United States Patent
Sanchez-Riera et al.

(10) Patent No.: US 11,434,512 B2
(45) Date of Patent: *Sep. 6, 2022

(54) PRODUCTION OF FATTY ACID ESTERS

(71) Applicant: GENOMATICA, INC., San Diego, CA (US)

(72) Inventors: Fernando Sanchez-Riera, South San Francisco, CA (US); Stephen Del Cardayre, South San Francisco, CA (US); Fernando Valle, South San Francisco, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/234,315

(22) Filed: Dec. 27, 2018

(65) Prior Publication Data
US 2020/0017890 A1     Jan. 16, 2020

Related U.S. Application Data

(63) Continuation of application No. 12/768,419, filed on Apr. 27, 2010, now abandoned, which is a continuation-in-part of application No. 12/278,957, filed as application No. PCT/US2007/011923 on May 18, 2007, now abandoned.

(60) Provisional application No. 61/182,564, filed on May 29, 2009, provisional application No. 61/173,016, filed on Apr. 27, 2009, provisional application No. 60/802,016, filed on May 19, 2006, provisional application No. 60/801,995, filed on May 19, 2006, provisional application No. 60/908,547, filed on Mar. 28, 2007.

(51) Int. Cl.
| | |
|---|---|
| C12P 7/64 | (2022.01) |
| C12P 7/06 | (2006.01) |
| C12N 1/21 | (2006.01) |
| C12N 1/19 | (2006.01) |
| C12N 9/18 | (2006.01) |
| C12N 9/00 | (2006.01) |
| C12N 9/10 | (2006.01) |
| C12P 7/649 | (2022.01) |
| C12N 9/02 | (2006.01) |
| C12N 9/52 | (2006.01) |
| C12N 9/04 | (2006.01) |

(52) U.S. Cl.
CPC ............ *C12P 7/649* (2013.01); *C12N 9/0006* (2013.01); *C12N 9/0008* (2013.01); *C12N 9/52* (2013.01); *C12P 7/065* (2013.01); *Y02E 50/10* (2013.01)

(58) Field of Classification Search
None
See application file for complete search history.

(56) References Cited

U.S. PATENT DOCUMENTS

| | | |
|---|---|---|
| 5,000,000 A | 3/1991 | Ingram et al. |
| 5,028,539 A | 7/1991 | Ingram et al. |
| 5,233,109 A | 8/1993 | Chow |
| 5,424,202 A | 6/1995 | Ingram et al. |
| 5,441,742 A | 8/1995 | Autant et al. |
| 5,445,947 A | 8/1995 | Metz et al. |
| 5,482,846 A | 1/1996 | Ingram et al. |
| 5,530,186 A | 6/1996 | Hitz et al. |
| 5,536,659 A | 7/1996 | Fukuda et al. |
| 5,602,030 A | 2/1997 | Ingrahm et al. |
| 5,807,893 A | 9/1998 | Voelker |
| 5,908,617 A | 6/1999 | Moore et al. |
| 5,939,250 A | 8/1999 | Short |
| 5,955,329 A | 9/1999 | Yuan et al. |
| 6,015,440 A | 1/2000 | Noureddini |
| 6,143,538 A | 11/2000 | Somerville et al. |
| 6,229,056 B1 | 5/2001 | Ansmann et al. |
| 6,491,927 B1 | 12/2002 | Arnaud et al. |
| 6,583,266 B1 | 6/2003 | Smith et al. |
| 6,596,538 B1 | 7/2003 | Lardizabal et al. |
| 6,750,048 B2 | 6/2004 | Ruecker et al. |
| 6,960,455 B2 | 11/2005 | Livshits et al. |
| 6,982,155 B1 | 1/2006 | Fukuda et al. |
| 7,056,714 B2 | 6/2006 | Rosazza et al. |
| 7,118,896 B2 | 10/2006 | Kalscheuer et al. |
| 7,169,588 B2 | 1/2007 | Burch et al. |
| 7,314,974 B2 | 1/2008 | Cao et al. |
| 7,425,433 B2 | 9/2008 | Rosazza et al. |
| 7,491,854 B2 | 2/2009 | Binder |
| 7,608,700 B2 | 10/2009 | Klaenhammer et al. |
| 7,691,159 B2 | 4/2010 | Li |
| 8,110,093 B2 | 2/2012 | Friedman et al. |
| 8,110,670 B2 | 2/2012 | Hu et al. |
| 8,268,599 B2 | 9/2012 | Schirmer et al. |
| 8,283,143 B2 | 10/2012 | Hu et al. |
| 8,313,934 B2 | 11/2012 | Bhatia et al. |

(Continued)

FOREIGN PATENT DOCUMENTS

| | | |
|---|---|---|
| BR | PI0712205 A2 | 2/2012 |
| CN | 1491282 A | 4/2004 |

(Continued)

OTHER PUBLICATIONS

Martinez-Force et al., Planta 211:67-678, 2000 (Year: 2000).*

(Continued)

*Primary Examiner* — David Steadman

(74) *Attorney, Agent, or Firm* — Harness Dickey & Pierce P.L.C.

(57) ABSTRACT

Methods of producing fatty acid esters, such as fatty acid ethyl esters, from genetically engineered microorganisms are described.

10 Claims, 12 Drawing Sheets

Specification includes a Sequence Listing.

(56) References Cited

U.S. PATENT DOCUMENTS

| | | | |
|---|---|---|---|
| 8,323,924 | B2 | 12/2012 | Schirmer et al. |
| 8,535,916 | B2 | 9/2013 | Del Cardayre et al. |
| 9,017,984 | B2 | 4/2015 | Hu et al. |
| 9,133,406 | B2 | 9/2015 | Gaertner |
| 9,587,231 | B2 * | 3/2017 | Hom .................... C12N 15/00 |
| 10,017,455 | B2 | 7/2018 | Hu et al. |
| 2003/0040474 | A1 | 2/2003 | Kapeller-Libermann et al. |
| 2003/0064328 | A1 | 4/2003 | Friedel |
| 2003/0097686 | A1 | 5/2003 | Knauf et al. |
| 2003/0129601 | A1 | 7/2003 | Cole |
| 2003/0233675 | A1 | 12/2003 | Cao et al. |
| 2004/0005678 | A1 | 1/2004 | Keasling et al. |
| 2004/0009576 | A1 | 1/2004 | Kalscheuer et al. |
| 2004/0072323 | A1 | 4/2004 | Matsuda et al. |
| 2004/0161833 | A1 | 8/2004 | Shah |
| 2004/0180400 | A1 | 9/2004 | Rosazza et al. |
| 2004/0197896 | A1 | 10/2004 | Cole |
| 2005/0019863 | A1 | 1/2005 | Sarmientos et al. |
| 2005/0130126 | A1 | 6/2005 | Durmaz et al. |
| 2005/0250135 | A1 | 11/2005 | Klaenhammer et al. |
| 2006/0014977 | A1 | 1/2006 | Miller et al. |
| 2006/0037237 | A1 | 2/2006 | Copeland et al. |
| 2006/0195947 | A1 | 8/2006 | Davis et al. |
| 2006/0206963 | A1 | 9/2006 | Voelker et al. |
| 2007/0003736 | A1 | 1/2007 | Saarvali et al. |
| 2007/0192900 | A1 | 8/2007 | Sticklen |
| 2007/0251141 | A1 | 11/2007 | Bist et al. |
| 2007/0261138 | A1 | 11/2007 | Graham et al. |
| 2007/0270319 | A1 | 11/2007 | Seggelkow et al. |
| 2007/0281345 | A1 | 12/2007 | Binder |
| 2008/0161595 | A1 | 7/2008 | Huang et al. |
| 2008/0221310 | A1 | 9/2008 | O'Sullivan et al. |
| 2008/0295388 | A1 | 12/2008 | Bazzani et al. |
| 2009/0038211 | A1 | 2/2009 | Sarin et al. |
| 2009/0047721 | A1 | 2/2009 | Trimbur et al. |
| 2009/0075333 | A1 | 3/2009 | Campbell et al. |
| 2009/0084025 | A1 | 4/2009 | Bhatia et al. |
| 2009/0117629 | A1 | 5/2009 | Schmidt-Dannert et al. |
| 2009/0136469 | A1 | 5/2009 | Senin et al. |
| 2009/0215140 | A1 | 8/2009 | Kurano et al. |
| 2009/0275097 | A1 | 11/2009 | Sun et al. |
| 2010/0071259 | A1 | 3/2010 | Hu et al. |
| 2010/0105955 | A1 | 4/2010 | Alibhai et al. |
| 2010/0105963 | A1 | 4/2010 | Hu |
| 2010/0185017 | A1 | 7/2010 | Yoshikuni et al. |
| 2010/0221798 | A1 | 9/2010 | Schirmer et al. |
| 2010/0242345 | A1 | 9/2010 | Keasling et al. |
| 2010/0249470 | A1 | 9/2010 | Schirmer et al. |
| 2010/0251601 | A1 | 10/2010 | Hu et al. |
| 2010/0257777 | A1 | 10/2010 | Sanchez-Riera et al. |
| 2010/0257778 | A1 | 10/2010 | Gaertner et al. |
| 2010/0274033 | A1 | 10/2010 | Sanchez-Riera et al. |
| 2011/0072714 | A1 | 3/2011 | Gaertner |
| 2011/0097769 | A1 | 4/2011 | Del Cardayre et al. |
| 2011/0146142 | A1 | 6/2011 | Lee et al. |
| 2011/0162259 | A1 | 7/2011 | Gaertner |
| 2012/0040426 | A1 | 2/2012 | Sun et al. |
| 2013/0084608 | A1 | 4/2013 | Szabo et al. |

FOREIGN PATENT DOCUMENTS

| | | |
|---|---|---|
| DE | 10 2004 052 115 | 4/2006 |
| EP | 1 241 262 A2 | 9/2002 |
| EP | 0 557 469 A1 | 3/2004 |
| EP | 2 024 491 | 11/2014 |
| GB | 2 090 611 | 7/1982 |
| JP | 08-173165 | 7/1996 |
| JP | 2002-223788 A | 8/2002 |
| JP | 2009-511091 A | 3/2009 |
| JP | 2010-505388 A | 2/2010 |
| KR | 10200717428 | 2/2007 |
| WO | WO-99/18118 A1 | 4/1999 |
| WO | WO-00/12725 A2 | 3/2000 |
| WO | WO-00/61740 | 10/2000 |
| WO | WO-00/78782 A1 | 12/2000 |
| WO | WO-02/40690 | 5/2002 |
| WO | WO-03/074676 | 9/2003 |
| WO | WO-2004/000871 | 12/2003 |
| WO | WO-2004/031376 A2 | 4/2004 |
| WO | WO-2004/081226 | 9/2004 |
| WO | WO-2005/007845 | 1/2005 |
| WO | WO-2005/052163 A2 | 6/2005 |
| WO | WO-2005/077495 A1 | 8/2005 |
| WO | WO-2006/014837 A1 | 2/2006 |
| WO | WO-2006/037947 A1 | 4/2006 |
| WO | WO-2007/022169 | 2/2007 |
| WO | WO-2007/032538 A1 | 3/2007 |
| WO | WO-2007/136762 A2 | 11/2007 |
| WO | WO-2008/058788 A1 | 5/2008 |
| WO | WO-2008/100251 | 8/2008 |
| WO | WO-2008/119082 A2 | 10/2008 |
| WO | WO-2009/042950 A1 | 4/2009 |
| WO | WO-2009/140695 A2 | 11/2009 |
| WO | WO-2009/140696 | 11/2009 |
| WO | WO-2010/021711 | 2/2010 |
| WO | WO-2010/022090 A1 | 2/2010 |
| WO | WO-201 0/033921 | 3/2010 |
| WO | WO-2010/042664 A1 | 4/2010 |
| WO | WO-2010/062480 A2 | 6/2010 |
| WO | WO-2010/118409 A1 | 10/2010 |
| WO | WO-2010/118410 A1 | 10/2010 |
| WO | WO-2010/126891 A1 | 11/2010 |
| WO | WO-2010/127318 | 11/2010 |
| WO | WO-2011/038132 A1 | 3/2011 |
| WO | WO-2011/038134 A1 | 3/2011 |
| WO | WO-2011/062987 | 5/2011 |

OTHER PUBLICATIONS

Chang et al., Proc. Natl. Acad. Sci. 86:8373-8376, 1989 (Year: 1989).*
Brenda information for EC 2.3.1.86, obtained from brenda-enzymes.org on May 11, 2021, 3 pages (Year: 2021).*
Brenda information for EC 3.1.2.20, obtained from brenda-enzymes.org on May 11, 2021, 8 pages (Year: 2021).*
Hunt et al., J. Lipid Res. 46:2029-2032, 2005 (Year: 2005).*
Magnuson et al., FEBS Lett. 299:262-266, 1992 (Year: 1992).*
Cho et al., J. Biol. Chem. 270:4216-4219, 1995 (Year: 1995).*
Final Office Action in U.S. Appl. No. 15/954,451 dated Apr. 20, 2020.
Preliminary Office Action in BR Patent Application No. PI1015313-6 dated Mar. 24, 2020 (with English translation) (6 pages).
Partial Search Report in EP Patent Application No. 19192374.7 dated Feb. 18, 2020 (10 pages).
Abbadi et al., "Knockout of the regulatory site of 3-ketoacyl-ACP synthase III enhances short-and medium-chain acyl-ACP synthesis", Plant Journal, Oct. 2000, vol. 24, Issue 1, pp. 1-9.
Abdel-Hamid et al., "Coordinate Expression of the Acetyl Coenzyme A Carboxylase Genes, accB and accC, Is Necessary for Normal Regulation of Biotin Synthesis in *Escherichia coli*", J. Bacteriol., Jan. 15, 2007, vol. 189, Issue 2, pp. 369-376.
Abdel-Hamid et al., "Pyruvate oxidase contributes to the aerobic growth efficiency of *Escherichia coli*", Microbiol. Jul. 2001, vol. 147, Issue 6, pp. 1483-1498.
Allen, E.E. et al., "Structure and regulation of the omega-3 polyunsaturated fatty acid synthase genes from the deep-sea bacterium Photobacterium profundum strain SS9," Microbiology, Jul. 2002, vol. 148, Issue 6, pp. 1903-1913.
Alper et al., "Engineering for Biofuels: Exploiting Innate Microbial Capacity or Importing Biosynthetic Potential?", NRM, Oct. 2009, vol. 7, pp. 715-723.
Altschul et al., "Basic Local Alignment Search Tool," Journal of Molecular Biology, May 15, 1990, vol. 215, pp. 403-410.
Alvarez et al., "Triacylglycerols in prokaryotic microorganisms", Appl. Microbiol. Biotechnol., Dec. 2002, vol. 60, Issue 4, pp. 367-376.
Antoni et al., "Biofuels from microbes," Appl. Microbial. Biotechnol., Nov. 2007, vol. 77, pp. 23-35.

(56) References Cited

OTHER PUBLICATIONS

Atsumi et al., "Metabolic engineering for advanced biofuels production from *Escherichia coli*", Current Opin. Biotech., Sep. 2008, vol. 19, pp. 414-419.
Atsumi et al., "Metabolic engineering of *Escherichia coli* for 1-butanol production", Metabolic Engineering, Nov. 2008, vol. 10, pp. 305-311.
Atsumi et al., "Non-fermentative pathways for synthesis of branched-chain higher alcohols as biofuels," Nature, Jan. 3, 2008, vol. 451, pp. 86-89.
Barnes, Jr. et al., "Studies on the Mechanism of Fatty Acid Synthesis. XIX. Preparation and General Properties of Palmityl Thioesterase", J. Biol. Chem., Jun. 10, 1968, vol. 243, Issue 11, pp. 2955-2962.
Beekwilder et al., "Functional Characterization of Enzymes Forming Volatile Esters from Strawberry and Banana", Plant Physiology, Aug. 2004, vol. 135, pp. 1865-1878.
Beinert., "Recent developments in the field of iron-sulfur proteins", FASEB J., May 1990, vol. 4, pp. 2483-2491.
Benoist et al., "In vivo sequence requirements of the SV40 early promoter region," Nature, Mar. 26, 1981, vol. 290, Issue 5804, pp. 304-310.
Benson et al., "Development of a Heterogeneous Catalytic Cracking Reactor Utilizing Online Mass Spectrometry Analysis", J. Chromatography, Nov. 23, 2007, vol. 1172, Issue 2, pp. 204-208.
Bergler et al., "Protein EnvM is the NADH-dependent Enoyl-ACP Reductase (FabI) of *Escherichia coli*," J. Biol. Chem., Feb. 25, 1994, vol. 269, Issue 8, pp. 5943-5946.
Bergler et al., "The enoyl-[acyl-carrier-protein] reductase (FabI) of *Escherichia coli*, which catalyzes a key regulatory step in fatty acid biosynthesis, accepts NADH and NADPH as cofactors and is inhibited by palmitoyl-CoA", Eur. J. Biochem., Dec. 15, 1996, vol. 242, pp. 689-694.
Berrios-Rivera et al., "The Effect of Increasing NADH Availability on the Redistribution of Metabolic Fluxes in *Escherichia coli* Chemostat Cultures", Metabolic Engineering, Jul. 2002, vol. 4, pp. 230-237.
Birge et al., "Acyl Carrier Protein. XVI.Intermediate Reactions of Unsaturated Fatty Acid Synthesis in *Escerichia coli* and Studies of fab B Mutants", J.Biol.Chem. Aug. 25, 1972, vol. 247, Issue 16, pp. 4921-4929.
Bitter et al., "Expression and Secretion Vectors for Yeast," Methods in Enzymology—Recombinant DNA, Jun. 28, 1989, vol. 153, Part D, pp. 516-544.
Black et al., "Cloning, Sequencing, and Expression of the fadD Gene of *Escherichia coli* Encoding Acyl Coenzyme A Synthetase", J. Biol. Chem., vol. 267, Dec. 15, 1992, No. 35, pp. 25513-25520.
Black et al., "Long-Chain Acyl-CoA-Dependent Regulation of Gene Expression in Bacteria, Yeast and Mammals", J. Nutrition, Feb. 2000, pp. 305S-309S.
Black et al., "Mutational Analysis of a Fatty Acyl-Coenzyme A Synthetase Signature Motif Identifies Seven Amino Acid Residues That Modulate Fatty Acid Substrate Specificity", J. Biol. Chem., Feb. 21, 1997, vol. 272, Issue 8, pp. 4896-4903.
Black., "Primary Sequence of the *Escherichia coli* fadL Gene Encoding an Outer Membrane Protein Required for Long-Chain Fatty Acid Transport", J. Bacteriology, Jan. 1991, vol. 173, Issue 2, pp. 435-442.
Blanchard et al., "Overexpression and Kinetic Characterization of the Carboxyltransferase Component of Acetyl-CoA Carboxylase", J. Biol. Chem., Jul. 24, 1998, vol. 273, Issue 30, pp. 19140-19145.
Bonamore et al., "The desaturase from Bacillus subtilis, a promising tool for the selective olefination of phospholipids", J.Biotechnology, Jan. 2, 2006, vol. 121, pp. 49-53.
Bond-Watts et al., "Enzyme mechanism as a kinetic control element for designing synthetic biofuel pathways", Nature Chem. Bio., Feb. 2011, vol. 537, pp. 1-6 (Suppl. S1-S28).
Bonner et al., "Purification and Properties of Fatty Acyl Thioesterase I from *Escherichia coli*", J.Biol.Chem. May 25, 1972, vol. 247, Issue 10, pp. 3123-3133.
Boonstra et al., "The udhA Gene of *Escherichia coli* Encodes a Soluble Pyridine Nucleotide Transhydrogenase", J. Bacteriol., Feb. 1, 1999, vol. 181, Issue 3, pp. 1030-1034.
Boulanger et al., "Purification and Structural and Functional Characterization of FhuA, a Transporter of the *Escherichia coli* Outer Membrane", Biochemistry, Nov. 12, 1996, vol. 35, Issue 45, pp. 14216-14224.
Bredwell et al., "Reactor Design Issues for Synthesis-Gas Fermentations", Biotechnol. Prog., Oct. 1, 1999, vol. 15, pp. 834-844.
Brenda—Information on EC 3.1.2.14—oleoyl-[acyl-carrier-protein] hydrolase, Aug. 6, 2019, 11 pages.
Broun et al., "A bifunctional oleate 12-hydroxylase: Desaturase from Lesquerella fend/err". Plant Journal, Nov. 13, 1998, vol. 13, Issue 2, pp. 201-210.
Bunch et al., "The IdhA gene encoding the fermentative lactate dehydrogenase of *Escherichia coli*", Microbiol., Feb. 1997, vol. 143, Issue 1, pp. 187-195.
Cahoon et al., "A Determinant of Substrate Specificity Predicted from the Acyl-Acyl Carrier Protein Desaturase of Developing Cat's Claw Seed", Plant Physiol, Jun. 1998, vol. 117, pp. 593-598.
Cahoon et al., "Modification of the Fatty Acid Composition of *Escherichia coli* by Coexpression of a Plant Acyl-Acyl Carrier Protein Desaturase and Ferredoxin", J.Bacteriol., Feb. 1996, vol. 178, Issue 3, pp. 936-939.
Cahoon et al., "Redesign of soluble fatty acid desaturases from plants for altered substrate specificity and double bond position", Proc. Natl. Acad. Sci., May 13, 1997, vol. 94, pp. 4872-4877.
Camilli et al., "Bacterial Small-Molecule Signaling Pathways", Science, Feb. 24, 2006, vol. 311, Issue 5764, pp. 1-9.
Campbell et al., "A New *Escherichia coli* metabolic competency: growth on fatty acids by a novel anaerobic .beta.-oxidation pathway", Mol. Microbiol., Feb. 2003, vol. 47, Issue 3, pp. 793-805.
Campbell et al., "*Escherichia coli* FadR Positively Regulates Transcription of the fabB Fatty Acid Biosynthetic Gene", J.Bacteriol., Oct. 2001, vol. 183, Issue 20, pp. 5982-5990.
Campbell et al., "The Enigmatic *Escherichia coli* fadE Gene is yafH", J. Bacteriol., Jul. 2002, vol. 184, Issue 13, pp. 3759-3764.
Cann et al., "Production of 2-methyl-1-butanol in engineered *Escherichia coli*," Appl. Microbiol Biotechnol., Nov. 2008, vol. 81, Issue 2, pp. 89-98.
Canoira et al., "Biodiesel from Jojoba oil-wax: Transesterification with methanol and properties as a fuel", Biomass and Bioenergy, Jan. 2006, vol. 30, pp. 76-81.
Canonaco et al., "Metabolic flux response to phosphoglucose isomerase knock-out in *Escherichia coli* and impact of overexpression ofthe soluble transhydrogenase UdhA", FEMS Microbiology Letters, Nov. 2001, vol. 204, pp. 247-252.
Causey et al., "Engineering *Escherichia coli* for efficient conversion of glucose to pyruvate," PNAS, Feb. 24, 2004, vol. 101, No. 8, pp. 2235-2240.
Caviglia et al., "Rat Long Chain Acyl-CoA Synthetase 5, but Not 1, 2, 3, or 4, Complements *Escherichia coli* fadD," J. Biol. Chem, Mar. 19, 2004, vol. 279, No. 12, pp. 11163-11169.
Chang et al., "Genetic and Biochemical Analyses of *Escherichia coli* Strains Having a Mutation in the Structural Gene (poxB) for Pyruvate Oxidase," J. Bacteriol., May 1983, vol. 154, Issue 2, pp. 756-762.
Chassagnole et al., "Dynamic Modeling of the Central Carbon Metabolism of *Escherichia coli*", Biotech & Engineering, Jul. 5, 2002, vol. 79, Issue 1, pp. 53-73.
Chen et al., "Biosynthesis of Ansatrienin (mycotrienin) and naphthomycin, Identification and Analysis of Two Separate Biosynthetic Gene Clusters in Streptomyces Collinus Tu 1892," Apr. 1999, Eur. J. Biochem., vol. 261, pp. 98-107.
Chen, "Permeability issues in whole-cell bioprocesses and cellular membrane engineering", Appl Microbiol Biotechnol., Mar. 2007, vol. 74, pp. 730-738.
Cheng et al., "Mammalian Wax Biosynthesis, II. Expression Cloning of a Wax Synthase cDNAs Encoding a Member of the Acyltransferase Enzyme Family*," J. Biol. Chem., Sep. 3, 2004, vol. 279, Issue 36, pp. 37798-37807.

(56) References Cited

OTHER PUBLICATIONS

Chica et al., "Semi-rational approaches to engineering enzyme activity: combining the benefits of directed evolution and rational design," Current Opinion in Biotechnology, Feb. 2005, vol. 16, pp. 378-384.

Cho et al., "Defective Export of a Periplasmic Enzyme Disrupts Regulation of Fatty Acid Synthesis," J. Biol. Chern., Mar. 3, 1995, vol. 270, No. 9, pp. 4216-4219.

Cho et al., "*Escherichia coli* thioesterase I, molecular cloning and sequencing of the structural gene and identification s a periplasmic enzyme", J. Biol. Chem., May 5, 1993, vol. 268, No. 13, pp. 9238-9245.

Cho et al., "Transcriptional regulation of the fad regulon genes of *Escherichia coli* by ArcA", Microbiology, Aug. 1, 2006, vol. 152, pp. 2207-2219.

Choi et al., ".beta.-Ketoacyl-acyl Carrier Protein Synthase III (FabH) Is a Determining Factor in Branched-Chain Fatty Acid Biosynthesis", J. of Bacteriology, Jan. 2000, vol. 182, Issue 2, pp. 365-370.

Coleman et al., "Enzymes of triacylglycerol synthesis and their regulation", Progress in Lipid Research, Mar. 2004, vol. 43, pp. 134-176.

Collister et al., "Modification of the petroleum system concept: Origins of alkanes and isoprenoids in crude oils", AAPG Bulletin, May 2004, vol. 88, Issue 5, pp. 587-611.

Conway et al., "Cloning and Sequencing of the Alcohol Dehydrogenase II Gene from Zymomonas mobilis," J. Bacteriol., Jun. 1987, vol. 169, Issue 6, pp. 2591-2597.

Corpet, "Multiple sequence alignment with hierarchical clustering," Nucleic Acids Research, Nov. 28, 1988, vol. 16, No. 22, pp. 10881-10890.

Costaglioli, P et al., "Profiling candidate genes involved in wax biosynthesis in *Arabidopsis thaliana* by mircroarray analysis," Biochimica et Biophysica Acta., Jun. 1, 2005, vol. 1734, pp. 247-258.

Costantino et al., "Enhanced levels of .lambda. Red-mediated recombinants in mismatch repair mutants", Proc. Natl. Acad. Sci. USA, Dec. 11, 2003, vol. 100, Issue 26, pp. 15748-15753.

Cropp et al., "Identification of a Cyclohexylcarbonyl CoA Biosynthetic Gene Cluster and Application in the Production of Doramectin", Nature Biotechnology, Sep. 2000, vol. 18, pp. 980-983.

Currie., "Source Apportionment of Atmospheric particles," Characterization of Environmental Particles, IUPAC Environmental Analytical Chemistry Series, vol. 1, Mar. 17, 1992, pp. 3-75.

Da Silva et al., "Comparison of the Genomes of Two Xanthomonas Pathogens with Differing Host Specificities", Nature, May 23, 2002, vol. 417, pp. 459-463.

Database EMBL (Online), Jul. 1996, "Synechococcus, PCC7942 Ribosomal Protein S1 of 30S Ribosome (rpsI), ORF271, ORF231, ORF341, Carboxyltransferase alpha subunit (accA), ORF245, ORF227, and GTP cyclohydrolase I (folE) genes, complete cds, and ORF205 gene, partial cds.," XP002564232, 2 pages.

Database GenBank Accession No. AAA34215, thioesterase [Umbellularia californica], URL https://www.ncbi.nlm.nih.gov/protein/AAA34215, 2 pages.

Database UniProt (Online), Nov. 1996, "SubName: Full=Putative uncharacterized CI2 protein; SubName: Full=Putative uncharacterized protein SEC0028;" XP002564231, retrieved from EBI accession No. UNIPROT: 054765, Database accession No. 054765, 1 page.

Database UniProt, Online, Nov. 1996, XP002545841, Retrieved from EBI Accession No. Uniprot:Q54764, 1 page.

Database UniProt, Online, Nov. 1996, XP002564231, Retrieved from EBI Accession No. UNIPROT:Q54765, 1 page.

Database Uniprot, Online, Nov. 1996, XP002564232, Retrieved from EBI Accession No. Uniprot:Q54765, 4 pages.

Datsenko et al., "One-step Inactivation of Chromosomal Genes in *Escherichia coli* K-12 using PCR Products", Proc. Natl. Acad. Sci USA, Jun. 6, 2000, vol. 97, No. 12, pp. 6640-6645.

Davis et al., "Inhibition of *Escherichia coli* Acetyl Coenzyme A Carboxylase by Acyl-Acyl Carrier Protein", J.Bacteriol., Feb. 2001, vol. 183, Issue 4, pp. 1499-1503.

Davis et al., "Overproduction of Acetyl-CoA Carboxylase Activity Increases the Rate of Fatty Acid Biosynthesis in *Escherichia coli*", J. Biol. Chem., Sep. 15, 2000, vol. 275, Issue 37, pp. 28593-28598.

Davis, J.B., "Microbial Incorporation of Fatty Acids Derived From n-Alkanes Into Glycerides and Waxes," Applied Microbiology, May 1964, vol. 12, No. 3, pp. 210-214.

De Lay et al., "In Vivo Functional Analyses of the Type II Acyl Carrier Proteins of Fatty Acid Biosynthesis", J. Biol. Chem., Jul. 13, 2007, vol. 282, No. 28, pp. 20319-20328.

De Mendoza et al., "Thermal Regulation of Membrane Fluidity in *Escherichia coli*. Effects of Overproduction of P-Ketoacylacyl Carrier Protein Synthase 1", J. Biol. Chem., Feb. 25, 1983, vol. 258, Issue 4, pp. 2098-2101.

Dehesh et al., "KAS IV: A 3-ketoacyl-ACP synthase from Cuphea sp. Is a medium chain specific condensing enzyme", The Plant Journal, Aug. 1998, vol. 15, Issue 3, pp. 383-390.

Dehesh et al., "Production of high levels of 8:0 and 10:0 fatty acids in transgenic canola by overexpression of Ch FatB2, a thioesterase cDNA from Cuphea hookeriana," The Plant Journal, Feb. 1996, vol. 9, Issue 2, pp. 167-172.

Dellomonaco et al., "Engineered Respiro-Fermentative Metabolism for the Production of Biofuels and Biochemicals from Fatty Acid-Rich Feedstocks", Applied & Environmental Microbiology, Aug. 2010, vol. 76, Issue 15, pp. 5067-5078.

Demirbas, A., "Progress and recent trends in biofuels", Progress in Energy and Combustion Science, Feb. 2007, vol. 33, pp. 1-18.

Demirbas, A., "Relationships derived from physical properties of vegetable oil and biodiesel fuels", Jul. 2008, Fuel, vol. 87, pp. 1743-1748.

Denoya, et al., "A Second Branded-Chain a-Keto Acid Dehydrogenase Gene Cluster (bkdFGH) from Streptomyces Avermitilis: Its Relationship to Avermectin Biosynthesis and the Construction of a bkdF Mutant Suitable for the Production of Novel Antiparasitic Avermectins", Journal of Bacteriology, Jun. 1995, vol. 177, No. 12, pp. 3504-3511.

DeVeaux et al., "Genetic and Biochemical Characterization of a Mutation (fatA) That Allows trans Unsaturated Fatty Acids to Replace the Essential cis Unsaturated Fatty Acids of *Escherichia coli*", J. Bacteriology, Mar. 1989, vol. 171, Issue 3, pp. 1562-1568.

Doan et al., "Functional expression of five *Arabidopsis* fatty acyl-CoA reductase genes in *Escherichia coli*", J. Plant Physiology, May 15, 2009, vol. 166, pp. 787-796.

Domergue et al., "Acyl Carriers Used as Substrates by the Desaturases and Elongases Involved in Very Long-chain Polyunsaturated Fatty Acids Biosynthesis Reconstituted in Yeast", J. Biol. Chem, vol. 278, Sep. 12, 2003, Issue 37, pp. 35115-35126.

Domka et al., "YliH (BssR) and YceP (BssS) Regulate *Escherichia coli* K-12 Biofilm Bormation by Influencing Cell Signaling", Appl. and Environ. Microbiol., Apr. 2006, vol. 72, Issue 4, pp. 2449-2459.

Dormann et al., "Specificities of the Acyl-Acyl Carrier Protein (ACP) Thioesterase and Glycerol-3-Phosphate Acyltransferase for Octadecenoyl-ACP Isomers (Identification of a Petroselinoyl-ACP Thioesterase in Umbelliferae)," Plant Physiol., Mar. 1994, vol. 104, pp. 839-844.

Doss, R.P., "Composition and Enzymatic Activity of the Extracellular Matrix Secreted by Germlings of Botrytis cinerea," Appl. and Environ. Microbiol., Feb. 1999, vol. 65, Issue 2, pp. 404-408.

Duan et al., "De novo Biosynthesis of Biodiesel by *Escherichia coli* in Optimized Fed-Batch Cultivation", PLoS ONE, May 2011, vol. 6, Issue 5, pp. 1-7.

Durre, P., "Fermentative Butanol Production: Bulk Chemical and Biofuel," Ann. N. Y. Acad. Sci., Mar. 2008, vol. 1125, pp. 353-362.

Dworkin et al., "The PspA Protein of *Escherichia coli* is a Negative Regulator of sigma54-Dependent Transcription", J. Bacteriol., Jan. 2000, vol. 182, Issue 2, pp. 311-319.

Edwards et al., "The *Escherichia coli* MG1655 in silico metabolic genotype: Its definition, characteristics, and capabilities", PNAS, May 9, 2000, vol. 97, Issue 10, pp. 5528-5533.

(56) References Cited

OTHER PUBLICATIONS

Elbahloul et al., "Pilot-Scale Production of Fatty Acid Ethyl Esters by an Engineered *Escherichia coli* Strain Harboring the p(Microdiesel) Plasmid", Appl. and Environ. Microbiol., Jun. 23, 2010, vol. 76, Issue 13, pp. 4560-4565.
European Search Report on EP Application 09013640.9, dated Jan. 25, 2010, 7 pages.
European Search report on EP Application 09013650.8, dated Aug. 23, 2010, 9 pages.
European Search Report on EP Application 11005423.6, dated Nov. 15, 2011, 7 pages.
European Search Report on EP Application 12194886.3, dated Apr. 24, 2013, 6 pages.
European Search Report on EP Application 12194886.3, dated Sep. 17, 2015, 7 pages.
European Search Report on EP Application 14193614.6, dated Mar. 5, 2015, 5 pages.
European Search Report on EP Application 18153966.9, dated Oct. 19, 2018, 13 pages.
Farewell et al., "Role of the *Escherichia coli* FadR Regulator in Stasis Survival and Growth Phase-Dependent Expression of the uspA, fad, and fab Genes", J. Bacteriol., Nov. 1996, vol. 178, Issue 22, pp. 6443-6450.
Fehler et al., "Biosynthesis of Hydrocarbons in Anabaena variabilis. Incorporation of [methyl-14C]-and [methy/-2H2] Methionine into 7- and 8-Methylheptadecanes*", Biochemistry, Jan. 20, 1970, vol. 9, No. 2, pp. 418-422.
Feng et al., "A New Member of the *Escherichia coli* fad Regulon: Transcriptional Regulation of fadM (ybaW)", J. Bacteriol., Oct. 2009, vol. 191, Issue 20, pp. 6320-6328.
Feng et al., "*Escherichia coli* Unsaturated Fatty Acid Synthesis: Complex Transcription of the fabA Gene and in Vivo Identification of the Essential Reaction Catalyzed by FabB", J.Biol. Chem., Oct. 23, 2009, vol. 284, Issue 43, pp. 1-19.
Feng et al., "Overlapping Repressor Binding Sites Result in Additive Regulation of *Escherichia coli* FadH by FadR and ArcA", J. of Bacteriology, Aug. 12, 2010, vol. 192, Issue 17, pp. 4289-4299.
Final Office Action on U.S. Appl. No. 12/278,957, dated Mar. 13, 2016, 22 pages.
Final Office Action on U.S. Appl. No. 12/278,957, dated May 1, 2017, 29 pages.
Final Office Action on U.S. Appl. No. 12/278,957, dated Nov. 8, 2011, 15 pages.
Final Office Action on U.S. Appl. No. 12/278,957, dated Sep. 15, 2014, 23 pages.
Final Office Action on U.S. Appl. No. 12/768,419, dated Aug. 19, 2015, 33 pages.
Final Office Action on U.S. Appl. No. 12/768,419, dated Dec. 1, 2017, 20 pages.
Final Office Action on U.S. Appl. No. 12/768,419, dated Jul. 14, 2016, 11 pages.
Final Office Action on U.S. Appl. No. 12/768,419, dated Mar. 21, 2013, 31 pages.
Final Office Action on U.S. Appl. No. 13/099,986, dated Jul. 11, 2012, 9 pages.
Final Office Action on U.S. Appl. No. 13/529,990, dated May 23, 2014, 15 pages.
Final Office Action on U.S. Appl. No. 13/870,426, dated Jun. 29, 2016, 14 pages.
Fischer et al., "Selection and optimization of microbial hosts for biofuels production", Metabolic Engineering, Jul. 3, 2008, vol. 10, pp. 295-304.
Flaman et al., "Site-directed Mutagenesis of Acyl Carrier Protein (ACP) Reveals Amino Acid Residues Involved in ACP Structure and Acyl-ACP Synthetase Activity," J. Biol. Chem., Sep. 21, 2001, vol. 276, Issue 38, pp. 35934-35939.
Fleischman et al., "Putative long-chain fatty-acid—CoA ligase [*Mycobactcterium smegmatis* str. MC2 155]", GenBank71854. 1(2006), 3 pages.
Foecking et al., "Powerful and versatile enhancer-promoter unit for mammalian expression vectors," Gene, Aug. 1986, vol. 45, Issue 1, pp. 101-105.
Foreign Action other than Search Report on IN 201618015610 dated Dec. 16, 2019.
Fozo et al., "The fabM Gene Product of Streptococcus mutans Is Responsible for the Synthesis of Monounsaturated Fatty Acids and Is Necessary for Survival at Low pH", J. Bacteriol., Jun. 17, 2004, vol. 186, Issue 13, pp. 4152-4158.
Fu et al., "Oleylethanolamide regulates feeding and body weight through activation of the nuclear receptor PPAR-beta)", Sep. 4, 2003, Nature, vol. 425, pp. 90-93.
Fujita et al., "Regulation of fatty acid metabolism in bacteria", Mol. Microbiology, Nov. 2007, vol. 66, Issue 4, pp. 829-839.
Fulda et al., "Two long-chain acyl-CoA synthetases from *Arabidopsis thaliana* involved in peroxisomal fatty acid beta-oxidation", The Plant Journal, Oct. 2002, vol. 32, pp. 93-103.
Ghisla et al., "Acyl-CoA dehydrogenases—A mechanistic overview," Eur. J. Biochem., Feb. 2004, vol. 271, pp. 494-508.
Glick et al., "Factors affecting the expression of foreign proteins in *Escherichia coli*," J Ind. Microbiol. and Biotech., Feb. 1987, vol. 1, Issue 5, p. 277-282.
Guo et al., "Protein tolerance to random amino acid change," Jun. 22, 2004, Natl. Acad. Sci., vol. 101, No. 25, pp. 9205-9210.
Hamer et al., "Regulation in vivo of a cloned mammalian gene: cadmium induces the transcription of a mouse metallothionein gene is SV40 vectors," J. Mol. Appl. Gen., Apr. 1982, vol. 1, pp. 273-288.
Hamilton-Kemp et al., "Production of the Long-Chain Alcohols Octanol, Decanol, and Dodecanol by *Escherichia coli*", Current Microbiology, May 2005, vol. 51, pp. 82-86.
Han et al., "A Novel Alternate Anaplerotic Pathway to the Glyoxylate Cycle in Streptomycetes," J. Bacteriol., Aug. 1997, vol. 179, Issue 16, pp. 5157-5164.
Han et al., "Biosynthesis of Alkanes in Nostoc Muscorum," Journal of the American Chemical Society, vol. 91, Issue 18, Aug. 1969, pp. 5156-5159.
Hancock et al., "SIMPLE34: an improved and enhanced implementation for VAX and Sun computers of the SIMPLE algorithm for analysis of clustered repetitive motifs in nucleotide seguences," Comput. Appl. Biosci., Feb. 1994, vol. 10, No. 1, pp. 67-70.
Hantke, K., "Ferrous iron transport mutants in *Escherichia coli* K12," FEMS Microbiology Letters, Sep. 1987, vol. 44, pp. 53-57.
He et al., "Nocardia sp. Carboxylic Acid Reductase: Cloning, Expression, and Characterization of a New Aldehyde Oxidoreductase Family," Applied and Environmental Microbiology, Mar. 2004, vol. 70 Issue 3, pp. 1874-1881.
Heath et al., "Inhibition of .beta.-Ketoacyl-Acyl Carrier Protein Synthase III (FabH) by Acyl-Acyl Carrier Protein in *Escherichia coli*", J.Biol. Chem., May 3, 1996, vol. 271, Issue 18, pp. 10996-11000.
Heath et al., "Lipid Biosynthesis as a Target for Antibacterial Agents," Prog. Lipid Res., Nov. 2001, vol. 40, Issue 6, pp. 467-497.
Heath et al., "Regulation of Fatty Acid Elongation and Initiation by Acyl-Acyl Carrier Protein in *Escherichia coli*", J. Biol. Chem., Jan. 26, 1996, vol. 271, Issue 4, pp. 1833-1836.
Heath et al., "Regulation of Malonyl-CoA Metabolism by Acyl-Acyl Carrier Protein and .beta.-Ketoacyl-Acyl Carrier Protein Synthases in *Escherichia coli*", J. Biol. Chem., Jun. 30, 1995, vol. 270, Issue 26, pp. 15531-15538.
Heath et al., "Roles of the FabA and FabZ .beta.-Hydroxyacyl-Acyl Carrier Protein Dehydratases in *Escherichia coli* Fatty Acid Biosynthesis", J. Biol. Chem., Nov. 1, 1996, vol. 271, Issue 44, pp. 27795-27801.
Henry et al., "*Escherichia coli* Transcription Factor That Both Activates Fatty Acid Synthesis and Represses Fatty Acid Degradation", J. Mol. Biol., Dec. 20, 1991, vol. 222, pp. 843-849.
Higgins et al., "CLUSTAL: a package for performing multiple seguence alignment on a microcomputer," Dec. 15, 1988, Gene, vol. 73, No. 1, pp. 237-244.
Higgins et al., "Using CLUSTAL for Multiple Seguence Alignments," Meth. Enzymol., vol. 266, Published online Jan. 7, 2004, pp. 383-402.

(56) References Cited

OTHER PUBLICATIONS

Higgins et al., "Fast and sensitive multiple sequence alignments on a microcomputer", Cabios Communications Apr. 1989, vol. 5, No. 2, pp. 151-153.

Hill et al., "Functional Analysis of conserved Histidines in ADP-Glucose Pyrophosphorylase from *Escherichia coli*," Biochem. Biophys. Res. Comm., Mar. 17, 1998, vol. 244, pp. 573-577.

Hoffmann et al., "Heat-Induced Aggregation of β-Lactoglobulin: Role of the Free Thiol Group and Disulfide Bonds," J. Agric. Food Chem., Aug. 18, 1997, vol. 45, Issue 8, pp. 2942-2948.

Hoffmeister et al., "Mitochondrial trans-2-Enoyl-CoA Reductase of Wax Ester Fermentation from Euglena gracilis Defines a New Family of Enzymes Involved in Lipid Synthesis*," The Journal of Biological Chemistry, vol. 280, Feb. 11, 2005, No. 6, pp. 4329-4338.

Holland-Staley et al., "Aerobic Activity of *Escherichia coli* Alcohol Dehydrogenase Is Determined by a Single Amino Acid," J. Bacteriol., Nov. 2000, vol. 182, No. 21, pp. 6049-6054.

Holtzapple et al., "Biosynthesis of Isoprenoid Wax Ester in Marinobacter hydrocarbonoclasticus DSM 8798: Identification and Characterization of Isoprenoid Coenzyme A Synthetase and Wax Ester Synthases," J.Bacteriology, May 2007, vol. 189, Issue 10, pp. 3804-3812.

Horton et al., "Heterologous expression of the *Saccharomyces cerevisiae* alcohol acetyltransferase genes in Clostridium acetobutylicum and *Escherichia coli* for the production of isoamyl acetate," Journal of Industrial Microbiology and Biotechnology, Jul. 2003, vol. 30, pp. 427-432.

Howell et al., "(R)-Citramalate Synthase in Methanogenic Archaea," J. Bacteriol., vol. 181, Jan. 1999, Issue 1, pp. 331-333.

Hsieh., "Pool Size and Mean Age of Stable Soil Organic Carbon in Cropland," Soil Sci. Soc. Am. J., Jan. 1, 1992, vol. 56, pp. 460-464.

Hu et al., "Microalgal triacylglycerols as feedstocks for biofuel production: perspectives and advances", The Plant Journal, May 2008, vol. 54, pp. 621-639.

Huang et al., "Parallelization of a local similarity algorithm," Bioinformatics, Apr. 1992, vol. 8, Issue 2, pp. 155-165.

Huber et al., "Branched-Chain Fatty Acids Produced by Mutants of Streptomyces fradiae, Putative Precursors of the Lactone Ring of Tylosin," Antimicrob. Agents Chemother., Aug. 1, 1990, vol. 34, Issue 8, pp. 1535-1541.

Huisman et al., "Towards novel processes for the fine-chemical and pharmaceutical industries," Curr. Opin. Biotechnol., Oct. 1, 2002, vol. 13, Issue 4, pp. 352-358.

Hunt et al., "Characterization of an Acyl-CoA Thioesterase That Functions as a Major Regulator of Peroxisomal Lipid Metabolism," J. Biol. Chem., Jan. 11, 2002, vol. 277, Issue 2, pp. 1128-1138.

Imahara et al., "Thermodynamic study on cloud point of biodiesel with its fatty acid composition", Fuel, vol. 85, Sep. 2006, pp. 1666-1670.

International Preliminary Report on Patentability for PCT/US2010/032580, dated Nov. 1, 2011, 5 pages.

International Preliminary Report on Patentability on PCT/US2007/003736, dated Aug. 2009, 6 pages.

International Preliminary Report on Patentability on PCT/US2007/011923, dated Nov. 21, 2008, 12 pages.

International Preliminary Report on Patentability on PCT/US2008/057127, dated Sep. 15, 2009, 6 pages.

International Preliminary Report on Patentability on PCT/US2008/058788, dated Sep. 29, 2009, 12 pages.

International Search Report and Written Opinion on PCT/US2007/003736, dated Aug. 24, 2007, 8 pages.

International Search Report and Written Opinion on PCT/US2007/011923, dated Feb. 22, 2008, 18 pages.

International Search Report and Written Opinion on PCT/US2008/057127, dated Sep. 5, 2008, 9 pages.

International Search Report and Written Opinion on PCT/US2008/058788, dated Jan. 27, 2009, 21 pages.

International Search Report and Written Opinion on PCT/US2009/004734, dated Nov. 17, 2009, 9 pages.

International Search Report and Written Opinion on PCT/US2009/044403, dated Sep. 25, 2009, 10 pages.

International Search Report and Written Opinion on PCT/US2009/044409, dated Jan. 29, 2010, 10 pages.

International Search Report and Written Opinion on PCT/US2009/054213, dated Oct. 6, 2009, 8 pages.

International Search Report and Written Opinion on PCT/US2009/59903, dated Jun. 2, 2010, 18 pages.

International Search Report and Written Opinion on PCT/US2009/59904, dated Apr. 5, 2010, 11 pages.

International Search Report and Written Opinion on PCT/US2010/032580, dated Jul. 6, 2010, 8 pages.

International Search Report and Written Opinion on PCT/US2010/050024, dated Jan. 27, 2011, 13 pages.

International Search Report and Written Opinion on PCT/US2010/050026, dated Jan. 6, 2011, 9 pages.

International Search Report on PCT/US2008/058788, dated Jan. 27, 2009, 10 pages.

Inui et al., "Fatty Acid Synthesis in Mitochondria of Euglena gracilis", Eur. J. Biochem., Jul. 1984, vol. 142, pp. 121-126.

Ishige et al., "Long-Chain Aldehyde Dehydrogenase That Participates in n-Alkane Utilization and Wax Ester Synthesis in Acinetobacter sp. Strain M-1", Appl. Environ. Microbiol., Aug. 2000, vol. 66, Issue 8, pp. 3481-3486.

Ishige et al., "Wax Ester Production from n-Alkanes by *Acinetobacter* sp. Strain M-1: Ultrastructure of Cellular Inclusions and Role of Acyl Coenzyme A Reductase", Appl. Environ. Microbiol., Mar. 2002, vol. 68, Issue 3, pp. 1192-1195.

IUBMB Enzyme Nomenclature. EC 1.2.1.50. 1986. p. 1.
IUBMB Enzyme Nomenclature. EC 2.3.1.75. 1984. p. 1.
IUBMB Enzyme Nomenclature. EC 2.3.1.84. 1984. p. 1.
IUBMB Enzyme Nomenclature. EC 6.4.1.2. 1961. p. 1.

Jahreis et al., "Adaptation of sucrose Metabolism in the *Escherichia coli* Wild-Type Strain EC3132", Oct. 2002, J. Bacteriol., vol. 184, Issue 19, pp. 5307-5316.

James et al., "Expression of Two *Escherichia coli* Acetyl-GoA Carboxylase Subunits is Autoregulated", The Journal of Biological Chemistry, vol. 279, No. 4, Jan. 23, 2004, pp. 2520-2527.

Jarboe, L.R. et al., "Development of Ethanologenic Bacteria", Adv. Biochem., Enqin./Biotechnol., Jul. 31, 2007, vol. 108, pp. 237-261.

Jayakumar et al., "Cloning and expression of the multifunctional human fatty acid synthase and its subdomains in *Escherichia coli*", PNAS, Dec. 1996, vol. 93, pp. 14509-14514.

Jiang et al., "Inhibition of Fatty Acid Synthesis in *Escherichia coli* in the Absence of Phospholipid Synthesis and Release of Inhibition by Thioesterase Action", Journal of Bacteriology, May 1994, vol. 176, No. 10, pp. 2814-2821.

Johnson et al., "Genetic Analysis of the Role of *Saccharomyces cerevisiae* Acyl-CoA Synthetase Genes in Regulating Protein N-Myristoylation", Jul. 8, 1994, J. Biol. Chem., vol. 269, No. 27, pp. 18037-18046.

Johnston et al., "Isolation of the yeast regulatory gene GAL4 and analysis of its dosage effects on the galactose/melibiose regulon". Proc. Natl. Acad. Sci. USA, Nov. 15, 1982, vol. 79, Issue 22, pp. 6971-6975.

Jones et al., "Palmitoyl-Acyl Carrier Protein (ACP) Thioesterase and the Evolutionary-Origin of Plant Acyl-ACP Thioesterases", Plant Cell, Mar. 1995, vol. 7, pp. 359-371.

Joshi et al., "Flow properties of biodiesel fuel blends at low temperatures", Jun. 2007, Fuel, vol. 86, pp. 143-151.

Juttner et al., "Environmental Factors Affecting the Formation of Mesityloxide, Dimethylallylic Alcohol and Other Volatile Compounds Excreted by Anabaena cylindrica," Journal of General Microbiology, Mar. 1983, vol. 129, pp. 407-412.

Juttner et al., "The reducing capacities of cyanobacteria for aldehydes and ketones," Appl. Microbiol. Biotechnol., Oct. 1986, vol. 25, pp. 52-54.

Kalscheuer et al., "A novel bifunctional wax ester synthase/acyl-CoA:diacylglycerol acyltransferase mediates wax ester and triacylglycerol biosynthesis in Acinetobacter calcoacetius ADP", Journal of Biological Chemistry, Mar. 7, 2003, vol. 278, No. 10, pp. 8075-8082.

(56) References Cited

OTHER PUBLICATIONS

Kalscheuer et al., "Analysis of Storage Lipid Accumulation in Alcanivorax borkumensis: Evidence for Alternative Triacylglycerol Biosynthesis Routes in Bacteria," J. Bacteriol., Feb. 2007, vol. 189, Issue 3, pp. 918-928.
Kalscheuer et al., "Microdiesel: *Escherichia coli* engineered for fuel production," Microbiology, vol. 152, Jan. 1, 2006, pp. 2529-2536.
Kalscheuer et al., "Neutral Lipid Biosynthesis in Engineered *Escherichia coli*: Jojoba Oil-like Wax Esters and Fatty Acid Butyl Esters," Applied and Environmental Microbiology, Feb. 1, 2006, vol. 72, No. 2, pp. 1373-1379.
Kalscheuer et al., "Synthesis of Novel Lipids in *Saccharomyces cerevisiae* by Heterologous Expression of an Unspecific Bacterial Acyltransferase", Appl. Environ. Microbiol., Dec. 2004, vol. 70, Issue 12, pp. 7119-7125.
Kameda et al., "Further purification, characterization and salt activation of acyl-CoA synthetase from *Escherichia coli*", Biochimica et Biophysica Acta, May 29, 1985, vol. 840, pp. 29-36.
Kameda et al., "Purification and Characterization of Acyl Coenzyme A Synthetase from *Escherichia coli*", J. Bacteriol. Chem., Jun. 10, 1981, vol. 256, Issue 11, pp. 5702-5707.
Kaneda, "Iso- and anteiso-fatty acids in bacteria: biosynthesis, function, and taxonomic significance," Microbiol. Rev., Jun. 1991, vol. 55, Issue 2, pp. 288-302.
Kazan et al., "Effect of Glucose Concentration on the Growth Rate and Some Intracellular Components of a Recombinant *E. coli* Culture," Process Biochem., vol. 30, Issue 3, pp. 269-273 (1995).
Keasling et al., "Metabolic engineering delivers next-generation biofuels", Nature Biotechology, Mar. 2008, vol. 26, Issue 3, pp. 298-299.
Kizer et al., "Application of Functional Genomics to Pathway Optimization for Increased Isoprenoid Production", Applied and Environmental Microbiology, May 2008, vol. 74, No. 10, pp. 3229-3241.
Knoll et al., "Biochemical Studies of Three *Saccharomyces cerevisiae* Acyl-CoA Synthetases, Faalp, Faa2p, and Faa3p", J. Biol. Chem., Jun. 10, 1994, vol. 269, Issue 23, pp. 16348-16356.
Knoll et al., "Use of *Escherichia coli* Strains Containing fad Mutations plus a Triple Plasmid Expression System to Study the Import of Myristate, Its Activation by *Saccharomyces cerevisiae* Acyl-CoA Synthetase, and Its Utilization by *S. cerevisiae* Myristoyl-Coa: Protein N-Myristoyltransferase," The Journal of Biological Chemistry, Feb. 25, 1993, vol. 268, No. 6, pp. 4281-4290.
Knothe et al., "Kinematic viscosity of biodiesel components (fatty acid alkyl esters) and related compounds at low temperatures", Nov. 2007, Fuel, vol. 86, pp. 2560-2567.
Knothe et al., "Kinematic viscosity of biodiesel fuel components and related compounds. Influence of compound structure and comparison to petrodiesel fuel components," Jun. 2005, Fuel, vol. 84, pp. 1059-1065.
Knothe, "'Designer' Biodiesel: Optimizing Fatty Ester Composition to Improve Fuel Properties," Energy & Fuels, Feb. 19, 2008, vol. 22, 25 pages.
Knothe., "Dependence of biodiesel fuel properties on the structure of fatty acid alkyl esters," Fuel Processing Technology, vol. 86, Jun. 2005, pp. 1059-1070.
Knudsen et al,. "Transacylation as a chain-termination mechanism in fatty acid synthesis by mammalian fatty acid synthetase: Synthesis of medium-chain-length (C8-C12) acyl-CoA esters by goat mammary-gland fatty acid synthetase", Biochem. J., Jan. 15, 1982, vol. 202, pp. 139-143.
Koffas, M.A.G., "Expanding the repertoire of biofuel alternatives through metabolic pathway evolution", PNAS, Jan. 27, 2009, vol. 106, Issue 4, pp. 965-966.
Koksharova et al., "Genetic tools for cyanobacteria", Appl. Microbiol. Biotechnol., Feb. 2002, vol. 58, Issue 2, pp. 123-137.
Kolkman et al., "Directed evolution of proteins by exon shuffling1", Nat Biotechnol., May 2001, vol. 19, pp. 423-427.
Kornberg et al., "Routes for Fructose Utilization by *Escherichia coli*", J. Mol. Microbiol. Biotechnol., Oct. 2001, vol. 3, Issue 3, pp. 355-359.
Kroumova et al., "A pathway for the biosynthesis of straight and branched, odd- and even-length, medium-chain fatty acids in plants", Proc. Natl. Acad. Sci. USA, Nov. 22, 1994, vol. 91, pp. 11437-11441.
Kumari et al., "Regulation of Acetyl Coenzyme A Synthetase in *Escherichia coli*", J. Bacteriol., Aug. 2000, vol. 182, Issue 15, pp. 4173-4179.
Ladygina et al., "A Review of Microbial Synthesis of Hydrocarbons," Process Biochemistry, Feb. 2006, vol. 41, pp. 1001-1014.
Lang et al., "Preparation and characterization of bio-diesels from various bio-oils", Bioresource Tech., Oct. 2001, vol. 80, pp. 53-62.
Lardizabal et al., "Purification of a Jojoba Embryo Wax Synthase, Cloning of its cDNA. & Production of High Levels of Wax in Seeds of Transgenic Arabidopsis," Plant Physiol., Mar. 1, 2000, vol. 122, Issue 3, pp. 645-655.
Lazar et al., "Transforming Growth Factor a: Mutation of Aspartic Acid 47 and Leucine 48 Results in Different Biological Activity", Mar. 1988, Mol. Cell. Biol., vol. 8, No. 3, pp. 1247-1252.
Lee et al., "Enhanced preference for .pi.-bond containing substrates is correlated to Pro110 in the substrate-binding tunnel of *Escherichia coli* thioesterase l/protease l/lysophospholipase L.sub.1", Biochim. Et Biophys. Acta, Aug. 2007, vol. 1774, pp. 959-967.
Lee et al., "Metabolic engineering of microorganisms for biofuels production: from bugs to synthetic biology to fuels", Current Opinion in Biotechnology, Nov. 2008, vol. 19, pp. 556-563.
Lee et al., "Prospects for Biodiesel as a Byproduct of Wood Pulping—A review," Peer-reviewed Review Article, ncsu.edu. bioresources,vol. 1, No. 1, Jul. 2006, pp. 150-171.
Lennen et al., "A Process for Microbial Hydrocarbon Synthesis: Overproduction of Fatty Acids in *Escherichia coli* and Catalytic Conversion to Alkanes", Biotech. Bioengineering, Jun. 1, 2010, vol. 106, Issue 2, pp. 193-202.
Leonard et al., "A Cuphea .beta.-ketoacyl-ACP synthase shifts the synthesis of fatty acids towards shorter chains in *Arabidopsis* seeds expressing Cuphea FatB thioesterases", Plant Journal, Mar. 1998, vol. 13, Issue 5, pp. 621-628.
Lerner et al., "Low copy number plasmids for regulated low-level expression of cloned genes in *Escherichia coli* with blue/white insert screening capability", Nucleic Acids Research, Aug. 11, 1990, vol. 18, Issue 15, p. 4631.
Li et al., "Alteration of the Fatty Acid Profile of Streptomyces Coelicolor by Replacement of the Initiation Enzyme 3-Ketoacyl Acyl Carrier Protein Synthase III (FabH)", J. Bacteriol., Jun. 2005, vol. 187, Issue 11, pp. 3795-3799.
Li et al., "Conversion of Fatty Aldehydes to Alka(e)nes and Formate by a Cyanobacterial Aldehyde Decarbonylase: Cryptic Redox by an Unusual Dimetal Oxygenase", J. Am. Chem. Soc., Apr. 27, 2011, vol. 133, pp. 6158-6161.
Li et al., "Growth Rate Regulation of *Escherichia coli* Acetyl Coenzyme A Carboxylase, Which Catalyzes the First Committed Step of Lipid Biosynthesis", J. Bacteriol., Jan. 1993, vol. 175, Issue 2, pp. 332-340.
Li et al., "Overexpression of a bacterial branched-chain a-keto acid dehydrogenase complex in *Arabidopsis* results in accumulation of branched-chain acyl-CoAs and alteration of free amino acid composition in seeds", Plant Science, Dec. 2003, vol. 165, Issue 6, pp. 1213-1219.
Li et al., "Purification, Characterization, and Properties of an Aryl Aldehyde Oxidoreductase from *Nocardia* Sp. Strain NRRL 5646," Journal of Bacteriology, Jun. 1997, vol. 179, No. 11, pp. 3482-3487.
Li et al., "The carboxylic acid reduction pathway in Nocardia. Purification and characterization of the aldehyde reductase", J. of Industrial Microbiology & Biotechnology, Jan. 2001, vol. 25, pp. 328-332.
Li et al., "The Gene Encoding the Biotin Carboxylase Subunit of *Escherichia coli* Acetyl-CoA carboxylase", J. Biol. Chem., Jan. 15, 1992, vol. 267, Issue 2, pp. 855-863.

(56) References Cited

OTHER PUBLICATIONS

Lin, "Fed-Batch Culture of a Metabolically Engineered *Escherichia coli* Strain Designed for High-Level Succinate Production and Yield Under Aerobic Conditions", Biotech. Engineering, Jun. 20, 2005, vol. 90, Issue 6, pp. 775-779.

Link et al., "Methods for Generating Precise Deletions and Insertions in the Genome of Wild-Type *Escherichia coli*: Application to Open Reading Frame Characterization", J. Bacteriol., Oct. 1997, vol. 179, Issue 20, pp. 6228-6237.

Liu, et al., "Production and secretion of fatty acids in genetically engineered cyanobacteria", Mar. 29, 2010, PNAS Early Edition, pp. 1-6.

Lu et al., "Overproduction of free fatty acids in *E. coli*: Implications for biodiesel production", Metabolic Engineering, Nov. 2008, vol. 10, pp. 333-339.

Lykidis et al., "Genomic Prospecting for Microbial Biodiesel Production", DOE-Joint Genome Institute, Jun. 2008, pp. 1-39.

Lynd et al., "Microbial Cellulose Utilization: Fundamentals and Biotechnology", Microbiol. Mol. Biol. Rev., Sep. 2002, vol. 66, Issue 3, pp. 506-577.

Lytle, "Involvement of Both Dockerin Subdomains in Assembly of the Clostridium thermocellum Cellulosome", J. Bacteriol., Dec. 1988, vol. 180, Issue 24, pp. 6581-6585.

Mackey et al., "Detection of Rhythmic Bioluminescense from Luciferase Reporters in Cyanobacteria," Methods in Molecular Biology, vol. 362, Feb. 2, 2007, pp. 115-129.

Magnuson et al., "Regulation of Fatty Acid Biosynthesis in *Escherichia coli*", Microbiol.Reviews, Sep. 1993, vol. 57, Issue 3, pp. 522-542.

Maniatis et al., "Regulation of Inducible and Tissue-Specific Gene Expression", Science, Jun. 5, 1987, vol. 236, pp. 1237-1245.

Marr et al., "Effect of Temperature on the Composition of Fatty Acids in *Escherichia coli*", J. Bacteriol., Jul. 19, 1962, vol. 84, pp. 1260-1267.

Marrakchi et al., "A New Mechanism for Anaerobic Unsaturated Fatty Acid Formation in Streptococcus pneumoniae*", J. Biol. Chem., Nov. 22, 2002, vol. 277 Issue 47, pp. 44809-44816.

Marrakchi et al., "Mechanistic Diversity and Regulation of Type II Fatty Acid Synthesis", Biochemical Society Transactions, vol. 30, Nov. 1, 2002, Part 6, pp. 1050-1055.

Massengo-Tiasse et al., "Vibrio cholerae FabV Defines a New Class of Enoyl-Acyl Carrier Protein Reductase", J. Biol. Chem., Jan. 18, 2008, vol. 283, Issue 3, pp. 1308-1316.

Mat-Jan et al., "Mutants of *Esherichia coli* Deficient in the Fermatative Lactate Dehydrogenase", J. Bacteriol., Jan. 1989, vol. 171, Issue 1, pp. 342-348.

Matsumoto et al., "Yeast whole-cell biocatalyst constructed by intracellular overproduction of Rhizopus oryzae lipase is applicable to biodiesel fuel production", Appl. Microbiol. Biotechnol., Nov. 2001, vol. 57, Issue 4, pp. 515-520.

Mayer et al., "Identification of amino acid residues involved in substrate specificity of plant acyl-ACP thioesterases using a bioinformatics-guided approach", BMC Plant Biology, Jan. 3, 2007, vol. 7, No. 1, pp. 1-11.

McCue et al., "Phylogenetic footprinting of transcription factor binding sites in proteobacterial aenomes", Nucleic Acids Res., Dec. 1, 2001, vol. 29, Issue 3, pp. 774-782.

McDaniel et al., Mandibular Gland Secretions of the Male Beewolves Philanthus crabroniformis, P. barbatus, and P. pulcher (Hymenoptera: Sphecidea), Jan. 1992, Journal of Chemical Ecology, vol. 18, No. 1, pp. 27-37.

McKnight., "Functional relationships between transcriptional control signals of the thymidine kinase gene of herpes simplex virus", Dec. 1982, Cell, vol. 31, pp. 355-365.

Metz et al., "Purification of a Jojoba Embryo Fatty Acyl-Coenzyme A Reductase and Expression of Its eDNA in High Erucic Acid Rapeseed", Plant Physiol., Mar. 2000, vol. 122, pp. 635-644.

Metzgar et al., "Acinetobacter sp. ADP1: an ideal model organism for genetic analysis and genome engineering", Nucleic Acid Res., Oct. 28, 2004, vol. 32, Issue 19, pp. 5780-5790.

Miller et al., "A Highly Catalytic and Selective Conversion of Carboxylic Acids to 1-Alkenes of One Less Carbon Atom", J. Org. Chem., Jan. 1, 1993, vol. 58, Issue 1, pp. 18-20.

Minshull et al., "Protein evolution by molecular breeding", Curr. Opin. Chem. Biol., Jun. 1999, vol. 3, pp. 284-290.

Mohan et al., "An *Escherichia coli* Gene (FabZ) Encoding (3R)-Hydroxymyristoyl Acyl Carrier Protein Dehydrase. Relation to fubA and Suppression of Mutations in Lipid A Biosynthesis", J.Biol.Chem., Dec. 30, 1994, vol. 269, Issue 52, pp. 32896-32903.

Moore, "Biosynthetic Studies of .omega.-Cycloheptyl Fatty Acids in Alicyclobacillus cycloheptanicus. Formation of Cycloheptanecarboxylic Acid from Phenylacetic Acid", Apr. 4, 1997, J. Org. Chem., vol. 62, pp. 2173-2185.

Morgan-Kiss et al., "The *Escherichia coli* fadK (ydiD) Gene Encodes an Anerobically Regulated Short Chain Acyl-CoA Synthetase", J. Biol. Chern., Sep. 3, 2004, vol. 279, Issue 36, pp. 37324-37333.

Morgan-Kiss et al., "The Lactococcus lactis FabF Fatty Acid Synthetic Enzyme can Functionally Replace both the FabB and FabF Proteins of *Escherichia coli* and the FabH Protein of Lactococcus lactis", Arch. Microbiol., Jun. 4, 2008, vol. 190, pp. 427-437.

Mudge, "Fatty Alcohols—a review of their natural synthesis and environmental distribution", School of Ocean Sciences, University of Wales-Bangor, Nov. 2005, pp. 1-74.

Murata, "Modes of Fatty-Acid Desaturation in Cyanobacteria", Oct. 1992, Plant Cell Physiol., vol. 33, pp. 933-941.

Murli et al., "A Role for the umuDC Gene Products of *Escherichia coli* in Increasing Resistance to DNA Damage in Stationary Phase by Inhibiting the Transition to Exponential Growth", J. Bacteriol., Feb. 2000, vol. 182, Issue 4, pp. 1127-1135.

Myong-Ok, P., "New Pathway for Long-Chain n-Alkane Synthesis via 1-Alcohol in Vibrio furnissii M1", Journal of Bacteriology, Feb. 1, 2005, vol. 187, No. 4, pp. 1426-1429.

Naccarato et al., "In Vivo and In Vitro Biosynthesis of Free Fatty Alcohols in *Escherichia coli* K-12", Lipids, Jun. 1974, vol. 9, No. 6, pp. 419-428.

NCBI Reference Sequence YP.sub.--889972.1, Putative Long-Chain Fatty-Acid-CoA Ligase [Microbacterium Smegmatis Str. MC2 155], retrieved from http://www.ncbi.nlm.nih.gov/protein/118469671, 4 pages.

NCBI Reference, Putative Alcohol Dehydrogenase [Acinetobacter sp. ADP1], 2010, 3 pages, retrieved from http://ncbi.nlm.nih.gov/protein/49532534.

Needleman et al., "A General Method Applicable to the Search for Similarities in the Amino Acid Sequence of Two Proteins", Mar. 28, 1970, J. Mol. Biol., vol. 48, pp. 443-453.

Ness et al., "Molecular breeding: The natural approach to protein design", Adv Protein Chem., Oct. 11, 2000, vol. 55, pp. 261-292.

Nomura et al., "Coexpression of Genetically Engineered 3-Ketoacyl-ACP Synthase III (fabH) and Polyhydroxyalkanoate Synthase (phaC) Genes Leads to Short-Chain-Length-Medium-Chain-Length Polyhydroxyalkanoate Copolymer Production from Glucose in *Escherichia coli* JM109", Appl Environ. Microbiol. Feb. 2004, vol. 70, Issue 2, pp. 999-1007.

Non-Final Office Action in U.S. Appl. No. 12/526,209, dated Dec. 14, 2012, 8 pages.

Non-Final Office Action in U.S. Appl. No. 15/451,881, dated Dec. 20, 2019, 10 pages.

Non-Final Office Action on U.S. Appl. No. 12/278,957 dated Apr. 15, 2011, 11 pages.

Non-Final Office Action on U.S. Appl. No. 12/278,957 dated Nov. 16, 2016, 30 pages.

Non-Final Office Action on U.S. Appl. No. 12/278,957, dated Dec. 24, 2013, 26 pages.

Non-Final Office Action on U.S. Appl. No. 12/278,957, dated Jun. 30, 2015, 20 pages.

Non-Final Office Action on U.S. Appl. No. 12/278,960, dated Jun. 30, 2011, 11 pages.

Non-Final Office Action on U.S. Appl. No. 12/278,960, dated Oct. 15, 2010, 14 pages.

Non-Final Office Action on U.S. Appl. No. 12/768,419, dated Dec. 26, 2014, 32 pages.

Non-Final Office Action on U.S. Appl. No. 12/768,419, dated Feb. 19, 2016, 27 pages.

(56) References Cited

OTHER PUBLICATIONS

Non-Final Office Action on U.S. Appl. No. 12/768,419, dated Mar. 30, 2017, 41 pages.
Non-Final Office Action on U.S. Appl. No. 12/768,419, dated Nov. 18, 2011, 31 pages.
Non-Final Office Action on U.S. Appl. No. 13/099,986, dated Dec. 6, 2011, 12 pages.
Non-Final Office action on U.S. Appl. No. 13/302,957, dated Oct. 29, 2012, 21 pages.
Non-Final Office Action on U.S. Appl. No. 13/529,990, dated Aug. 21, 2013, 12 pages.
Non-Final Office Action on U.S. Appl. No. 13/870,426, dated Oct. 13, 2015, 20 pages.
Non-Final Office Action on U.S. Appl. No. 15/619,290, dated Oct. 27, 2017, 7 pages.
Non-Final Office Action on U.S. Appl. No. 15/954,451 dated Nov. 11, 2019, 14 pages.
Non-Final Office Action on U.S. Appl. No. 12/278,961, dated Nov. 10, 2010, 6 pages.
Non-Final Office Action on U.S. Appl. No. 14/661,219 dated Oct. 16, 2017, 19 pages.
Non-Final Office Action on U.S. Appl. No. 14/952,720, dated Jul. 14, 2017, 18 pages.
Notice of Acceptance on AU Application No. 2014200805, dated Sep. 4, 2015, 3 pages.
Notice of Allowance in U.S. Appl. No. 12/526,209, dated Jul. 26, 2013, 8 pages.
Notice of Allowance on U.S. Appl. No. 13/870,426, dated Nov. 16, 2016, 9 pages.
Notice of Allowance on U.S. Appl. No. 12/278,960, dated Nov. 23, 2011, 11 pages.
Notice of Allowance on U.S. Appl. No. 12/278,961, dated Dec. 12, 2011, 5 pages.
Notice of Allowance on U.S. Appl. No. 12/278,961, dated Jul. 14, 2011, 6 pages.
Notice of Allowance on U.S. Appl. No. 13/099,986, dated Aug. 21, 2012, 8 pages.
Notice of Allowance on U.S. Appl. No. 13/529,990, dated Jan. 28, 2015, 9 pages.
Notice of Allowance on U.S. Appl. No. 15/619,290, dated Mar. 14, 2018, 8 pages.
Notice of Reasons for Rejection in JP Patent Application No. 2015-211435, dated Aug. 26, 2019, (with English translation) (12 pages).
Notice of Reasons for Rejection in JP Patent Application No. 2018-207088, dated Sep. 2, 2019 (with English translation) (8 pages).
Nunn et al., "Role for fadR in Unsaturated Fatty Acid Biosynthesis in *Escherichia coli*", J.Bacteriol., May 1983, vol. 154, Issue 2, pp. 554-560.
Nunn et al., "Transport of long-chain fatty acids by *Escherichia coli*: Mapping and characterization of mutants in the fadL gene", PNAS, Jul. 1978, vol. 75, Issue 7, pp. 3377-3381.
Nunn, W., "A Molecular View of Fatty Acid Catabolism in *Escherichia coli*", Jun. 1986, Microbiol. Rev., vol. 50, Issue 2, pp. 179-192.
Office Action in CA 3035878 dated Jan. 28, 2020, 4 pages.
Office Action in CN 201710052351.0 dated Feb. 3, 2020, 17 pages (with translation).
Office Action on AU Application 015238773, dated Nov. 10, 2016, 2 pages.
Office Action on AU Application 2007254151, dated May 22, 2012, 2 pages.
Office Action on AU Application 2008230735, dated Aug. 16, 2012, 4 pages.
Office Action on AU Application 2014200805, dated Mar. 26, 2015, 5 pages.
Office Action on AU Application 2017203360, dated Jun. 14, 2018, 3 pages.
Office Action on BR Application 1220170101145, dated Apr. 10, 2018, 19 pages with translation of relevant parts.
Office Action on BR Application PI0712205.5, dated Feb. 8, 2017, 22 pages with translation of relevant parts.
Office Action on BR Application PI0712205-5, dated Feb. 15, 2018, 30 pages, with translation.
Office Action on BR Application PI0809345-8, dated Dec. 6, 2017, 10 pages, English language version of relevant parts.
Office Action on BR Application PI0809345-8, dated Jun. 27, 2017, 15 pages with summary translation.
Office Action on CA Application 2678915, dated Dec. 7, 2015, 5 pages.
Office Action on CA Application 2678915, dated Feb. 2, 2018, 3 pages.
Office Action on CA Application 2678915, dated Mar. 8, 2017, 4 pages.
Office Action on CA Application 2722441, dated Sep. 24, 2015, 5 pages.
Office Action on CA Application 2759273, dated Mar. 31, 2016, 5 pages.
Office Action on CA Application 2759273, dated Nov. 23, 2016, 3 pages.
Office Action on CN Application 200880009283.9, dated May 10, 2016, 5 pages with translation.
Office Action on CN Application 201080027865.7, dated Jan. 30, 2015, 13 pages with translation.
Office Action on CN Application 201080027865.7, dated May 15, 2014, 12 pages with translation.
Office Action on CN Application 201080027865.7, dated Dec. 14, 2016, 13 pages with translation.
Office Action on CN Application 201080027865.7, dated Jul. 10, 2017, 14 pages with translation.
Office Action on CN Application 201080027865.7, dated Mar. 16, 2016, 10 pages with translation.
Office Action on CN Application 201080027865.7, dated Sep. 22, 2015, 11 pages with translation.
Office Action on CN Application 201080027865.7, mailed Sep. 30, 2018, 7 pages with translation.
Office Action on CN Application 201510244069.3, dated Jan. 29, 2018, 12 pages with translation.
Office Action on CN Application 201510244069.3, dated May 25, 2017, 16 pages, with translation.
Office Action on CN Application 201610085050.3, dated Feb. 1, 2019, 16 pages with translation.
Office Action on CN Application 201610085050.3, dated Jan. 29, 2018 14 pages with translation.
Office Action on CN Application 201610085050.3, dated Jul. 26, 2017, 11 pages with translation.
Office Action on CN Application 201610085050.3, dated Nov. 3, 2016, 17 pages with translation.
Office Action on EP 12194886.3, dated Jun. 8, 2016, 6 pages.
Office Action on EP Application 07809099.0, dated Apr. 26, 2010, 5 pages.
Office Action on EP Application 07809099.0, dated Feb. 6, 2013, 8 pages.
Office Action on EP Application 07809099.0, dated Jan. 7, 2011, 7 pages.
Office Action on EP Application 07809099.0, dated Jun. 22, 2009, 3 pages.
Office Action on EP Application 07809099.0, dated Nov. 18, 2009, 4 pages.
Office Action on EP Application 08744695.1, dated Apr. 20, 2012, 7 pages.
Office Action on EP Application 08744695.1, dated Feb. 17, 2010, 5 pages.
Office Action on EP Application 08744695.1, dated May 28, 2013, 7 pages.
Office Action on EP Application 08744695.1, dated Nov. 19, 2010, 4 pages.
Office Action on EP Application 09013640.9, dated May 7, 2012, 5 pages.
Office Action on EP Application 09013640.9, dated Sep. 20, 2010, 1 page.
Office Action on EP Application 09013650.8, dated Jul. 11, 2012, 6 pages.

(56) References Cited

OTHER PUBLICATIONS

Office Action on EP Application 09013650.8, dated Jun. 11, 2013, 5 pages.
Office Action on EP Application 09747776.4, dated Aug. 28, 2015, 3 pages.
Office Action on EP Application 10770203.7, dated Jun. 19, 2017, 8 pages.
Office Action on EP Application 11005423.6, dated Jul. 5, 2012, 6 pages.
Office Action on EP Application 11005423.6, dated Nov. 11, 2013, 5 pages.
Office Action on EP Application 12194886.3, dated May 16, 2014, 7 pages.
Office Action on EP Application 14193614.6, dated Jan. 9, 2018, 4 pages.
Office Action on EP Application 14193614.6, dated Mar. 8, 2017, 4 pages.
Office Action on EP Application 15179791.7, dated Dec. 16, 2016, 4 pages.
Office Action on IN Application 201618015610, dated Dec. 16, 2019, 6 pages with translation.
Office Action on IN Application 6112/DELNP/2009, dated May 1, 2015, 6 pages, with translation.
Office Action on IN Application 734/DELNP/2014, dated Nov. 20, 2018, 5 pages with translation.
Office Action on IN Application 9257/DELNP/2011, dated Oct. 6, 2017, 7 pages with translation.
Office Action on IN Application 9659/DELNP/2008, dated Nov. 1, 2013, 4 pages with translation.
Office Action on JP Application 2009-511091, dated Aug. 2, 2012, 6 pages with translation.
Office Action on JP Application 2009-511091, dated Feb. 4, 2014, 6 pages with translation.
Office Action on JP Application 2009-511091, dated Jan. 29, 2013, 7 pages with translation.
Office Action on JP Application 2009-511091, dated Sep. 28, 2015, 11 pages with translation.
Office Action on JP Application 2010-501269, dated Apr. 1, 2014, 5 pages with translation.
Office Action on JP Application 2010-501269, dated May 21, 2013, 10 pages with translation.
Office Action on JP Application 2010-501269, dated Sep. 9, 2015, 7 pages with translation.
Office Action on JP Application 2014-115874, dated Aug. 5, 2015, 8 pages with translation.
Office Action on JP Application 2014-249577, dated Nov. 28, 2016, 5 pages with translation.
Office Action on JP Application 2015-211435, dated Aug. 2, 2017, 5 pages with translation.
Office Action on JP Application 2015-211435, dated Aug. 22, 2016, 6 pages with translation.
Office Action on JP Application 2015-211435, dated Feb. 14, 2019, 6 pages with translation.
Office Action on JP Application 2016-126210, dated Jun. 5, 2017, 10 pages with translation.
Office Action on JP Application 2016-126210, dated Sep. 12, 2016, 13 pages with translation.
Office Action on JP Application 2105-211435, dated Jul. 5, 2018, 6 pages with translation.
Office Action on U.S. Appl. No. 12/526,209, dated Oct. 17, 2012, 9 pages.
Office Action on U.S. Appl. No. 12/768,419, dated Mar. 6, 2014, 27 pages.
Ohmiya, K. et al., "Application of Microbial Genes to Recalcitrant Biomass Utilization and Environmental Conservation", J. Bioscience and Bioengineering, Jan. 31, 2003, vol. 95, No. 6, pp. 549-561.
Omelchenko et al., "Non-homologous isofunctinal enzymes: A systematic analysis of alternative solutions in enzyme evolution", Biol. Direct, Apr. 30, 2010, vol. 5, No. 31, pp. 1-20.
Orlandi et al., "Cloning Immunoglobulin Variable Domains for Expression by the Polymerase Chain Reaction," Proc. Natl. Acad. Sci. USA, May 1989, vol. 86, Issue 10, pp. 3833-3837.
Overath et al., "Fatty Acid Degradation in *Escherichia coli*, An Inducible Acyl-CoA synthetase, the Mapping of old-Mutations, and the Isolation of Regulatory Mutants", European J. Biochem., Feb. 1969, vol. 7, pp. 559-574.
P0AGG2 (last viewed on Sep. 30, 2015) 6 pages.
Pages et al., "Interaction between the Endoglucanase CelA and the Scaffolding Protein CipC of the Clostridium cellulolyticum Cellulosome", J. Bacteriol., Apr. 1996, vol. 178, Issue 8, pp. 2279-2286.
Palaniappan et al., "Enhancement and Selective Production of Phoslactomycin B, a Protein Phosphatase IIa Inhibitor, through Identification and Engineering of the Corresponding Biosynthetic Gene Cluster*", The Journal of Biological Chemistry, Sep. 12, 2003, vol. 278, No. 37, pp. 35552-35557.
Park, "New Pathway for Long-Chain n-Alkane Synthesis via 1-Alcohol in Vibrio furnissii M1", J. Bacteriol., Feb. 2005, vol. 187, pp. 1426-1429.
Patton et al., "A Novel Delta3, Delta2-Enoyl-CoA Isomerase Involved in the Biosynthesis of the Cyclohexanecarboxylic Acid-Derived Moiety of the Polyketide Ansatrienin A" Biochemistry, Jun. 1, 2000, vol. 39, pp. 7595-7604.
Pearson et al., "Improved tools for biological sequence comparison", Proc. Natl. Acad. Sci. USA, Apr. 1988, vol. 85, Issue 8, pp. 2444-2448.
Pearson et al., "Using the FASTA program to search protein and DNA sequence database," Chapter 26, Computer Analysis of Sequence Data, Part I, ed. by Annette Griffin, Hugh G. Griffin, p. 307-331, 1994.
Peng et al., "Effect of fadR gene knockout on the metabolism of *Escherichia coli* based on analyses of protein expressions, enzyme activities and intracellular metabolite concentrations", Enzyme and Microbial Tech., Feb. 2006, vol. 38, pp. 512-520.
Perez et al., "*Escherichia coli* YqhD Exhibits Aldehyde Reductase Activity and Protects from the Harmful Effect of Lipid Peroxidation-derived Aldehydes", J. Biol. Chem., Mar. 21, 2008, vol. 283, Issue 12, pp. 7346-7353.
Peterson & Ingram, "Anaerobic Respiration in Engineered *Escherichia coli* with an Internal Electron Acceptor to Produce Fuel Ethanol", Ann. N.Y. Acad. Sci., Feb. 29, 2008, vol. 1125, pp. 363-372.
Phung et al., "Genes for Fatty Acids Biosynthesis in the *Cyanobacterium synechococcus* sp. Strain PCC 7942", Jan. 1995, Abstracts of the General Meeting of the American Society of Microbiology, The Society, Washington, DC, p. 524, 1 page.
Pillai et al., "Functional characterization of .beta.-ketoacyl-ACP reductase (FabG) from Plasmodium falciparum", Biochem. and Biophysical Research, Comm., Mar. 18, 2003, vol. 303, pp. 387-392.
Prather et al., "De novo biosynthentic pathways: rational design of microbial chemical factories," Current Opinion in Biotechnology, Oct. 2008, vol. 19, pp. 468-474.
Database UniProt, Online, Retrieved from Accession No. Q7CWB7, dated Jan. 16, 2020, 1 page.
Database UniProt, Online, Retrieved from Accession No. Q7CXR6, dated Jan. 16, 2020, 1 page.
Database UniProt, Online, Retrieved from Accession No. Q8UG62, dated Jan. 16, 2020, 1 page.
Qiu et al., "Crystal structure and substrate specificity of the .beta.-ketoacyl-acyl carrier protein synthase III (FabH) from *Staphylococcus aureus*", Aug. 2005, Protein Science, vol. 14, pp. 2087-2094.
Qiu et al., "Metabolic Engineering of Aeromonas hydrophilia for the Enhanced Production of Poly(3-hydroxybutyrate-co-3-hydroxyhexanoate)," Feb. 2006, Applied Microbiology & Biotechnology, vol. 69, Issue 5, pp. 537-542.
Rafi et al., "Structure of Acyl Carrier Protein Bound to FabI, the FASII Enoyl Reductase from *Escherichia coli*", J. Biol. Chem., Sep. 29, 2006, vol. 281, Issue 51, pp. 1-21.
Rawlings et al., "Biosynthesis of fatty acids and related metabolites", Natural Product Reports, Jul. 15, 1998, Issue 3, pp. 275-308.

(56) References Cited

OTHER PUBLICATIONS

Rawlings et al., "The Gene Encoding *Escherichia coli* Acyl Carrier Protein Lies within a Cluster of Fatty Acid Biosynthetic Genes", J.Biol.Chem., Mar. 25, 1992, vol. 267, Issue 9, pp. 5751-5754.
Ray et al., "Activation of long chain fatty acids with acyl carrier protein: Demonstration of a new enzyme, acyl-acyl carrier protein synthetase, in *Escherichia coli*" PNAS, Dec. 1976, vol. 73, Issue 12, pp. 4374-4378.
Reading et al., "Quorum sensing: the many languages of bacteria," FEMS Microbiol. Lett., vol. 254, Jan. 2006, pp. 1-11.
Rehm et al., "Heterologous expression of the acyl-acyl carrier protein thioesterase gene from the plant Umbellularia californica mediates polyhydroxyalkanoate biosynthesis in recombinant *Escherichia coli*", Appl. Microbiol, and Biotech., Feb. 9, 2001, vol. 55, pp. 205-209.
Reiser et al., "Isolation of Mutants of Acinetobacter calcoaceticus Deficient in Wax Ester Synthesis of Complementation of One Mutation with a Gene Encoding a Fatty Acyl Coenzyme A Reductase", J. Bacteriol., May 1997, vol. 179, Issue 9, pp. 2969-2975.
Ren et al., "FabG, an NADPH-Dependent 3-Ketoacyl Reductase of Pseudomonas aeruginosa, Provides Precursors for Medium-Chain-Length Poly-3-Hydroxyalkanoate Biosynthesis in *Escherichia coli*", J. Bacteriol., May 2000, vol. 182, Issue 10, pp. 2978-2981.
Rock et al., "Acyl-Acyl Carrier Protein Synthetase from *Escherichia coli*", Meth. Enzymol., Jul. 12, 1981, vol. 71, pp. 163-168.
Rock et al., "Increased unsaturated fatty acid production associated with a suppressor of the fabA6(Ts) mutation in *Escherichia coli*", J. Bacteriol., Sep. 1996, vol. 178, Issue 18, pp. 5382-5387.
Rock et al., "Pathways for the incorporation of exogenous fatty acids into phosphatidylethanolamine in *Escherichia coli*.", The Journal of Biological Chemistry, vol. 260, No. 23, Oct. 15, 1985, pp. 12720-12724.
Romero et al., "Metabolic Engineering of Bacillus Subtilis for Ethanol Production: Lactate Dehydrogenase Plays a Key Role in Fermentative Metabolism", Applied & Environmental Microbiology, Aug. 10, 2007, vol. 73, Issue 16, pp. 5190-5198.
Rude et al., "New microbial fuels: a biotech perspective", Current Opinion in Microbiology, Jun. 2009, vol. 12, pp. 274-281.
Rude et al., "Terminal Olefin (1-Alkene) Biosynthesis by a Novel P450 Fatty Acid Decarboxylase from *Jeotgalicoccus* Species", Appl. Environ. Microbiol., Mar. 2011, vol. 77, No. 5, pp. 1718-1727.
Ruyter et al., "Controlled Gene Expression Systems for Lactococcus lactis with the Food-Grade Inducer Nisin", Applied and Environmental Microbiology, Oct. 1996, vol. 6 2, No. 10, pp. 3662-3667.
Sabirova et al., "Mutation in a "tesB-Like" Hydroxyacyl-Coenzyme A—Specific Thioesterase Gene Causes Hyperproduction of Extracellular Polyhydroxyalkanoates by Alcanivorax borkumensis SK2", J. Bacteriol., Dec. 2006, vol. 188, Issue 23, pp. 8452-8459.
Saito et al., "Crystal structure of enoyl-acyl carrier protein reductase (FabK) from *Streptococcus neumonia* reveals the binding mode of an inhibitor", Protein Science, Jan. 2, 2008, Issue 17, pp. 691-699.
Salas et al., "Characterization of substrate specificity of plant FatA and FatB acyl-ACP thioesterases", Archives of Biochem. and Biophysics, Aug. 2002, vol. 403, pp. 25-34.
Sambrook et al., "Molecular Cloning: A Laboratory Manual," 2nd Ed., Cold Spring Harbor Laboratory Press, Dec. 1989, pp. 16.30-16.37.
Sanchez et al., "Effect of Overexpression of a Soluble Pyridine Nucleotide Transhydrogenase (UdhA) on the Production of Poly(3-hydroxybutyrate) in *Escherichia coli*", Mar.-Apr. 2006, Biotechnol. Prog., vol. 22, pp. 420-425.
Schirmer et al., "Microbial iosynthesis of Alkanes", Science, Jul. 30, 2010, vol. 329, Issue 5991, pp. 559-562.
Schneider-Belhaddad et al., "Solubilization, Partial Purification, and Characterization of a Fatty Aldehyde Decarbonylase from a Higher Plant, Pisum sativum," Archives Biochem. Biophys., May 15, 2000, vol. 377, Issue 2, pp. 341-349.

Schujman et al., "A malonyl-CoA-dependent switch in the bacterial response to a dysfunction of lipid metabolism," Molecular Microbiology, Jun. 2008, vol. 68, Issue 4, pp. 987-996.
Schweizer et al., "Microbial Type I Fatty Acid Synthases (FAS): Major Players in a Network of Cellular FAS Systems", Microbiol. Mol. Biol. Rev. Sep. 2004, vol. 68, Issue 3, pp. 501-517.
Shahid et al., "A review of biodiesel as vehicular fuel", Renew. Sustain.Ener.Reviews, Dec. 2008, vol. 12, pp. 2484-2494.
Shockey et al., "*Arabidopsis* Contains a Large Superfamily of Acyl-Activating Enzymes. Phylogenetic and Biochemical Analysis Reveals a New Class of Acyl-Coenzyme A Synthetases," Plant Physiol. Jun. 2003, vol. 132, Issue 2, pp. 1065-1076.
Shockey et al., "*Arabidopsis* Contains Nine Long-Chain Acyl-Coenzyme A Synthetase Genes that Participate in Fatty Acid and Glycerolipid Metabolism," Plant Physiology, Aug. 2002, vol. 129, pp. 1710-1722.
Silver et al., "Amino terminus of the yeast GAL4 gene product is sufficient for nuclear localization," Proc. Natl. Acad. Sci. USA, Oct. 1984, vol. 81, Issue 19, pp. 5951-5955.
Singh et al., "Protein Engineering Approaches in the Post-Genomic Era," Current Protein Peptide Science 2017, vol. 18, pp. 1-11.
Smith et al., "Comparison of Biosequences," Advances in Applied Mathematics, Dec. 1981, vol. 2, Issue 4, pp. 482-489.
Soriano et al., "Crystallization behavior of neat biodiesel and biodiesel treated with ozonized vegetable oil", European Journal of Lipid Science and Technology, vol. 107, No. 9, Sep. 2005, pp. 689-696.
Spencer et al., "Thioesterases I and II of *Escherichia coli*," J. Biol. Chem., Sep. 10, 1978, vol. 253, Issue 17, pp. 5922-5926.
Steen et al., "Microbial production of fatty-acid-derived fuels and chemicals from plant biomass", Nature, vol. 463, No. 7280, Jan. 28, 2010, pp. 559-562.
Stemmer, "DNA shuffling by random fragmentation and reassembly: In vitro recombination for molecular evolution," Proc. Natl. Acad. Sci., Oct. 1994, vol. 91, pp. 10747-10751.
Stephens et al., "The Pyruvate Dehydrogenase Complex of *Escherichia coli* K12," Eur. J. Biochem., Jul. 1, 1983, vol. 133, pp. 155-162.
Stoveken et al., "The Wax Ester Synthase/Acyl Coenzyme A:Diacylglycerol Acyltransferase from Acinetobacter sp. Strain ADP1: Characterization of a Novel Type of Acyltransferase", J. Bacteriology, Feb. 2005, vol. 187, Issue 4, pp. 1369-1376.
Subrahmanyam et al., "Overproduction of a Functional Fatty Acid Biosynthetic Enzyme Blocks Fatty Acid Synthesis in *Escherichia coli*," J. Bacteriol., Sep. 1998, vol. 180, Issue 17, pp. 4596-4602.
Sukovich, Thesis, Hydrocarbon Biosynthesis by Bacteria: Genes and Hydrocarbon Products, Dec. 2010, 190 pages.
Sulzenbacher et al., "Crystal Structure of *E. coli* Alcohol Dehydrogenase YqhD: Evidence of a Covalently Modified NADP Coenzyme," J. Mol. Biol., Sep. 10, 2004, vol. 342, pp. 489-502.
Supplementary European Search Report on EP Application 10762559.2, dated Oct. 5, 2015, 9 pages.
Supplementary European Search Report on EP Application 10770203.7, dated Dec. 3, 2012, 19 pages.
Ta et al., "Cloning, Sequencing, and Overexpression oaf [2Fe-2S] Ferredoxin Gene from *Escherichia coli*", J. Biol. Chem., Jun. 5, 1992, vol. 267, Issue 16, pp. 11120-11125.
Teerawanichpan et al., "Fatty Acyl-CoA Reductase and Wax Synthase from Euglena gracilis in the Biosynthesis of Medium-Chain Wax Esters", Lipids 45, Mar. 2010, Issue 3, pp. 263-273.
Thelen et al., Metabolic Engineering of Fatty Acid Biosynthesis in Plants, Metabolic Engineering, Jan. 2002, vol. 4, pp. 12-21.
Thiel, "Genetic Analysis of cyanobacteria," in The Molecular Biology of Cyanobacteria, Advances in Photosynthesis and Respiration, Kluwer Academic Publishers, pp. 581-611 (1994).
Thomason et al., "Identification of the *Escherichia coli* K-12 ybhE Gene as pgl, Encoding 6-Phosphogluconolactonase", J. Bacteriol., Dec. 2004, vol. 186, Issue 24, pp. 8248-8253.
Thorpe et al., "Structure and mechanism of action of the Acyl-CoA dehydrogenases," FASEB J., Jun. 1995, vol. 9, pp. 718-725.
Tong et al., "Acetyl-Coenzyme A Carboxylases: Versatile Targets for Drug Discovery", J. Cellular Biochem., Dec. 15, 2006, vol. 99, pp. 1476-1488.

(56) References Cited

OTHER PUBLICATIONS

Toomey et al., "Studies on the Mechanism of Fatty Acid Synthesis XVI. Preparation and General Properties of Acyl-Malonyl Acyl Carrier Proteincondensing Enzyme From *Escherichia coli*," J. Biol. Chem., Mar. 10, 1966, vol. 241, Issue 5, pp. 1159-1165.
Tsay et al., "Isolation and Characterization of the .beta.-Ketoacyl-acyl Carrier Protein Synthase I11 Gene (fabH) from *Escherichia coli* K-12", J. Biol. Chem., Apr. 5, 1992, vol. 267, Issue 10, pp. 6807-6814.
Tucci et al., "A Novel Prokaryotic trans-2-enoyl-CoA reductase from the Spirochete Treponema denticola", FEBS Letters 581, Apr. 17, 2007, pp. 1561-1566, 6 pages.
Twaig, Farouq A.A et al., "Performance of Composite Catalysts in Palm Oil Cracking for the Production of Liquid Fuels and Chemicals", Fuel Processing Technology, Aug. 15, 2004, vol. 85, pp. 1283-1300.
UniProt accession No. Q325A2 "Subname: Full=Acyl-CoA thioesterase I" (2005), 1 page.
Vadali et al., "Cofactor engineering of intracellular CoA/acetyl-CoA and its effect on metabolic flux redistribution in *Escherichia coli*", Metabolic Engineering, Apr. 2004, vol. 6, pp. 133-139.
Valle et al., "Overexpression of Chromosomal Genes in *Escherichia coli*", Methods Mol. Biol., vol. 267 pp. 113-122 (2006).
Van Den Berg et al., "The FadL family: unusual transporters for unusual substrates", Curr. Opin. Struct. Biol., Aug. 2005, vol. 15, pp. 401-407.
Van Der Hoeven et al., "Biosynthesis and Elongation of Short- and Medium-Chain-Length Fatty Acids," Plant Physiol., Jan. 2000, vol. 122, pp. 275-282.
Venkitasubramanian et al., "Reduction of Carboxylic Acids by Nocardia Aldehyde Oxidoreductase Requires a Phosphopantetheinylated Enzyme*", The Journal of Biological Chemistry, Jan. 5, 2007, vol. 282, No. 1, pp. 478-485.
Venturi, "Regulation of quorum sensing in Pseudomonas", FEMS Microbiol. Rev., Mar. 2006, vol. 30, pp. 274-291.
Vicente et al., Integrated biodiesel production: a comparison of different homogeneous catalysts systems, Bioresource Technology, Jan. 1, 2004, vol. 92, No. 3, pp. 295-305.
Voelker et al., "Alteration of the Specificity and Regulation of Fatty Acid Synthesis of *Escherichia coli* by Expression of a Plant Medium-Chain Acyl-Acyl Carrier Protein Thioesterase", Journal of Bacteriology, Dec. 1994, vol. 176, No. 23, pp. 7320-7327.
Voss et al., "The role of enhancers in the regulation of cell-type-specific transcriptional control", Trends Biochem Sci., Jul. 1986, vol. 11, Issue 7, pp. 287-289.
Wacey et al., "Disentangling the perturbational effects of amino acid substitutions in the DNA-binding domain of p53.", Hum Genet, Feb. 1999, vol. 104, pp. 15-22.
Wang et al., "Functional Replacement of the FabA and FabB Proteins of *Escherichia coli* Fatty Acid Synthesis by Enterococcus faecalis FabZ and FabF Homologues", J. Biol. Chem., Aug. 13, 2004, vol. 279, Issue 33, pp. 34489-34495.
Wang et al., Biosynthetic pathway for poly(3-hydroxypropionate) in recombinant *Escherichia coli*, J Microbiol., Aug. 2012, vol. 50, No. 4, pp. 693-697.
Watson et al., "Molecular Biology of the Gene", 4th Ed., Benjamin Cummins, May 1987, 23 pages.

Weber et al., "13C-pattern of glycerol: Origin and practical importance", Journal of Agricultural and Food Chemistry, vol. 45, No. 6, Jan. 1, 1997, pp. 2042-2046.
White et al., "Carboxylic acid reductase: a new tungsten enzyme catalyzes the reduction of non-activated carboxylic acids to aldehydes", Eur. J. Biochem., Sep. 1, 1989, vol. 184, pp. 89-96.
White et al., "Production of Long-chain Alcohols by Yeasts", J. Gen. Microbio., Aug. 1987, vol. 133, Issue 8, pp. 2181-2090.
Wootton et al., "Statistics of local complexity in amino acid sequences and sequence databases", Computers in Chemistry, Jun. 1993, vol. 17, Issue 2, pp. 149-163.
Wu et al., "Studies of Biosynthesis of Waxes by Developing Jojoba Seed: III. Biosynthesis of Wax Esters of Acyl CoA and Long Chain Alcohols", Dec. 1981 Lipids 16, Issue 12, pp. 897-902.
Xu et al., "The FadRzDNA Complex. Transcriptional Control of Fatty Acid Metabolism in *Escherichia coli*", J. Biol. Chem., May 18, 2001, vol. 276, Issue 20, pp. 17373-17379.
Yomano, L.P. et al., "Re-Engineering *Escherichia coli* for ethanol production", Biotechnol. Lett., Dec. 2008, vol. 30, pp. 2097-2103.
Yoo et al., "Determination of the native form of FadD, the *Escherichia coli* fatty acyl-CoA synthetase, and characterization of limited proteolysis by outer membrane protease OmpT", Biochem. J., Dec. 15, 2001, vol. 360, pp. 699-706.
Zang et al., "Optimum Conditions for Transformation of Synechocystis sp. PCC 6803", The Journal of Microbiology, Jun. 2007, vol. 45, No. 3, pp. 241-245.
Zhang et al., "Inhibiting Bacterial Fatty Acid Synthesis", J. Biol. Chem., Jun. 30, 2006, vol. 281, Issue 26, pp. 17541-17544.
Zhang et al., "Structural Basis for Catalytic and Inhibitory Mechanisms of .beta.-Hydroxyacyl-acyl Carrier Protein Dehydratase (FabZ)", J. Biol. Chem., Feb. 29, 2008, vol. 283, Issue 9, pp. 5370-5379.
Zhang et al., "The FabR (YijC) Transcription Factor Regulates Unsaturated Fatty Acid Biosynthesis in *Escherichia coli*\*", J. Biol. Chem., May 3, 2002, vol. 277, Issue 18, pp. 15558-15565.
Zhang Hanxing et al., "Molecular effect of FadD on the regulation and metabolism of fatty acid 1n *Escherichia coli*", FEMS Microbiology Letters, Jun. 2006, vol. 259, No. 2, pp. 249-253.
Zheng et al., "Thioesterase II of *Escherichia coli* Plays an Important Role in 3-Hydroxydecanoic Acid Production", Applied and Environmental Microbiology, Jul. 2004, vol. 70, No. 7, pp. 3807-3813.
Zhu et al., "Functions of the Clostridium acetobutylicium FabF and FabZ proteins in unsaturated fatty acid biosynthesis", BMC Microbiology, Jun. 4, 2009, vol. 9, pp. 1-11.
Zimhony et al., "Characterization of *Mycobacterium smegmatis* Expressing the *Mycobacterium tuberculosis* Fatty Acid Synthase I (fas1) Gene", J. Bacteriol., Jul. 2004, vol. 186, Issue 13, pp. 4051-4055.
Extended European Search Report in EP Patent Application No. 19192374.7 dated Jun. 24, 2020 (11 pages).
Notice of Allowance in U.S. Appl. No. 15/451,881 dated Aug. 5, 2020.
Notice of Allowance in U.S. Appl. No. 15/451,881 dated Jul. 22, 2020.
Notice of Allowance in U.S. Appl. No. 15/451,881 dated Sep. 4, 2020.
Notice of Reasons for Rejection in JP Patent Application No. 2018-207088 dated Aug. 17, 2020 (with English Translation) (6 pages).
Office Action in BR Patent Application No. PI1015313-6 dated Jul. 14, 2020 (with English translation) (26 pages).

\* cited by examiner

SEQUENCE LISTING

```
<160> NUMBER OF SEQ ID NOS: 32

<210> SEQ ID NO 1
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaaaacagca acaatgtgag ctttgttgta attatattgt aaacatattg attccgggga      60
tccgtcgacc                                                            70

<210> SEQ ID NO 2
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaacggagcc tttcggctcc gttattcatt tacgcggctt caactttcct gtaggctgga      60
gctgcttc                                                              68

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgggcaggtg ctatgaccag gac                                             23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 4
cgcggcgttg accggcagcc tgg    23

<210> SEQ ID NO 5
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atgtttattt gcgttaccgt tcattcacaa tactggagca atccagtatg catatgaata    60
tcctccttag ttcc    74

<210> SEQ ID NO 6
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgtacctcta tcttgatttg cttgtttcat tactcgtcct tcacatttcc gtgtaggctg    60
gagctgcttc g    71

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaccggccaa agaattgcag    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
taagccagca actaacgcca    20

<210> SEQ ID NO 9
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gatgaactaa acttgttacc gttatcacat tcaggagatg gagaaccatg catatgaata    60
tcctccttag ttcc    74

<210> SEQ ID NO 10
<211> LENGTH: 71

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccttattatg acgggaaatg ccacccttt taccttagcc agtttgtttt gtgtaggctg     60
gagctgcttc g                                                         71

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgggctattt aaccgttagt                                                20

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agagcattaa cggtaggg                                                  18

<210> SEQ ID NO 13
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tatttttagt agcttaaatg tgattcaaca tcactggaga aagtcttatg catatgaata    60
tcctccttag ttcc                                                      74

<210> SEQ ID NO 14
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctcccctgga atgcagggga gcggcaagat taaaccagtt cgttcgggca gtgtaggctg    60
gagctgcttc g                                                         71

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
```

```
caatatcgcc atagctttc                                                  19
```

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
tacagtttct gactcagg                                                   18
```

<210> SEQ ID NO 17
<211> LENGTH: 6700
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
ggggaattgt gagcggataa caattcccct gtagaaataa ttttgtttaa ctttaataag     60
gagatatacc atggtgaaga aggtttggct taaccgttat cccgcggacg ttccgacgga    120
gatcaaccct gaccgttatc aatctctggt agatatgttt gagcagtcgg tcgcgcgcta    180
cgccgatcaa cctgcgtttg tgaatatggg ggaggtaatg accttccgca agctggaaga    240
acgcagtcgc gcgtttgccg cttatttgca acaaggggttg gggctgaaga aaggcgatcg    300
cgttgcgttg atgatgccta atttattgca atatccggtg gcgctgtttg cattttgcg    360
tgccgggatg atcgtcgtaa acgttaaccc gttgtatacc ccgcgtgagc ttgagcatca    420
gcttaacgat agcggcgcat cggcgattgt tatcgtgtct aactttgctc acacactgga    480
aaaagtggtt gataaaaccg ccgttcagca cgtaattctg acccgtatgg gcgatcagct    540
atctacggca aaaggcacgg tagtcaattt cgttgttaaa tacatcaagc gtttggtgcc    600
gaaataccat ctgccagatg ccatttcatt tcgtagcgca ctgcataacg gctaccggat    660
gcagtacgtc aaacccgaac tggtgccgga agatttagct tttctgcaat acaccggcgg    720
caccactggt gtggcgaaag gcgcgatgct gactcaccgc aatatgctgg cgaacctgga    780
acaggttaac gcgacctatg gtccgctgtt gcatccgggc aaagagctgg tggtgacggc    840
gctgccgctg tatcacattt ttgccctgac cattaactgc ctgctgttta tcgaactggg    900
tgggcagaac ctgcttatca ctaacccgcg cgatattcca gggttggtaa agagttagc    960
gaaatatccg tttaccgcta tcacgggcgt taacaccttg ttcaatgcgt tgctgaacaa   1020
taaagagttc cagcagctgg atttctccag tctgcatctt tccgcaggcg agggatgcc    1080
agtgcagcaa gtggtggcag agcgttgggt gaaactgaca ggacagtatc tgctggaagg   1140
ctatggcctt accgagtgtg cgccgctggt cagcgttaac ccatatgata ttgattatca   1200
tagtggtagc atcggtttgc cggtgccgtc gacggaagcc aaactggtgg atgatgatga   1260
taatgaagta ccaccgggtc aaccgggtga gctttgtgtc aaaggaccgc aggtgatgct   1320
gggttactgg cagcgtccgg atgctacaga tgagatcatc aaaaatggct ggttacacac   1380
cggcgacatc gcggtgatgg atgaagaagg gttcctgcgc attgtcgatc gtaaaaaaga   1440
catgattctg gtttccggtt ttaacgtcta tcccaacgag attgaagatg tcgtcatgca   1500
gcatcctggc gtacaggaag tcgcggctgt tggcgtacct tccggctcca gtggtgaagc   1560
ggtgaaaatc ttcgtagtga aaaaagatcc atcgcttacc gaagagtcac tggtgacctt   1620
```

```
ttgccgccgt cagctcacgg gctacaaagt accgaagctg gtggagtttc gtgatgagtt    1680
accgaaatct aacgtcggaa aaattttgcg acgagaatta cgtgacgaag cgcgcggcaa    1740
agtggacaat aaagcctgaa agcttgcggc cgcataatgc ttaagtcgaa cagaaagtaa    1800
tcgtattgta cacggccgca taatcgaaat taatacgact cactataggg gaattgtgag    1860
cggataacaa ttccccatct tagtatatta gttaagtata agaaggagat atacatatgc    1920
gcccattaca tccgattgat tttatattcc tgtcactaga aaaagacaaa cagcctatgc    1980
atgtaggtgg tttatttttg tttcagattc ctgataacgc cccagacacc tttattcaag    2040
atctggtgaa tgatatccgg atatcaaaat caatccctgt tccaccattc aacaataaac    2100
tgaatgggct tttttgggat gaagatgaag agtttgattt agatcatcat tttcgtcata    2160
ttgcactgcc tcatcctggt cgtattcgtg aattgcttat ttatatttca caagagcaca    2220
gtacgctgct agatcgggca aagcccttgt ggacctgcaa tattattgaa ggaattgaag    2280
gcaatcgttt tgccatgtac ttcaaaattc accatgcgat ggtcgatggc gttgctggta    2340
tgcggttaat tgaaaaatca ctctcccatg atgtaacaga aaaaagtatc gtgccacctt    2400
ggtgtgttga gggaaaacgt gcaaagcgct taagagaacc taaaacaggt aaaattaaga    2460
aaatcatgtc tggtattaag agtcagcttc aggcgacacc cacagtcatt caagagcttt    2520
ctcagacagt atttaaagat attggacgta atcctgatca tgtttcaagc tttcaggcgc    2580
cttgttctat tttgaatcag cgtgtgagct catcgcgacg ttttgcagca cagtcttttg    2640
acctagatcg ttttcgtaat attgccaaat cgttgaatgt gaccattaat gatgttgtac    2700
tagcggtatg ttctggtgca ttacgtgcgt atttgatgag tcataatagt ttgccttcaa    2760
aaccattaat tgccatggtt ccagcctcta ttcgcaatga cgattcagat gtcagcaacc    2820
gtattacgat gattctggca aatttggcaa cccacaaaga tgatcctttta caacgtcttg    2880 aaattatccg ccgtagtgtt caaaactcaa agcaacgctt caaacgtatg accagcgatc    2940
agattctaaa ttatagtgct gtcgtatatg gccctgcagg actcaacata atttctggca    3000
tgatgccaaa acgccaagcc ttcaatctgg ttatttccaa tgtgcctggc ccaagagagc    3060
cactttactg gaatggtgcc aaacttgatg cactctaccc agcttcaatt gtattagacg    3120
gtcaagcatt gaatattaca atgaccagtt atttagataa acttgaagtt ggtttgattg    3180
catgccgtaa tgcattgcca agaatgcaga atttactgac acatttagaa gaagaaattc    3240
aactatttga aggcgtaatt gcaaagcagg aagatattaa acagccaat taaaaacaat    3300 aaacttgatt ttttaattta tcagataaaa ctaaagggct aaattagccc tcctaggctg    3360
ctgccaccgc tgagcaataa ctagcataac cccttggggc ctctaaacgg gtcttgaggg    3420
gttttttgct gaaacctcag gcatttgaga agcacacggt cacactgctt ccggtagtca    3480
ataaaccggt aaaccagcaa tagacataag cggctattta acgaccctgc cctgaaccga    3540
cgaccgggtc atcgtggccg gatcttgcgg cccctcggct tgaacgaatt gttagacatt    3600
atttgccgac taccttggtg atctcgcctt tcacgtagtg gacaaattct tccaactgat    3660
ctgcgcgcga ggccaagcga tcttcttctt gtccaagata agcctgtcta gcttcaagta    3720
tgacgggctg atactgggcc ggcaggcgct ccattgccca gtcggcagcg acatccttcg    3780
gcgcgatttt gccggttact gcgctgtacc aaatgcggga caacgtaagc actacatttc    3840
gctcatcgcc agcccagtcg ggcggcgagt tccatagcgt taaggtttca tttagcgcct    3900
caaatagatc ctgttcagga accggatcaa agagttcctc cgccgctgga cctaccaagg    3960
```

```
caacgctatg ttctcttgct tttgtcagca agatagccag atcaatgtcg atcgtggctg    4020
gctcgaagat acctgcaaga atgtcattgc gctgccattc tccaaattgc agttcgcgct    4080
tagctggata acgccacgga atgatgtcgt cgtgcacaac aatggtgact tctacagcgc    4140
ggagaatctc gctctctcca ggggaagccg aagtttccaa aaggtcgttg atcaaagctc    4200
gccgcgttgt ttcatcaagc cttacggtca ccgtaaccag caaatcaata tcactgtgtg    4260
gcttcaggcc gccatccact gcggagccgt acaaatgtac ggccagcaac gtcggttcga    4320
gatggcgctc gatgacgcca actacctctg atagttgagt cgatacttcg gcgatcaccg    4380
cttccctcat actcttcctt tttcaatatt attgaagcat ttatcagggt tattgtctca    4440
tgagcggata catatttgaa tgtatttaga aaaataaaca aatagctagc tcactcggtc    4500
gctacgctcc gggcgtgaga ctgcggcggg cgctgcggac acatacaaag ttacccacag    4560
attccgtgga taagcagggg actaacatgt gaggcaaaac agcagggccg cgccggtggc    4620
gtttttccat aggctccgcc ctcctgccag agttcacata aacagacgct tttccggtgc    4680
atctgtggga gccgtgaggc tcaaccatga atctgacagt acgggcgaaa cccgacagga    4740
cttaaagatc cccaccgttt ccggcgggtc gctccctctt gcgctctcct gttccgaccc    4800
tgccgtttac cggatacctg ttccgccttt ctcccttacg ggaagtgtgg cgctttctca    4860
tagctcacac actggtatct cggctcggtg taggtcgttc gctccaagct gggctgtaag    4920
caagaactcc ccgttcagcc cgactgctgc gccttatccg gtaactgttc acttgagtcc    4980
aacccggaaa agcacggtaa aacgccactg gcagcagcca ttggtaactg ggagttcgca    5040
gaggatttgt ttagctaaac acgcggttgc tcttgaagtg tgcgccaaag tccggctaca    5100
ctggaaggac agatttggtt gctgtgctct gcgaaagcca gttaccacgg ttaagcagtt    5160
ccccaactga cttaaccttc gatcaaacca cctccccagg tggttttttc gtttacaggg    5220
caaaagatta cgcgcagaaa aaaggatct caagaagatc ctttgatctt ttctactgaa    5280
ccgctctaga tttcagtgca atttatctct tcaaatgtag cacctgaagt cagccccata    5340
cgatataagt tgtaattctc atgttagtca tgccccgcgc ccaccggaag gagctgactg    5400
ggttgaaggc tctcaagggc atcggtcgag atcccggtgc ctaatgagtg agctaactta    5460
cattaattgc gttgcgctca ctgcccgctt tccagtcggg aaacctgtcg tgccagctgc    5520
attaatgaat cggccaacgc gcggggagag gcggtttgcg tattgggcgc cagggtggtt    5580
tttcttttca ccagtgagac gggcaacagc tgattgccct tcaccgcctg gccctgagag    5640
agttgcagca agcggtccac gctggtttgc cccagcaggc gaaaatcctg tttgatggtg    5700
gttaacggcg ggatataaca tgagctgtct tcggtatcgt cgtatcccac taccgagatg    5760
tccgcaccaa cgcgcagccc ggactcggta atggcgcgca ttgcgcccag cgccatctga    5820
tcgttggcaa ccagcatcgc agtgggaacg atgccctcat tcagcatttg catggtttgt    5880
tgaaaaccgg acatggcact ccagtcgcct tcccgttccg ctatcggctg aatttgattg    5940
cgagtgagat atttatgcca gccagccaga cgcagacgcg ccgagacaga acttaatggg    6000
cccgctaaca gcgcgatttg ctggtgaccc aatgcgacca gatgctccac gcccagtcgc    6060
gtaccgtctt catgggagaa aataatactg ttgatgggtg tctggtcaga gacatcaaga    6120
aataacgccg gaacattagt gcaggcagct tccacagcaa tggcatcctg gtcatccagc    6180
ggatagttaa tgatcagccc actgacgcgt tgcgcgagaa gattgtgcac cgccgcttta    6240
caggcttcga cgccgcttcg ttctaccatc gacaccacca cgctggcacc cagttgatcg    6300
gcgcgagatt taatcgccgc gacaatttgc gacggcgcgt gcagggccag actggaggtg    6360
```

```
gcaacgccaa tcagcaacga ctgtttgccc gccagttgtt gtgccacgcg gttgggaatg    6420
taattcagct ccgccatcgc cgcttccact tttccccgcg ttttcgcaga aacgtggctg    6480
gcctggttca ccacgcggga aacggtctga taagagacac cggcatactc tgcgacatcg    6540
tataacgtta ctggtttcac attcaccacc ctgaattgac tctcttccgg gcgctatcat    6600
gccataccgc gaaaggtttt gcgccattcg atggtgtccg ggatctcgac gctctccctt    6660
atgcgactcc tgcattagga aattaatacg actcactata                          6700

<210> SEQ ID NO 18
<211> LENGTH: 4963
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
ggggaattgt gagcggataa caattcccct gtagaaataa ttttgtttaa ctttaataag     60
gagatatacc atgggcagca gccatcacca tcatcaccac agccaggatc cgaattcgag    120
ctcggcgcgc ctgcaggtcg acaagcttgc ggccgcataa tgcttaagtc gaacagaaag    180
taatcgtatt gtacacggcc gcataatcga attaatacg actcactata ggggaattgt     240
gagcggataa caattcccca tcttagtata ttagttaagt ataagaagga gatatacata    300
tgaaagcgct tagcccagtg gatcaactgt tcctgtggct ggaaaaacga cagcaaccca    360
tgcacgtagg cggtttgcag ctgttttcct tcccggaagg tgccggcccc aagtatgtga    420
gtgagctggc ccagcaaatg cgggattact gccacccagt ggcgccattc aaccagcgcc    480
tgacccgtcg actcggccag tattactgga ctagagacaa acagttcgat atcgaccacc    540
acttccgcca cgaagcactc cccaaacccg gtcgcattcg cgaactgctt tctttggtct    600
ccgccgaaca ttccaacctg ctggaccggg agcgccccat gtgggaagcc catttgatcg    660
aagggatccg cggtcgccag ttcgctctct attataagat ccaccattcg gtgatggatg    720
gcatatccgc catgcgtatc gcctccaaaa cgctttccac tgaccccagt gaacgtgaaa    780
tggctccggc ttgggcgttc aacaccaaaa aacgctcccg ctcactgccc agcaacccgg    840
ttgacatggc ctccagcatg gcgcgcctaa ccgcgagcat aagcaaacaa gctgccacag    900
tgcccggtct cgcgcgggag gtttacaaag tcacccaaaa agccaaaaaa gatgaaaact    960
atgtgtctat ttttcaggct cccgacacga ttctgaataa taccatcacc ggttcacgcc   1020
gctttgccgc ccagagcttt ccattaccgc gcctgaaagt tatcgccaag gcctataact   1080
gcaccattaa caccgtggtg ctctccatgt gtggccacgc tctgcgcgaa tacttgatta   1140
gccaacacgc gctgcccgat gagccactga ttgcaatggt gccatgagc ctgcggcagg    1200 acgacagcac tggcggcaac cagatcggta tgatcttggc taacctgggc acccacatct   1260
gtgatccagc taatcgcctg cgcgtcatcc acgattccgt cgaggaagcc aaatcccgct   1320
tctcgcagat gagcccggaa gaaattctca atttcaccgc cctcactatg gctcccaccg   1380
gcttgaactt actgaccggc ctagcgccaa atggcgggc cttcaacgtg gtgatttcca   1440
acatacccgg gccgaaagag ccgctgtact ggaatggtgc acagctgcaa ggagtgtatc   1500
cagtatccat tgccttggat cgcatcgccc taaatatcac cctcaccagt tatgtagacc   1560
agatggaatt tgggcttatc gcctgccgcc gtactctgcc ttccatgcag cgactactgg   1620
attacctgga acagtccatc cgcgaattgg aaatcggtgc aggaattaaa tagtaaccta   1680
```

```
ggctgctgcc accgctgagc aataactagc ataacccctt ggggcctcta acgggtctt      1740
gagggtttt  ttgctgaaac ctcaggcatt tgagaagcac acggtcacac tgcttccggt     1800
agtcaataaa ccggtaaacc agcaatagac ataagcggct atttaacgac cctgccctga    1860
accgacgaca agctgacgac cgggtctccg caagtggcac ttttcgggga aatgtgcgcg    1920
gaacccctat ttgtttattt ttctaaaatac attcaaatat gtatccgctc atgaattaat  1980
tcttagaaaa actcatcgag catcaaatga aactgcaatt tattcatatc aggattatca    2040
ataccatatt tttgaaaaag ccgtttctgt aatgaaggag aaaactcacc gaggcagttc    2100
cataggatgg caagatcctg gtatcggtct gcgattccga ctcgtccaac atcaatacaa    2160
cctattaatt tcccctcgtc aaaaataagg ttatcaagtg agaaatcacc atgagtgacg    2220
actgaatccg gtgagaatgg caaaagttta tgcatttctt tccagacttg ttcaacaggc   2280
cagccattac gctcgtcatc aaaatcactc gcatcaacca aaccgttatt cattcgtgat    2340
tgcgcctgag cgagacgaaa tacgcggtcg ctgttaaaag acaattaca  aacaggaatc    2400
gaatgcaacc ggcgcaggaa cactgccagc gcatcaacaa tattttcacc tgaatcagga    2460
tattcttcta atacctggaa tgctgttttc ccggggatcg cagtggtgag taaccatgca    2520
tcatcaggag tacggataaa atgcttgatg gtcggaagag gcataaattc cgtcagccag    2580
tttagtctga ccatctcatc tgtaacatca ttggcaacgc tacctttgcc atgtttcaga    2640
aacaactctg gcgcatcggg cttcccatac aatcgataga ttgtcgcacc tgattgcccg    2700
acattatcgc gagcccattt atacccatat aaatcagcat ccatgttgga atttaatcgc    2760
ggcctagagc aagacgtttc ccgttgaata tggctcatac tcttcctttt tcaatattat    2820
tgaagcattt atcagggtta ttgtctcatg agcggataca tatttgaatg tatttagaaa    2880
aataaacaaa taggcatgct agcgcagaaa cgtcctagaa gatgccagga ggatacttag    2940
cagagagaca ataaggccgg agcgaagccg ttttttccata ggctccgccc ccctgacgaa    3000
catcacgaaa tctgacgctc aaatcagtgg tggcgaaacc cgacaggact ataaagatac    3060
caggcgtttc cccctgatgg ctcccctcttg cgctctcctg ttcccgtcct gcggcgtccg    3120
tgttgtggtg gaggctttac ccaaatcacc acgtcccgtt ccgtgtagac agttcgctcc    3180
aagctgggct gtgtgcaaga acccccccgtt cagcccgact gctgcgcctt atccggtaac    3240
tatcatcttg agtccaaccc ggaaagacac gacaaaacgc cactggcagc agccattggt    3300
aactgagaat tagtggattt agatatcgag agtcttgaag tggtggccta acagaggcta    3360
cactgaaagg acagtatttg gtatctgcgc tccactaaag ccagttacca ggttaagcag    3420
ttccccaact gacttaaccct tcgatcaaac cgcctcccca ggcggttttt tcgtttacag    3480
agcaggagat tacgacgatc gtaaaaggat ctcaagaaga tcctttacgg attcccgaca    3540
ccatcactct agatttcagt gcaatttatc tcttcaaatg tagcacctga agtcagcccc    3600
atacgatata agttgtaatt ctcatgttag tcatgccccg cgcccaccgg aaggagctga    3660
ctgggttgaa ggctctcaag ggcatcggtc gagatcccgg tgcctaatga gtgagctaac    3720
ttacattaat tgcgttgcgc tcactgcccg ctttccagtc gggaaacctg tcgtgccagc    3780
tgcattaatg aatcggccaa cgcgcgggga gaggcggttt gcgtattggg cgccagggtg    3840
gtttttcttt tcaccagtga cgggcaac agctgattgc ccttcaccgc ctggccctga    3900
gagagttgca gcaagcggtc cacgctggtt tgccccagca ggcgaaaatc ctgtttgatg    3960
gtggttaacg gcgggatata acatgagctg tcttcggtat cgtcgtatcc cactaccgag    4020
```

| | |
|---|---|
| atgtccgcac caacgcgcag cccggactcg gtaatggcgc gcattgcgcc cagcgccatc | 4080 |
| tgatcgttgg caaccagcat cgcagtggga acgatgccct cattcagcat ttgcatggtt | 4140 |
| tgttgaaaac cggacatggc actccagtcg ccttcccgtt ccgctatcgg ctgaatttga | 4200 |
| ttgcgagtga gatatttatg ccagccagcc agacgcagac gcgccgagac agaacttaat | 4260 |
| gggcccgcta acagcgcgat tgctggtga cccaatgcga ccagatgctc cacgcccagt | 4320 |
| cgcgtaccgt cttcatggga gaaaataata ctgttgatgg gtgtctggtc agagacatca | 4380 |
| agaaataacg ccggaacatt agtgcaggca gcttccacag caatggcatc ctggtcatcc | 4440 |
| agcggatagt taatgatcag cccactgacg cgttgcgcga aagattgtg caccgccgct | 4500 |
| ttacaggctt cgacgccgct tcgttctacc atcgacacca ccacgctggc acccagttga | 4560 |
| tcggcgcgag atttaatcgc cgcgacaatt tgcgacggcg cgtgcagggc cagactggag | 4620 |
| gtggcaacgc caatcagcaa cgactgtttg cccgccagtt gttgtgccac gcggttggga | 4680 |
| atgtaattca gctccgccat cgccgcttcc acttttttccc gcgttttcgc agaaacgtgg | 4740 |
| ctggcctggt tcaccacgcg ggaaacggtc tgataagaga caccggcata ctctgcgaca | 4800 |
| tcgtataacg ttactggttt cacattcacc accctgaatt gactctcttc cgggcgctat | 4860 |
| catgccatac cgcgaaaggt tttgcgccat tcgatggtgt ccgggatctc gacgctctcc | 4920 |
| cttatgcgac tcctgcatta ggaaattaat acgactcact ata | 4963 |

```
<210> SEQ ID NO 19
<211> LENGTH: 5733
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
```

| | |
|---|---|
| actcaccagt cacagaaaag catcttacgg atggcatgac agtaagagaa ttatgcagtg | 60 |
| ctgccataac catgagtgat aacactgcgg ccaacttact tctgacaacg atcggaggac | 120 |
| cgaaggagct aaccgctttt ttgcacaaca tgggggatca tgtaactcgc cttgatcgtt | 180 |
| gggaaccgga gctgaatgaa gccataccaa acgacgagcg tgacaccacg atgcctgcag | 240 |
| caatggcaac aacgttgcgc aaactattaa ctggcgaact acttactcta gcttcccggc | 300 |
| aacaattaat agactggatg gaggcggata agttgcagg accacttctg cgctcggccc | 360 |
| ttccggctgg ctggtttatt gctgataaat ctggagccgg tgagcgtggg tctcgcggta | 420 |
| tcattgcagc actggggcca gatggtaagc cctcccgtat cgtagttatc tacacgacgg | 480 |
| ggagtcaggc aactatggat gaacgaaata gacagatcgc tgagataggt gcctcactga | 540 |
| ttaagcattg gtaactgtca gaccaagttt actcatatat actttagatt gatttaaaac | 600 |
| ttcattttta atttaaaagg atctaggtga agatcctttt tgataatctc atgaccaaaa | 660 |
| tcccttaacg tgagttttcg ttccactgag cgtcagaccc cttaataaga tgatcttctt | 720 |
| gagatcgttt tggtctgcgc gtaatctctt gctctgaaaa cgaaaaaacc gccttgcagg | 780 |
| gcggttttc gaaggttctc tgagctacca actctttgaa ccgaggtaac tggcttggag | 840 |
| gagcgcagtc accaaaactt gtcctttcag tttagcctta accggcgcat gacttcaaga | 900 |
| ctaactcctc taaatcaatt accagtggct gctgccagtg gtgcttttgc atgtctttcc | 960 |
| gggttggact caagacgata gttaccggat aaggcgcagc ggtcggactg aacgggggt | 1020 |
| tcgtgcatac agtccagctt ggagcgaact gcctacccgg aactgagtgt caggcgtgga | 1080 |

-continued

```
atgagacaaa cgcggccata acagcggaat gacaccggta aaccgaaagg caggaacagg    1140
agagcgcacg agggagccgc caggggggaaa cgcctggtat ctttatagtc ctgtcgggtt    1200
tcgccaccac tgatttgagc gtcagatttc gtgatgcttg tcagggggggc ggagcctatg    1260 gaaaaacggc tttgccgcgg ccctctcact tccctgttaa gtatcttcct ggcatcttcc    1320
aggaaatctc cgccccgttc gtaagccatt tccgctcgcc gcagtcgaac gaccgagcgt    1380
agcgagtcag tgagcgagga agcggaatat atcctgtatc acatattctg ctgacgcacc    1440
ggtgcagcct ttttttctcct gccacatgaa gcacttcact gacaccctca tcagtgccaa    1500
catagtaagc cagtatacac tccgctagcg ctgaggtctg cctcgtgaag aaggtgttgc    1560
tgactcatac caggcctgaa tcgccccatc atccagccag aaagtgaggg agccacggtt    1620
gatgagagct tgttgtagg tggaccagtt ggtgattttg aacttttgct ttgccacgga    1680
acggtctgcg ttgtcgggaa gatgcgtgat ctgatccttc aactcagcaa aagttcgatt    1740
tattcaacaa agccacgttg tgtctcaaaa tctctgatgt tacattgcac aagataaaaa    1800
tatatcatca tgaacaataa aactgtctgc ttacataaac agtaatacaa ggggtgttat    1860
gagccatatt caacgggaaa cgtcttgctc gaggccgcga ttaaattcca acatggatgc    1920
tgatttatat gggtataaat gggctcgcga taatgtcggg caatcaggtg cgacaatcta    1980
tcgattgtat gggaagcccg atgcgccaga gttgtttctg aaacatggca aaggtagcgt    2040
tgccaatgat gttacagatg agatggtcag actaaactgg ctgacggaat ttatgcctct    2100
tccgaccatc aagcatttta tccgtactcc tgatgatgca tggttactca ccactgcgat    2160
ccccgggaaa acagcattcc aggtattaga agaatatcct gattcaggtg aaaatattgt    2220
tgatgcgctg gcagtgttcc tgcgccggtt gcattcgatt cctgtttgta attgtccttt    2280
taacagcgat cgcgtatttc gtctcgctca ggcgcaatca cgaatgaata acggtttggt    2340
tgatgcgagt gattttgatg acgagcgtaa tggctggcct gttgaacaag tctggaaaga    2400
aatgcataag cttttgccat tctcaccgga ttcagtcgtc actcatggtg atttctcact    2460
tgataacctt atttttgacg aggggaaatt aataggttgt attgatgttg gacgagtcgg    2520
aatcgcagac cgataccagg atcttgccat cctatggaac tgcctcggtg agttttctcc    2580
ttcattacag aaacggcttt tcaaaaata tggtattgat aatcctgata tgaataaatt    2640
gcagtttcat ttgatgctcg atgagttttt ctaatcagaa ttggttaatt ggttgtaaca    2700
ctggcagagc attacgctga cttgacggga cggcggcttt gttgaataaa tcgaactttt    2760
gctgagttga aggatcagat cacgcatctt cccgacaacg cagaccgttc cgtggcaaag    2820
caaaagttca aaatcaccaa ctggtccacc tacaacaaag ctctcatcaa ccgtggctcc    2880
ctcactttct ggctggatga tggggcgatt caggcctggt atgagtcagc aacaccttct    2940
tcacgaggca gacctcagcg ctcaaagatg caggggtaaa agctaaccgc atctttaccg    3000
acaaggcatc cggcagttca acagatcggg aagggctgga tttgctgagg atgaaggtgg    3060
aggaaggtga tgtcattctg gtgaagaagc tcgaccgtct tggccgcgac accgccgaca    3120
tgatccaact gataaaagag tttgatgctc agggtgtagc ggttcggttt attgacgacg    3180
ggatcagtac cgacggtgat atggggcaaa tggtggtcac catcctgtcg gctgtggcac    3240
aggctgaacg ccggaggatc ctagagcgca cgaatgaggg ccgacaggaa gcaaagctga    3300
aaggaatcaa atttggccgc aggcgtaccg tggacaggaa cgtcgtgctg acgcttcatc    3360
agaagggcac tggtgcaacg gaaattgctc atcagctcag tattgcccgc tccacggttt    3420
ataaaattct tgaagacgaa agggcctcgt gatacgccta tttttatagg ttaatgtcat    3480
```

```
gataataatg gtttcttaga cgtcttaatt aatcaggaga gcgttcaccg acaaacaaca    3540
gataaaacga aaggcccagt ctttcgactg agcctttcgt tttatttgat gcctggcagt    3600
tccctactct cgcatgggga accccacac taccatcggc gctacggcgt ttcacttctg     3660
agttcggcat ggggtcaggt gggaccaccg cgctactgcc gccaggcaaa ttctgtttta    3720
tcagaccgct tctgcgttct gatttaatct gtatcaggct gaaaatcttc tctcatccgc    3780
caaaacagcc aagctggaga ccgtttaaac tcaatgatga tgatgatgat ggtcgacggc    3840
gctattcaga tcctcttctg agatgagttt tgttcgggc ccaagcttcg aattcccata     3900
tggtaccagc tgcagatctc gagctcggat ccatggttta ttcctcctta tttaatcgat    3960
acattaatat atacctcttt aattttttaat aataaagtta atcgataatt ccggtcgagt   4020
gcccacacag attgtctgat aaattgttaa agagcagtgc cgcttcgctt tttctcagcg    4080
gcgctgtttc ctgtgtgaaa ttgttatccg ctcacaattc cacacattat acgagccgga   4140
tgattaattg tcaacagctc atttcagaat atttgccaga accgttatga tgtcggcgca    4200
aaaaacatta tccagaacgg gagtgcgcct tgagcgacac gaattatgca gtgatttacg    4260
acctgcacag ccataccaca gcttccgatg gctgcctgac gccagaagca ttggtgcacc    4320
gtgcagtcga tgataagctg tcaaaccaga tcaattcgcg ctaactcaca ttaattgcgt   4380
tgcgctcact gcccgctttc cagtcgggaa acctgtcgtg ccagctgcat taatgaatcg    4440
gccaacgcgc ggggagaggc ggtttgcgta ttgggcgcca gggtggtttt cttttcacc    4500 agtgagacgg gcaacagctg attgcccttc accgcctggc cctgagagag ttgcagcaag   4560
cggtccacgc tggtttgccc cagcaggcga aaatcctgtt tgatggtggt tgacggcggg   4620
atataacatg agctgtcttc ggtatcgtcg tatcccacta ccgagatatc cgcaccaacg    4680
cgcagcccgg actcggtaat ggcgcgcatt gcgcccagcg ccatctgatc gttggcaacc    4740
agcatcgcag tgggaacgat gccctcattc agcatttgca tggtttgttg aaaaccggac   4800
atggcactcc agtcgccttc ccgttccgct atcggctgaa tttgattgcg agtgagatat    4860
ttatgccagc cagccagacg cagacgcgcc gagacagaac ttaatgggcc cgctaacagc    4920
gcgatttgct ggtgacccaa tgcgaccaga tgctccacgc ccagtcgcgt accgtcttca    4980
tgggagaaaa taatactgtt gatgggtgtc tggtcagaga catcaagaaa taacgccgga   5040
acattagtgc aggcagcttc cacagcaatg gcatcctggt catccagcgg atagttaatg    5100
atcagcccac tgacgcgttg cgcgagaaga ttgtgcaccg ccgctttaca ggcttcgacg   5160
ccgcttcgtt ctaccatcga caccaccacg ctggcaccca gttgatcggc gcgagattta    5220
atcgccgcga caatttgcga cggcgcgtgc agggccagac tggaggtggc aacgccaatc    5280
agcaacgact gtttgcccgc cagttgttgt gccacgcggt tgggaatgta attcagctcc    5340
gccatcgccg cttccacttt ttcccgcgtt ttcgcagaaa cgtggctggc ctggttcacc   5400
acgcgggaaa cggtctgata agagacaccg gcatactctg cgacatcgta taacgttact   5460
ggtttcacat tcaccaccct gaattgactc tcttccgggc gctatcatgc cataccgcga    5520
aaggttttgc accattcgat ggtgtcaacg taaatgcatg ccgcttcgcc ttcgcgcgcg    5580
aattgatctg ctgcctcgcg cgtttcggtg atgacggtga aaacctctga cacatgcagc    5640
tcccggagac ggtcacagct tgtctgtaag cggatgccgg gagcagacaa gcccgtcagg   5700
gcgcgtcagc gggtgttggc ggggccggcc tcg                                5733
```

<210> SEQ ID NO 20

```
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 20
ctctagaaat aatttaactt taagtaggag auaggtaccc atggcggaca cgttattgat      60

<210> SEQ ID NO 21
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cttcgaattc catttaaatt atttctagag tcattatgag tcatgattta ctaaaggc        58

<210> SEQ ID NO 22
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctctagaaat aattttagtt aagtataaga aggagatata ccatggtgaa gaaggtttgg      60
cttaa                                                                 65

<210> SEQ ID NO 23
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cttcgaattc catttaaatt atttctagag ttatcaggct ttattgtcca c               51

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctctagaaat aatttagtta agtataagaa ggagatatac at                        42

<210> SEQ ID NO 25
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
```

```
cttcgaattc catttaaatt atttctagag ttactattta attcctgcac cgatttcc      58
```

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
atatgacgtc ggcatccgct tacagaca                                        28
```

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
aattcttaag tcaggagagc gttcaccgac aa                                   32
```

<210> SEQ ID NO 28
<211> LENGTH: 4311
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
ctagtaacgg ccgccagtgt gctggaattc aggcagttca acctgttgat agtacgtact      60
aagctctcat gtttcacgta ctaagctctc atgtttaacg tactaagctc tcatgtttaa     120
cgaactaaac cctcatggct aacgtactaa gctctcatgg ctaacgtact aagctctcat     180
gtttcacgta ctaagctctc atgtttgaac aataaaatta atataaatca gcaacttaaa     240
tagcctctaa ggttttaagt tttataagaa aaaaaagaat atataaggct tttaaagctt     300
ttaaggttta acggttgtgg acaacaagcc agggatgtaa cgcactgaga agcccttaga     360
gcctctcaaa gcaattttca gtgacacagg aacacttaac ggctgacagc ctgaattctg     420
cagatctggc gtaatagcga agaggcccgc accgatcgcc cttcccaaca gttgcgcagc     480
ctgaatggcg aatggcgctt tgcctggttt ccggtaccag aagcggtgcc ggaaagctgg     540
ctggagtgcg atcttcctga ggccgatact gtcgtcgtcc cctcaaactg gcagatgcac     600
ggttacgatg cgcccatcta caccaacgta acctatccca ttacggtcaa tccgccgttt     660
gttcccacgg agaatccgac gggttgttac tcgctcacat ttaatgttga tgaaagctgg     720
ctacaggaag gccagacgcg aattattttt gatggcgtta actggcgtt tcatctgtgg     780 tgcaacgggc gctgggtcgg ttacggccag acagtcgtt tgccgtctga atttgacctg     840
agcgcatttt tacgcgccgg agaaaaccgc ctcgcggtga tggtgctgcg ttggagtgac     900
ggcagttatc tggaagatca ggatatgtgg cggatgagcg gcattttccg tgacgtctcg     960
ttgctgcata aaccgactac acaaatcagc gatttccatg ttgccactcg ctttaatgat    1020
gatttcagcc gcgctgtact ggaggctgaa gttcagatgt gcggcgagtt gcgtgactac    1080
ctacgggtaa cagtttcttt atggcagggt gaaacgcagg tcgccagcgg caccgcgcct    1140
ttcggcggtg aaattatcga tgagcgtggt ggttatgccg atcgcgtcac actacgtctg    1200
```

```
aacgtcgaaa acccgaaact gtggagcgcc gaaatcccga atctctatcg tgcggtggtt   1260
gaactgcaca ccgccgacgg cacgctgatt gaagcagaag cctgcgatgt cggtttccgc   1320
gaggtgcgga ttgaaaatgg tctgctgctg ctgaacggca agccgttgct gattcgaggc   1380
gttaaccgtc acgagcatca tcctctgcat ggtcaggtca tggatgagca acgatggtg    1440 caggatatcc tgctgatgaa gcagaacaac tttaacgccg tgcgctgttc gcattatccg   1500
aaccatccgc tgtggtacac gctgtgcgac cgctacggcc tgtatgtggt ggatgaagcc   1560
aatattgaaa cccacggcat ggtgccaatg aatcgtctga ccgatgatcc gcgctggcta   1620
ccggcgatga gcgaacgcgt aacgcgaatg gtgcagcgcg atcgtaatca cccgagtgtg   1680
atcatctggt cgctggggaa tgaatcaggc cacggcgcta atcacgacgc gctgtatcgc   1740
tggatcaaat ctgtcgatcc ttcccgcccg gtgcagtatg aaggcggcgg agccgacacc   1800
acggccaccg atattatttg cccgatgtac gcgcgcgtgg atgaagacca gcccttcccg   1860
gctgtgccga atggtccat caaaaaatgg cttttcgctac ctggagagac gcgcccgctg   1920
atcctttgcg aatacgccca cgcgatgggt aacagtcttg gcggtttcgc taaatactgg   1980
caggcgtttc gtcagtatcc ccgtttacag ggcggcttcg tctgggactg ggtggatcag   2040
tcgctgatta aatatgatga aaacggcaac ccgtggtcgg cttacggcgg tgattttggc   2100
gatacgccga acgatcgcca gttctgtatg aacggtctgg tctttgccga ccgcacgccg   2160
catccagcgc tgacggaagc aaaacaccag cagcagtttt tccagttccg tttatccggg   2220
caaaccatcg aagtgaccag cgaatacctg ttccgtcata gcgataacga gctcctgcac   2280
tggatggtgg cgctgatgg taagccgctg gcaagcggtg aagtgcctct ggatgtcgct   2340
ccacaaggta acagttgat tgaactgcct gaactaccgc agccggagag cgccgggcaa   2400
ctctggctca cagtacgcgt agtgcaaccg aacgcgaccg catggtcaga agccgggcac   2460
atcagcgcct ggcagcagtg gcgtctggcg gaaaacctca gtgtgacgct ccccgccgcg   2520
tcccacgcca tcccgcatct gaccaccagc gaaatggatt tttgcatcga gctgggtaat   2580
aagcgttggc aatttaaccg ccagtcaggc tttctttcac agatgtggat tggcgataaa   2640
aaacaactgc tgacgccgct gcgcgatcag ttcacccgtg cacgtctgct gtcagataaa   2700
gtctcccgtg aactttaccc ggtggtgcat atcggggatg aaagctggcg catgatgacc   2760
accgatatgg ccagtgtgcc ggtctccgtt atcggggaag aagtggctga tctcagccac   2820
cgcgaaaatg acatcaaaaa cgccattaac ctgatgttct ggggaatata atgtcaggc   2880 atgagattat caaaaaggat cttcacctag atccttttca cgtagaaagc cagtccgcag   2940
aaacggtgct gaccccggat gaatgtcagc tactgggcta tctggacaag gaaaacgca    3000 agcgcaaaga gaaagcaggt agcttgcagt gggcttacat ggcgatagct agactgggcg   3060
gttttatgga cagcaagcga accggaattg ccagctgggg cgccctctgg taaggttggg   3120
aagccctgca aagtaaactg gatggctttc tcgccgccaa ggatctgatg cgcaggggga   3180
tcaagctctg atcaagagac aggatgagga tcgtttcgca tgattgaaca agatggattg   3240
cacgcaggtt ctccggccgc ttgggtggag aggctattcg gctatgactg gcacaacag    3300 acaatcggct gctctgatgc cgccgtgttc cggctgtcag cgcaggggcg cccggttctt   3360
tttgtcaaga ccgacctgtc cggtgccctg aatgaactgc aagacgaggc agcgcggcta   3420
tcgtggctgg ccacgacggg cgttccttgc gcagctgtgc tcgacgttgt cactgaagcg   3480
ggaagggact ggctgctatt gggcgaagtg ccggggcagg atctcctgtc atctcacctt   3540
gctcctgccg agaaagtatc catcatggct gatgcaatgc ggcggctgca tacgcttgat   3600
```

```
ccggctacct gcccattcga ccaccaagcg aaacatcgca tcgagcgagc acgtactcgg    3660
atggaagccg gtcttgtcga tcaggatgat ctggacgaag agcatcaggg gctcgcgcca    3720
gccgaactgt tcgccaggct caaggcgagc atgcccgacg gcgaggatct cgtcgtgacc    3780
catggcgatg cctgcttgcc gaatatcatg gtggaaaatg gccgcttttc tggattcatc    3840
gactgtggcc ggctgggtgt ggcggaccgc tatcaggaca tagcgttggc tacccgtgat    3900
attgctgaag agcttggcgg cgaatgggct gaccgcttcc tcgtgcttta cggtatcgcc    3960
gctcccgatt cgcagcgcat cgccttctat cgccttcttg acgagttctt ctgaattatt    4020
aacgcttaca atttcctgat gcggtatttt ctccttacgc atctgtgcgg tatttcacac    4080
cgcatacagg tggcactttt cggggaaatg tgcgcggaac ccctatttgt ttatttttct    4140
aaatacattc aaatatgtat ccgctcatga gacaataacc ctgataaatg cttcaataat    4200
agcacgtgag gagggccacc atggccaagt tgaccagtgc cgttccggtg ctcaccgcgc    4260
gcgacgtcgc cggagcggtc gagttctgga ccgaccggct cgggttctcc c             4311
```

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
caaccagcgg ccgcgcagac gatggtgcag gatatc                              36

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccacacacta gtcagatctg cagaattcag gctgtc                              36

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggctggctgg cataaatatc tc                                             22

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
catcgcgtgg gcgtattcg                                                 19

PRODUCTION OF FATTY ACID ESTERS

CROSS REFERENCE TO RELATED APPLICATIONS

This application is a continuation of U.S. application Ser. No. 12/768,419, filed Apr. 27, 2010, now abandoned, which claims the benefit of U.S. Provisional Application No. 61/173,016, filed Apr. 27, 2009, and U.S. Provisional Application No. 61/182,564, filed May 29, 2009, U.S. patent application Ser. No. 12/768,419 is a continuation-in-part of U.S. application Ser. No. 12/278,957, filed Apr. 20, 2010, now abandoned, which is the U.S. National Stage of International Application No. PCT/US2007/011923, filed May 18, 2007, which claims the benefit of U.S. Provisional Application No. 60/802,016, filed May 19, 2006, U.S. Provisional Application No. 60/801,995 filed May 19, 2006, and U.S. Provisional Application 60/908,547 filed Mar. 28, 2007. The contents of these applications is hereby incorporated by reference in their entirety.

SEQUENCE LISTING

This application contains a Sequence Listing which has been submitted electronically in ASCII format and is hereby incorporation by reference in its entirety. Said ASCII copy, created on Oct. 1, 2019 is named 109112-0805 SL.txt and is 36,409 bytes in size.

TECHNICAL FIELD

This disclosure relates generally to methods of using genetically engineered cells and microorganisms to produce fatty acid esters, and to the fatty acid esters produced by these methods. The products are particularly useful as biofuels.

BACKGROUND

Petroleum is a limited, natural resource found in the Earth in liquid, gaseous, or solid forms. Petroleum is primarily composed of hydrocarbons, which are comprised mainly of carbon and hydrogen. It also contains significant amounts of other elements, such as, nitrogen, oxygen, or sulfur, in different forms.

Petroleum is a valuable resource, but petroleum products are developed at considerable costs, both financial and environmental. First, sources of petroleum must be discovered. Petroleum exploration is an expensive and risky venture. The cost of exploring deep water wells can exceed $100 million. In addition to the economic cost, petroleum exploration carries a high environmental cost. For example, offshore exploration disturbs the surrounding marine environments.

After a productive well is discovered, the petroleum must be extracted from the Earth at great expense. Even under the best circumstances, only 50% of the petroleum in a well can be extracted. Petroleum extraction also carries an environmental cost. For example, petroleum extraction can result in large seepages of petroleum rising to the surface. Offshore drilling involves dredging the seabed which disrupts or destroys the surrounding marine environment.

After extraction, petroleum must be transported over great distances from petroleum producing regions to petroleum consuming regions. In addition to the shipping costs, there is also the environmental risk of devastating oil spills.

In its natural form, crude petroleum extracted from the Earth has few commercial uses. It is a mixture of hydrocarbons (e.g., paraffins (or alkanes), olefins (or alkenes), alkynes, napthenes (or cylcoalkanes), aliphatic compounds, aromatic compounds, etc.) of varying length and complexity. In addition, crude petroleum contains other organic compounds (e.g., organic compounds containing nitrogen, oxygen, sulfur, etc.) and impurities (e.g., sulfur, salt, acid, metals, etc.).

Hence, crude petroleum must be refined and purified before it can be used commercially. Due to its high energy density and its easy transportability, most petroleum is refined into fuels, such as transportation fuels (e.g., gasoline, diesel, aviation fuel, etc.), heating oil, liquefied petroleum gas, etc.

Crude petroleum is also a primary source of raw materials for producing petrochemicals. The two main classes of raw materials derived from petroleum are short chain olefins (e.g., ethylene and propylene) and aromatics (e.g., benzene and xylene isomers). These raw materials are derived from the longer chain hydrocarbons in crude petroleum by cracking the long chain hydrocarbons at considerable expense using a variety of methods, such as catalytic cracking, steam cracking, or catalytic reforming. These raw materials are used to make petrochemicals, which cannot be directly refined from crude petroleum, such as monomers, solvents, detergents, or adhesives.

One example of a raw material derived from crude petroleum is ethylene. Ethylene is used to produce petrochemicals such as, polyethylene, ethanol, ethylene oxide, ethylene glycol, polyester, glycol ether, ethoxylate, vinyl acetate, 1,2-dichloroethane, trichloroethylene, tetrachloroethylene, vinyl chloride, and polyvinyl chloride. Another example of a raw material derived from crude petroleum is propylene. Propylene is used to produce isopropyl alcohol, acrylonitrile, polypropylene, propylene oxide, propylene glycol, glycol ethers, butylene, isobutylene, 1,3-butadiene, synthetic elastomers, polyolefins, alpha-olefins, fatty alcohols, acrylic acid, acrylic polymers, allyl chloride, epichlorohydrin, and epoxy resins.

Petrochemicals can be used to make specialty chemicals, such as plastics, resins, fibers, elastomers, pharmaceuticals, lubricants, or gels. Examples of specialty chemicals which can be produced from petrochemical raw materials are: fatty acids, hydrocarbons (e.g., long chain hydrocarbons, branched chain hydrocarbons, saturated hydrocarbons, unsaturated hydrocarbons, etc.), fatty alcohols, esters, fatty aldehydes, ketones, lubricants, etc.

Specialty chemicals have many commercial uses. Fatty acids are used commercially as surfactants. Surfactants can be found in detergents and soaps. Fatty acids can also be used as additives in fuels, lubricating oils, paints, lacquers, candles, salad oils, shortenings, cosmetics, and emulsifiers. In addition, fatty acids are used as accelerator activators in rubber products. Fatty acids can also be used as a feedstock to produce methyl esters, amides, amines, acid chlorides, anhydrides, ketene dimers, and peroxy acids and esters.

Hydrocarbons have many commercial uses. For example, shorter chain alkanes are used as fuels. Methane and ethane are the main constituents of natural gas. Longer chain alkanes (e.g., from five to sixteen carbons) are used as transportation fuels (e.g., gasoline, diesel, or aviation fuel). Alkanes having more than sixteen carbon atoms are important components of fuel oils and lubricating oils. Even longer alkanes, which are solid at room temperature, can be used, for example, as a paraffin wax. Alkanes that contain approximately thirty-five carbons are found in bitumen, which is used for road surfacing. In addition, longer chain alkanes can be cracked to produce commercially useful shorter chain hydrocarbons.

Like short chain alkanes, short chain alkenes are used in transportation fuels. Longer chain alkenes are used in plastics, lubricants, and synthetic lubricants. In addition, alkenes are used as a feedstock to produce alcohols, esters, plasticizers, surfactants, tertiary amines, enhanced oil recovery agents, fatty acids, thiols, alkenylsuccinic anhydrides, epoxides, chlorinated alkanes, chlorinated alkenes, waxes, fuel additives, and drag flow reducers.

Fatty alcohols have many commercial uses. The shorter chain fatty alcohols are used in the cosmetic and food industries as emulsifiers, emollients, and thickeners. Due to their amphiphilic nature, fatty alcohols behave as nonionic surfactants, which are useful in detergents. In addition, fatty alcohols are used in waxes, gums, resins, pharmaceutical salves and lotions, lubricating oil additives, textile antistatic and finishing agents, plasticizers, cosmetics, industrial solvents, and solvents for fats.

Esters have many commercial uses. For example, biodiesel, an alternative fuel, is comprised of esters (e.g., fatty acid methyl ester, fatty acid ethyl esters, etc.). Some low molecular weight esters are volatile with a pleasant odor which makes them useful as fragrances or flavoring agents. In addition, esters are used as solvents for lacquers, paints, and varnishes. Furthermore, some naturally occurring substances, such as waxes, fats, and oils are comprised of esters. Esters are also used as softening agents in resins and plastics, plasticizers, flame retardants, and additives in gasoline and oil. In addition, esters can be used in the manufacture of polymers, films, textiles, dyes, and pharmaceuticals.

Aldehydes are used to produce many specialty chemicals. For example, aldehydes are used to produce polymers, resins, dyes, flavorings, plasticizers, perfumes, pharmaceuticals, and other chemicals. Some are used as solvents, preservatives, or disinfectants. Some natural and synthetic compounds, such as vitamins and hormones, are aldehydes. In addition, many sugars contain aldehyde groups.

Ketones are used commercially as solvents. For example, acetone is frequently used as a solvent, but it is also a raw material for making polymers. Ketones are also used in lacquers, paints, explosives, perfumes, and textile processing. In addition, ketones are used to produce alcohols, alkenes, alkanes, imines, and enamines.

In addition, crude petroleum is a source of lubricants. Lubricants derived petroleum are typically composed of olefins, particularly polyolefins and alpha-olefins. Lubricants can either be refined from crude petroleum or manufactured using the raw materials refined from crude petroleum.

Obtaining these specialty chemicals from crude petroleum requires a significant financial investment as well as a great deal of energy. It is also an inefficient process because frequently the long chain hydrocarbons in crude petroleum are cracked to produce smaller monomers. These monomers are then used as the raw material to manufacture the more complex specialty chemicals.

In addition to the problems with exploring, extracting, transporting, and refining petroleum, petroleum is a limited and dwindling resource. One estimate of current world petroleum consumption is 30 billion barrels per year. By some estimates, it is predicted that at current production levels, the world's petroleum reserves could be depleted before the year 2050.

Finally, the burning of petroleum based fuels releases greenhouse gases (e.g., carbon dioxide) and other forms of air pollution (e.g., carbon monoxide, sulfur dioxide, etc.). As the world's demand for fuel increases, the emission of greenhouse gases and other forms of air pollution also increases. The accumulation of greenhouse gases in the atmosphere leads to an increase in global warming. Hence, in addition to damaging the environment locally (e.g., oil spills, dredging of marine environments, etc.), burning petroleum also damages the environment globally.

Due to the inherent challenges posed by petroleum, there is a need for a renewable petroleum source which does not need to be explored, extracted, transported over long distances, or substantially refined like petroleum. There is also a need for a renewable petroleum source that can be produced economically. In addition, there is a need for a renewable petroleum source that does not create the type of environmental damage produced by the petroleum industry and the burning of petroleum based fuels. For similar reasons, there is also a need for a renewable source of chemicals that are typically derived from petroleum.

SUMMARY

This disclosure relates to the production of fatty acid esters, such as fatty acid ethyl esters ("FAEE"), from genetically engineered microorganisms without providing exogenous alcohol to the microorganisms. Generally, the fatty acid esters are produced by culturing a microorganism that is genetically engineered to produce a fatty acid and at least one ester synthase, in the absence of exogenous alcohol, such as exogenous ethanol or exogenous methanol. The microorganism can also be genetically engineered to increase ethanol production compared to a wild type microorganism.

In one aspect, the invention features a method of producing a fatty acid ester by culturing a genetically engineered microorganism in the absence of exogenous alcohol, wherein the microorganism is genetically engineered to produce an alcohol, a fatty acid, and at least one ester synthase. In some embodiments, the method further includes the step of isolating the fatty acid ester. In other embodiments, the alcohol is ethanol. In still other embodiments, the fatty acid ester is a fatty acid ethyl ester.

In some embodiments, the microorganism is cultured in a culture medium comprising an initial concentration of about 2 g/L to about 50 g/L of a carbon source. In other embodiments, the microorganism is cultured in a culture medium comprising an initial concentration of about 2 g/L to about 10 g/L of a carbon source. In other embodiments, the microorganism is cultured in a culture medium comprising an initial concentration of about 10 g/L to about 20 g/L of a carbon source. In other embodiments, the microorganism is cultured in a culture medium comprising an initial concentration of about 20 g/L to about 30 g/L of a carbon source. In other embodiments, the microorganism is cultured in a culture medium comprising an initial concentration of about 30 g/L to about 40 g/L of a carbon source. In other embodiments, the microorganism is cultured in a culture medium comprising an initial concentration of about 40 g/L to about 50 g/L of a carbon source.

In some embodiments, the method further includes the step of monitoring the level of the carbon source in the culture medium. In some embodiments, the method further includes adding a supplemental carbon source to the culture medium when the level of the carbon source in the medium is less than about 0.5 g/L. In some embodiments, the method further includes adding a supplemental carbon source to the culture medium when the level of the carbon source in the medium is less than about 0.4 g/L. In some embodiments, the method further includes adding a supplemental carbon source to the culture medium when the level of the carbon source in the medium is less than about 0.3 g/L. In some embodiments, the method further includes adding a supplemental carbon source to the culture medium when the level of the carbon source in the medium is less than about 0.2 g/L. In some embodiments, the method further includes adding a supplemental carbon source to the culture medium when the level of the carbon source in the medium is less than about 0.1 g/L.

In some embodiments, the supplemental carbon source is added to maintain a carbon source level of about 2 g/L to about 5 g/L. In some embodiments, the supplemental carbon source is added to maintain a carbon source level of about 2 g/L to about 3 g/L. In some embodiments, the supplemental carbon source is added to maintain a carbon source level of about 3 g/L to about 4 g/L. In some embodiments, the supplemental carbon source is added to maintain a carbon source level of about 4 g/L to about 5 g/L. In some embodiments, the carbon source is glucose.

In some embodiments, the microorganism is cultured in aerobic conditions. In some embodiments, the aerobic conditions include about 10% to about 50% dissolved oxygen. In some embodiments, the aerobic conditions include about 10% to about 20% dissolved oxygen. In some embodiments, the aerobic conditions include about 20% to about 30% dissolved oxygen. In some embodiments, the aerobic conditions include about 30% to about 40% dissolved oxygen. In some embodiments, the aerobic conditions include about 40% to about 50% dissolved oxygen.

In other embodiments, the microorganism is cultured at a temperature of about 30° C. to about 35° C. In other embodiments, the microorganism is cultured at a temperature of about 30° C. to about 31° C. In other embodiments, the microorganism is cultured at a temperature of about 31° C. to about 32° C. In other embodiments, the microorganism is cultured at a temperature of about 32° C. to about 33° C. In other embodiments, the microorganism is cultured at a temperature of about 33° C. to about 34° C. In other embodiments, the microorganism is cultured at a temperature of about 34° C. to about 35° C.

In some embodiments, the microorganism is cultured at a pH of about 6.6 to about 7.0. In some embodiments, the microorganism is cultured at a pH of about 6.6 to about 6.7. In some embodiments, the microorganism is cultured at a pH of about 6.7 to about 6.8. In some embodiments, the microorganism is cultured at a pH of about 6.8 to about 6.9. In some embodiments, the microorganism is cultured at a pH of about 6.9 to about 7.0.

In some embodiments, the method further includes adding about 1 mM isopropyl β-D-1-thiogalactopyranoside to the culture medium. In some embodiments, the fatty acid ethyl ester is produced at a concentration of about 1 g/L to about 170 g/L, such as about 1 g/L to about 10 g/L; or such as about 40 g/L to about 170 g/L; or such as about 100 g/L to about 170 g/L. In some embodiments, the fatty acid ethyl ester is produced at a concentration of about 10 g/L to about 100 g/L. In some embodiments, the fatty acid ethyl ester is produced at a concentration of about 1 g/L to about 40 g/L. In some embodiments, the fatty acid ethyl ester is produced at a concentration of about 40 g/L to about 100 g/L. In some embodiments, the fatty acid ethyl ester is produced at a concentration of about 1 g/L to about 100 g/L.

In some embodiments, the microorganism is genetically engineered to overexpress at least one gene selected from the group consisting of pdc, adh, adhA, adhB, pdh, and casAB, relative to a corresponding wild type microorganism. In other embodiments, the microorganism is genetically engineered to have reduced expression of at least one gene selected from the group consisting of frd, ldhA, pflA, pflB, adhE, ackA, and focA, relative to a corresponding wild type organism. In certain embodiments, the microorganism is genetically engineered to have reduced expression of a lactate dehydrogenase gene, for example, one encoding an enzyme of EC 1.1.1.27. In some embodiments, one or more of the endogenous lactate dehydrogenase genes are functionally deleted or knocked-out. In particular embodiments, the lactate dehydrogenase gene encodes an NAD-linked fermentative D-lactate dehydrogenase (e.g., Mat-Jan et al., *J. Bacteriol.* 171(1):342-8 (1989); Bunch et al., *Microbiol.* 143(1):187-95 (1997)). In further embodiments, the lactate dehydrogenase is encoded by an ldhA gene.

In some embodiments, the microorganism overexpresses a gene encoding a thioesterase or a gene encoding an acyl-CoA synthase, relative to a wild type microorganism. In other embodiments, the microorganism overexpresses a gene encoding a thioesterase and a gene encoding an acyl-CoA synthase, relative to a wild type microorganism. In some embodiments, the gene encoding a thioesterase is selected from the group consisting of tesA, 'tesA, fatB1, fatB2, fatB3, fatA1, atfata, and fatA. In other embodiments, the gene encoding an acyl-CoA synthase is fadD. In yet other embodiments, the gene encoding an ester synthase is selected from the group consisting of atfA1, wax-dgat, and mWS.

In some embodiments, the microorganism is a recombinant *E. coli* cell. In certain embodiments, the recombinant *E. coli* cell includes a genetic modification that has reduced expression of a fatty acid biosynthesis regulator gene. In some embodiments, one or more endogenous fatty acid biosynthesis regulator genes are functionally deleted or knocked-out. In certain embodiments, the fatty acid biosynthesis regulator gene is a transcriptional repressor, for example, a repressor of *E. coli* genes fabA, fabB and/or yqfA. (see, e.g., McCue et al., *Nucleic Acids Res.,* 29(3): 774-82 (2001); Zhang et al., *J. Biol. Chem.* 277 (18):15558-65) (2002)). In particular embodiments, the fatty acid biosynthesis regulator gene is fabR. In certain other embodiments, the recombinant *E. coli* cell includes a genetic modification that has reduced expression of a pyruvate oxidase gene, for example, one encoding an enzyme of EC 1.2.3.3. (see, e.g., Chang et al., *J. Bacteriol.* 154 (2):756-62 (1983); Abdel-Ahmid et al., *Micribiol.* 147 (6):1483-98 (2001)). In some embodiments, one or more endogenous pyruvate oxidase genes are functionally deleted or knocked-out. In particular embodiments, the pyruvate oxidase gene is poxB. In certain other embodiments, the recombinant *E. coli* cell includes a genetic modification that has reduced expression or a functional deletion of a fadE gene.

In certain preferred embodiments, the fatty acid synthesis regulator gene is deleted. In an alternate embodiment the recombinant *E. coli* cell further comprises a pyruvate oxidase gene, wherein the pyruvate oxidase gene has reduced expression relative to a wild type *E. coli* cell. In one embodiment, the pyruvate oxidase gene is deleted. In an alternative embodiment, the recombinant *E. coli* cell further comprises a lactate dehydrogenase gene, wherein the lactate dehydrogenase gene has reduced expression relative to a wild type *E. coli* cell. In one embodiment, the lactate dehydrogenase is deleted. In an alternative embodiment, the recombinant *E. coli* cell further comprises (1) a pyruvate oxidase gene, wherein the pyruvate oxidase gene has reduced expression relative to a wild type *E. coli* cell, and (2) a lactate dehydrogenase gene, wherein the lactate dehydrogenase gene has reduced expression relative to a wild type *E. coli* cell.

In certain preferred embodiments, the pyruvate oxidase gene is deleted. In an alternate embodiment the recombinant *E. coli* cell further comprises a fatty acid synthesis regulator gene, wherein the fatty acid synthesis regulator gene has reduced expression relative to a wild type *E. coli* cell. In one embodiment, the fatty acid synthesis regulator gene is deleted. In an alternative embodiment, the recombinant *E. coli* cell further comprises a lactate dehydrogenase gene, wherein the lactate dehydrogenase gene has reduced expression relative to a wild type *E. coli* cell. In one embodiment, the lactate dehydrogenase is deleted. In an alternative embodiment, the recombinant *E. coli* cell further comprises (1) a fatty acid synthesis regulator gene, wherein the fatty acid synthesis regulator gene has reduced expression relative to a wild type *E. coli* cell, and (2) a lactate dehydrogenase gene, wherein the lactate dehydrogenase gene has reduced expression relative to a wild type *E. coli* cell.

In certain preferred embodiments, the lactate dehydrogenase gene is deleted. In an alternate embodiment the recombinant *E. coli* cell further comprises a pyruvate oxidase gene, wherein the pyruvate oxidase gene has reduced expression relative to a wild type *E. coli* cell. In one embodiment, the pyruvate oxidase gene is deleted. In an alternative embodiment, the recombinant *E. coli* cell further comprises a fatty acid synthesis regulator gene, wherein the fatty acid synthesis regulator gene has reduced expression relative to a wild type *E. coli* cell. In one embodiment, the fatty acid synthesis regulator gene is deleted. In an alternative embodiment, the recombinant *E. coli* cell further comprises (1) a pyruvate oxidase gene, wherein the pyruvate oxidase gene has reduced expression relative to a wild type *E. coli* cell, and (2) a fatty acid synthesis regulator gene, wherein the fatty acid synthesis regulator gene has reduced expression relative to a wild type *E. coli* cell.

In a preferred embodiment, the recombinant *E. coli* cell comprises at least one of the following gene deletions: poxB, ldhA, and/or fabR. In some embodiments, the recombinant *E. coli* cell includes a genetic modification that attenuates expression of at least one gene selected from the group consisting of fadE, fabR, poxB, and ldhA, relative to a wild type *E. coli* cell.

In some embodiments, the fatty acid ester is produced at a yield of about 0.5 g to about 50 g of fatty acid ester per 100 g of glucose in the fermentation medium. In particular embodiments, the fatty acid ester is produced at a yield of about 0.5 g to about 40 g of fatty acid ester per 100 g of glucose, about 0.5 g to about 30 g of fatty acid ester per 100 g of glucose, about 0.5 g to about 20 g of fatty acid ester per 100 g of glucose, about 0.5 g to about 10 g of fatty acid ester per 100 g of glucose, about 0.5 g to about 5 g of fatty acid ester per 100 g of glucose, or about 0.5 g to about 4 g of fatty acid ester per 100 g of glucose in the fermentation medium. In particular embodiments, the fatty acid ester is produced at a yield of at least 0.5 g of fatty acid ester, at least 4 g of fatty acid ester, at least 5 g of fatty acid ester, at least 10 g of fatty acid ester, at least 20 g of fatty acid ester, at least 30 g of fatty acid ester, at least 40 g of fatty acid ester, or at least 50 g of fatty acid ester per 100 g of glucose in the fermentation medium. In particular embodiments, the fatty acid ester is produced at a yield of no more than 50 g of fatty acid ester per 100 g of glucose in the fermentation medium.

In some embodiments, the fatty acid ester is produced at a yield of about 0.5% to about 50% by mass of the glucose in the fermentation medium. In particular embodiments, the fatty acid ester is produced at a yield of about 0.5% to about 40%, about 0.5% to about 30%, about 0.5% to about 20%, about 0.5% to about 10%, about 0.5% to about 5%, or about 0.5% to about 4% by mass of the glucose in the fermentation medium. In particular embodiments, the fatty acid ester is produced at a yield of at least about 0.5%, at least about 4%, at least about 5%, at least about 10%, at least about 20%, at least about 30%, at least about 40%, or at least about 50% by mass of glucose in the fermentation medium. In particular embodiments, the fatty acid ester is produced at a yield of no more than 50% by mass of glucose in the fermentation medium.

In some embodiments, the fatty acid ester is produced at a yield of about 10% to about 95% by mass of carbon in the carbon source in the fermentation medium. In particular embodiments, the fatty acid ester is produced at a yield of about 15% to about 90%, about 20% to about 80%, or about 30% to about 70% by mass of carbon in the carbon source in the fermentation medium. In particular embodiments, the fatty acid ester is produced at a yield of at least about 10%, at least about 20%, at least about 30%, at least about 40%, at least about 50%, at least about 60%, at least about 70%, at least about 80%, at least about 90%, or at least about 95% by mass of carbon in the carbon source in the fermentation medium. In particular embodiments, the fatty acid ester is produced at a yield of no more than 95% by mass of carbon in the carbon source in the fermentation medium.

In some embodiments, the fatty acid ethyl ester is produced at a yield of about 0.5 g to about 50 g of fatty acid ethyl ester per 100 g of glucose in the fermentation medium. In particular embodiments, the fatty acid ethyl ester is produced at a yield of about 0.5 g to about 40 g of fatty acid ethyl ester per 100 g of glucose, about 0.5 g to about 30 g of fatty acid ethyl ester per 100 g of glucose, about 0.5 g to about 20 g of fatty acid ethyl ester per 100 g of glucose, about 0.5 g to about 10 g of fatty acid ethyl ester per 100 g of glucose, about 0.5 g to about 5 g of fatty acid ethyl ester per 100 g of glucose, or about 0.5 g to about 4 g of fatty acid ethyl ester per 100 g of glucose in the fermentation medium. In particular embodiments, the fatty acid ethyl ester is produced at a yield of at least 0.5 g of fatty acid ethyl ester, at least 4 g of fatty acid ester, at least 5 g of fatty acid ethyl ester, at least 10 g of fatty acid ethyl ester, at least 20 g of fatty acid ethyl ester, at least 30 g of fatty acid ethyl ester, at least 40 g of fatty acid ethyl ester, or at least 50 g of fatty acid ethyl ester per 100 g of glucose in the fermentation medium. In particular embodiments, the fatty acid ethyl ester is produced at a yield of no more than 50 g of fatty acid ethyl ester per 100 g of glucose in the fermentation medium.

In some embodiments, the fatty acid ethyl ester is produced at a yield of about 0.5% to about 50% by mass of the glucose in the fermentation medium. In particular embodiments, the fatty acid ethyl ester is produced at a yield of about 0.5% to about 40%, about 0.5% to about 30%, about 0.5% to about 20%, about 0.5% to about 10%, about 0.5% to about 5%, or about 0.5% to about 4% by mass of the glucose in the fermentation medium. In particular embodiments, the fatty acid ethyl ester is produced at a yield of at least about 0.5%, at least about 4%, at least about 5%, at least about 10%, at least about 20%, at least about 30%, at least about 40%, or at least about 50% by mass of glucose in the fermentation medium. In particular embodiments, the fatty acid ethyl ester is produced at a yield of no more than 50% by mass of glucose in the fermentation medium.

In some embodiments, the fatty acid ethyl ester is produced at a yield of about 10% to about 95% by mass of carbon in the carbon source in the fermentation medium. In particular embodiments, the fatty acid ethyl ester is produced at a yield of about 15% to about 90%, about 20% to about 80%, or about 30% to about 70% by mass of carbon in the carbon source in the fermentation medium. In particular embodiments, the fatty acid ethyl ester is produced at a yield of at least about 10%, at least about 20%, at least about 30%, at least about 40%, at least about 50%, at least about 60%, at least about 70%, at least about 80%, at least about 90%, or at least about 95% by mass of carbon in the carbon source in the fermentation medium. In particular embodiments, the fatty acid ethyl ester is produced at a yield of no more than 95% by mass of carbon in the carbon source in the fermentation medium.

In some embodiments, the fatty acid ester is a fatty acid methyl ester.

In some embodiments, the fatty acid methyl ester is produced at a yield of about 0.5 g to about 50 g of fatty acid methyl ester per 100 g of glucose in the fermentation medium. In some embodiments, the fatty acid methyl ester is produced at a yield of about 0.5 g to about 40 g of fatty acid methyl ester per 100 g of glucose, about 0.5 g to about 30 g of fatty acid methyl ester per 100 g of glucose, about 0.5 g to about 20 g of fatty acid methyl ester per 100 g of glucose, about 0.5 g to about 10 g of fatty acid methyl ester per 100 g of glucose, about 0.5 g to about 5 g of fatty acid methyl ester per 100 g of glucose, or about 0.5 g to about 4 g of fatty acid methyl ester per 100 g of glucose in the fermentation medium. In particular embodiments, the fatty acid methyl ester is produced at a yield of at least 0.5 g of fatty acid methyl ester, at least 4 g of fatty acid ester, at least 5 g of fatty acid methyl ester, at least 10 g of fatty acid methyl ester, at least 20 g of fatty acid methyl ester, at least 30 g of fatty acid methyl ester, at least 40 g of fatty acid methyl ester, or at least 50 g of fatty acid methyl ester per 100 g of glucose in the fermentation medium. In particular embodiments, the fatty acid methyl ester is produced at a yield of no more than 50 g of fatty acid methyl ester per 100 g of glucose in the fermentation medium.

In some embodiments, the fatty acid methyl ester is produced at a yield of about 0.5% to about 50% by mass of the glucose in the fermentation medium. In particular embodiments, the fatty acid methyl ester is produced at a yield of about 0.5% to about 40%, about 0.5% to about 30%, about 0.5% to about 20%, about 0.5% to about 10%, about 0.5% to about 5%, or about 0.5% to about 4% by mass of the glucose in the fermentation medium. In particular embodiments, the fatty acid methyl ester is produced at a yield of at least about 0.5%, at least about 4%, at least about 5%, at least about 10%, at least about 20%, at least about 30%, at least about 40%, or at least about 50% by mass of glucose in the fermentation medium. In particular embodiments, the fatty acid methyl ester is produced at a yield of no more than 50% by mass of glucose in the fermentation medium.

In some embodiments, the fatty acid methyl ester is produced at a yield of about 10% to about 95% by mass of carbon in the carbon source in the fermentation medium. In particular embodiments, the fatty acid methyl ester is produced at a yield of about 15% to about 90%, about 20% to about 80%, or about 30% to about 70% by mass of carbon in the carbon source in the fermentation medium. In particular embodiments, the fatty acid methyl ester is produced at a yield of at least about 10%, at least about 20%, at least about 30%, at least about 40%, at least about 50%, at least about 60%, at least about 70%, at least about 80%, at least about 90%, or at least about 95% by mass of carbon in the carbon source in the fermentation medium. In particular embodiments, the fatty acid methyl ester is produced at a yield of no more than 95% by mass of carbon in the carbon source in the fermentation medium.

In another aspect, the invention features a fatty acid ester produced by a method of the present disclosure. In some embodiments, the fatty acid ester is a fatty acid ethyl ester. In some embodiments, the fatty acid ethyl ester is at least about 4, 6, 8, 10, 12, 14, 16, or 18 carbons in length.

In some embodiments, the fatty acid ethyl ester comprises an A side and a B side. In some embodiments, the B side of the fatty acid ethyl ester includes a straight chain. In other embodiments, the B side of the fatty acid ethyl ester includes a branched chain. In still other embodiments, the B side of the fatty acid ethyl ester comprises at least one cyclic moiety.

In some embodiments, the fatty acid ethyl ester is saturated. In other embodiments, the fatty acid ethyl ester is unsaturated. In other embodiments, the fatty acid ethyl ester is monounsaturated.

In another aspect, the invention features a method of producing a fatty acid ethyl ester by culturing a genetically engineered microorganism in the absence of exogenous alcohol, wherein the microorganism is genetically engineered to produce a fatty acid and at least one ester synthase.

In some embodiments, the microorganism is genetically engineered to produce ethanol. In some embodiments, the microorganism is genetically engineered to overexpress of at least one gene selected from the group consisting of pdc, adh, adhA, adhB, pdh, and casAB, relative to a wild type microorganism. In other embodiments, the microorganism is genetically engineered to have reduced expression of at least one gene selected from the group consisting of frd, ldhA, pflA, pflB, adhE, ackA, and focA, relative to a wild type microorganism. In certain embodiments, the microorganism is genetically engineered to have reduced expression of a lactate dehydrogenase gene, for example, one encoding an enzyme of EC 1.1.1.27. In some embodiments, one or more endogenous lactate dehydrogenase genes are functionally deleted or knocked out. In particular embodiments, the lactate dehydrogenase gene encodes an NAD-linked fermentative D-lactate dehydrogenase. In further embodiments, the lactate dehydrogenase is encoded by an ldhA gene.

In some embodiments, the method further includes isolating the fatty acid ethyl ester. In other embodiments, the method further includes monitoring the level of the carbon source in the culture medium. In some embodiments, the method further includes adding about 1 mM isopropyl β-D-1-thiogalactopyranoside to the culture medium.

In some embodiments, the microorganism is cultured in a culture medium comprising an initial concentration of about 2 g/L to about 50 g/L of a carbon source. In some embodiments, the microorganism is cultured in a culture medium comprising an initial concentration of about 2 g/L to about 10 g/L of a carbon source. In some embodiments, the microorganism is cultured in a culture medium comprising an initial concentration of about 10 g/L to about 20 g/L of a carbon source. In some embodiments, the microorganism is cultured in a culture medium comprising an initial concentration of about 20 g/L to about 30 g/L of a carbon source. In some embodiments, the microorganism is cultured in a culture medium comprising an initial concentration of about 30 g/L to about 40 g/L of a carbon source. In some embodiments, the microorganism is cultured in a culture medium comprising an initial concentration of about 40 g/L to about 50 g/L of a carbon source.

In some embodiments, the method includes adding a supplemental carbon source to the culture medium when the level of the carbon source in the medium is less than about 0.5 g/L. In some embodiments, the method includes adding a supplemental carbon source to the culture medium when the level of the carbon source in the medium is less than about 0.4 g/L. In some embodiments, the method includes adding a supplemental carbon source to the culture medium when the level of the carbon source in the medium is less than about 0.3 g/L. In some embodiments, the method includes adding a supplemental carbon source to the culture medium when the level of the carbon source in the medium is less than about 0.2 g/L. In some embodiments, the method includes adding a supplemental carbon source to the culture medium when the level of the carbon source in the medium is less than about 0.1 g/L.

In some embodiments, the supplemental carbon source is added to maintain a carbon source concentration of about 2 g/L to about 5 g/L. In some embodiments, the supplemental carbon source is added to maintain a carbon source concentration of about 2 g/L to about 3 g/L. In some embodiments, the supplemental carbon source is added to maintain a carbon source concentration of about 3 g/L to about 4 g/L. In some embodiments, the supplemental carbon source is added to maintain a carbon source concentration of about 4 g/L to about 5 g/L.

In some embodiments, the carbon source is glucose.

In some embodiments, the microorganism is cultured in aerobic conditions. In some embodiments, the aerobic conditions comprise about 10% to about 50% dissolved oxygen. In some embodiments, the aerobic conditions include about 10% to about 20% dissolved oxygen. In some embodiments, the aerobic conditions include about 20% to about 30% dissolved oxygen. In some embodiments, the aerobic conditions include about 30% to about 40% dissolved oxygen. In some embodiments, the aerobic conditions include about 40% to about 50% dissolved oxygen.

In some embodiments, the microorganism is cultured at a temperature of about 30° C. to about 35° C. In other embodiments, the microorganism is cultured at a temperature of about 30° C. to about 31° C. In other embodiments, the microorganism is cultured at a temperature of about 31° C. to about 32° C. In other embodiments, the microorganism is cultured at a temperature of about 32° C. to about 33° C. In other embodiments, the microorganism is cultured at a temperature of about 33° C. to about 34° C. In other embodiments, the microorganism is cultured at a temperature of about 34° C. to about 35° C.

In other embodiments, the microorganism is cultured at a pH of about 6.6 to about 7.0. In some embodiments, the microorganism is cultured at a pH of about 6.6 to about 6.7. In some embodiments, the microorganism is cultured at a pH of about 6.7 to about 6.8. In some embodiments, the microorganism is cultured at a pH of about 6.8 to about 6.9. In some embodiments, the microorganism is cultured at a pH of about 6.9 to about 7.0.

In some embodiments, the fatty acid ethyl ester is produced at a concentration of about 1 g/L to about 170 g/L, such as about 1 g/L to about 10 g/L; or such as about 40 g/L to about 170 g/L; or such as about 100 g/L to about 170 g/L. In some embodiments, the fatty acid ethyl ester is produced at a concentration of about 10 g/L to about 100 g/L. In some embodiments, the fatty acid ethyl ester is produced at a concentration of about 1 g/L to about 40 g/L. In some embodiments, the fatty acid ethyl ester is produced at a concentration of about 40 g/L to about 100 g/L. In some embodiments, the fatty acid ethyl ester is produced at a concentration of about 1 g/L to about 100 g/L.

In some embodiments, the microorganism is genetically engineered to overexpress a gene encoding a thioesterase or a gene encoding an acyl-CoA synthase, relative to a wild type microorganism. In other embodiments, the microorganism is genetically engineered to overexpress a gene encoding a thioesterase and a gene encoding an acyl-CoA synthase, relative to a wild type microorganism. In some embodiments, the gene encoding a thioesterase is selected from the group consisting of tesA, 'tesA, fatB1, fatB2, fatB3, fatA1, atfata, and fatA. In other embodiments, the gene encoding a thioesterase is 'tesA. In some embodiments, the gene encoding an acyl-CoA synthase is fadD. In other embodiments, the gene encoding an ester synthase is selected from the group consisting of atfA1, wax-dgat, and mWS. In other embodiments, the gene encoding an ester synthase is atfA1.

In some embodiments, the microorganism is a recombinant $E.$ $coli$ cell. In certain embodiments, the recombinant $E.$ $coli$ cell includes a genetic modification that has reduced expression of a fatty acid biosynthesis regulator gene. In some embodiments, one or more endogenous fatty acid biosynthesis regulator genes are functionally deleted or knocked-out. In certain embodiments, the fatty acid biosynthesis regulator gene is a transcriptional repressor, for example, a repressor of $E.$ $coli$ genes fabA, fabB and/or yqfA. In particular embodiments, the fatty acid biosynthesis regulator gene is fabR. In certain other embodiments, the recombinant $E.$ $coli$ cell includes a genetic modification that has reduced expression of a pyruvate oxidase gene, for example, one encoding an enzyme of EC 1.2.3.3. In some embodiments, one or more endogenous pyruvate oxidase genes are functionally deleted or knocked-out. In particular embodiments, the pyruvate oxidase gene is poxB. In certain other embodiments, the recombinant $E.$ $coli$ cell includes a genetic modification that has reduced expression or a functional deletion of a fadE gene. In other embodiments, the recombinant $E.$ $coli$ cell includes a genetic modification that attenuates expression of at least one gene selected from the group consisting of fadE,fabR, poxB, and ldhA, relative to a wild type $E.$ $coli$ cell.

In certain preferred embodiments, the fatty acid synthesis regulator gene is deleted. In an alternate embodiment the microorganism further comprises a pyruvate oxidase gene, wherein the pyruvate oxidase gene has reduced expression relative to a wild type microorganism. In one embodiment, the pyruvate oxidase gene is deleted. In an alternative embodiment, the microorganism further comprises a lactate dehydrogenase gene, wherein the lactate dehydrogenase gene has reduced expression relative to a wild type microorganism. In one embodiment, the lactate dehydrogenase is deleted. In an alternative embodiment, the microorganism further comprises (1) a pyruvate oxidase gene, wherein the pyruvate oxidase gene has reduced expression relative to a wild type microorganism, and (2) a lactate dehydrogenase gene, wherein the lactate dehydrogenase gene has reduced expression relative to a wild type microorganism.

In certain preferred embodiments, the pyruvate oxidase gene is deleted. In an alternate embodiment the microorganism further comprises a fatty acid synthesis regulator gene, wherein the fatty acid synthesis regulator gene has reduced expression relative to a wild type microorganism. In one embodiment, the fatty acid synthesis regulator gene is deleted. In an alternative embodiment, the microorganism further comprises a lactate dehydrogenase gene, wherein the lactate dehydrogenase gene has reduced expression relative to a wild type microorganism. In one embodiment, the lactate dehydrogenase is deleted. In an alternative embodiment, the microorganism further comprises (1) a fatty acid synthesis regulator gene, wherein the fatty acid synthesis regulator gene has reduced expression relative to a wild type microorganism, and (2) a lactate dehydrogenase gene, wherein the lactate dehydrogenase gene has reduced expression relative to a wild type microorganism.

In certain preferred embodiments, the lactate dehydrogenase gene is deleted. In an alternate embodiment the microorganism further comprises a pyruvate oxidase gene, wherein the pyruvate oxidase gene has reduced expression relative to a wild type microorganism. In one embodiment, the pyruvate oxidase gene is deleted. In an alternative embodiment, the microorganism further comprises a fatty acid synthesis regulator gene, wherein the fatty acid synthesis regulator gene has reduced expression relative to a wild type microorganism. In one embodiment, the fatty acid synthesis regulator gene is deleted. In an alternative embodiment, the microorganism further comprises (1) a pyruvate oxidase gene, wherein the pyruvate oxidase gene has reduced expression relative to a wild type microorganism, and (2) a fatty acid synthesis regulator gene, wherein the fatty acid synthesis regulator gene has reduced expression relative to a wild type microorganism.

In a preferred embodiment, the microorganism comprises at least one of the following gene deletions: poxB, ldhA, and/or fabR.

In another aspect, the invention features a fatty acid ethyl ester produced by a method described herein. In some embodiments, the fatty acid ethyl ester includes an A side and a B side. In some embodiments, the B side of the fatty acid ethyl ester is at least about 4, 6, 8, 10, 12, 14, 16, or 18 carbons in length.

In some embodiments, the B side of the fatty acid ethyl ester comprises a straight chain. In other embodiments, the B side of the fatty acid ethyl ester comprises a branched chain. In still other embodiments, the B side of the fatty acid ethyl ester comprises at least one cyclic moiety.

In some embodiments, the fatty acid ethyl ester is saturated. In other embodiments, the fatty acid ethyl ester is unsaturated. In still other embodiments, the fatty acid ethyl ester is monounsaturated.

In some embodiments, the invention features a method of producing by a host cell an alcohol, a fatty acid and at least one ester synthase. In some embodiments, the method comprises expressing in the host cell a recombinant vector comprising at least one gene selected from the group consisting of pdc, adh, adhA, adhB, pdh, and casAB. In some embodiments, the method further includes isolating the fatty acid esters from the host cell. In other embodiments, the alcohol is ethanol. In still other embodiments, the fatty acid ester is a fatty acid ethyl ester.

In some embodiments, the recombinant vector further comprises a promoter operably linked to the nucleotide sequence. In certain embodiments, the promoter is a developmentally-regulated, an organelle-specific, a tissue-specific, an inducible, a constitutive, or a cell-specific promoter. In some embodiments, the recombinant vector comprises at least one sequence selected from the group consisting of (a) a regulatory sequence operably coupled to the nucleotide sequence; (b) a selection marker operatively coupled to the nucleotide sequence; (c) a marker sequence operatively coupled to the nucleotide sequence; (d) a purification moiety operably coupled to the nucleotide sequence; (e) a secretion sequence operatively coupled to the nucleotide sequence; and (f) a targeting sequence operatively coupled to the nucleotide sequence.

In certain embodiments, the recombinant vector is a plasmid.

In some embodiments, the host cell expresses a polypeptide, such as, for example, a Pdc, Adh, AdhA, AdhB, Pdh, or CasAB polypeptide, encoded by the recombinant vector. In some embodiments, the nucleotide sequence is stably incorporated into the genomic DNA of the host cell, and the expression of the nucleotide sequence is under the control of the regulated promoter.

In some embodiments, the method further comprises modifying the expression of one or more genes selected from the group consisting of frd, ldhA, pflA, pflB, adhE, ackA, and focA. In certain embodiments, modifying the expression of such a gene includes expressing it and/or increasing the expression or activity of it in the host cell. In alternative embodiments, modifying the expression of such a gene includes attenuating such a gene or decreasing the expression or activity of such a gene in the host cell. In some embodiments, modifying the expression of such a gene includes deleting or knocking out the gene in the host cell. In particular embodiments, the method comprises modifying the expression of a lactate dehydrogenase gene, for example, one encoding an enzyme of EC 1.1.1.27. In certain embodiments, the expression of lactate dehydrogenase is reduced. In some embodiments, one or more endogenous lactate dehydrogenase genes are functionally deleted or knocked out. In certain embodiments, the lactate dehydrogenase gene encodes an NAD-linked fermentative D-lactate dehydrogenase. In further embodiments, the lactate dehydrogenase is encoded by an ldhA gene.

In another aspect, the invention features a genetically engineered microorganism, which produces an alcohol, a fatty acid, and at least one ester synthase. In some embodiments, the microorganism is engineered to overexpress at least one gene selected from the group consisting of pdc, adh, adhA, adhB, pdh, and casAB, relative to a corresponding wild type microorganism. In other embodiments, the microorganism is genetically engineered to have reduced expression of at least one gene selected from the group consisting of frd, ldhA, pflA, pflB, adhE, ackA, and focA, relative to a corresponding wild type organism.

In certain embodiments, the genetically engineered microorganism comprises an exogenous control sequence stably incorporated into the genomic DNA of the microorganism upstream of a gene selected from the group consisting of pdc, adh, adhA, adhB, pdh, and casAB, wherein the microorganism produces an increased level of an alcohol relative to a wild-type microorganism. In certain embodiments, the microorganism produces an increased level of ethanol relative to a wild-type microorganism. In further embodiments, the microorganism further produces an increased level of fatty acid ester relative to a wild-type microorganism. In yet other embodiments, the microorganism produces an increased level of a fatty acid ethyl ester relative to a wild-type microorganism.

In some embodiments, the microorganism overexpresses a gene encoding a thioesterase or a gene encoding an acyl-CoA synthase, relative to a wild type microorganism. In other embodiments, the microorganism overexpresses a gene encoding a thioesterase and a gene encoding an acyl-CoA synthase, relative to a wild type microorganism. In some embodiments, the gene encoding a thioesterase is selected from the group consisting of tesA, 'tesA, fatB1, fatB2, fatB3, fatA1, atfata, and fatA. In other embodiments, the gene encoding an acyl-CoA synthase is fadD. In yet other embodiments, the gene encoding an ester synthase is selected from the group consisting of atfA1, wax-dgat, and mWS.

In some embodiments, the microorganism is a recombinant *E. coli* cell. In certain embodiments, the microorganism is an *E. coli* strain B, strain C, strain K, or strain W. In certain embodiments, the recombinant *E. coli* cell includes a genetic modification that has reduced expression of a fatty acid biosynthesis regulator gene. In some embodiments, one or more endogenous fatty acid biosynthesis regulator genes are functionally deleted or knocked-out. In certain embodiments, the fatty acid biosynthesis regulator gene is a transcriptional repressor, for example, a repressor of *E. coli* genes fabA, fabB and/or yqfA. In particular embodiments, the fatty acid biosynthesis regulator gene is fabR. In certain other embodiments, the recombinant *E. coli* cell includes a genetic modification that has reduced expression of a pyruvate oxidase gene, for example, one encoding an enzyme of EC 1.2.3.3. In some embodiments, one or more endogenous pyruvate oxidase genes are functionally deleted or knocked-out. In particular embodiments, the pyruvate oxidase gene is poxB. In certain other embodiments, the recombinant *E. coli* cell includes a genetic modification that has reduced expression or a functional deletion of a fadE gene. In some embodiments, the recombinant *E. coli* cell includes a genetic modification that attenuates expression of at least one gene selected from the group consisting of fadE, fabR, poxB, and ldhA, relative to a wild type *E. coli* cell.

In certain preferred embodiments, the fatty acid synthesis regulator gene is deleted. In an alternate embodiment the microorganism further comprises a pyruvate oxidase gene, wherein the pyruvate oxidase gene has reduced expression relative to a wild type microorganism. In one embodiment, the pyruvate oxidase gene is deleted. In an alternative embodiment, the microorganism further comprises a lactate dehydrogenase gene, wherein the lactate dehydrogenase gene has reduced expression relative to a wild type microorganism. In one embodiment, the lactate dehydrogenase is deleted. In an alternative embodiment, the microorganism further comprises (1) a pyruvate oxidase gene, wherein the pyruvate oxidase gene has reduced expression relative to a wild type microorgansim, and (2) a lactate dehydrogenase gene, wherein the lactate dehydrogenase gene has reduced expression relative to a wild type microorganism.

In certain preferred embodiments, the pyruvate oxidase gene is deleted. In an alternate embodiment the microorganism further comprises a fatty acid synthesis regulator gene, wherein the fatty acid synthesis regulator gene has reduced expression relative to a wild type microorganism. In one embodiment, the fatty acid synthesis regulator gene is deleted. In an alternative embodiment, the microorganism further comprises a lactate dehydrogenase gene, wherein the lactate dehydrogenase gene has reduced expression relative to a wild type microorganism. In one embodiment, the lactate dehydrogenase is deleted. In an alternative embodiment, the microorganism further comprises (1) a fatty acid synthesis regulator gene, wherein the fatty acid synthesis regulator gene has reduced expression relative to a wild type microorganism, and (2) a lactate dehydrogenase gene, wherein the lactate dehydrogenase gene has reduced expression relative to a wild type microorganism.

In certain preferred embodiments, the lactate dehydrogenase gene is deleted. In an alternate embodiment the microorganism further comprises a pyruvate oxidase gene, wherein the pyruvate oxidase gene has reduced expression relative to a wild type microorganism. In one embodiment, the pyruvate oxidase gene is deleted. In an alternative embodiment, the microorganism further comprises a fatty acid synthesis regulator gene, wherein the fatty acid synthesis regulator gene has reduced expression relative to a wild type microorganism. In one embodiment, the fatty acid synthesis regulator gene is deleted. In an alternative embodiment, the microorganism further comprises (1) a pyruvate oxidase gene, wherein the pyruvate oxidase gene has reduced expression relative to a wild type microorganism, and (2) a fatty acid synthesis regulator gene, wherein the fatty acid synthesis regulator gene has reduced expression relative to a wild type microorganism.

In a preferred embodiment, the genetically engineered microorganism comprises at least one of the following gene deletions: poxB, ldhA, and/or fabR.

In some embodiments, the microorganism is a bacterium. In certain embodiments, the bacterium is a Gram-negative or a Gram-positive bacterium. In some embodiments, the microorganism is a mycobacterium selected from the group consisting of *Mycobacterium smegmatis, Mycobacterium abscessus, Mycobacterium avium, Mycobacterium bovis, Mycobacterium tuberculosis, Mycobacterium leprae, Mycobacterium marinum,* and *Mycobacterium ulcerans*. In certain embodiments, the microorganism is a cyanobacterium, including, for example, *Synechococcus* sp. PCC 7002, *Synechococcus elongatus* PCC 7942, or *Synechocystis* sp. PCC6803. In some embodiments, the microorganism is a yeast, including an oleaginous yeast such as, for example, a *Yarrowia*, a *Candida*, a *Rhodotorula*, a *Rhodosporidium*, a *Cryptococcus*, a *Trichosporon*, or a *Lypomyces*.

In other embodiments, the microorganism is a green-sulfur bacterium, green-non-sulfur bacterium, purple sulfur bacterium, purple non-sulfur bacterium, extremophile, or a synthetic organism. In some embodiments, the wild type and/or the engineered microorganism can be one that is light-dependent or fixes carbon. In other embodiments, the wild-type and/or engineered microorganism has autotrophic activity, such as, for example, photoautotrophic activity in the presence of light. In some embodiments, the wild-type and/or engineered microorganism is heterotrophic or mixotrophic in the absence of light. In some embodiments, the microorganism is selected from an *Arabidopsis thaliana, Panicum virgatum, Miscanthus giganteus, Zea mays, Botryococcus braunii, Chlamydomonas reinhardtii, Dunaliala salina, Synechococcus* sp. PCC7002, *Synechoccus elongatus* PCC7942, *Synechocystis* sp. PCC 6803, *thermosynechococcus elongatus* BP-1, *Chlorobium tepidum, Chloroflexus auranticus, Chromatiumm vinosum, Rhodospirillum rubrum, Rhodobacter capsulatus, Rhodopseudomonas palusris, Clostridium ljungdahlii, Clostridiuthermocellum, Pencillium chrysogenum, Pichia pastoris, Saccharomyces cerevisiae, Yarrowia lipolytica, Schizosacchromyces pombe, Pseudomonas fluorescens,* or *Zymomonas mobils*.

In another aspect, the invention features a fatty acid ester produced by any of the methods or any of the microorganisms described herein, or a biofuel or surfactant composition comprising a fatty acid ester produced by any of the methods or any of the microorganisms described herein.

In another aspect, the invention features a genetically engineered microorganism comprising a fatty acid synthesis regulator gene, wherein the fatty acid synthesis regulator gene has reduced expression relative to a wild type microorganism. In some embodiments, the genetically engineered microorganism further comprises (1) a pyruvate oxidase gene, wherein the pyruvate oxidase gene has reduced expression relative to a wild type microorganism, and (2) a lactate dehydrogenase gene, wherein the lactate dehydrogenase gene has reduced expression relative to a wild type microorganism.

In another aspect, the invention features a genetically engineered microorganism comprising a pyruvate oxidase gene, wherein the pyruvate oxidase gene has reduced expression relative to a wild type microorganism.

In another aspect, the invention features a genetically engineered microorganism comprising a lactate dehydrogenase gene, wherein the lactate dehydrogenase gene has reduced expression relative to a wild type microorganism.

DEFINITIONS

Figure 1:
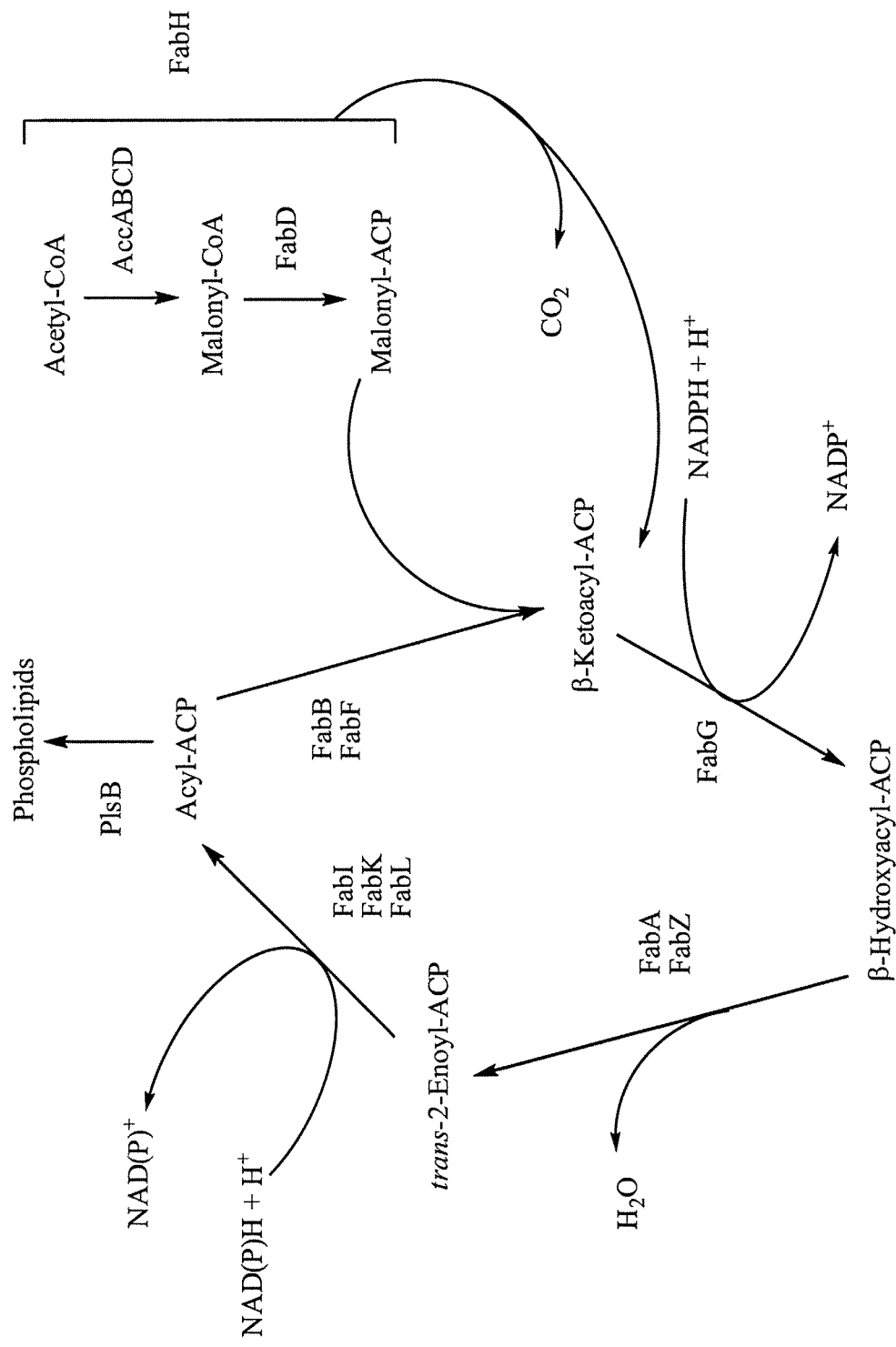
FIG. 1 is a diagram illustrating the FAS biosynthetic pathway.
Figure 2:
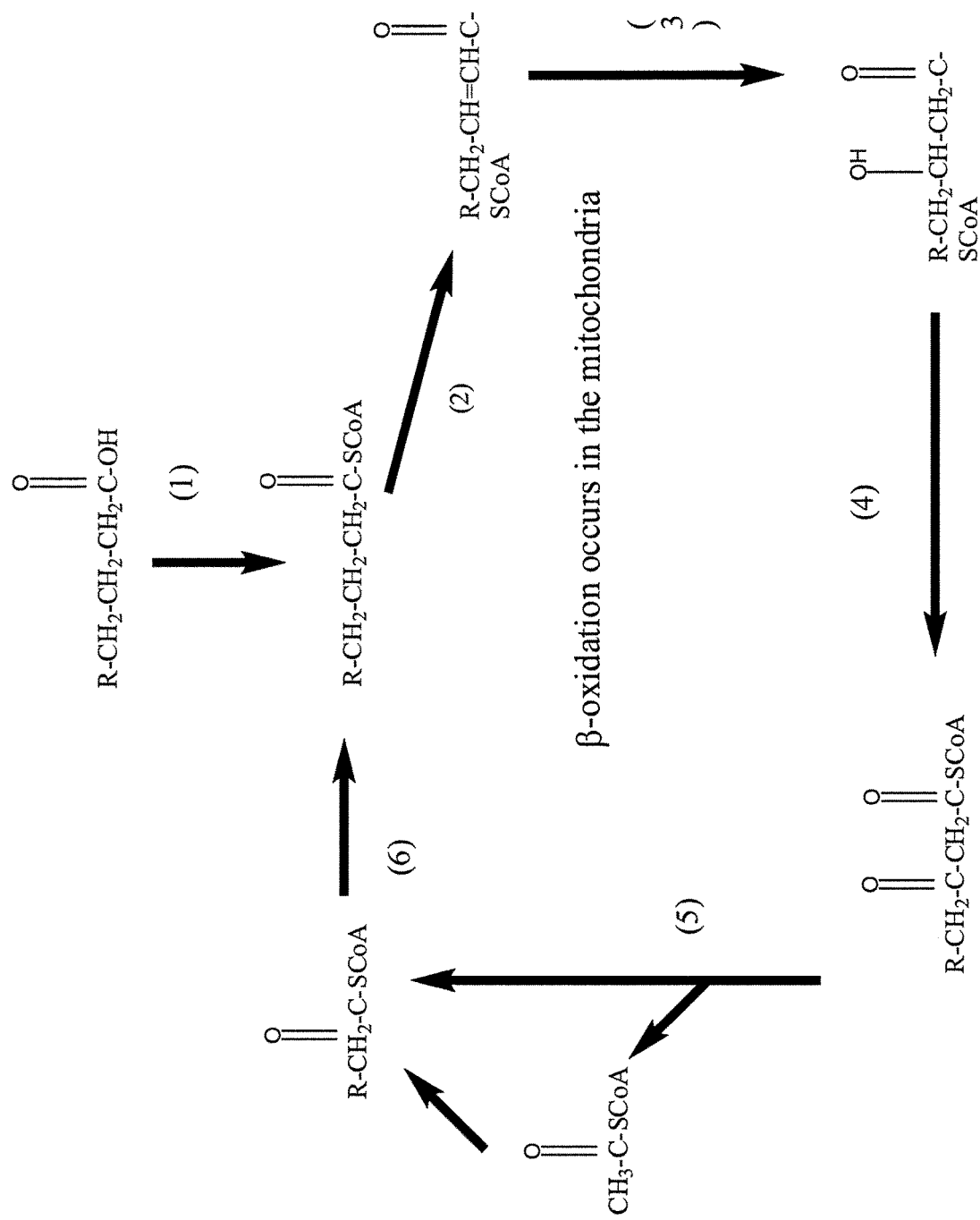
FIG. 2 is a diagram illustrating the beta-oxidation pathway, including steps catalyzed by the following enzymes (1) acyl-CoA synthase (EC 6.2.1.-); (2) acyl-CoA dehydrogenase (EC 1.3.99.3); (3) enoyl-CoA hydratase (EC 4.2.1.17); (4) 3-hydroxybutyryl-CoA epimerase (EC 5.1.2.3); and (5) 3-ketoacyl-CoA thiolase (EC 2.3.1.16). This final reaction of the β-oxidation cycle releases acetyl-CoA and an acyl-CoA fatty acid two carbons shorter, ready to go through β-oxidation reactions again.

The articles "a" and "an" are used herein to refer to one or to more than one (i.e., to at least one) of the grammatical object of the article. By way of example, "an element" means one element or more than one element.

As used herein, the term "biocrude" refers to a product derived from biomass, biomass derivatives, or other biological sources that, like petroleum crude, can be converted into other fuels. For example, biocrude can be converted into gasoline, diesel, jet fuel, or heating oil. Moreover, biocrude, like petroleum crude, can be converted into other industrially useful chemicals for use in, for example, pharmaceuticals, cosmetics, consumer goods, industrial processes, and the like.

Biocrude may include, for example, hydrocarbons, hydrocarbon products, fatty acid esters, and/or aliphatic ketones. In a preferred embodiment, biocrude is comprised of hydrocarbons, for example aliphatic (e.g., alkanes, alkenes, alkynes) or aromatic hydrocarbons.

As used herein, the term "biodiesel" means a biofuel that can be a substitute of diesel, which is derived from petroleum. Biodiesel can be used in internal combustion diesel engines in either a pure form, which is referred to as "neat" biodiesel, or as a mixture in any concentration with petroleum-based diesel. In one embodiment, biodiesel can include esters or hydrocarbons, such as aldehydes, alkanes, or alkenes.

As used herein, the term "biofuel" refers to any fuel derived from biomass, biomass derivatives, or other biological sources. Biofuels can be substituted for petroleum based fuels. For example, biofuels are inclusive of transportation fuels (e.g., gasoline, diesel, jet fuel, etc.), heating fuels, and electricity-generating fuels. Biofuels are a renewable energy source. As used herein, the term "biomass" refers to a carbon source derived from biological material. Biomass can be converted into a biofuel. One exemplary source of biomass is plant matter. For example, corn, sugar cane, or switchgrass can be used as biomass. Another non-limiting example of biomass is animal matter, for example cow manure. Biomass also includes waste products from industry, agriculture, forestry, and households. Examples of such waste products that can be used as biomass are fermentation waste, straw, lumber, sewage, garbage, and food leftovers. Biomass also includes sources of carbon, such as carbohydrates (e.g., monosaccharides, disaccharides, or polysaccharides).

As used herein, the phrase "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). These include, for example, various monosaccharides, such as glucose, fructose, mannose, and galactose; oligosaccharides, such as fructo-oligosaccharide and galacto-oligosaccharide; polysaccharides such as xylose and arabinose; disaccharides, such as sucrose, maltose, and turanose; cellulosic material, such as methyl cellulose and sodium carboxymethyl cellulose; saturated or unsaturated fatty acid esters, such as succinate, lactate, and acetate; alcohols, such as methanol, ethanol, propanol, or mixtures thereof. The carbon source can also be a product of photosynthesis, including, but not limited to, glucose. A preferred carbon source is biomass. Another preferred carbon source is glucose.

As used herein, a "cloud point lowering additive" is an additive added to a composition to decrease or lower the cloud point of a solution.

As used herein, the phrase "cloud point of a fluid" means the temperature at which dissolved solids are no longer completely soluble. Below this temperature, solids begin precipitating as a second phase giving the fluid a cloudy appearance. In the petroleum industry, cloud point refers to the temperature below which a solidified material or other heavy hydrocarbon crystallizes in a crude oil, refined oil, or fuel to form a cloudy appearance. The presence of solidified materials influences the flowing behavior of the fluid, the tendency of the fluid to clog fuel filters, injectors, etc., the accumulation of solidified materials on cold surfaces (e.g., a pipeline or heat exchanger fouling), and the emulsion characteristics of the fluid with water.

The terms "comprising," "having," "including," and "containing" are to be construed as open-ended terms (e.g., meaning "including, but not limited to,") unless otherwise noted.

As used herein, the term "conditions sufficient to allow expression" means any conditions that allow a host cell or production host to produce a desired product, such as a polypeptide, acyl-CoA, fatty acid derivative (e.g., fatty acids, hydrocarbons, fatty alcohols, fatty esters, etc.), or other product described herein. Suitable conditions include, for example, fermentation conditions. Fermentation conditions can comprise many parameters. Exemplary conditions include temperature ranges, levels of aeration, and media composition. Each of these conditions, individually and in combination, allows the host cell to grow.

Exemplary culture media include broths or gels. Generally, the medium includes a carbon source, such as glucose, fructose, cellulose, or the like, that can be metabolized by a host cell directly. In addition, enzymes can be used in the medium to facilitate the mobilization (e.g., the depolymerization of starch or cellulose to fermentable sugars) and subsequent metabolism of the carbon source.

To determine if conditions are sufficient to allow expression, a host cell can be cultured, for example, for about 4, 8, 12, 24, 36, or 48 hours. During and/or after culturing, samples can be obtained and analyzed to determine if the conditions allow expression. For example, the host cells in the sample or the medium in which the host cells were grown can be tested for the presence of a desired product. When testing for the presence of a product, assays, such as, but not limited to, TLC, HPLC, GC/FID, GC/MS, LC/MS, MS, can be used.

As used herein, "conditions that permit product production" refers to any fermentation conditions that allow a production host to produce a desired product, such as acyl-CoA or fatty acid derivatives (e.g., fatty acids, hydrocarbons, fatty alcohols, waxes, or fatty esters). Fermentation conditions usually comprise many parameters. Exemplary conditions include, but are not limited to, temperature ranges, levels of aeration, and media composition. Each of these conditions, individually and/or in combination, allows the production host to grow.

Exemplary media include broths and/or gels. Generally, a suitable medium includes a carbon source (e.g., glucose, fructose, cellulose, etc.) that can be metabolized by the microorganism directly. In addition, enzymes can be used in the medium to facilitate the mobilization (e.g., the depolymerization of starch or cellulose to fermentable sugars) and subsequent metabolism of the carbon source.

To determine if the fermentation conditions permit product production, the production host can be cultured for about 4, 8, 12, 24, 36, or 48 hours. During culturing or after culturing, samples can be obtained and analyzed to determine if the fermentation conditions have permitted product production. For example, the production hosts in the sample or the medium in which the production hosts are grown can be tested for the presence of the desired product. Exemplary assays, such as TLC, HPLC, GC/FID, GC/MS, LC/MS, MS, as well as those provided herein, can be used identify and quantify the presence of a product.

As used herein, "control element" means a transcriptional control element. Control elements include promoters and enhancers. The term "promoter element," "promoter," or "promoter sequence" refers to a DNA sequence that functions as a switch that activates the expression of a gene. If the gene is activated, it is said to be transcribed or participating in transcription. Transcription involves the synthesis of mRNA from the gene. A promoter, therefore, serves as a transcriptional regulatory element and also provides a site for initiation of transcription of the gene into mRNA. Control elements interact specifically with cellular proteins involved in transcription (Maniatis et al., *Science* 236:1237, 1987).

As used herein, the term "deletion" or "knockout" means modifying or inactivating a polynucleotide sequence that encodes a target protein in order to reduce or eliminate the function of the target protein. A polynucleotide deletion can be performed by methods well known in the art (See, e.g., Datsenko et al., *Proc. Nat. Acad. Sci. USA*, 97:6640-45, 2000 or International Patent Application Nos. PCT/US2007/011923 and PCT/US2008/058788)

As used herein, the term "endogenous" means a polynucleotide that is in the cell and was not introduced into the cell using recombinant genetic engineering techniques. For example, a gene that was present in the cell when the cell was originally isolated from nature. A polynucleotide is still considered endogenous if the control sequences, such as a promoter or enhancer sequences which activate transcription or translation, have been altered through recombinant techniques.

As used herein, the term "ester synthase" means a peptide capable of producing fatty esters. More specifically, an ester synthase is a peptide which converts a thioester to a fatty ester. In a preferred embodiment, the ester synthase converts a thioester (e.g., acyl-CoA) to a fatty ester.

In an alternate embodiment, an ester synthase uses a thioester and an alcohol as substrates to produce a fatty ester. Ester synthases are capable of using short and long chain thioesters as substrates. In addition, ester synthases are capable of using short and long chain alcohols as substrates.

Non-limiting examples of ester synthases are wax synthases, wax-ester synthases, acyl CoA:alcohol transacylases, acyltransferases, and fatty acyl-coenzyme A:fatty alcohol acyltransferases. Exemplary ester synthases are classified in enzyme classification number EC 2.3.1.75. A number of these enzymes, as well as other useful enzymes for making the products described herein, have been disclosed in, for example, International Patent Application Nos. PCT/US2007/011923 and PCT/US2008/058788 (e.g., FIG. 1), which are incorporated herein by reference.

As used herein, the term "exogenous" means a polynucleotide that does not originate from a particular cell as found in nature. For example, "exogenous polynucleotide" could refer to a polynucleotide that was inserted within the genomic polynucleotide sequence of a microorganism or to an extra chromosomal polynucleotide that was introduced into the microorganism. Thus, a non-naturally-occurring polynucleotide is considered to be exogenous to a cell once introduced into the cell. A polynucleotide that is naturally-occurring can also be exogenous to a particular cell. For example, an entire polynucleotide isolated from a first cell can be an exogenous polynucleotide with respect to a second cell if that polynucleotide from the first cell is introduced into the second cell.

As used herein, the term "fatty acid" means a carboxylic acid having the formula RCOOH. R represents an aliphatic group, preferably an alkyl group. R can comprise between about 4 and about 22 carbon atoms. Fatty acids can be saturated, monounsaturated, or polyunsaturated. In a preferred embodiment, the fatty acid is made from a fatty acid biosynthetic pathway.

As used herein, the term "fatty acid biosynthetic pathway" means a biosynthetic pathway that produces fatty acids. The fatty acid biosynthetic pathway includes fatty acid enzymes that can be engineered, as described herein, to produce fatty acids, and in some embodiments can be expressed with additional enzymes to produce fatty acids having desired carbon chain characteristics.

As used herein, the term "fatty acid degradation enzyme" means an enzyme involved in the breakdown or conversion of a fatty acid or fatty acid derivative into another product. A nonlimiting example of a fatty acid degradation enzyme is an acyl-CoA synthase. A number of these enzymes, as well as other useful enzymes for making the products described herein, have been disclosed in, for example, International Patent Application Nos. PCT/US2007/011923 and PCT/US2008/058788 (e.g., FIG. 1), which are incorporated herein by reference. Additional examples of fatty acid degradation enzymes are described herein.

As used herein, the term "fatty acid derivative" means products made in part from the fatty acid biosynthetic pathway of the production host. "Fatty acid derivative" also includes products made in part from acyl-ACP or acyl-ACP derivatives. The fatty acid biosynthetic pathway includes fatty acid synthase enzymes which can be engineered as described herein to produce fatty acid derivatives, and in some examples can be expressed with additional enzymes to produce fatty acid derivatives having desired carbon chain characteristics. Exemplary fatty acid derivatives include for example, fatty acids, acyl-CoAs, fatty aldehydes, short and long chain alcohols, hydrocarbons, fatty alcohols, ketones, and esters (e.g., waxes, fatty acid esters, or fatty esters).

As used herein, the term "fatty acid derivative enzymes" means all enzymes that may be expressed or overexpressed in the production of fatty acid derivatives. These enzymes are collectively referred to herein as fatty acid derivative enzymes. These enzymes may be part of the fatty acid biosynthetic pathway. Non-limiting examples of fatty acid derivative enzymes include fatty acid synthases, thioesterases, acyl-CoA synthases, acyl-CoA reductases, alcohol dehydrogenases, alcohol acyltransferases, carboxylic acid reductases, fatty alcohol-forming acyl-CoA reductase, ester synthases, aldehyde biosynthetic polypeptides, and alkane biosynthetic polypeptides. Fatty acid derivative enzymes convert a substrate into a fatty acid derivative. In some examples, the substrate may be a fatty acid derivative which the fatty acid derivative enzyme converts into a different fatty acid derivative. A number of these enzymes, as well as other useful enzymes for making the products described herein, have been disclosed in, for example, International Patent Application Nos. PCT/US2007/011923 and PCT/US2008/058788 (e.g., FIG. 1), which are incorporated herein by reference.

As used herein, "fatty acid enzyme" means any enzyme involved in fatty acid biosynthesis. Fatty acid enzymes can be expressed or overexpressed in host cells to produce fatty acids. Non-limiting examples of fatty acid enzymes include fatty acid synthases and thioesterases. A number of these enzymes, as well as other useful enzymes for making the products described herein, have been disclosed in, for example, International Patent Application Nos. PCT/US2007/011923 and PCT/US2008/058788 (e.g., FIG. 1), which are incorporated herein by reference.

As used herein, the term "fatty ester" means an ester. In a preferred embodiment, a fatty ester is any ester made from a fatty acid to produce, for example, a fatty acid ester. In one embodiment, a fatty ester contains an A side (i.e., the carbon chain attached to the carboxylate oxygen) and a B side (i.e., the carbon chain comprising the parent carboxylate). In a preferred embodiment, when the fatty ester is derived from the fatty acid biosynthetic pathway, the A side is contributed by an alcohol, and the B side is contributed by a fatty acid. Any alcohol can be used to form the A side of the fatty esters. For example, the alcohol can be derived from the fatty acid biosynthetic pathway. Alternatively, the alcohol can be produced through non-fatty acid biosynthetic pathways. Moreover, the alcohol can be provided exogenously. For example, the alcohol can be supplied in the fermentation broth in instances where the fatty ester is produced by an organism that can also produce the fatty acid. Alternatively, a carboxylic acid, such as a fatty acid or acetic acid, can be supplied exogenously in instances where the fatty ester is produced by an organism that can also produce alcohol.

The carbon chains comprising the A side or B side can be of any length. In one embodiment, the A side of the ester is at least about 1, 2, 3, 4, 5, 6, 7, 8, 10, 12, 14, 16, or 18 carbons in length. The B side of the ester is at least about 4, 6, 8, 10, 12, 14, 16, 18, 20, 22, 24, or 26 carbons in length. The A side and/or the B side can be straight or branched chain. The branched chains may have one or more points of branching. In addition, the branched chains may include cyclic branches. Furthermore, the A side and/or B side can be saturated or unsaturated. If unsaturated, the A side and/or B side can have one or more points of unsaturation.

In one embodiment, the fatty ester is produced biosynthetically. In this embodiment, first the fatty acid is "activated." Non-limiting examples of "activated" fatty acids are acyl-CoA, acyl-ACP, and acyl phosphate. Acyl-CoA can be a direct product of fatty acid biosynthesis or degradation. In addition, acyl-CoA can be synthesized from a free fatty acid, a CoA, or an adenosine nucleotide triphosphate (ATP). An example of an enzyme which produces acyl-CoA is acyl-CoA synthase After the fatty acid is activated, it can be readily transferred to a recipient nucleophile. Exemplary nucleophiles are alcohols, thiols, or phosphates.

In one embodiment, the fatty ester is a wax. The wax can be derived from a long chain alcohol and a long chain fatty acid. In another embodiment, the fatty ester can be derived from a fatty acyl-thioester and an alcohol. In another embodiment, the fatty ester is a fatty acid thioester, for example fatty acyl Coenzyme A (CoA). In other embodiments, the fatty ester is a fatty acyl panthothenate, an acyl carrier protein (ACP), or a fatty phosphate ester. Fatty esters have many uses. For example, fatty esters can be used as biofuels, surfactants, or formulated into additives that provide lubrication and other benefits to fuels and industrial chemicals.

As used herein, "fraction of modern carbon" or "$f_M$" has the same meaning as defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (e.g., plant material), $f_M$ is approximately 1.1.

Calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence that is aligned for comparison purposes is at least about 30%, preferably at least about 40%, more preferably at least about 50%, even more preferably at least about 60%, and even more preferably at least about 70%, at least about 80%, at least about 90%, or about 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology"). The percent identity between the two sequences is a function of the number of identical positions shared by the sequences, taking into account the number of gaps and the length of each gap, which need to be introduced for optimal alignment of the two sequences.

The comparison of sequences and determination of percent homology between two sequences can be accomplished using a mathematical algorithm. In a preferred embodiment, the percent homology between two amino acid sequences is determined using the Needleman and Wunsch (1970), *J. Mol. Biol.* 48:444 453, algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent homology between two nucleotide sequences is determined using the GAP program in the GCG software package, using a NWSgapdna. CMP matrix and a gap weight of about 40, 50, 60, 70, or 80 and a length weight of about 1, 2, 3, 4, 5, or 6. A particularly preferred set of parameters (and the one that should be used if the practitioner is uncertain about which parameters should be applied to determine if a molecule is within a homology limitation of the claims) are a Blossum 62 scoring matrix with a gap penalty of 12, a gap extend penalty of 4, and a frameshift gap penalty of 5.

Other methods for aligning sequences for comparison are well known in the art. Various programs and alignment algorithms are described in, for example, Smith & Waterman, *Adv. Appl. Math.* 2:482, 1981; Pearson & Lipman, *Proc. Natl. Acad. Sci. USA* 85:2444, 1988; Higgins & Sharp, *Gene* 73:237 244, 1988; Higgins & Sharp, *CABIOS* 5:151-153, 1989; Corpet et al., *Nucleic Acids Research* 16:10881-10890, 1988; Huang et al., *CABIOS* 8:155-165, 1992; and Pearson et al., *Methods in Molecular Biology* 24:307-331, 1994. and Altschul et al., *J. Mol. Biol.* 215:403-410, 1990.

As used herein, a "host cell" is a cell used to produce a product described herein (e.g., an aldehyde or alkane). A host cell can be modified to express or overexpress selected genes or to have attenuated expression of selected genes. Non-limiting examples of host cells include plant, animal, human, bacteria, cyanobacteria, yeast, or filamentous fungi cells.

As used herein, the term "microorganism" means prokaryotic and eukaryotic microbial species from the domains Archaea, Bacteria and Eucarya, the latter including yeast and filamentous fungi, protozoa, algae, or higher Protista. The term "microbial cell", as used herein, means a cell from a microorganism.

As used herein, the term "nucleic acid" refers to a polynucleotide, such as deoxyribonucleic acid (DNA), and, where appropriate, ribonucleic acid (RNA). The term also includes analogs of either RNA or DNA made from nucleotide analogs, and, as applicable to the embodiment being described, single (sense or antisense) and double-stranded polynucleotides, ESTs, chromosomes, cDNAs, mRNAs, and rRNAs. The term "nucleic acid" may be used interchangeably with "polynucleotide," "DNA," "nucleic acid molecule," "nucleotide sequence," and/or "gene" unless otherwise indicated herein or otherwise clearly contradicted by context.

As used herein, the term "operably linked" means that a selected nucleotide sequence (e.g., encoding a polypeptide described herein) is in proximity with a promoter to allow the promoter to regulate expression of the selected nucleotide sequence. In addition, the promoter is located upstream of the selected nucleotide sequence in terms of the direction of transcription and translation. By "operably linked" is meant that a nucleotide sequence and a regulatory sequence(s) are connected in such a way as to permit gene expression when the appropriate molecules (e.g., transcriptional activator proteins) are bound to the regulatory sequence(s).

The term "or" is used herein to mean, and is used interchangeably with, the term "and/or," unless context clearly indicates otherwise.

As used herein, "overexpress" means to express or cause to be expressed or produced a nucleic acid, polypeptide, or hydrocarbon in a cell at a greater concentration than is normally expressed in a corresponding wild-type cell. For example, a polypeptide can be "overexpressed" in a recombinant host cell when the polypeptide is present in a greater concentration in the recombinant host cell compared to its concentration in a non-recombinant host cell of the same species.

As used herein, "partition coefficient" or "P," is defined as the equilibrium concentration of a compound in an organic phase divided by the concentration at equilibrium in an aqueous phase (e.g., fermentation broth). In one embodiment of a bi-phasic system described herein, the organic phase is formed by the aldehyde or alkane during the production process. However, in some examples, an organic phase can be provided, such as by providing a layer of octane, to facilitate product separation. When describing a two phase system, the partition characteristics of a compound can be described as log P. For example, a compound with a log P of 1 would partition 10:1 to the organic phase. A compound with a log P of −1 would partition 1:10 to the organic phase. By choosing an appropriate fermentation broth and organic phase, an organic fatty acid derivative or product with a high log P value can separate into the organic phase even at very low concentrations in the fermentation vessel.

As used herein, the term "polypeptide" may be used interchangeably with "protein," "peptide," and/or "enzyme" unless otherwise indicated herein or otherwise clearly contradicted by context.

As used herein, the term "production host" means a cell used to produce the products disclosed herein. The production host is modified to express, overexpress, attenuate or delete expression of selected polynucleotides. Non-limiting examples of production hosts include plant, algal, animal, human, bacteria, yeast, and filamentous fungi cells.

As used herein, the term "purify," "purified," or "purification" means the removal or isolation of a molecule from its environment by, for example, isolation or separation. "Substantially purified" molecules are at least about 60% free, preferably at least about 75% free, and more preferably at least about 90% free from other components with which they are associated. As used herein, these terms also refer to the removal of contaminants from a sample. For example, the removal of contaminants can result in an increase in the percentage of a fatty acid derivative or product in a sample. For example, when a fatty acid derivatives or products are produced in a host cell, the fatty acid derivatives or products can be purified by the removal of host cell proteins. After purification, the percentage of fatty acid derivatives or products in the sample is increased.

The terms "purify," "purified," and "purification" do not require absolute purity. They are relative terms. Thus, for example, when the fatty acid derivatives or products are produced in host cells, a purified fatty acid derivative or product is one that is substantially separated from other cellular components (e.g., nucleic acids, polypeptides, lipids, carbohydrates, or other fatty acid derivatives or products). In another example, a purified fatty acid derivative or purified product preparation is one in which the fatty acid derivative or product is substantially free from contaminants, such as those that might be present following fermentation. In some embodiments, a fatty acid derivative or product is purified when at least about 50% by weight of a sample is composed of the fatty acid derivative or product. In other embodiments, a fatty acid derivative or product is purified when at least about 60%, 70%, 80%, 85%, 90%, 92%, 95%, 98%, or 99% or more by weight of a sample is composed of the fatty acid derivative or product.

As used herein, the term "recombinant polypeptide" refers to a polypeptide that is produced by recombinant DNA techniques, wherein generally DNA encoding the expressed polypeptide or RNA is inserted into a suitable expression vector and that is in turn used to transform a host cell to produce the polypeptide or RNA.

As used herein, the term "substantially identical" (or "substantially homologous") is used to refer to a first amino acid or nucleotide sequence that contains a sufficient number of identical or equivalent (e.g., with a similar side chain) amino acid residues (e.g., conserved amino acid substitutions) or nucleotides to a second amino acid or nucleotide sequence such that the first and second amino acid or nucleotide sequences have similar activities.

As used herein, the term "surfactants" means a substance capable of reducing the surface tension of a liquid in which it is dissolved. A surfactant is typically composed of a water-soluble head and a hydrocarbon chain or tail. The water soluble head is hydrophilic and can be either ionic or nonionic. The hydrocarbon chain is hydrophobic. Surfactants are used in a variety of products. For example, surfactants are used in the compositions or manufacture of detergents, cleaners, textiles, leather, paper, cosmetics, pharmaceuticals, processed foods, and agricultural products. In addition, surfactants can be used in the extraction and isolation of crude oils.

There are four major categories of surfactants which are characterized by their uses. Anionic surfactants have detergent-like activity and are generally used for cleaning applications. Cationic surfactants contain long chain hydrocarbons and are often used to treat proteins and synthetic polymers or are components of fabric softeners and hair conditioners. Amphoteric surfactants also contain long chain hydrocarbons, but are typically used in shampoos. Non-ionic surfactants are generally used in cleaning products.

As used herein, the term "synthase" means an enzyme which catalyzes a synthesis process. As used herein, the term synthase includes synthases, synthetases, and ligases.

As used herein, the term "transfection" means the introduction of a nucleic acid (e.g., via an expression vector) into a recipient cell by nucleic acid-mediated gene transfer.

As used herein, the term "transformation" refers to a process in which a cell's genotype is changed as a result of the cellular uptake of exogenous nucleic acid. This may result in the transformed cell expressing a recombinant form of a RNA or polypeptide. In the case of antisense expression from the transferred gene, the expression of a naturally-occurring form of the polypeptide is disrupted.

As used herein, the term "transport protein" means a polypeptide that facilitates the movement of one or more compounds in and/or out of a cellular organelle and/or a cell. A number of these proteins, as well as other useful proteins for making the products described herein, have been disclosed in, for example, International Patent Application Nos. PCT/US2007/011923 and PCT/US2008/058788 (e.g., FIG. 1), which are incorporated herein by reference.

As used herein, the term "vector" refers to a nucleic acid molecule capable of transporting another nucleic acid to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids," which refer generally to circular double stranded DNA loops that, in their vector form, are not bound to the chromosome. In the present specification, "plasmid" and "vector" are used interchangeably, as the plasmid is the most commonly used form of vector. However, also included are such other forms of expression vectors that serve equivalent functions and that become known in the art subsequently hereto.

As used herein, the term "wax" means a composition comprised of fatty esters. In a preferred embodiment, the fatty ester in the wax is comprised of medium to long carbon chains. In addition to fatty esters, a wax may comprise other components (e.g., hydrocarbons, sterol esters, aliphatic aldehydes, alcohols, ketones, beta-diketones, triacylglycerols, etc.).

Throughout the specification, a reference may be made using an abbreviated gene name or polypeptide name, but it is understood that such an abbreviated gene or polypeptide name represents the genus of genes or polypeptides. Such gene names include all genes encoding the same polypeptide and homologous polypeptides having the same physiological function. Polypeptide names include all polypeptides that have the same activity (e.g., that catalyze the same fundamental chemical reaction).

The accession numbers referenced herein are derived from the NCBI database (National Center for Biotechnology Information) maintained by the National Institute of Health, U.S.A. Unless otherwise indicated, the accession numbers are as provided in the database as of April 2009.

EC numbers are established by the Nomenclature Committee of the International Union of Biochemistry and Molecular Biology (NC-IUBMB) (available at www.chem.qmul.ac.uk/iubmb/enzyme/). The EC numbers referenced herein are derived from the KEGG Ligand database, maintained by the Kyoto Encyclopedia of Genes and Genomics, sponsored in part by the University of Tokyo. Unless otherwise indicated, the EC numbers are as provided in the database as of April 2009.

Unless otherwise defined, all technical and scientific terms used herein have the same meaning as commonly understood by one of ordinary skill in the art to which this invention belongs.

Although methods and materials similar or equivalent to those described herein can be used in the practice or testing of the present invention, suitable methods and materials are described below. All methods described herein can be performed in any suitable order unless otherwise indicated herein or otherwise clearly contradicted by context.

Unless otherwise stated, amounts listed in percentage (%) are in weight percent, based on the total weight of the composition.

All publications, patent applications, patents, and other references mentioned herein are incorporated by reference in their entirety. In case of conflict, the present specification, including definitions, will control. In addition, the materials, methods, and examples are illustrative only and not intended to be limiting.

Recitation of ranges of values herein are merely intended to serve as a shorthand method of referring individually to each separate value falling within the range, unless otherwise indicated herein, and each separate value is incorporated into the specification as if it were individually recited herein.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Other features and advantages of the invention will be apparent from the following detailed description and from the claims.

DETAILED DESCRIPTION

This disclosure relates to the production of fatty acid esters, such as fatty acid ethyl esters ("FAEE"), from recombinant cells without providing exogenous alcohol, such as exogenous ethanol or methanol, to the cells. Producing fatty acid esters without providing exogenous alcohol simplifies the fermentation process, reduces the costs and handling of additional raw materials, and avoids the need to store flammable alcohols. This provides an economic advantage.

Many cells and microorganisms can use fatty acids as energy sources and therefore contain β-oxidation pathways that metabolize fatty acids to make energy. It was found that over-expressing a peptide having acyl-CoA synthase activity (the first enzymatic activity found in the β oxidation pathway), and/or attenuating other genes in the beta oxidation pathway, could increase the amount of acyl-CoA produced, while maintaining the viability of the cell or microorganism. Similarly, over-expressing a peptide having acyl-CoA synthase activity in combination with over-expression of peptides that form fatty acid derivatives can improve fatty acid derivative production. Methods of improving fatty acid derivative production in cell culture are disclosed in WO2008/119082.

It has been discovered that, surprisingly, recombinant cells can be modified to produce fatty acid esters, such as FAEE, without the need to provide exogenous alcohol to the cells. In some methods, neither exogenous ethanol nor exogenous methanol is provided to the cells. In other methods, no exogenous alcohol is provided to the cells. In some methods, the recombinant cell is a recombinant E. coli cell.

Without being bound by any particular theory, it is believed that the methods of producing FAEE disclosed herein increase production of ethanol by the recombinant cells. Additionally, the recombinant cells are modified to produce fatty acids, and to express a gene encoding an ester synthase enzyme. Without being bound by any particular theory, it is believed that fatty acids and the endogenous ethanol produced by the recombinant cells act as raw materials for the wax synthase enzyme to form fatty acid esters, such as FAEE.

Fatty acids produced by the methods described herein are not limited to esters of any particular length or other characteristics. For example, a microorganism can be genetically engineered to produce any of the fatty esters described in Knothe, Fuel Processing Technology 86:1059-1070, 2005, using the teachings provided herein. Such fatty esters can be characterized by centane number (CN), viscosity, melting point, and heat of combustion.

I. Production of Fatty Acid Derivatives and Modifications for Increasing Production The production host used to produce acyl-CoA and/or fatty acid derivatives can be recombinantly modified to include nucleic acid sequences that over-express peptides. For example, the production host can be modified to increase the production of acyl-CoA and reduce the catabolism of fatty acid derivatives and intermediates in the fatty acid biosynthetic pathway, such as acyl-CoA, or to reduce feedback inhibition at specific points in the fatty acid biosynthetic pathway. In addition to modifying the genes described herein, additional cellular resources can be diverted to over-produce fatty acids, for example, the lactate, succinate and/or acetate pathways can be attenuated, and acetyl-CoA carboxylase (acc) can be over-expressed. The modifications to the production host described herein can be through genomic alterations, addition of recombinant expression systems, or combinations thereof.

The fatty acid biosynthetic pathways involved are illustrated in FIG. 1 through FIG. 5. Subsections A-G below describe the steps in these pathways. Different steps in the pathway are catalyzed by different enzymes. Each step is a potential place for overexpression of the gene to produce more enzyme and thus drive the production of more fatty acids and fatty acid derivatives. Genes encoding enzymes required for the pathway can also be recombinantly added to a production host lacking such enzymes. Finally, steps that would compete with the pathway leading to production of fatty acids and fatty acid derivatives can be attenuated or blocked in order to increase the production of the desired products. Methods of producing fatty acid derivatives are described in WO2008/119082, which is herein incorporated by reference in its entirety.

A. Acetyl-CoA-Malonyl-CoA to Acyl-ACP

Fatty acid synthase (FAS) is a group of peptides that catalyze the initiation and elongation of acyl chains (Marrakchi et al., *Biochemical Society*, 30:1050-1055, 2002). The acyl carrier protein (ACP) along with the enzymes in the FAS pathway control the length, degree of saturation, and branching of the fatty acids produced. The steps in this pathway are catalyzed by enzymes of the fatty acid biosynthesis (fab) and acetyl-CoA carboxylase (acc) gene families. Depending upon the desired product, one or more of these genes can be attenuated or over-expressed. 1. Fatty Acid Biosynthetic Pathway: acetyl-CoA or malonyl-CoA to acyl-ACP The fatty acid biosynthetic pathway in the production host uses the precursors acetyl-CoA and malonyl-CoA (FIG. 1). The steps in this pathway are catalyzed by enzymes of the fatty acid biosynthesis (fab) and acetyl-CoA carboxylase (acc) gene families. This pathway is described in Heath et al., *Prog. Lipid Res.* 40(6):467-97 (2001), which is incorporated herein by reference in its entirety.

Acetyl-CoA is carboxylated by acetyl-CoA carboxylase (Acc, a multisubunit enzyme encoded by four separate genes, accABCD), to form malonyl-CoA. The malonate group is transferred to ACP by malonyl-CoA:ACP transacylase (FabD) to form malonyl-ACP. A condensation reaction then occurs, where malonyl-ACP merges with acetyl-CoA, resulting in β-ketoacyl-ACP. β-ketoacyl-ACP synthase III (FabH) initiates the FAS cycle, while β-ketoacyl-ACP synthase I (FabB) and β-ketoacyl-ACP synthase II (FabF) are involved in subsequent cycles.

Next, a cycle of steps is repeated until a saturated fatty acid of the appropriate length is made. First, the β-ketoacyl-ACP is reduced by NADPH to form β-hydroxyacyl-ACP. This step is catalyzed by β-ketoacyl-ACP reductase (FabG). β-hydroxyacyl-ACP is then dehydrated to form trans-2-enoyl-ACP. β-hydroxyacyl-ACP dehydratase/isomerase (FabA) or β-hydroxyacyl-ACP dehydratase (FabZ) catalyze this step. NADPH-dependent trans-2-enoyl-ACP reductase I, II, or III (FabI, FabK, and FabL, respectively) reduces trans-2-enoyl-ACP to form acyl-ACP. Subsequent cycles are started by the condensation of malonyl-ACP with acyl-ACP by β-ketoacyl-ACP synthase I or β-ketoacyl-ACP synthase II (FabB and FabF, respectively).

2. Modifications to the Fatty Acid Biosynthetic Pathway to Increase acyl-ACP Production Production hosts can be engineered to overproduce acetyl-CoA and malonyl-CoA. Such production hosts include plant, animal, algal, bacterial, cyanobacterial, fungal, or human cells. Cells of microorganisms such as, for example, bacteria, cyanobacterial, algae, yeast, or filamentous fungi can also be used as production hosts. Non-limiting examples of microorganisms that can be used as production hosts include *E. coli, Saccharomyces cerevisiae, Candida lipolytica, Arthrobacter* AK 19, *Rhodotorula glutinins, Acinetobacter* sp. strain M-1, *Candida lipolytica,* and other oleaginous microorganisms. Other suitable microorganisms include, without limitation, *Synechococcus* sp. PCC7002, *Synechococcus elongatus.* PCC7942, and *Synechocystis* sp. PCC6803. Several different modifications can be made, either in combination or individually, to the production host to obtain increased acetyl-CoA/malonyl-CoA/fatty acid and fatty acid derivative production.

For example, to increase acetyl-CoA production, one or more of the following genes can be expressed in a production host: pdh, panK, aceEF (encoding the E1p dehydrogenase component and the E2p dihydrolipoamide acyltransferase component of the pyruvate and 2-oxoglutarate dehydrogenase complexes), fabH, fabD, fabG, acpP, fabF. In other examples, additional DNA sequence encoding fatty-acyl-CoA reductases and aldehyde decarbonylases can be expressed in the production host. It is well known in the art that a plasmid containing one or more of the aforementioned genes, all under the control of a constitutive, or otherwise controllable promoter, can be constructed. Exemplary GenBank accession numbers for these genes are: pdh (BAB34380, AAC73227, AAC73226), panK (also known as coaA, AAC76952), aceEF (AAC73227, AAC73226),fabH (AAC74175), fabD (AAC74176), fabG (AAC74177), acpP (AAC74178),fabF (AAC74179).

Additionally, the expression level of an acyl-CoA dehydrogenase gene can be reduced or functionally deleted in the engineered microorganism by transformation with conditionally replicative or non-replicative plasmids containing null or deletion mutations of the corresponding gene, or by substituting promoters or enhancer sequences. In some embodiment, the acyl-CoA dehydrogenase gene encodes an enzyme of, for example, EC 1.3.99.3. In particular embodiments, the acyl-CoA dehydrogenase gene is fadE.

In some embodiments, the expression level of a fatty acid biosynthesis regulator gene can be reduced or functionally deleted in the engineered microorganism by transformation with conditionally replicative or non-replicative plasmids containing null or deletion mutations of the corresponding gene, or by substituting promoters or enhancer sequences. In some embodiments, the fatty acid biosynthesis regulator gene is a transcriptional repressor, for example a repressor of the fabA, fabB and/or yqfA genes (see, e.g., McCue et al., *Nucleic Acids Res.,* 29(3):774-82 (2001); Zhang et al., *J. Biol. Chem.* 277 (18):15558-65 (2002)). In particular embodiments, the fatty acid biosynthesis regulator gene is afabR gene.

In other embodiments, the expression levels of a pyruvate oxidase gene (see, e.g., Chang et al.,*J. Bacteriol.* 154(2): 756-62 (1983); Abdel-Ahmid et al., *Microbiol.* 147(6): 2001)) can be reduced or functionally deleted in the engineered microorganism by transformation with conditionally replicative or non-replicative plasmids containing null or deletion mutations of the corresponding genes, or by substituting promoters or enhancer sequences. In some embodiments, the pyruvate oxidase gene encodes an enzyme of, for example, EC 1.2.3.3. In particular embodiments, the pyruvate oxidase gene is a poxB gene.

In other embodiments, the expression levels of a lactate dehydrogenase gene (see, e.g., Mat-Jan et al., *J. Bacteriol.* 171(1):342-8; Bunch et al., *Microbiol.* 143(1):187-95 (1997)) can be reduced or functionally deleted in the engineered microorganism by transformation with conditionally replicative or non-replicative plasmids containing null or deletion mutations of the corresponding gene, or by substituting promoters or enhancer sequences. In some embodiments, the lactate dehydrogenase gene encodes an enzyme of, for example, EC 1.1.1.27. In particular embodiments, the lactate dehydrogenase gene is an NAD-linked fermentative D-lactate dehydrogenase gene. In further embodiments, the lactate dehydrogenase gene is a ldhA gene.

In certain embodiments, the expression levels of fadE, fabR, gpsA, ldhA, pflA, pflB, adhE, pta, poxB, ackA, and/or ackB can be reduced or knocked-out in the engineered microorganism by transformation with conditionally replicative or non-replicative plasmids containing null or deletion mutations of the corresponding genes, or by substituting promoter or enhancer sequences. Exemplary GenBank accession numbers for these genes are: fadE (AAC73325), gspA (AAC76632), ldhA (AAC74462), pflA (AP_001532), pflB (AAC73989), adhE (AAC74323), pta (AAC75357), poxB (AAC73958), ackA (AAC75356), and ackB (BAB81430). The resulting engineered production hosts can produce increased levels of acetyl-CoA when grown in an appropriate environment.

Moreover, malonyl-CoA overproduction can be affected by engineering the production hosts as described above with accABCD (e.g., accession number AAC73296, EC 6.4.1.2) included in the plasmid synthesized de novo. Fatty acid overproduction can be achieved by further including a DNA sequence encoding lipase (e.g., Accession numbers CAA89087, CAA98876) in the plasmid synthesized de novo.

As a result, in some examples, acetyl-CoA carboxylase can be over-expressed to increase the intracellular concentration thereof by at least about 2-fold, preferably at least about 5-fold, or more preferably at least about 10-fold, relative to native expression levels.

In addition, the plsB (e.g., Accession number AAC77011) D311E mutation can be used to increase the amount of available acyl-CoA.

In addition, over-expression of a sfa gene (suppressor of FabA, e.g., Accession number AAN79592) can be included in the production hosts to increase production of monounsaturated fatty acids (Rock et al., *J. Bacteriology* 178:5382-5387 (1996)).

B. Acyl-ACP to Fatty Acid

1. Fatty Acid Biosynthetic Pathway: acyl-ACP to Fatty Acids

As described above, acetyl-CoA and malonyl-CoA are processed in several steps to form acyl-ACP chains. The enzyme sn-glycerol-3-phosphate acyltransferase (PlsB) catalyzes the transfer of an acyl group from acyl-ACP or acyl-CoA to the sn-1 position of glycerol-3-phosphate. Thus, PlsB is a regulatory enzyme in phospholipid synthesis, which is part of the fatty acid pathway Inhibiting PlsB can lead to an increase in the levels of long chain acyl-ACP, which feedback can inhibit early steps in the pathway (e.g., accABCD, fabH, and fabI). Uncoupling of this regulation, for example by thioesterase overexpression, can lead to increased fatty acid production. The tes and fat gene families express thioesterase. FabI can also be inhibited in vitro by long-chain acyl-CoA.

2. Modifications to the Fatty Acid Biosynthetic Pathway to Produce Desired Fatty Acids To engineer a production host for the production of a homogeneous population of fatty acid derivatives, one or more endogenous genes can be attenuated or functionally deleted and, as a result, one or more thioesterases can be expressed. For example, $C_{10}$ fatty acid derivatives can be produced by attenuating thioesterase $C_{18}$ (e.g., accession numbers AAC73596 and POADA1), which uses $C_{18:1}$-ACP and expressing thioesterase $C_{10}$ (e.g., accession number Q39513), which uses $C_{10}$-ACP. This can result in a relatively homogeneous population of fatty acid derivatives that have a carbon chain length of 10. In another example, $C_{14}$ fatty acid derivatives can be produced by attenuating endogenous thioesterases that produce non-$C_{14}$ fatty acids and expressing the thioesterase accession number Q39473 (which uses $C_{14}$-ACP). In yet another example, $C_{12}$ fatty acid derivatives can be produced by expressing thioesterases that use $C_{12}$-ACP (for example, accession number Q41635) and attenuating thioesterases that produce non-$C_{12}$ fatty acids. Acetyl-CoA, malonyl-CoA, and fatty acid overproduction can be verified using methods known in the art, for example by using radioactive precursors, HPLC, and GC-MS subsequent to cell lysis. Non-limiting examples of thioesterases useful in the claimed methods and production hosts are listed Table 1.

TABLE 1

Thioesterases

| Accession Number | Source Organism | Gene | Preferential product produced |
| --- | --- | --- | --- |
| AAC73596 | E. coli | tesA without leader sequence | $C_{18:1}$ |
| AAC73555 | E. coli | tesB | |
| Q41635, AAA34215 | Umbellularia california | fatB | $C_{12:0}$ |
| Q39513; AAC49269 | Cuphea hookeriana | fatB2 | $C_{8:0}$-$C_{10:0}$ |

TABLE 1-continued

Thioesterases

| Accession Number | Source Organism | Gene | Preferential product produced |
| --- | --- | --- | --- |
| AAC49269; AAC72881 | Cuphea hookeriana | fatB3 | $C_{14:0}$-$C_{16:0}$ |
| Q39473, AAC49151 | Cinnamonum camphorum | fatB | $C_{14:0}$ |
| CAA85388 | Arabidopsis thaliana | fatB [M141T]* | $C_{16:1}$ |
| NP 189147; NP 193041 | Arabidopsis thaliana | fatA | $C_{18:1}$ |
| CAC39106 | Bradyrhiizobium japonicum | fatA | $C_{18:1}$ |
| AAC72883 | Cuphea hookeriana | fatA | $C_{18:1}$ |
| AAL79361 | Helianthus annus | fatA1 | |

*Caner et al., *BMC Plant Biology* 7: 1-11, 2007

C. Fatty Acid to Acyl-CoA

1. Conversion of Fatty Acids to Acyl-CoA

Acyl-CoA synthase (ACS) esterifies free fatty acids to acyl-CoA by a two-step mechanism. The free fatty acid first is converted to an acyl-AMP intermediate (an adenylate) through the pyrophosphorolysis of ATP. The activated carbonyl carbon of the adenylate is then coupled to the thiol group of CoA, releasing AMP and the acyl-CoA final product. See Shockey et al., *Plant. Physiol.* 129:1710-1722 (2002).

The *E. coli* ACS enzyme FadD and the fatty acid transport protein FadL are essential components of a fatty acid uptake system. FadL mediates transport of fatty acids into the bacterial cell, and FadD mediates formation of acyl-CoA esters. When no other carbon source is available, exogenous fatty acids are taken up by bacteria and converted to acyl-CoA esters, which can bind to the transcription factor FadR and derepress the expression of the fad genes that encode proteins responsible for fatty acid transport (FadL), activation (FadD), and β-oxidation (FadA, FadB, FadE, and FadH). When alternative sources of carbon are available, bacteria synthesize fatty acids as acyl-ACPs, which are used for phospholipid synthesis, but are not substrates for β-oxidation. Thus, acyl-CoA and acyl-ACP are both independent sources of fatty acids that can result in different end-products. See Caviglia et al., *J. Biol. Chem.* 279(12):1163-1169 (2004).

2. Modifications to Increase Conversion of Fatty Acids to Acyl-CoA

Production hosts can be engineered using known peptides to produce fatty acids of various lengths which can be converted to acyl-CoA. One exemplary method includes increasing the expression of, or expressing more active forms of, one or more acyl-CoA synthase peptides (EC 6.2.1.-). A list of acyl-CoA synthases that can be expressed to produce acyl-CoA and fatty acid derivatives is shown in Table 2.

TABLE 2

Acyl-CoA synthases

| Gene Name/Locus | Source | NCBI ID | % Identity to E. coli FadD | % Similarity to E. coli FadD |
|---|---|---|---|---|
| fadD | E. coli | NP_416319 | — | — |
| fadK | E. coli | YP_416216 | 45 | 27 |
| fadD | Acinetobacter sp. ADP1 | YP_045024 | 51 | 70 |
| fadD | Haemophilus influenza RdKW20 | NP_438551 | 64 | 78 |
| BH3103 | Bacillus halodurans C-125 | NP_243969 | 40 | 58 |
| yhfL | Bacillus subtilis | NP_388908 | 39 | 57 |
| Pfl-4354 | Pseudomonas fluorescens Pfo-1 | YP_350082 | 52 | 71 |
| EAV15023 | Comamonas testosterone KF-1 | ZP_01520072 | 55 | 72 |
| fadD1 | Pseudomonas aeruginosa | NP_251989 | 54 | 72 |
| fadD2 | Pseudomonas aeruginosa PAO1 | NP_251990 | 55 | 72 |
| fadD | Rhizobium etli CFN42 | YP_533919 | 55 | 72 |
| RPC_4074 | Rhodopseudomonas palustris Bis B18 | YP_533919 | 56 | 72 |
| fadD1 | Rasltonia Solanacearum GMI 1000 | NP_520978 | 56 | 72 |
| fadDD35 | Mycobacterium tuberculosis H37Rv | NP_217021 | 28 | 46 |
| fadDD22 | Mycobacterium tuberculosis H37Rv | NP_217464 | 23 | 42 |
| PRK0059 | Stenotrophomonas MaltophiliaR551-3 | ZP_01644857 | 59 | 75 |

Based on their degree of similarity to E. coli FadD, the following homologous genes were selected to be synthesized and evaluated: fadDD35 from M tuberculosis HR7Rv [NP_217021]; yhfL from B. subtilis [NP_388908]; fadD1 from P. aeruginosa PAO1 [NP_251989]; and fadD homolog, Faa3p from Saccharomyces cerevisiae [NP_012257].

Additional fatty acid acyl-CoA synthases from eukaryotic organisms which can be used to produce acyl-CoA, as well as fatty acid derivatives, include those described in Shockey et al., *Plant. Physiol.* 129: 1710-1722 (2002) (Arabidopsis), Caviglia et al., *J. Biol. Chem.* 279: 1163-1169 (2004) (rat), and Knoll et al., *J. Biol. Chem.* 269(23):16348-56 (1994) (yeast). Gene sequences encoding these synthetases are known in the art. See, e.g., Johnson et al., *J. Biol. Chem.* 269: 18037-18046 (1994); Shockey et al., *Plant. Physiol.* 129: 1710-1722 (2002); Black et al., *J. Biol Chem.* 267: 25513-25520 (1992). These eukaryotic acyl-CoA synthases, despite their lack of high homology to E. coli fadD sequences, can complement FadD activity in E. coli fadD knockouts.

D. Acyl-CoA to Fatty Alcohol

1. Conversion of Acyl-CoA to Fatty Alcohol

Acyl-CoA is reduced to a fatty aldehyde by NADH-dependent acyl-CoA reductase (e.g., Acr1). The fatty aldehyde is then reduced to a fatty alcohol by NADPH-dependent alcohol dehydrogenase (e.g., YqhD). Alternatively, fatty alcohol forming acyl-CoA reductase (FAR) catalyzes the reduction of an acyl-CoA into a fatty alcohol and CoASH. FAR uses NADH or NADPH as a cofactor in this four-electron reduction. Although the alcohol-generating FAR reactions proceed through an aldehyde intermediate, a free aldehyde is not released. Thus, the alcohol-forming FARs are distinct from those enzymes that carry out two-electron reductions of acyl-CoA and yield free fatty aldehyde as a product. (See Cheng et al., *J. Biol. Chem.*, 279(36):37789-37797 (2004); Metz et al., *Plant Physiol.*, 122:635-644 (2000)).

2. Modifications to Increase Conversion of Acyl-CoA to Fatty Alcohol

Production hosts can be engineered using known polypeptides to produce fatty alcohols from acyl-CoA. One exemplary method includes increasing the expression of, or expressing more active forms of, either fatty alcohol forming acyl-CoA reductases (encode by a gene such as acr1 from FAR, EC 1.2.1.50/1.1.1) or acyl-CoA reductases (EC 1.2.1.50), as well as alcohol dehydrogenase (EC 1.1.1.1).

Exemplary GenBank Accession Numbers of these genes include, without limitation, acr1 [GenBank Accession No. YP_047869, or AAC45217]. Other suitable genes have been described in, for example, International Application PCT/US08/058788 (e.g., FIG. 1), which is incorporated herein by reference.

Fatty alcohols can be described as hydrocarbon-based surfactants. For surfactant production, the production host can be modified to produce a surfactant from a renewable carbon source. Such a production host can include a first exogenous DNA sequence encoding a protein capable of converting a fatty acid to a fatty aldehyde and a second exogenous DNA sequence encoding a protein capable of converting a fatty aldehyde to an alcohol. In some examples, the first exogenous DNA sequence can encode a fatty acid reductase. In one embodiment, the second exogenous DNA sequence can encode a mammalian microsomal aldehyde reductase or long-chain aldehyde dehydrogenase. In a further example, the first and second exogenous DNA sequences can be from *Arthrobacter* AK 19, *Rhodotorula glutinins*, *Acinetobacter* sp. strain M-1, or *Candida lipolytica*. In one embodiment, the first and second heterologous DNA sequences can be from a multienzyme complex from *Acinetobacter* sp. strain M-1 or *Candida lipolytica*.

Additional sources of heterologous DNA sequences encoding fatty acid to long chain alcohol converting proteins that can be used in surfactant production include, but are not limited to, *Mortierella alpina* (ATCC 32222), *Cryptococcus curvatus*, (also referred to as *Apiotricum curvatum*), *Alcanivorax jadensis* (T9T =DSM 12718 =ATCC 700854), *Acinetobacter* sp. HO1-N (ATCC 14987) and *Rhodococcus opacus* (PD630 DSMZ 44193).

In one example, the fatty acid derivative is a saturated or unsaturated surfactant product having a carbon chain length of about 6 to about 36 carbon atoms, about 8 to about 30 carbon atoms, about 10 to about 26 carbon atoms, about 12 to about 20 carbon atoms, or about 12 to about 16 carbon atoms. In another example, the surfactant product has a carbon chain length of about 10 to about 18 carbon atoms, or about 12 to about 14 carbon atoms.

Appropriate production hosts for producing surfactants can be from either eukaryotic or prokaryotic microorganisms. Exemplary production hosts include cells of *Arthrobacter* AK 19, *Rhodotorula glutinins*, *Acinetobacter* sp strain M-1, *Arabidopsis thalania, Candida lipolytica, Saccharomyces cerevisiae,* and *E. coli* engineered to express acetyl-CoA carboxylase. Production hosts that synthesize high levels of surfactant precursors in the form of lipids and oils, such as cells of *Rhodococcus opacus, Arthrobacter* AK 19, and *Rhodotorula glutinins E. coli* engineered to express acetyl CoA carboxylase, and other oleaginous bacteria, yeast, and fungi can also be used.

IV. Genetic Engineering of Production Strain to Increase Ethanol Production

The production hosts used to produce fatty acid esters, such as FAEE, can be recombinantly modified to express or over-express specific genes, or to attenuate the expression of specific genes, and thus allows the production hosts to produce ethanol or to increase production of ethanol. Recombinant modifications suitable for use in the present methods to produce ethanol or to increase production of ethanol are described in, e.g., Jarboe et al., *Adv. Biochem. Engin./Biotechnol.* 108:237-261 (2007); Peterson & Ingram, *Ann. N.Y. Acad. Sci.* 1125:363-372 (2008); and Yomano et al., *Biotechnol. Lett.* 30:2097-2103 (2008), which are incorporated herein by reference in their entirety.

Non-limiting examples of genes that can be expressed, overexpressed, or attenuated to produce ethanol include pdc [e.g., GenBank Accession No. YP_163095], adh [e.g., GenBank Accession No. YP_162971], adhA [e.g., GenBank Accession No. AAA71935], adhB [e.g., GenBank Accession No. AAC70367], pflA [e.g., GenBank Accession No. AP_001532], pflB [GenBank Accession No. AAC73989], casA [e.g., GenBank Accession No. AAB51563], casB [GenBank Accession No. AAB51564], frd [e.g., GenBank Accession No. AAT36479], idhA [GenBank Accession No. NP_415898], adhE [e.g., GenBank Accession No. NP_415757], ackA [e.g., GenBank Accession No. AAC75356], focA [e.g., GenBank Accession No. NP_415424], among others. Specifically, non-limiting examples of genes than can be expressed or over-expressed to produce ethanol or increase ethanol production in the present methods include pdc, adh, adhA, adhB, pdh, and casAB. Non-limiting examples of genes than can be attenuated to produce ethanol or increase ethanol production in the present methods include frd, ldhA, pflA, pflB, adhE, ackA, and focA.

E. Genetic Engineering of Production Strain to Increase Ethanol Production

The production hosts used to produce fatty acid esters, such as FAEE, can be recombinantly modified to express or over-express specific genes, or to attenuate the expression of specific genes, and thus allows the production hosts to produce ethanol or to increase production of ethanol. Recombinant modifications suitable for use in the present methods to produce ethanol or to increase production of ethanol are described in, e.g., Jarboe et al., *Adv. Biochem. Engin./Biotechnol.* 108:237-261 (2007); Peterson et al., *Ann. N.Y. Acad. Sci.* 1125:363-372 (2008); and Yomano et al., *Biotechnol. Lett.* 30:2097-2103 (2008), which are incorporated herein by reference in their entirety.

Specifically, non-limiting examples of genes than can be expressed or over-expressed to produce ethanol or increase ethanol production in the present methods include pdc, adh, adhA, adhB, pdh, and casAB. Non-limiting examples of genes than can be attenuated to produce ethanol or increase ethanol production in the present methods include frd, ldhA, pflA, pflB, adhE, ackA, and focA.

F. Fatty Alcohols to Fatty Esters

Production hosts can be engineered using known polypeptides to produce fatty esters of various lengths. One exemplary method includes increasing the expression of, or expressing more active forms of, one or more alcohol O-acetyltransferase peptides (EC 2.3.1.84). These peptides catalyze the acetylation of an alcohol by converting an acetyl-CoA and an alcohol to a CoA and an ester. In some examples, the alcohol O-acetyltransferase peptides can be expressed in conjunction with selected thioesterase peptides, FAS peptides, and fatty alcohol forming peptides, thus allowing the carbon chain length, saturation, and degree of branching to be controlled. In some cases, the bkd operon can be coexpressed to enable branched fatty acid precursors to be produced.

As used herein, alcohol O-acetyltransferase peptides include peptides in enzyme classification number EC 2.3.1.84, as well as any other peptide capable of catalyzing the conversion of acetyl-CoA and an alcohol to form a CoA and an ester. Additionally, one of ordinary skill in the art will appreciate that alcohol O-acetyltransferase peptides will catalyze other reactions.

For example, some alcohol O-acetyltransferase peptides accept other substrates in addition to fatty alcohols or acetyl-CoA thioester, such as other alcohols and other acyl-CoA thioesters. Such non-specific or divergent-specificity alcohol O-acetyltransferase peptides are, therefore, also included. Alcohol O-acetyltransferase peptide sequences are publicly available. Exemplary genes encoding alcohol O-acetyltransferases include, without limitation, aat [GenBank Accession No. AAG13130]. Other O-acetyltransferases have been described in, for example, International Application PCT/US08/058788, (e.g., FIG. 1) which is incorporated herein by reference.

Assays for characterizing the activity of particular alcohol O-acetyltransferase peptides are well known in the art. O-acyltransferases can be engineered to have new activities and specificities for the donor acyl group or acceptor alcohol moiety. Engineered enzymes can be generated through well-documented rational and evolutionary approaches.

G. Acyl-CoA to Fatty Esters

1. Production of Fatty Esters

Fatty esters are synthesized by acyl-CoA:fatty alcohol acyltransferase (e.g., ester synthase), which conjugate an alcohol to a fatty acyl-CoA via an ester linkage. Ester synthases and encoding genes are known from the jojoba plant and the bacterium *Acinetobacter* sp. strain ADP1 (formerly *Acinetobacter calcoaceticus* ADP1). The bacterial ester synthase is a bifunctional enzyme, exhibiting ester synthase activity and the ability to form triacylglycerols from diacylglycerol substrates and fatty acyl-CoAs (acyl-CoA:diglycerol acyltransferase (DGAT) activity). The gene wax/dgat encodes both ester synthase and DGAT. See Cheng et al., *J. Biol. Chem.* 279(36):37798-37807, 2004; Kalscheuer and Steinbuchel, *J. Biol. Chem.* 278:8075-8082, 2003. Ester synthases can also be used to produce certain fatty esters that can be used as a fuel, such as biodiesel, as described herein.

2. Modifications to Produce Fatty Esters

Fatty esters, including waxes, from acyl-CoA and alcohols can be produced using known polypeptides. One exemplary method includes increasing the expression of, or expressing more active forms of, one or more ester synthases (EC 2.3.1.20, 2.3.1.75). Ester synthase peptide sequences are publicly available, a number of which have been described in, for example, International Application PCT/US08/058788 (e.g., FIG. 1) which is incorporated herein by reference. Methods to identify ester synthase activity are provided in, e.g., U.S. Pat. No. 7,118,896, which is herein incorporated by reference in its entirety.

In particular examples, if the desired product is an ester-based biofuel, the production host is modified so that it produces an ester generated from a renewable energy source. Such a production host can include an exogenous DNA sequence encoding an ester synthase that is expressed so as to confer upon said production host the ability to synthesize a saturated, unsaturated, or branched fatty ester from a renewable energy source. In some embodiments, the organism can also express DNA sequence encoding the following exemplary proteins: fatty acid elongases, acyl-CoA reductases, acyltransferases, ester synthases, fatty acyl transferases, diacylglycerol acyltransferases, acyl-coA wax alcohol acyltransferases. In an alternate embodiment, the organism can express a DNA sequence encoding a bifunctional ester synthase/acyl-CoA: diacylglycerol acyltransferase. For example, the bifunctional ester synthase/acyl-CoA: diacylglycerol acyltransferase can be selected from the multienzyme complexes from *Simmondsia chinensis, Acinetobacter* sp. strain ADP1 (formerly *Acinetobacter calcoaceticus* ADP1), *Alcanivorax borkumensis, Pseudomonas aeruginosa, Fundibacter jadensis, Arabidopsis thaliana,* or *Alcaligenes eutrophus* (later renamed *Ralstonia eutropha*). In one embodiment, the fatty acid elongases, acyl-CoA reductases or wax synthases can be from a multienzyme complex from *Alcaligenes eutrophus* (later renamed *Ralstonia eutropha*) or other organisms known in the literature to produce esters, such as wax or fatty esters.

Additional sources of heterologous DNA sequence encoding ester synthesis proteins that can be used in fatty ester production include, but are not limited to, *Mortierella alpina* (e.g., ATCC 32222), *Cryptococcus curvatus* (also referred to as *Apiotricum curvatum*), *Alcanivorax jadensis* (for example T9T =DSM 12718 =ATCC 700854), *Acinetobacter* sp. HO1-N, (e.g., ATCC 14987) and *Rhodococcus opacus* (e.g., PD630, DSMZ 44193).

Production hosts for producing fatty esters can be either eukaryotic or prokaryotic microorganisms. Non-limiting examples of production hosts for producing fatty esters include *Saccharomyces cerevisiae, Candida lipolytica, E. coli Arthrobacter* AK 19, *Rhodotorula glutinins, Acinetobacter* sp. strain M-1, *Candida lipolytica,* and other oleaginous microorganisms.

In one instance, the ester synthase from *Acinetobacter* sp. ADP1 at locus AA017391 (described in Kalscheuer et al., *J. Biol. Chem.* 278:8075-8082 (2003), herein incorporated by reference) is used. In another instance, the ester synthase from *Simmondsia chinensis* at locus AAD38041 is used. Optionally, an ester exporter such as a member of the FATP family can be used to facilitate the release of esters into the extracellular environment. A non-limiting example of an ester exporter that can be used is fatty acid (long chain) transport protein CG7400-PA, isoform A, from *Drosophila melanogaster,* at locus NP_524723.

H. Enhanced Production of FAEE

To enhance production of FAEE, the production host can be engineered to over-express a gene encoding a thioesterase, a gene encoding an acyl-CoA synthase, and a gene encoding an ester synthase. The ester synthase can be a bifunctional wax ester synthase/acyl-CoA: diacylglycerol acyltransferase. Exemplary bifunctional wax ester synthase/acyl-CoA: diacylglycerol acyltransferase genes include, without limitation, atfA1 [GenBank Accession No. AA017391], as well as those described in, for example, International Application PCT/US08/058788 (e.g., FIG. 1), which is incorporated herein by reference. To enhance production of FAEE, any one of or any combination of fadE, fabR, poxB, pflA, pflB, and ldhA can optionally be attenuated, deleted, functionally deleted, or knocked-out. Exemplary GenBank Accession Numbers of these genes include, without limitation, fabR [GenBank Accession No. NP_418398], fadE [GenBank Accession No. AAC73325], poxB [GenBank Accession No. AAC73958 or NP_415392], pflA [GenBank Accession No. AP_001532], pflB [GenBank Accession No. AAC73989], and ldhA [GenBank Accession No. AAC74462 or NP_415898], as well as those described in, for example, International Application PCT/US08/058788 (e.g., FIG. 1), which is incorporated herein by reference. Non-limiting examples of *E. coli* production hosts suitable for use in the instant method include *E. coli* strain ID1 (MG1655 ΔfadE with an operon containing the genes 'tesA, fadD and atfA1 integrated in the chromosome under the control of the Trc promoter) and *E. coli* strain Δ4 (MG1655 ΔfadE ΔfabR ΔpoxB ΔldhA carrying a plasmid containing 'tesA, fadD, and atfA1).

I. Release of Fatty Acid Derivatives—Transport Proteins

Transport proteins can export fatty acid derivatives out of the production host and into the culture medium. Many transport and efflux proteins serve to excrete a large variety of compounds and can be modified to be selective for particular types of fatty acid derivatives. Non-limiting examples of suitable transport proteins include ATP-Binding Cassette (ABC) transport proteins, efflux proteins, and fatty acid transporter proteins (FATP). Additional non-limiting examples of transport proteins include the ABC transport proteins from organisms such as *Caenorhabditis elegans, Arabidopsis thalania, Alkaligenes eutrophus, Rhodococcus erythropolis.* Exemplary ABC transport proteins include CER5, AtMRP5, AmiS2, and AtPGP1. In a preferred embodiment, the ABC transport protein is CER5 [e.g., GenBank Accesion No. AY734542]. Other exemplary transport proteins include, without limitation, AtMRP5 [GenBank Accession No. NP_171908], AmiS2 [Accession No. JC5491], AtPGP1 [GenBank Accession No. NP_181228], as well as those described in, for example, International Application PCT/US08/058788 (e.g., FIG. 1), which is incorporated herein by reference. Vectors containing genes that express suitable transport proteins can be inserted into a production host to increase the release of fatty acid derivatives.

Production hosts can also be chosen for their endogenous ability to release fatty acid derivatives. The efficiency of product production and release into the fermentation broth can be expressed as a ratio of intracellular product to extracellular product. In some examples, the ratio can be about 5:1, 4:1, 3:1, 2:1, 1:1, 1:2, 1:3, 1:4, or 1:5.

II. Selection of Carbon Chain Characteristics of Fatty Acid Derivatives

Fatty acid derivatives with particular branch points, levels of saturation, carbon chain length, and ester characteristics can be produced. Microorganisms that naturally produce particular derivatives can be chosen. Alternatively, microorganisms can be genetically modified to express genes that encode enzymes that can produce particular fatty acid derivatives. Non-limiting examples of enzymes and genes that can be used alone or in combination to make fatty acid derivatives with desired characteristics have been disclosed in, for example, International Application PCT/US08/058788 (e.g., FIG. 1), which is incorporated herein by reference.

In some examples, the expression of exogenous FAS genes originating from different species or engineered variants can be introduced into the production host to result in the biosynthesis of fatty acids that are structurally different (in length, branching, degree of unsaturation, etc.) from those of the native production host. These heterologous gene products can also be chosen or engineered to be unaffected by the natural regulatory mechanisms in the production host, and therefore allow for control of the production of the desired commercial product. For example, the FAS enzymes from *Bacillus subtilis, Saccharomyces cerevisiae, Streptomyces* spp., *Ralstonia, Rhodococcus, Corynebacteria, Brevibacteria, Mycobacteria,* oleaginous yeast, and the like can be expressed in the production host. The expression of such exogenous enzymes can alter the structure of the fatty acid produced.

When a production host is engineered to produce a fatty acid with a specific level of unsaturation, branching, or carbon chain length, the resulting engineered fatty acid can be used in the production of fatty acid derivatives. Fatty acid derivatives generated from such production hosts can display the characteristics of the engineered fatty acid.

For example, a production host can be engineered to make branched, short chain fatty acids, which can then be used by the production host to produce branched, short chain fatty alcohols. Similarly, a hydrocarbon can be produced by engineering a production host to produce a fatty acid having a defined level of branching, unsaturation, and/or carbon chain length, thus, producing a homogeneous hydrocarbon population. Additional steps can be employed to improve the homogeneity of the resulting product. For example, when an unsaturated alcohol, fatty ester, or hydrocarbon is desired, the production host can be engineered to produce low levels of saturated fatty acids and in addition can be modified to express an additional desaturase and thus reduce the production of saturated product.

A. Branched and Cyclic Moieties

1. Engineering Branched and Cyclic Fatty Acid Derivatives

Fatty acids are a key intermediate in the production of fatty acid derivatives. Fatty acid derivatives can be produced that contain branch points, cyclic moieties, and combinations thereof, by using branched or cyclic fatty acids to make the fatty acid derivatives.

For example, *E. coli* naturally produces straight chain fatty acids (sFAs). To engineer *E. coli* to produce branched chain fatty acids (brFAs), several genes that provide branched precursors (e.g., bkd operon) can be introduced into the production host and expressed to allow initiation of fatty acid biosynthesis from branched precursors (e.g., fabH). For example, bkd, ilv, icm, and/or fab gene families can be expressed or over-expressed to produce branched chain fatty acid derivatives. Similarly, to produce cyclic fatty acids, genes that provide cyclic precursors can be introduced into the production host and expressed to allow initiation of fatty acid biosynthesis from cyclic precursors. The ans, chc, and plm gene families can be expressed or over-expressed to produce cyclic fatty acids. Non-limiting examples of genes in these gene families include ansJ, ansK, ansL, chcA [GenBank Accession No. U72144, or AAQ84160], ansM, plmJ [GenBank Accession No. AAQ84158], plmK [GenBank Accession No. AAQ84158], plmL [GenBank Accession No. AAQ84159], plmM [GenBank Accession No. AAQ84161], chcB [GenBank Accession No. AF268489], as well as others including those described in, for example, International Application PCT/US08/058788 (e.g., FIG. 1), which is incorporated herein by reference.

Additionally, the production host can be engineered to express genes encoding proteins for the elongation of brFAs (e.g., ACP, FabF, etc.) and/or to delete or attenuate the corresponding *E. coli* genes that normally lead to sFAs. In this regard, endogenous genes that would compete with the introduced genes (e.g., fabH, fabF) are deleted or attenuated.

The branched acyl-CoA (e.g., 2-methyl-butyryl-CoA, isovaleryl-CoA, isobutyryl-CoA, etc.) are the precursors of brFA. In most microorganisms containing brFA, the brFA are synthesized in two steps from branched amino acids (e.g., isoleucine, leucine, and valine) (Kadena, *Microbiol. Rev.* 55:288 (1991)). A production host can be engineered to express or over-express one or more of the enzymes involved in these two steps to produce brFAs, or to overproduce brFAs. For example, the production host can have an endogenous enzyme that can accomplish one step leading to brFA, therefore only genes encoding enzymes involved in the second step need to be introduced recombinantly.

2. Formation of Branched Fatty Acids and Branched Fatty Acid Derivatives

The first step in forming brFAs is the production of the corresponding α-keto acids by a branched-chain amino acid aminotransferase. Production hosts can endogenously include genes encoding such enzymes or such genes can be recombinantly introduced. *E. coli,* for example, endogenously expresses such an enzyme, IlvE (EC 2.6.1.42; GenBank accession YP_026247). In some production hosts, a heterologous branched-chain amino acid aminotransferase cannot be expressed. However, *E. coli* IlvE or any other branched-chain amino acid aminotransferase (e.g., IlvE from *Lactococcus lactis* (GenBank accession AAF34406), IlvE from *Pseudomonas putida* (GenBank accession NP_745648), or IlvE from *Streptomyces coelicolor* (GenBank accession NP_629657)), if not endogenous, can be introduced. If the aminotransferase reaction is rate limiting in brFA biosynthesis in the chosen production host, then the aminotransferase can be over-expressed.

The second step is the oxidative decarboxylation of the α-ketoacids to the corresponding branched-chain acyl-CoA. This reaction can be catalyzed by a branched-chain α-keto acid dehydrogenase complex (bkd; EC 1.2.4.4.) (Denoya et al., *J. Bacteriol.* 177:3504 (1995)), which consists of E1α/β (decarboxylase), E2 (dihydrolipoyl transacylase) and E3 (dihydrolipoyl dehydrogenase) subunits. These branched-chain α-keto acid dehydrogenase complexes are similar to pyruvate and α-ketoglutarate dehydrogenase complexes. Every microorganism that possesses brFAs and/or grows on branched-chain amino acids can be used as a source to isolate bkd genes for expression in production hosts such as, for example, *E. coli.* Furthermore, *E. coli* has the E3 component as part of its pyruvate dehydrogenase complex (lpd, EC 1.8.1.4, GenBank accession NP_414658). In some methods, only the E1 α/β and E2 bkd genes are expressed in the production host. Table 3 recites non-limiting examples of bkd genes from several microorganisms that can be recombinantly introduced and expressed in a production host to provide branched-chain acyl-CoA precursors. Microorganisms having such bkd genes can also be used as production hosts.

TABLE 3

Bkd genes from selected microorganisms

| Organism | Gene | GenBank Accession # |
| --- | --- | --- |
| *Streptomyces coelicolor* | bkdA1 (E1α) | NP_628006 |
| | bkdB1 (E1β) | NP_628005 |
| | bkdC1 (E2) | NP_628004 |

TABLE 3-continued

Bkd genes from selected microorganisms

| Organism | Gene | GenBank Accession # |
|---|---|---|
| Streptomyces coelicolor | bkdA2 (E1α) | NP_733618 |
| | bkdB2 (E1β) | NP_628019 |
| | bkdC2 (E2) | NP_628018 |
| Streptomyces avermitilis | bkdA (E1a) | BAC72074 |
| | bkdB (E1b) | BAC72075 |
| | bkdC (E2) | BAC72076 |
| Streptomyces avermitilis | bkdF (E1α) | BAC72088 |
| | bkdG (E1β) | BAC72089 |
| | bkdH (E2) | BAC72090 |
| Bacillus subtilis | bkdAA (E1α) | NP_390288 |
| | bkdAB (E1β) | NP_390288 |
| | bkdB (E2) | NP_390288 |
| Pseudomonas putida | bkdA1 (E1α) | AAA65614 |
| | bkdA2 (E1β) | AAA65615 |
| | bkdC (E2) | AAA65617 |

In another example, isobutyryl-CoA can be made in a production host, for example in *E. coli*, through the coexpression of a crotonyl-CoA reductase (Ccr, EC 1.6.5.5, 1.1.1.1) and isobutyryl-CoA mutase (large subunit IcmA, EC 5.4.99.2; small subunit IcmB, EC 5.4.99.2) (Han and Reynolds, *J. Bacteriol.* 179:5157, 1997). Crotonyl-CoA is an intermediate in fatty acid biosynthesis in *E. coli* and other microorganisms. Non-limiting examples of ccr and icm genes from selected microorganisms are given in Table 4.

TABLE 4

Ccr and icm genes from selected microorganisms

| Organism | Gene | GenBank Accession # |
|---|---|---|
| Streptomyces coelicolor | Ccr | NP_630556 |
| | icmA | NP_629554 |
| | icmB | NP_630904 |
| Streptomyces cinnamonensis | ccr | AAD53915 |
| | icmA | AAC08713 |
| | icmB | AJ246005 |

In addition to expression of the bkd genes, the initiation of brFA biosynthesis utilizes β-ketoacyl-acyl-carrier-protein synthase III (FabH, EC 2.3.1.41) with specificity for branched chain acyl-CoAs (Li et al., *J. Bacteriol.* 187:3795-3799, 2005). Non-limiting examples of such FabH enzymes are listed in Table 5. fabH genes that are involved in fatty acid biosynthesis of any brFA-containing microorganism can be expressed in a production host. The Bkd and FabH enzymes from production hosts that do not naturally make brFA can not support brFA production, therefore Bkd and FabH can be expressed recombinantly. Vectors containing the bkd and fabH genes can be inserted into such a production host. Similarly, the endogenous level of Bkd and FabH production can not be sufficient to produce brFA, therefore, they can be over-expressed. Additionally, other components of fatty acid biosynthesis pathway can be expressed or over-expressed, such as acyl carrier proteins (ACPs) and β-ketoacyl-acyl-carrier-protein synthase II (fabF, EC 2.3.1.41) (non-limiting examples of candidates are listed in Table 5). In addition to expressing these genes, some genes in the endogenous fatty acid biosynthesis pathway can be attenuated in the production host. Genes encoding enzymes that would compete for substrate with the enzymes of the pathway that result in brFA production can be attenuated to increase brFA production. For example, in *E. coli* the most likely candidates to interfere with brFA biosynthesis are fabH (GenBank accession # NP_415609) and/or fabF genes (GenBank accession # NP_415613).

TABLE 5

FabH, ACP and fabF genes from selected microorganisms with brFAs

| Organism | Gene | GenBank Accession # |
|---|---|---|
| Streptomyces coelicolor | fabH1 | NP_626634 |
| | ACP | NP_626635 |
| | fabF | NP_626636 |
| Streptomyces avermitilis | fabH3 | NP_823466 |
| | fabC3 (ACP) | NP_823467 |
| | fabF | NP_823468 |
| Bacillus subtilis | fabH_A | NP_389015 |
| | fabH_B | NP_388898 |
| | ACP | NP_389474 |
| | fabF | NP_389016 |
| Stenotrophomonas maltophilia | SmalDRAFT_0818 (FabH) | ZP_01643059 |
| | SmalDRAFT_0821 (ACP) | ZP_01643063 |
| | SmalDRAFT_0822 (FabF) | ZP_01643064 |
| Legionella pneumophila | FabH | YP_123672 |
| | ACP | YP_123675 |
| | fabF | YP_123676 |

As mentioned above, branched chain alcohols can be produced through the combination of expressing genes that support brFA synthesis and alcohol synthesis. For example, when an alcohol reductase, such as Acr1 from *Acinetobacter baylyi* ADP1, is coexpressed with a bkd operon, *E. coli* can synthesize isopentanol, isobutanol or 2-methyl butanol. Similarly, when Acr1 is coexpressed with ccr/icm genes, *E. coli* can synthesize isobutanol.

3. Formation of Cyclic Fatty Acids and Cyclic Fatty Acid Derivatives

To convert a production host such as *E. coli* cell into a cell capable of synthesizing w-cyclic fatty acids (cyFA), a gene that provides the cyclic precursor cyclohexylcarbonyl-CoA (CHC-CoA) (Cropp et al., *Nature Biotech.* 18:980-983, 2000) is introduced and expressed in the production host. A similar conversion is possible for other production hosts, for example, cells of bacteria, yeast, cyanobacteria, and filamentous fungi.

Non-limiting examples of genes that provide CHC-CoA in *E. coli* include: ansJ, ansK, ansL, chcA and ansM from the ansatrienin gene cluster of *Streptomyces collinus* (Chen et al., *Eur. J. Biochem.* 261: 98-107 (1999)) or plmJ, plmK, plmL, chcA and plmM from the phoslactomycin B gene cluster of *Streptomyces* sp. HK803 (Palaniappan et al., *J. Biol. Chem.* 278:35552-35557 (2003)) together with the chcB gene (Patton et al., *Biochem.* 39:7595-7604 (2000)) from *S. collinus, S. avermifilis* or *S. coelicolor* (see Table 6 for GenBank accession numbers). The genes listed above in Table 5 can then be expressed to allow initiation and elongation of w-cyclic fatty acids. Alternatively, the homologous genes can be isolated from microorganisms that make cyFA and expressed in *E. coli*.

TABLE 6

Genes for the synthesis of CHC-CoA

| Organism | Gene | GenBank Accession # |
|---|---|---|
| Streptomyces collinus | ansJK | U72144* |
| | ansL | |
| | chcA | |
| | ansM | |
| | chcB | AF268489 |

TABLE 6-continued

Genes for the synthesis of CHC-CoA

| Organism | Gene | GenBank Accession # |
|---|---|---|
| Streptomyces sp. HK803 | pmlJK | AAQ84158 |
| | pmlL | AAQ84159 |
| | chcA | AAQ84160 |
| | pmlM | AAQ84161 |
| Streptomyces coelicolor | chcB/caiD | NP_629292 |
| Streptomyces avermitilis | chcB/caiD | NP_629292 |

*Only chcA is annotated in GenBank entry U72144 ansJKLM and according to Chen et al. (*Eur. J. Biochem.* 261: 98-107 (1999)).

The genes listed in Table 5 (fabH, ACP and fabF) are sufficient to allow initiation and elongation of w-cyclic fatty acids because they can have broad substrate specificity. If the coexpression of any of these genes with the ansJKLM/chcAB or pmlJKLM/chcAB genes from Table 5 does not yield cyFA, then fabH, ACP and/or fabF homologs from microorganisms that make cyFAs can be isolated (e.g., by using degenerate PCR primers or heterologous DNA sequence probes) and coexpressed. Table 7 lists non-limiting examples of microorganisms that contain w-cyclic fatty acids.

TABLE 7

Non-limiting examples of microorganisms that contain ω-cyclic fatty acids

| Organism | Reference |
|---|---|
| *Curtobacterium pusillum* | ATCC19096 |
| *Alicyclobacillus acidoterrestris* | ATCC49025 |
| *Alicyclobacillus acidocaldarius* | ATCC27009 |
| *Alicyclobacillus cycloheptanicus* * | Moore, *J. Org. Chem.* 62: pp. 2173, 1997. |

* Uses cycloheptylcarbonyl-CoA and not cyclohexylcarbonyl-CoA as precursor for cyFA biosynthesis.

B. Saturation

Fatty acids are a key intermediate in the production of fatty acid derivatives. The degree of saturation in fatty acid derivatives can be controlled by regulating the degree of saturation of the fatty acid intermediates. The sfa, gns, and fab families of genes can be expressed or over-expressed to control the saturation of fatty acids. Exemplary genes from these families include, without limitation, sfa [GenBank Accession Nos. AAN79590, ACC44390]; gnsA [GenBank Accession No. ABD 18647.1], gnsB [GenBank Accession No. AAC74076.1], fabB [GenBank Accession No. BAA16180], fabK [GenBank Accession No. AAF98273], fabL [GenBank Accession No. AAU39821], and fabM [GenBank Accession No. DAA05501], as well as those described in, for example, International Application PCT/US08/058788 (e.g., FIG. 1), which is incorporated herein by reference.

Production hosts can be engineered to produce unsaturated fatty acids by engineering the production host to over-express fabB, or by growing the production host at low temperatures (e.g., less than 37° C.). FabB has preference to cis-δ³decenoyl-ACP and results in unsaturated fatty acid production in *E. coli*. Over-expression of fabB results in the production of a significant percentage of unsaturated fatty acids (de Mendoza et al., *J. Biol. Chem.*, 258:2098-101 (1983)). fabB can be inserted into and expressed in production hosts not naturally having the gene. These unsaturated fatty acids can then be used as intermediates in production hosts that are engineered to produce fatty acid derivatives, such as fatty alcohols, fatty esters, waxes, olefins, alkanes, and the like.

Alternatively, the repressor of fatty acid biosynthesis, for example, fabR (GenBank accession NP_418398), can be deleted, which will also result in increased unsaturated fatty acid production in *E. coli* (Zhang et al., *J. Biol. Chem.* 277:15558 (2002)). Similar deletions can be made in other production hosts. Further increase in unsaturated fatty acids can be achieved, for example, by over-expression of fabM (trans-2, cis-3-decenoyl-ACP isomerase, GenBank accession DAA05501) and controlled expression of fabK (trans-2-enoyl-ACP reductase II, GenBank accession NP_357969) from *Streptococcus pneumoniae* (Marrakchi et al., *J. Biol. Chem.* 277: 44809, 2002), while deleting *E. coli* fabI (trans-2-enoyl-ACP reductase, GenBank accession NP_415804). Additionally, to increase the percentage of unsaturated fatty esters, the production host can also over-express fabB (encoding β-ketoacyl-ACP synthase I, Accessions: BAA16180, EC:2.3.1.41), sfa (encoding a suppressor of fabA, Accession: AAC44390), and gnsA and gnsB (both encoding secG null mutant suppressors, (i.e., cold shock proteins), Accession:ABD18647.1, AAC74076.1). In some examples, the endogenous fabF gene can be attenuated, thus increasing the percentage of palmitoleate ($C_{16:1}$) produced.

C. Chain Length and Ester Characteristics 1. Chain Length and Production of Odd-Numbered Chains The methods described herein permit production of fatty esters and fatty acid derivatives of varied lengths. Chain length is controlled by thioesterase, which is produced by expression of the tes and fat gene families. By expressing specific thioesterases, fatty acids and fatty acid derivatives having a desired carbon chain length can be produced. Non-limiting examples of suitable thioesterases include TesA [GenBank Accession No. POADA1], TesA without leader sequence [GenBank Accession No. AAC73596, NP_415027, or POADA1], FatB1 [GenBank Accession No. Q41635], FatB2 [GenBank Accession No. AAC49269], FatB3 [GenBank Accession No. AAC72881], FatB [GenBank Accession No. Q39473, or CAA85388], FatA1 [GenBank Accession No. AAL79361], AtFatA [GenBank Accession No. NP_189147, NP_193041], FatA [GenBank Accession No. CAC 39106 or AAC72883] and others described in, for example, International Application PCT/US08/058788 (e.g., FIG. 1), which is incorporated herein by reference. A gene encoding a particular thioesterase can be introduced into a production host so that a fatty acid or fatty acid derivative of a particular carbon chain length is produced. Expression of endogenous thioesterases should then be suppressed.

In one embodiment, the fatty acid derivative contain a carbon chain of about 4 to 36 carbon atoms, about 6 to 32 carbon atoms, about 10 to 30 carbon atoms, about 10 to 18 carbon atoms, about 24 to 32 carbon atoms, about 26 to 30 carbon atoms, about 26 to 32 carbon atoms, about 5 to 10 carbon atoms, about 10 to 16 carbon atoms, or about 12 to 18 carbon atoms. In an alternate embodiment, the fatty acid derivative contain a carbon chain less than about 20 carbon atoms, less than about 18 carbon atoms, or less than about 16 carbon atoms. In another embodiment, the fatty ester product is a saturated or unsaturated fatty ester product having a carbon atom content between 24 and 46 carbon atoms. In one embodiment, the fatty ester product has a carbon atom content between 24 and 32 carbon atoms. In another embodiment, the fatty ester product has a carbon content of 14 and 20 carbons. In another embodiment, the fatty ester is the methyl ester of $C_{18:1}$. In another embodiment, the fatty ester is the ethyl ester of $C_{16:1}$. In another embodiment, the fatty ester is the methyl ester of $C_{16:1}$.

Some microorganisms preferentially produce even- or odd-numbered carbon chain fatty acids and fatty acid derivatives. For example, *E. coli* normally produce even-numbered carbon chain fatty acids and fatty acid ethyl esters (FAEE). Surprisingly, the methods disclosed herein can be used to alter that production. For example, *E. coli* can be made to produce odd-numbered carbon chain fatty acids and FAEE.

2. Ester Characteristics

An ester includes what is designated an "A" side and a "B" side. The A side is the carbon chain attached to the carboxylate oxygen of the ester. The B side is the carbon chain comprising the parent carboxylate of the ester. The B side can be contributed by a fatty acid produced from de novo synthesis in the production host. In some embodiments where the production host is additionally engineered to make alcohols (including fatty alcohols) the A side is also produced by the production host. In yet other embodiments, the A side can be provided exogenously, e.g., in the culture medium. By selecting the desired thioesterase genes, the B side (and the A side when fatty alcohols are being made) can be designed to be have certain carbon chain characteristics. These characteristics include points of branching, unsaturation, and desired carbon chain lengths.

When particular thioesterase genes are selected, the A side and B side will have similar carbon chain characteristics when they are both contributed by the production host using fatty acid biosynthetic pathway intermediates. For example, at least about 50%, 60%, 70%, or 80% of the fatty esters produced will have A sides and B sides that vary by about 2, 4, 6, 8, 10, 12, or 14 carbons in length. The A side and the B side can also display similar branching and saturation levels.

In addition to producing fatty alcohols for contribution to the A side, the production host can produce other short chain alcohols such as ethanol, propanol, isopropanol, isobutanol, and butanol for incorporation into the A side using techniques well known in the art. For example, butanol can be made by the production host. To create butanol producing cells, the LS9001 strain, for example, can be further engineered to express atoB (acetyl-CoA acetyltransferase) from *E. coli* K12, β-hydroxybutyryl-CoA dehydrogenase from *Butyrivibrio fibrisolvens*, crotonase from *Clostridium beijerinckii*, butyryl CoA dehydrogenase from *Clostridium beijerinckii*, CoA-acylating aldehyde dehydrogenase (ALDH) from *Cladosporium fulvum*, and adhE encoding an aldehyde-alcohol dehydrogenase of *Clostridium acetobutylicum* in the pBAD24 expression vector under the prpBCDE promoter system. Other production hosts can be similarly modified to produce butanol or other short chain alcohols. For example, ethanol can be produced in a production host using the methods taught by Kalscheuer et al., *Microbiology* 152:2529-2536 (2006), which is herein incorporated by reference.

III. Genetic Engineering of Production Strain to Increase Fatty Acid Derivative Production Heterologous DNA sequences involved in a biosynthetic pathway for the production of fatty acid derivatives can be introduced stably or transiently into a production host using techniques well known in the art (non-limiting examples include electroporation, calcium phosphate precipitation, DEAE-dextran mediated transfection, liposome-mediated transfection, conjugation, transduction, and genomic integration). For stable transformation, a DNA sequence can further include a selectable marker, including non-limiting examples such as antibiotic resistance and genes that complement auxotrophic deficiencies.

Various embodiments of this disclosure can utilize an expression vector that includes a heterologous DNA sequence encoding a protein involved in a metabolic or biosynthetic pathway. Suitable expression vectors include, but are not limited to, viral vectors (such as baculovirus vectors), phage vectors (such as bacteriophage vectors), plasmids, phagemids, cosmids, fosmids, bacterial artificial chromosomes, viral vectors (e.g., viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors for specific production hosts of interest (such as cells of *E. coli, Pseudomonas pisum,* and *Saccharomyces cerevisiae*).

Useful expression vectors can include one or more selectable marker genes to provide a phenotypic trait for selection of transformed production hosts. The selectable marker gene encodes a protein necessary for the survival or growth of transformed production hosts grown in a selective culture medium. Production hosts not transformed with the vector containing the selectable marker gene will not survive in the culture medium. Typical selection genes encode proteins that (a) confer resistance to antibiotics or other toxins (e.g., ampicillin, neomycin, methotrexate, or tetracycline); (b) complement auxotrophic deficiencies; or (c) supply critical nutrients not available from complex media (e.g., the gene encoding D-alanine racemate for *Bacilli*). In alternative embodiments, the selectable marker gene is one that encodes dihydrofolate reductase or confers neomycin resistance (for use in eukaryotic cell culture), or one that confers tetracycline or ampicillin resistance (for use in a prokaryotic production host, such as a cell of *E. coli*).

In the expression vector, the DNA sequence encoding the gene in the biosynthetic pathway is operably linked to an appropriate expression control sequence, (promoters, enhancers, and the like) to direct synthesis of the encoded gene product. Such promoters can be derived from microbial or viral sources, including CMV and SV40. Depending on the production host/vector system utilized, any number of suitable transcription and translation control elements can be used in the expression vector, including constitutive and inducible promoters, transcription enhancer elements, transcription terminators, etc. (see, e.g., Bitter et al., *Methods in Enzymology,* 153:516-544 (1987)).

Suitable promoters for use in prokaryotic production hosts include, but are not limited to, promoters capable of recognizing the T4, T3, Sp6 and T7 polymerases, the $P_R$ and $P_L$ promoters of bacteriophage lambda, the Trp, recA, heat shock, and lacZ promoters of *E. coli,* the alpha-amylase and the sigma-specific promoters of *B. subtilis,* the promoters of the bacteriophages of *Bacillus, Streptomyces* promoters, the int promoter of bacteriophage lambda, the bla promoter of the beta-lactamase gene of pBR322, and the CAT promoter of the chloramphenicol acetyl transferase gene. Additional prokaryotic promoters are described in Glick, *J. Ind. Microbiol.* 1:277 (1987); Watson et al., MOLECULAR BIOLOGY OF THE GENE, 4th Ed. (1987), Benjamin Cummins (1987); and Sambrook et al., MOLECULAR CLONING: A LABORATORY MANUAL, 2nd Ed. (Cold Spring Harbor Laboratory Press (1989)). Non-limiting examples of suitable eukaryotic promoters for use within a eukaryotic production host are viral in origin and include the promoter of the mouse metallothionein I gene (Hamer et al., *J. Mol. Appl. Gen.* 1:273 (1982)); the TK promoter of herpes virus (McKnight, *Cell* 31:355 (1982)); the SV40 early promoter (Benoist et al., *Nature* 290:304

(1981)); the cytomegalovirus promoter (Foecking et al., *Gene* 45:101 (1980)); the yeast gal4 gene promoter (Johnston et al., *PNAS* (USA) 79:6971 (1982); Silver et al., *PNAS* 81:5951 (1984)); and the IgG promoter (Orlandi et al., *PNAS* (*USA*) 86:3833 (1989)).

The production host can be genetically modified with a heterologous DNA sequence encoding a biosynthetic pathway gene product that is operably linked to an inducible promoter. Inducible promoters are well known in the art. Non-limiting examples of suitable inducible promoters include promoters that are affected by proteins, metabolites, or chemicals. These include, but are not limited to: a bovine leukemia virus promoter, a metallothionein promoter, a dexamethasone-inducible MMTV promoter, an SV40 promoter, an MRP polIII promoter, a tetracycline-inducible CMV promoter (such as the human immediate-early CMV promoter) as well as those from the Trp and lac operons.

In some examples, a production host is genetically modified with a heterologous DNA sequence encoding a biosynthetic pathway gene product that is operably linked to a constitutive promoter. Suitable constitutive promoters are known in the art and include constitutive adenovirus major late promoter, a constitutive MPSV promoter, or a constitutive CMV promoter.

In some examples, a modified production host is one that is genetically modified with an exogenous DNA sequence encoding a single protein involved in a biosynthesis pathway. In other embodiments, a modified production host is one that is genetically modified with exogenous DNA sequences encoding two or more proteins involved in a biosynthesis pathway, for example, the first and second enzymes in a biosynthetic pathway.

Where the production host is genetically modified to express two or more proteins involved in a biosynthetic pathway, those DNA sequences can each be contained in a single or in separate expression vectors. When those DNA sequences are contained in a single expression vector, in some embodiments, the nucleotide sequences will be operably linked to a common control element where the common control element controls expression of all of the biosynthetic pathway protein-encoding DNA sequences in the single expression vector (e.g., a promoter).

When a modified production host is genetically modified with heterologous DNA sequences encoding two or more proteins involved in a biosynthesis pathway, one of the DNA sequences can be operably linked to an inducible promoter, and one or more of the DNA sequences can be operably linked to a constitutive promoter.

In some embodiments, the intracellular concentration (e.g., the concentration of the intermediate in the genetically modified production host) of the biosynthetic pathway intermediate can be increased to further boost the yield of the final product. The intracellular concentration of the intermediate can be increased in a number of ways, including, but not limited to, increasing the concentration in the culture medium of a substrate for a biosynthetic pathway; increasing the catalytic activity of an enzyme that is active in the biosynthetic pathway; increasing the intracellular amount of a substrate (e.g., a primary substrate) for an enzyme that is active in the biosynthetic pathway; and the like.

In some examples, the fatty acid derivative or intermediate is produced in the cytoplasm of the production host. The cytoplasmic concentration can be increased in a number of ways, including, but not limited to, increasing the amount of carbon flux through the fatty acid pathway. Additionally, the concentration of acyl-CoA can be increased by increasing the biosynthesis of CoA in the cell, such as by over-expressing genes associated with pantothenate biosynthesis (e.g., panD) or knocking out the genes associated with glutathione biosynthesis (e.g., glutathione synthase).

Regulatory sequences, coding sequences, and combinations thereof, can be introduced or altered in the chromosome of the production host. In some examples, the integration of the desired recombinant sequence into the production host genomic sequence does not require the use of a selectable marker such as an antibiotic. In some examples, the genomic alterations include changing the control sequence of the target genes by replacing the native promoter(s) with a promoter that is insensitive to regulation. There are numerous approaches for doing this. For example, Valle and Flores, Methods Mol. Biol. 267:113-122, 2006, describes a PCR-based method to over-express chromosomal genes in *E. coli*. Another approach is based on the use of single-strand oligonucleotides to create specific mutations directly in the chromosome, using the technology developed by Court et al., *Proc. Nat. Acad. Sci.* 100:15748-15753, 2003. This technology is based on the use of the over-expression of the Beta protein from the bacteriophage lambda to enhance genetic recombination. The advantages of this approach are that synthetic oligonucleotides 70 bases long (or more) can be used to create point mutations, insertions, and deletions, thus eliminating any cloning steps. Furthermore, the system is sufficiently efficient that no markers are necessary to isolate the desired mutations.

With this approach the regulatory region of a gene can be changed to create a stronger promoter and/or eliminate the binding site of a repressor. In such a manner, a desired gene can be overexpressed in the production host.

IV. Fermentation

A. Maximizing Production Efficiency

The production and isolation of fatty acid derivatives can be enhanced by employing specific fermentation techniques. One method for maximizing production while reducing costs is increasing the percentage of the carbon source that is converted to hydrocarbon products.

During normal cellular lifecycles carbon is used in cellular functions including producing lipids, saccharides, proteins, organic acids, and nucleic acids. Reducing the amount of carbon necessary for growth-related activities can increase the efficiency of carbon source conversion to output. This can be achieved by first growing microorganisms to a desired density, such as a density achieved at the peak of the log phase of growth. At such a point, replication checkpoint genes can be harnessed to stop the growth of cells. Specifically, quorum sensing mechanisms (reviewed in Camilli et al., *Science* 311:1113 (2006); Venturi, *FEMS Microbio. Rev.* 30:274-291 (2006); and Reading et al., *FEMS Microbiol. Lett.* 254:1-11 (2006), which references are incorporated by reference herein) can be used to activate genes such as p53, p21, or other checkpoint genes.

Genes that can be activated to stop cell replication and growth in *E. coli* include umuDC genes, the over-expression of which stops the progression from stationary phase to exponential growth (Murli et al., *J. of Bact.* 182:1127 (2000)). UmuC is a DNA polymerase that can carry out translesion synthesis over non-coding lesions—the mechanistic basis of most UV and chemical mutagenesis. The umuDC gene products are used for the process of translesion synthesis and also serve as a DNA sequence damage checkpoint. The umuDC gene products include UmuC, UmuD, umuD', UmuD'$_2$C, UmuD'$_2$ and UmuD'$_2$. Simultaneously, the product-producing genes could be activated, thus minimizing the need for replication and maintenance pathways to be used while the fatty acid derivative is being made.

Production hosts s can also be engineered to express umuC and umuD from *E. coli* in pBAD24 under the prpBCDE promoter system through de novo synthesis of this gene with the appropriate end-product production genes.

The percentage of input carbons converted to fatty esters or hydrocarbon products is a cost driver. The more efficient the process is (i.e., the higher the percentage of input carbons converted to fatty esters or hydrocarbon products), the less expensive the process will be. For oxygen-containing carbon sources (e.g., glucose and other carbohydrate based sources), the oxygen must be released in the form of carbon dioxide. For every 2 oxygen atoms released, a carbon atom is also released leading to a maximal theoretical metabolic efficiency of ~34% (w/w) (for fatty acid derived products). This figure, however, changes for other hydrocarbon products and carbon sources. Typical efficiencies in the literature are approximately <5%. Production hosts engineered to produce hydrocarbon products can have greater than 1, 3, 5, 10, 15, 20, 25, and 30% efficiency. In one example, production hosts will exhibit an efficiency of about 10% to about 25%. In other examples, such production hosts will exhibit an efficiency of about 25% to about 30%. In other examples, such production hosts will exhibit >30% efficiency.

The production host can be additionally engineered to express recombinant cellulosomes, such as those described in PCT publication number WO/2008/100251, incorporated herein by reference in its entirety, which could allow the production host to use cellulosic material as a carbon source. For example, the production host can be additionally engineered to express invertases (EC 3.2.1.26) so that sucrose can be used as a carbon source.

Similarly, the production host can be engineered using the teachings described in U.S. Pat. Nos. 5,000,000; 5,028,539; 5,424,202; 5,482,846; and 5,602,030 to Ingram et al., all incorporated herein by reference in their entirety, so that the production host can assimilate carbon efficiently and use cellulosic materials as carbon sources.

In one example, the fermentation chamber will enclose a fermentation that is undergoing a continuous reduction. In this instance, a stable reductive environment would be created. The electron balance would be maintained by the release of carbon dioxide (in gaseous form). Efforts to augment the NAD/H and NADP/H balance can also facilitate in stabilizing the electron balance. The availability of intracellular NADPH can also be enhanced by engineering the production host to express an NADH:NADPH transhydrogenase. The expression of one or more NADH:NADPH transhydrogenase converts the NADH produced in glycolysis to NADPH which enhances the production of fatty acid derivatives.

B. Use of Glucose

In some instances, the methods disclosed herein are performed using glucose as a carbon source. In certain instances, microorganisms are grown in a culture medium containing an initial glucose concentration of about 2 g/L to about 50 g/L, such as about 5 g/L to about 20 g/L. In some instances, the glucose concentration of the culture medium decreases from the initial glucose concentration as the microorganisms consume the glucose, and a concentration of about 0 g/L to about 5 g/L glucose is maintained in the culture medium during the fatty acid ester production process. In certain instances, glucose is fed to the microorganisms in a solution of about 50% to about 65% glucose.

In some instances, the feed rate of glucose is set to match the cells' growth rate to avoid excess accumulation of glucose (i.e., >0% glucose) in the fermentor. In other instances, and a low concentration of excess glucose (e.g., about 2 g/L to about 5 g/L) is maintained. In certain instances, fatty acid esters can be produced from carbohydrates other than glucose, including but not limited to fructose, hydrolyzed sucrose, hydrolyzed molasses and glycerol.

C. FAEE Production With or Without Exogenous Alcohol

In some instances, the fatty acid ester production methods disclosed herein are performed in fermentors, e.g., as described in. For example, a cell culture is grown overnight, and an aliquot of the culture is used to inoculate an appropriate culture medium containing about 5 g/L to about 50 g/L of glucose in a fermentor with temperature, pH, agitation, aeration and dissolved oxygen control. An initial glucose concentration of about 5 g/L to about 20 g/L is preferred. Suitable conditions can include, e.g., a temperature of about 30° C. to about 35° C., a pH of about 6.6 to about 7.0, and a dissolved oxygen (DO) concentration of about 10% to about 50% of saturation. pH can be maintained by the addition of appropriate acids or bases, e.g., $NH_4OH$. In particular instances, the cells are maintained in aerobic conditions.

In some instances, about 0 g/L to about 5 g/L glucose is maintained in the fermentor during the fatty acid ester production process. Without being bound by any theory, it is believed that this process limits formation of acetate while allowing for production of ethanol. In certain instances, a glucose solution of about 50% to about 65% glucose is used in the feed stream.

In some methods, exogenous alcohol is added to the fermentor. In such instances, the feed rate of glucose is set to match the cells' growth rate to avoid excess accumulation of glucose (i.e., >0% glucose) in the fermentor. In other methods, exogenous alcohol is not supplied, and a low concentration of excess glucose (e.g., about 2 g/L to about 5 g/L) is maintained.

Most industrial and pharmaceutical fermentation processes using *E. coli* are fed batch processes where the initial glucose feed rate responds to an exponential pattern that supports a desired growth rate, followed by a production phase in which the glucose feed rate is kept constant. During the growth phase, it is common to use glucose feed rates that correspond to growth rates between about 0.1 $h^{-1}$ and about 0.4 $h^{-1}$. Faster glucose feed rates can also be used if a complex medium is supplied. The glucose feed rate during the production phase depends on factors such as cell density, glucose uptake rate and oxygen supply. In some of the methods described herein, glucose feed rates from about 4 g/L/h to about 15 g/L/h are used, such as glucose feed rates between about 8 g/L/h and about 12 g/L/h.

Any medium suitable to sustain *E. coli* growth can be used in the methods described herein. Non-limiting examples of suitable media are described in Molecular Cloning: A Laboratory Manual, 2nd Ed., ed. by Sambrook, Fritsch and Maniatis (Cold Spring Harbor Laboratory Press: 1989), which is incorporated herein by reference in its entirety. The media and feed concentrations of nutrients such as sugars, nitrogen, phosphorous, magnesium, sulfur and potassium will determine the maximum cell density obtained in the fermentation. Micronutrients such as trace elements and vitamins are not required for *E. coli* growth, but usually allow for faster growth and can be required to improve the efficiency of the production pathway. This is also the case when complex nutrient sources are added. Non-limiting examples of such sources include yeast extract, protein hydrolysates (of milk, soy, cotton and other sources), peptones, and corn steep liquor. In the present fermentation process, the addition of amino acids improves both the initial growth and production rates.

In certain methods, during the early phases of cell growth, the production of esters can be induced by the addition of 1 mM isopropyl β-D-1-thiogalactopyranoside (IPTG). When exogenous alcohol is supplied, the alcohol is added at the time of induction (i.e., when IPTG is added) at a concentration of 20 mL/L. When exogenous alcohol is supplied, the alcohol is added several times during the run to maintain a concentration of about 10 mL/L to about 30 mL/L.

EXAMPLES

The examples that follow illustrate the engineering of production hosts to produce fatty acid esters, such as FAEE. The biosynthetic pathway involved in the production of fatty acid derivatives, such as FAEE, are illustrated in the figures.

For example, FIG. 1 is a diagram of the FAS pathway showing the enzymes directly involved in the synthesis of acyl-ACP. To increase the production of fatty acid derivatives, such as waxes, fatty esters, fatty alcohols, and hydrocarbons one or more of the enzymes in FIG. 1 can be over expressed or mutated to reduce feedback inhibition to increase the amount of acyl-ACP produced. Additionally, enzymes that metabolize the intermediates to make non-fatty acid based products (side reactions) can be functionally deleted or attenuated to increase the flux of carbon through the fatty acid biosynthetic pathway. In the examples below, many production hosts are described that have been modified to increase fatty acid production.

Figure 3:
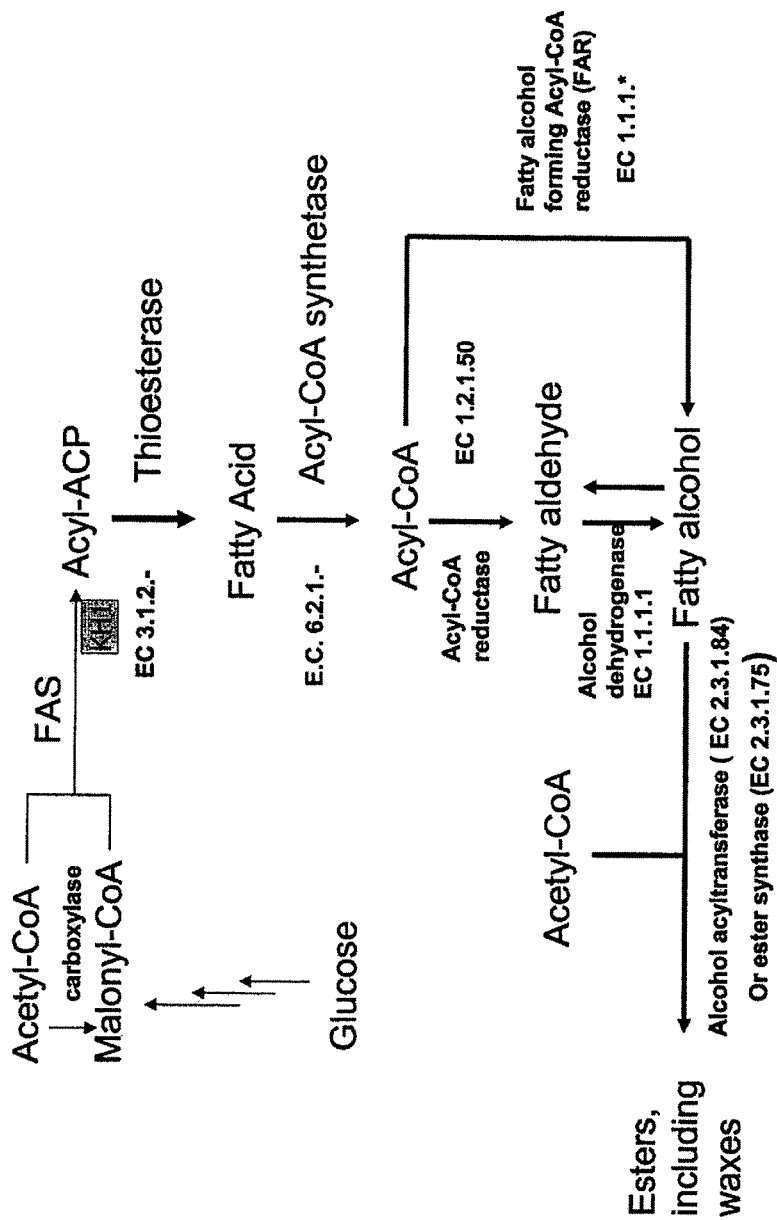
FIG. 3 is a diagram illustrating biosynthetic pathways that produce fatty esters depending upon the substrates provided.
Figure 4:
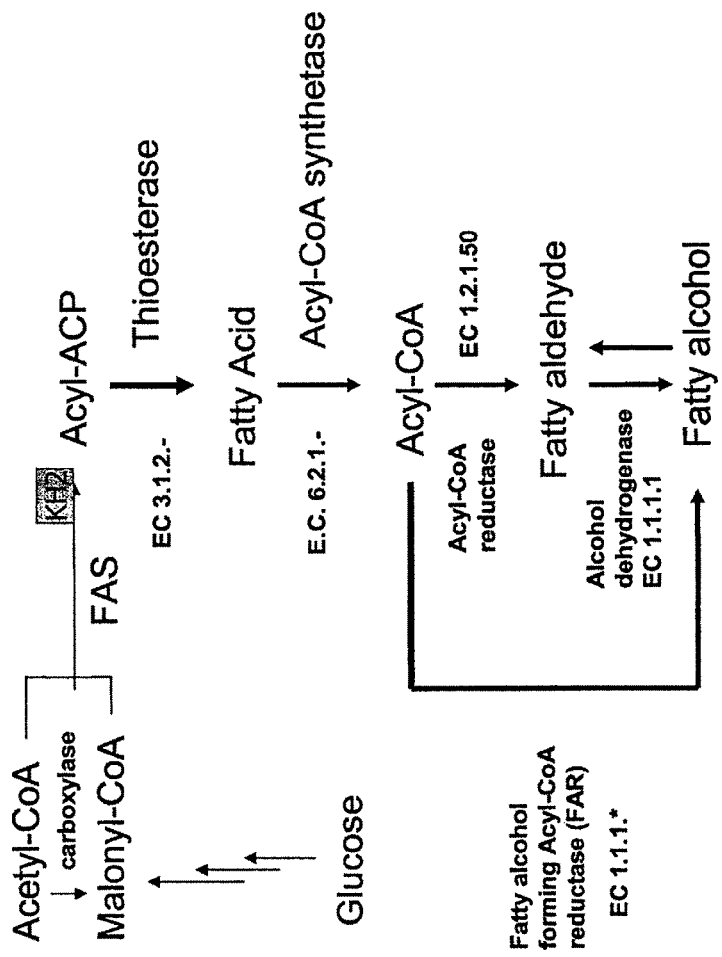
FIG. 4 is a diagram illustrating biosynthetic pathways that produce fatty alcohols.
Figure 5:
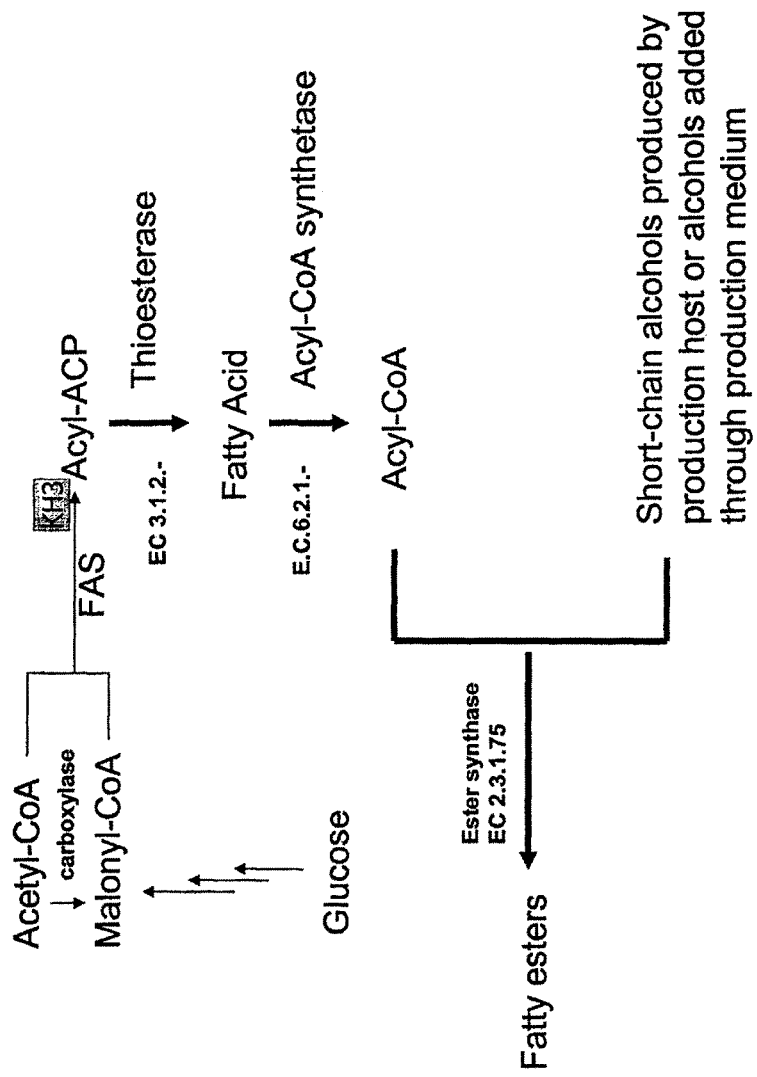
FIG. 5 is a diagram illustrating biosynthetic pathways that produce fatty esters.

FIG. 3, FIG. 4, and FIG. 5 show biosynthetic pathways that can be engineered to make fatty alcohols and fatty esters, respectively. As illustrated in FIG. 4, the conversion of each substrate (e.g., acetyl-CoA, malonyl-CoA, acyl-ACP, fatty acid, and acyl-CoA) to each product (e.g., acetyl-CoA, malonyl-CoA, acyl-ACP, fatty acid, and acyl-CoA) can be accomplished using several different polypeptides that are members of the enzyme classes indicated.

The examples below describe methods of producing FAEE by fermenting microorganisms with or without exogenous alcohol.

Methods

The following methods were used in the Examples described below.

Glucose Concentration

Glucose concentration throughout the fermentation was analyzed by High Pressure Liquid Chromatography (HPLC). The HPLC analysis was performed according to the following conditions: Agilent HPLC 1200 Series with Refractive Index detector; Column: Aminex HPX-87H, 300 mm×7.8 mm; column temperature: 35° C.; mobile phase: 0.01 M $H_2SO_4$ (aqueous); flow rate: 0.6 mL/min; injection volume: 20 μL.

Fatty Acid Ester Concentration

The production of fatty acid methyl esters (referred to herein as "FAME") and FAEE was analyzed by gas chromatography with flame ionization detector (GC-FID). The samples from fermentation broth were extracted with ethyl acetate in a ratio of 1:1 vol/vol. After strong vortexing, the samples were centrifuged and the organic phase was analyzed by gas chromatography (GC). The analysis conditions were as follows: instrument: Trace GC Ultra, Thermo Electron Corporation with Flame ionization detector (FID) detector; column: DB-1 (1% diphenyl siloxane; 99% dimethyl siloxane) CO1 UFM 1/0.1/5 01 DET from Thermo Electron Corporation, phase pH 5, FT: 0.4 μm, length 5 m, id: 0.1 mm; inlet conditions: 250° C. splitless, 3.8 min 1/25 split method used depending upon sample concentration with split flow of 75 mL/min; carrier gas, flow rate: Helium, 3.0 mL/min; block temperature: 330° C.; oven temperature: 0.5 minute hold at 50° C.; 100° C./minute to 330° C.; 0.5 minute hold at 330° C.; detector temperature: 300° C.; injection volume: 2 μL; run time/flow rate: 6.3 min/3.0 mL/min (splitless method), 3.8 min/1.5 mL/min (split 1/25 method), 3.04 min/1.2 mL/min (split 1/50 method).

Fermentation Conditions

Fermentations were performed in 2 L fermentors. Cells from a frozen stock were grown in a defined media of: 1.5 g/L of $KH_2PO_4$, 4.54 g/L of $K_2HPO_4$ trihydrate, 4 g/L of $(NH_4)_2SO_4$, 0.15 g/L of $MgSO_4$ heptahydrate, 20 g/L of glucose, 200 mM of Bis-Tris buffer (pH 7.2), 1.25 ml/L of trace minerals and 1.25 mL/L of a vitamin solution. The trace minerals solution was composed of 27 g/L of $FeCl_3.6H_2O$, 2 g/L of $ZnCl_2.4H_2O$, 2 g/L of $CaCl_2.6H_2O$, 2 g/L of $Na_2MoO_4.2H_2O$, 1.9 g/L of $CuSO_4.5H_2O$, 0.5 g/L of $H_3BO_3$, and 100 mL/L of concentrated HCl. The vitamin solution was composed of 0.42 g/L of riboflavin, 5.4 g/L of pantothenic acid, 6 g/L of niacin, 1.4 g/L of pyridoxine, 0.06 g/L of biotin, and 0.04 g/L of folic acid.

After the cells from the frozen stock were cultured overnight, 50 mL of the culture was used to inoculate 1 L of the same medium described above, but with only 5 g/L of glucose, in a fermentor with temperature, pH, agitation, aeration and dissolved oxygen control. The conditions for the fermentation were 32° C., pH 6.8 and dissolved oxygen (DO) equal to 30% of saturation. pH was maintained by adding $NH_4OH$, which also acted as a nitrogen source for cell growth. When the initial 5 g/L of glucose was almost consumed (e.g., less than about 0.5 g/L glucose), a feed consisting of 60% glucose, 3.9 g/L $MgSO_4$ heptahydrate and 10 mL/L of the trace minerals solution was supplied to the fermentor.

When exogenous alcohol was supplied, the feed rate was set to match the cells' growth rate to avoid accumulation of glucose in the fermentor. When exogenous alcohol was not supplied, a low concentration of excess glucose (e.g., about 2 g/L to about 5 g/L) was maintained.

In the early phases of the growth, the production of esters was induced by the addition of 1 mM isopropyl β-D-1-thiogalactopyranoside (IPTG). When exogenous alcohol was supplied, the alcohol was added at the time of induction (i.e., when IPTG was added) at a concentration of 20 mL/L. The fermentation continued for 3 days. When exogenous alcohol was supplied, the alcohol was added several times during the run to maintain a concentration of about 10 mL/L to about 30 mL/L.

Example 1

FAEE Production Without Exogenous Ethanol, Multiple Methanol Feeds

Modified *E. coli* strain Δ4 (MG1655 ΔfadE ΔfabR ΔpoxB ΔldhA) carrying a plasmid containing 'tesA,fadD, and atfA1 was first constructed.

1. Construction of the Δ4 strain:

The fadE gene of *E. coli* MG1655 (an *E. coli* K strain) was deleted using the Lambda Red (also known as the Red-Driven Integration) system described in Datsenko et al., *Proc. Natl. Acad. Sci. USA* 97: 6640-6645 (2000), with the following modifications.

Two primers were used to create the deletion:

```
                                           (SEQ ID NO: 1)
Del-fadE-F 5'-AAAAACAGCAACAATGTGAGCTTTGTTGTAATTATA

TTGTAAACATATTGATTCCGGGGATCCGTCGACC (SEQ ID NO: 2)
Del-fadE-R 5'-AAACGGAGCCTTTCGGCTCCGTTATTCATTTACGCG

GCTTCAACTTTCCTGTAGGCTGGAGCTGCTTC
```

The Del-fadE-F and Del-fadE-R primers were used to amplify the Kanamycin resistance ($Km^R$) cassette from plasmid pKD13 (as described in Datsenko et al., supra) by PCR. The PCR product was then used to transform electro-competent *E. coli* MG1655 cells containing pKD46 (described in Datsenko et al., supra). These cells had been previously induced with arabinose for 3-4 h. Following a 3 h outgrowth in a super optimal broth with catabolite repression (SOC) medium at 37° C., the cells were plated on Luria agar plates containing 50 µg/mL Kanamycin. Resistant colonies were identified and isolated after an overnight incubation at 37° C. Disruption of the fadE gene was confirmed in select colonies using PCR amplification with primers fadE-L2 andfadE-R1, which were designed to flank the fadE gene:

```
                          (SEQ ID NO: 3)
    fadE-L2    5'-CGGGCAGGTGCTATGACCAGGAC (SEQ ID NO: 4)
    fadE-R1    5'-CGCGGCGTTGACCGGCAGCCTGG
```

After the fadE deletion was confirmed, a single colony was used to remove the $Km^R$ marker, using the pCP20 plasmid as described in Datsenko et al., supra. The resulting MG1655 *E. coli* strain with the fadE gene deleted and the $Km^R$ marker removed was named *E. coli* MG1655 ΔfadE, or *E. coli* MG1655 D1.

The fabR gene of *E. coli*, which encodes a fatty acid biosynthesis regulator, and has been reported as a repressor of *E. coli* fabA, fabB and yqfA (see, e.g., McCue et al., *Nucleic Acids Res.*, 29(3):774-82 (2001); Zhang et al., *J. Biol. Chem.* 277(18):15558-65 (2002)), was deleted from *E. coli* MG1655 D1 using the Lambda Red system described in Datsenko et al., supra, but with the following modifications.

Two primers were used to create the deletion:

```
Del-fabR-F:
                                             (SEQ ID NO: 5)
5'- ATGTTTTATTGCGTTACCGTTCATTCACAATACTGGAGCAATCCAG

TATGCATATGAATATCCTCCTTAGTTCC-3'

Del-fabR-R:
                                             (SEQ ID NO: 6)
5'-CGTACCTCTATCTTGATTTGCTTGTTTCATTACTCGTCCTTCACATT

TCCGTGTAGGCTGGAGCTGCTTCG-3'
```

The Del-fabR-F and Del-fabR-R primers were used to amplify the $Km^R$ cassette from plasmid pKD13 by PCR. The PCR product obtained was used to transform the electro-competent *E. coli* MG1655 D1 cells containing pKD46 (see above). These cells had been previously induced with arabinose for 3-4 h. Following a 3 h outgrowth in SOC medium at 37° C., the cells were plated on Luria agar plates containing 50 µg/mL Kanamycin. Kanamycin resistant colonies were identified and isolated after an overnight incubation at 37° C. Disruption of the fabR gene was confirmed in select colonies by PCR amplification with primers fabR-verF and fabR-verR, which were designed to flank the fabR gene.

```
                                  (SEQ ID NO: 7)
    fabR-verF:    5'-AACCGGCCAAAGAATTGCAG-3'

(SEQ ID NO: 8)
    fabR-verR:    5'-TAAGCCAGCAACTAACGCCA-3'
```

After the fabR deletion was confirmed, a single colony was used to remove the $Km^R$ marker, using the pCP20 plasmid as described in Datsenko et al., supra. The resulting MG1655 *E. coli* strain having the fadE and fabR gene deletions was given the name Δ2, and used for further gene deletions.

The poxB gene of *E. coli*, which encodes a pyruvate oxidase (see, e.g., Chang et al., *J. Bacteriol.* 154(2):756-62 (1983); Abdel-Ahmid et al., *Microbiol.* 147(6):1483-98 (2001)) was deleted from the *E. coli* MG1655 Δ2 strain using the Lambda Red system described in Datsenko et al., supra, but with the following modifications.

Two primers were used to create the deletion:

```
Del-poxB-F:
                                             (SEQ ID NO: 9)
5'-GATGAACTAAACTTGTTACCGTTATCACATTCAGGAGATGGAGAACC

ATGCATATGAATATCCTCCTTAGTTCC-3'

Del-poxB-R:
                                             (SEQ ID NO: 10)
5'-CCTTATTATGACGGGAAATGCCACCCTTTTTACCTTAGCCAGTTTGT

TTTGTGTAGGCTGGAGCTGCTTCG-3'
```

The Del-poxB-F and Del-poxB-R primers were used to amplify the $Km^R$ cassette from plasmid pKD13 by PCR. The PCR product obtained was used to transform the electro-competent *E. coli* MG1655 Δ2 cells containing pKD46 (see above). These cells had been previously induced with arabinose for 3-4 h. Following a 3 h outgrowth in SOC medium at 37° C., the cells were plated on Luria agar plates containing 50 µg/mL Kanamycin. Kanamycin resistant colonies were identified and isolated after an overnight incubation at 37° C. Disruption of the poxB gene was confirmed in select colonies by PCR amplification with primers poxB-verF and poxB-verR, which were designed to flank the poxB gene.

```
                                 (SEQ ID NO: 11)
    poxB-verF:    5'-CGGGCTATTTAACCGTTAGT-3'

(SEQ ID NO: 12)
    poxB-verR:    5'-AGAGCATTAACGGTAGGG-3'
```

After the poxB deletion was confirmed, a single colony was used to remove the $Km^R$ marker, using the pCP20 plasmid as described in Datsenko et al., supra. The resulting MG1655 *E. coli* strain was given the name Δ3, and was used for further gene deletions.

The ldhA gene of *E. coli*, which encodes a lactate dehydrogenases, specifically an NAD-linked fermentative D-lactate dehydrogenase (see, e.g., Mat-Jan et al., *J. Bacteriol.* 171(1):342-8 (1989); Bunch et al., *Microbiol.* 143(1):187-95 (1997)) was then deleted from the *E. coli* strain A3, using the Lambda Red system described in Datsenko et al., supra, but with the following modifications.

Two primers were used to create the deletion:

```
Del-ldhA-F:
                                          (SEQ ID NO: 13)
5'-TATTTTTAGTAGCTTAAATGTGATTCAACATCACTGGAGAAAGTCTT

ATGCATATGAATATCCTCCTTAGTTCC-3'

Del-ldhA-R:
                                          (SEQ ID NO: 14)
5' CTCCCCTGGAATGCAGGGGAGCGGCAAGATTAAACCAGTTCGTTCGG

GCAGTGTAGGCTGGAGCTGCTTCG-3'
```

Disruption of the ldhA gene was confirmed in select colonies by PCR amplification with primers ldhA-verF and ldhA-verR, which were designed to flank the ldhA gene.

```
                                          (SEQ ID NO: 15)
    ldhA-verF:    5'-CAATATCGCCATAGCTTTC-3'

(SEQ ID NO: 16)
    ldhA-verR:    5'-TACAGTTTCTGACTCAGG-3'
```

After the ldhA deletion was confirmed, a single colony was used to remove the Km$^R$ marker, using the pCP20 plasmid as described in Datsenko et al., supra. The resulting MG1655 *E. coli* strain having the fadE, fabR, poxB, and ldhA gene deletions was given the name Δ4.

2. Creation of the tesA, fadD, and atfA1 plasmid

*E. coli* 'tesA is a nucleotide sequence comprising a leaderless *E. coli* tesA (GenBank Accession No. AAC73596, refseq accession U00096.2). 'tesA encodes an *E. coli* thioesterase (EC 3.1.1.5, 3.1.2.-) in which the first twenty-five amino acids were deleted and the amino acid in position 26, alanine, was replaced with methionine. That methionine then became the first amino acid of 'tesA. See Cho et al., *J. Biol. Chem.*, 270:4216-4219 (1995). *E. coli* fadD (GenBank Accession No. AAC74875; REFSEQ: accession U00096.2) encodes an acyl-CoA synthase. Alcanivorax borkumensis strain SK2 atfA1 (GenBank entry YP_694462; REFSEQ: accession NC_008260.1) encodes an ester synthase.

a) Construction of the 'tesA Plasmid

'tesA was amplified from a pETDuet-1-'tesA plasmid constructed as described below. (see also, e.g., WO 2007/136762 A2, which is incorporated by reference). The 'tesA gene was cloned into an NdeI/AvrII digested pETDuet-1 plasmid (Novagen, Madison, Wis.).

b) Construction of the fadD Plasmid fadD was amplified from a pHZ1.61 plasmid constructed as described below. A fadD gene was cloned into a pCDF-Duet-1 plasmid (Novagen, Madison, Wis.) under the control of a T7 promoter, generating a pHZ1.61 plasmid containing the following nucleotide sequence:

```
                                          (SEQ ID NO: 17)
GGGGAATTGTGAGCGGATAACAATTCCCCTGTAGAAATAATTTTGTTTAA

CTTTAATAAGGAGATATACCATGGTGAAGAAGGTTTGGCTTAACCGTTAT

CCCGCGGACGTTCCGACGGAGATCAACCCTGACCGTTATCAATCTCTGGT

AGATATGTTTGAGCAGTCGGTCGCGCGCTACGCCGATCAACCTGCGTTTG

TGAATATGGGGGAGGTAATGACCTTCCGCAAGCTGGAAGAACGCAGTCGC

GCGTTTGCCGCTTATTTGCAACAAGGGTTGGGGCTGAAGAAAGGCGATCG

CGTTGCGTTGATGATGCCTAATTTATTGCAATATCCGGTGGCGCTGTTTG

GCATTTTGCGTGCCGGGATGATCGTCGTAAACGTTAACCCGTTGTATACC

CCGCGTGAGCTTGAGCATCAGCTTAACGATAGCGGCGCATCGGCGATTGT

TATCGTGTCTAACTTTGCTCACACACTGGAAAAAGTGGTTGATAAAACCG

CCGTTCAGCACGTAATTCTGACCCGTATGGGCGATCAGCTATCTACGGCA

AAAGGCACGGTAGTCAATTTCGTTGTTAAATACATCAAGCGTTTGGTGCC

GAAATACCATCTGCCAGATGCCATTTCATTTCGTAGCGCACTGCATAACG

GCTACCGGATGCAGTACGTCAAACCCGAACTGGTGCCGGAAGATTTAGCT

TTTCTGCAATACACCGGCGGCACCACTGGTGTGGCGAAAGGCGCGATGCT

GACTCACCGCAATATGCTGGCGAACCTGGAACAGGTTAACGCGACCTATG

GTCCGCTGTTGCATCCGGGCAAAGAGCTGGTGGTGACGGCGCTGCCGCTG

TATCACATTTTTGCCCTGACCATTAACTGCCTGCTGTTTATCGAACTGGG

TGGGCAGAACCTGCTTATCACTAACCCGCGCGATATTCCAGGGTTGGTAA

AAGAGTTAGCGAAATATCCGTTTACCGCTATCACGGGCGTTAACACCTTG

TTCAATGCGTTGCTGAACAATAAAGAGTTCCAGCAGCTGGATTTCTCCAG

TCTGCATCTTTCCGCAGGCGGAGGGATGCCAGTGCAGCAAGTGGTGGCAG

AGCGTTGGGTGAAACTGACAGGACAGTATCTGCTGGAAGGCTATGGCCTT

ACCGAGTGTGCGCCGCTGGTCAGCGTTAACCCATATGATATTGATTATCA

TAGTGGTAGCATCGGTTTGCCGGTGCCGTCGACGGAAGCCAAACTGGTGG

ATGATGATGATAATGAAGTACCACCGGGTCAACCGGGTGAGCTTTGTGTC

AAAGGACCGCAGGTGATGCTGGGTTACTGGCAGCGTCCGGATGCTACAGA

TGAGATCATCAAAAATGGCTGGTTACACACCGGCGACATCGCGGTGATGG

ATGAAGAAGGGTTCCTGCGCATTGTCGATCGTAAAAAAGACATGATTCTG

GTTTCCGGTTTTAACGTCTATCCCAACGAGATTGAAGATGTCGTCATGCA

GCATCCTGGCGTACAGGAAGTCGCGGCTGTTGGCGTACCTTCCGGCTCCA

GTGGTGAAGCGGTGAAAATCTTCGTAGTGAAAAAAGATCCATCGCTTACC

GAAGAGTCACTGGTGACCTTTTGCCGCCGTCAGCTCACGGGCTACAAAGT

ACCGAAGCTGGTGGAGTTTCGTGATGAGTTACCGAAATCTAACGTCGGAA

AAATTTTGCGACGAGAATTACGTGACGAAGCGCGCGGCAAAGTGGACAAT

AAAGCCTGAAAGCTTGCGGCCGCATAATGCTTAAGTCGAACAGAAAGTAA

TCGTATTGTACACGGCCGCATAATCGAAATTAATACGACTCACTATAGGG

GAATTGTGAGCGGATAACAATTCCCCATCTTAGTATATTAGTTAAGTATA

AGAAGGAGATATACATATGCGCCCATTACATCCGATTGATTTTATATTCC

TGTCACTAGAAAAAAGACAACAGCCTATGCATGTAGGTGGTTTATTTTTG

TTTCAGATTCCTGATAACGCCCCAGACACCTTTATTCAAGATCTGGTGAA

TGATATCCGGATATCAAAATCAATCCCTGTTCCACCATTCAACAATAAAC

TGAATGGGCTTTTTTGGGATGAAGATGAAGAGTTTGATTTAGATCATCAT

TTTCGTCATATTGCACTGCCTCATCCTGGTCGTATTCGTGAATTGCTTAT

TTATATTTCACAAGAGCACAGTACGCTGCTAGATCGGGCAAAGCCCTTGT

GGACCTGCAATATTATTGAAGGAATTGAAGGCAATCGTTTTGCCATGTAC

TTCAAAATTCACCATGCGATGGTCGATGGCGTTGCTGGTATGCGGTTAAT

TGAAAAATCACTCTCCCATGATGTAACAGAAAAAGTATCGTGCCACCTT
```

```
GGTGTGTTGAGGGAAAACGTGCAAAGCGCTTAAGAGAACCTAAAACAGGT
AAAATTAAGAAAATCATGTCTGGTATTAAGAGTCAGCTTCAGGCGACACC
CACAGTCATTCAAGAGCTTTCTCAGACAGTATTTAAAGATATTGGACGTA
ATCCTGATCATGTTTCAAGCTTTCAGGCGCCTTGTTCTATTTTGAATCAG
CGTGTGAGCTCATCGCGACGTTTTGCAGCACAGTCTTTTGACCTAGATCG
TTTTCGTAATATTGCCAAATCGTTGAATGTGACCATTAATGATGTTGTAC
TAGCGGTATGTTCTGGTGCATTACGTGCGTATTTGATGAGTCATAATAGT
TTGCCTTCAAAACCATTAATTGCCATGGTTCCAGCCTCTATTCGCAATGA
CGATTCAGATGTCAGCAACCGTATTACGATGATTCTGGCAAATTTGGCAA
CCCACAAAGATGATCCTTTACAACGTCTTGAAATTATCCGCCGTAGTGTT
CAAAACTCAAAGCAACGCTTCAAACGTATGACCAGCGATCAGATTCTAAA
TTATAGTGCTGTCGTATATGGCCCTGCAGGACTCAACATAATTTCTGGCA
TGATGCCAAAACGCCAAGCCTTCAATCTGGTTATTTCCAATGTGCCTGGC
CCAAGAGAGCCACTTTACTGGAATGGTGCCAAACTTGATGCACTCTACCC
AGCTTCAATTGTATTAGACGGTCAAGCATTGAATATTACAATGACCAGTT
ATTTAGATAAACTTGAAGTTGGTTTGATTGCATGCCGTAATGCATTGCCA
AGAATGCAGAATTTACTGACACATTTAGAAGAAGAAATTCAACTATTTGA
AGGCGTAATTGCAAAGCAGGAAGATATTAAAACAGCCAATTAAAAACAAT
AAACTTGATTTTTTAATTTATCAGATAAAACTAAAGGGCTAAATTAGCCC
TCCTAGGCTGCTGCCACCGCTGAGCAATAACTAGCATAACCCCTTGGGGC
CTCTAAACGGGTCTTGAGGGGTTTTTGCTGAAACCTCAGGCATTTGAGA
AGCACACGGTCACACTGCTTCCGGTAGTCAATAAACCGGTAAACCAGCAA
TAGACATAAGCGGCTATTTAACGACCCTGCCCTGAACCGACGACCGGGTC
ATCGTGGCCGGATCTTGCGGCCCCTCGGCTTGAACGAATTGTTAGACATT
ATTTGCCGACTACCTTGGTGATCTCGCCTTTCACGTAGTGGACAAATTCT
TCCAACTGATCTGCGCGCGAGGCCAAGCGATCTTCTTCTTGTCCAAGATA
AGCCTGTCTAGCTTCAAGTATGACGGGCTGATACTGGGCCGGCAGGCGCT
CCATTGCCCAGTCGGCAGCGACATCCTTCGGCGCGATTTTGCCGGTTACT
GCGCTGTACCAAATGCGGGACAACGTAAGCACTACATTTCGCTCATCGCC
AGCCCAGTCGGGCGGCGAGTTCCATAGCGTTAAGGTTTCATTTAGCGCCT
CAAATAGATCCTGTTCAGGAACCGGATCAAAGAGTTCCTCCGCCGCTGGA
CCTACCAAGGCAACGCTATGTTCTCTTGCTTTTGTCAGCAAGATAGCCAG
ATCAATGTCGATCGTGGCTGGCTCGAAGATACCTGCAAGAATGTCATTGC
GCTGCCATTCTCCAAATTGCAGTTCGCGCTTAGCTGGATAACGCCACGGA
ATGATGTCGTCGTGCACAACAATGGTGACTTCTACAGCGCGGAGAATCTC
GCTCTCTCCAGGGGAAGCCGAAGTTTCCAAAAGGTCGTTGATCAAAGCTC
GCCGCGTTGTTTCATCAAGCCTTACGGTCACCGTAACCAGCAAATCAATA
TCACTGTGTGGCTTCAGGCCGCCATCCACTGCGGAGCCGTACAAATGTAC
GGCCAGCAACGTCGGTTCGAGATGGCGCTCGATGACGCCAACTACCTCTG
ATAGTTGAGTCGATACTTCGGCGATCACCGCTTCCCTCATACTCTTCCTT

TTTCAATATTATTGAAGCATTTATCAGGGTTATTGTCTCATGAGCGGATA
CATATTTGAATGTATTTAGAAAAATAAACAAATAGCTAGCTCACTCGGTC
GCTACGCTCCGGGCGTGAGACTGCGGCGGGCGCTGCGGACACATACAAAG
TTACCCACAGATTCCGTGGATAAGCAGGGGACTAACATGTGAGGCAAAAC
AGCAGGGCCGCGCCGGTGGCGTTTTTCCATAGGCTCCGCCCTCCTGCCAG
AGTTCACATAAACAGACGCTTTTCCGGTGCATCTGTGGGAGCCGTGAGGC
TCAACCATGAATCTGACAGTACGGGCGAAACCCGACAGGACTTAAAGATC
CCCACCGTTTCCGGCGGGTCGCTCCCTCTTGCGCTCTCCTGTTCCGACCC
TGCCGTTTACCGGATACCTGTTCCGCCTTTCTCCCTTACGGGAAGTGTGG
CGCTTTCTCATAGCTCACACACTGGTATCTCGGCTCGGTGTAGGTCGTTC
GCTCCAAGCTGGGCTGTAAGCAAGAACTCCCCGTTCAGCCCGACTGCTGC
GCCTTATCCGGTAACTGTTCACTTGAGTCCAACCCGGAAAAGCACGGTAA
AACGCCACTGGCAGCAGCCATTGGTAACTGGGAGTTCGCAGAGGATTTGT
TTAGCTAAACACGCGGTTGCTCTTGAAGTGTGCGCCAAAGTCCGGCTACA
CTGGAAGGACAGATTTGGTTGCTGTGCTCTGCGAAAGCCAGTTACCACGG
TTAAGCAGTTCCCCAACTGACTTAACCTTCGATCAAACCACCTCCCCAGG
TGGTTTTTTCGTTTACAGGGCAAAAGATTACGCGCAGAAAAAAGGATCT
CAAGAAGATCCTTTGATCTTTTCTACTGAACCGCTCTAGATTTCAGTGCA
ATTTATCTCTTCAAATGTAGCACCTGAAGTCAGCCCCATACGATATAAGT
TGTAATTCTCATGTTAGTCATGCCCCGCGCCCACCGGAAGGAGCTGACTG
GGTTGAAGGCTCTCAAGGGCATCGGTCGAGATCCCGGTGCCTAATGAGTG
AGCTAACTTACATTAATTGCGTTGCGCTCACTGCCCGCTTTCCAGTCGGG
AAACCTGTCGTGCCAGCTGCATTAATGAATCGGCCAACGCGCGGGGAGAG
GCGGTTTGCGTATTGGGCGCCAGGGTGGTTTTTCTTTTCACCAGTGAGAC
GGGCAACAGCTGATTGCCCTTCACCGCCTGGCCCTGAGAGAGTTGCAGCA
AGCGGTCCACGCTGGTTTGCCCCAGCAGGCGAAAATCCTGTTTGATGGTG
GTTAACGGCGGGATATAACATGAGCTGTCTTCGGTATCGTCGTATCCCAC
TACCGAGATGTCCGCACCAACGCGCAGCCCGGACTCGGTAATGGCGCGCA
TTGCGCCCAGCGCCATCTGATCGTTGGCAACCAGCATCGCAGTGGGAACG
ATGCCCTCATTCAGCATTTGCATGGTTTGTTGAAAACCGGACATGGCACT
CCAGTCGCCTTCCCGTTCCGCTATCGGCTGAATTTGATTGCGAGTGAGAT
ATTTATGCCAGCCAGCCAGACGCAGACGCGCCGAGACAGAACTTAATGGG
CCCGCTAACAGCGCGATTTGCTGGTGACCCAATGCGACCAGATGCTCCAC
GCCCAGTCGCGTACCGTCTTCATGGGAGAAAATAATACTGTTGATGGGTG
TCTGGTCAGAGACATCAAGAAATAACGCCGGAACATTAGTGCAGGCAGCT
TCCACAGCAATGGCATCCTGGTCATCCAGCGGATAGTTAATGATCAGCCC
ACTGACGCGTTGCGCGAGAAGATTGTGCACCGCCGCTTTACAGGCTTCGA
CGCCGCTTCGTTCTACCATCGACACCACCACGCTGGCACCCAGTTGATCG
GCGCGAGATTTAATCGCCGCGACAATTTGCGACGGCGCGTGCAGGGCCAG
ACTGGAGGTGGCAACGCCAATCAGCAACGACTGTTTGCCCGCCAGTTGTT
GTGCCACGCGGTTGGGAATGTAATTCAGCTCCGCCATCGCCGCTTCCACT
```

TTTTCCCGCGTTTTCGCAGAAACGTGGCTGGCCTGGTTCACCACGCGGGA

AACGGTCTGATAAGAGACACCGGCATACTCTGCGACATCGTATAACGTTA

CTGGTTTCACATTCACCACCCTGAATTGACTCTCTTCCGGGCGCTATCAT

GCCATACCGCGAAAGGTTTTGCGCCATTCGATGGTGTCCGGGATCTCGAC

GCTCTCCCTTATGCGACTCCTGCATTAGGAAATTAATACGACTCACTATA c) Construction of the atfA1 Plasmid atfA1 was amplified from a pHZ1.97-atfA1 plasmid constructed as described below. The atfA1 gene was synthesized by DNA2.0 (Menlo Park, Calif.) and cloned into an NdeI and AvrII digested pCOLA-Duet-1 plasmid (Novagen, Madison, Wis.), generating a pHZ1.97-atfA1plasmid having the following nucleotide sequence:

(SEQ ID NO: 18)
GGGGAATTGTGAGCGGATAACAATTCCCCTGTAGAAATAATTTTGTTTAA

CTTTAATAAGGAGATATACCATGGGCAGCAGCCATCACCATCATCACCAC

AGCCAGGATCCGAATTCGAGCTCGGCGCGCCTGCAGGTCGACAAGCTTGC

GGCCGCATAATGCTTAAGTCGAACAGAAAGTAATCGTATTGTACACGGCC

GCATAATCGAAATTAATACGACTCACTATAGGGGAATTGTGAGCGGATAA

CAATTCCCCATCTTAGTATATTAGTTAAGTATAAGAAGGAGATATACATA

TGAAAGCGCTTAGCCCAGTGGATCAACTGTTCCTGTGGCTGGAAAAACGA

CAGCAACCCATGCACGTAGGCGGTTTGCAGCTGTTTTCCTTCCCGGAAGG

TGCCGGCCCCAAGTATGTGAGTGAGCTGGCCCAGCAAATGCGGGATTACT

GCCACCCAGTGGCGCCATTCAACCAGCGCCTGACCCGTCGACTCGGCCAG

TATTACTGGACTAGAGACAAACAGTTCGATATCGACCACCACTTCCGCCA

CGAAGCACTCCCCAAACCCGGTCGCATTCGCGAACTGCTTTCTTTGGTCT

CCGCCGAACATTCCAACCTGCTGGACCGGGAGCGCCCCATGTGGGAAGCC

CATTTGATCGAAGGGATCCGCGGTCGCCAGTTCGCTCTCTATTATAAGAT

CCACCATTCGGTGATGGATGGCATATCCGCCATGCGTATCGCCTCCAAAA

CGCTTTCCACTGACCCCAGTGAACGTGAAATGGCTCCGGCTTGGGCGTTC

AACACCAAAAAACGCTCCCGCTCACTGCCCAGCAACCCGGTTGACATGGC

CTCCAGCATGGCGCGCCTAACCGCGAGCATAAGCAAACAAGCTGCCACAG

TGCCCGGTCTCGCGCGGGAGGTTTACAAAGTCACCCAAAAAGCCAAAAAA

GATGAAAACTATGTGTCTATTTTTCAGGCTCCCGACACGATTCTGAATAA

TACCATCACCGGTTCACGCCGCTTTGCCGCCCAGAGCTTTCCATTACCGC

GCCTGAAAGTTATCGCCAAGGCCTATAACTGCACCATTAACACCGTGGTG

CTCTCCATGTGTGGCCACGCTCTGCGCGAATACTTGATTAGCCAACACGC

GCTGCCCGATGAGCCACTGATTGCAATGGTGCCCATGAGCCTGCGGCAGG

ACGACAGCACTGGCGGCAACCAGATCGGTATGATCTTGGCTAACCTGGGC

ACCCACATCTGTGATCCAGCTAATCGCCTGCGCGTCATCCACGATTCCGT

CGAGGAAGCCAAATCCCGCTTCTCGCAGATGAGCCCGGAAGAAATTCTCA

ATTTCACCGCCCTCACTATGGCTCCCACCGGCTTGAACTTACTGACCGGC

CTAGCGCCAAAATGGCGGGCCTTCAACGTGGTGATTTCCAACATACCCGG

GCCGAAAGAGCCGCTGTACTGGAATGGTGCACAGCTGCAAGGAGTGTATC

CAGTATCCATTGCCTTGGATCGCATCGCCCTAAATATCACCCTCACCAGT

TATGTAGACCAGATGGAATTTGGGCTTATCGCCTGCCGCCGTACTCTGCC

TTCCATGCAGCGACTACTGGATTACCTGGAACAGTCCATCCGCGAATTGG

AAATCGGTGCAGGAATTAAATAGTAACCTAGGCTGCTGCCACCGCTGAGC

AATAACTAGCATAACCCCTTGGGGCCTCTAAACGGGTCTTGAGGGGTTTT

TTGCTGAAACCTCAGGCATTTGAGAAGCACACGGTCACACTGCTTCCGGT

AGTCAATAAACCGGTAAACCAGCAATAGACATAAGCGGCTATTTAACGAC

CCTGCCCTGAACCGACGACAAGCTGACGACCGGGTCTCCGCAAGTGGCAC

TTTTCGGGGAAATGTGCGCGGAACCCCTATTTGTTTATTTTTCTAAATAC

ATTCAAATATGTATCCGCTCATGAATTAATTCTTAGAAAAACTCATCGAG

CATCAAATGAAACTGCAATTTATTCATATCAGGATTATCAATACCATATT

TTTGAAAAAGCCGTTTCTGTAATGAAGGAGAAAACTCACCGAGGCAGTTC

CATAGGATGGCAAGATCCTGGTATCGGTCTGCGATTCCGACTCGTCCAAC

ATCAATACAACCTATTAATTTCCCCTCGTCAAAAATAAGGTTATCAAGTG

AGAAATCACCATGAGTGACGACTGAATCCGGTGAGAATGGCAAAAGTTTA

TGCATTTCTTTCCAGACTTGTTCAACAGGCCAGCCATTACGCTCGTCATC

AAAATCACTCGCATCAACCAAACCGTTATTCATTCGTGATTGCGCCTGAG

CGAGACGAAATACGCGGTCGCTGTTAAAGGACAATTACAAACAGGAATC

GAATGCAACCGGCGCAGGAACACTGCCAGCGCATCAACAATATTTTCACC

TGAATCAGGATATTCTTCTAATACCTGGAATGCTGTTTTCCCGGGGATCG

CAGTGGTGAGTAACCATGCATCATCAGGAGTACGGATAAAATGCTTGATG

GTCGGAAGAGGCATAAATTCCGTCAGCCAGTTTAGTCTGACCATCTCATC

TGTAACATCATTGGCAACGCTACCTTTGCCATGTTTCAGAAACAACTCTG

GCGCATCGGGCTTCCCATACAATCGATAGATTGTCGCACCTGATTGCCCG

ACATTATCGCGAGCCCATTTATACCCATATAAATCAGCATCCATGTTGGA

ATTTAATCGCGGCCTAGAGCAAGACGTTTCCCGTTGAATATGGCTCATAC

TCTTCCTTTTTCAATATTATTGAAGCATTTATCAGGGTTATTGTCTCATG

AGCGGATACATATTTGAATGTATTTAGAAAAATAAACAAATAGGCATGCT

AGCGCAGAAACGTCCTAGAAGATGCCAGGAGGATACTTAGCAGAGAGACA

ATAAGGCCGGAGCGAAGCCGTTTTTCCATAGGCTCCGCCCCCCTGACGAA

CATCACGAAATCTGACGCTCAAATCAGTGGTGGCGAAACCCGACAGGACT

ATAAAGATACCAGGCGTTTCCCCCTGATGGCTCCCTCTTGCGCTCTCCTG

TTCCCGTCCTGCGGCGTCCGTGTTGTGGTGGAGGCTTTACCCAAATCACC

ACGTCCCGTTCCGTGTAGACAGTTCGCTCCAAGCTGGGCTGTGTGCAAGA

ACCCCCCGTTCAGCCCGACTGCTGCGCCTTATCCGGTAACTATCATCTTG

AGTCCAACCCGGAAAGACACGACAAAACGCCACTGGCAGCAGCCATTGGT

AACTGAGAATTAGTGGATTTAGATATCGAGAGTCTTGAAGTGGTGGCCTA

ACAGAGGCTACACTGAAAGGACAGTATTTGGTATCTGCGCTCCACTAAAG

CCAGTTACCAGGTTAAGCAGTTCCCCAACTGACTTAACCTTCGATCAAAC

CGCCTCCCCAGGCGGTTTTTTCGTTTACAGAGCAGGAGATTACGACGATC

-continued

```
GTAAAAGGATCTCAAGAAGATCCTTTACGGATTCCCGACACCATCACTCT
AGATTTCAGTGCAATTTATCTCTTCAAATGTAGCACCTGAAGTCAGCCCC
ATACGATATAAGTTGTAATTCTCATGTTAGTCATGCCCCGCGCCCACCGG
AAGGAGCTGACTGGGTTGAAGGCTCTCAAGGGCATCGGTCGAGATCCCGG
TGCCTAATGAGTGAGCTAACTTACATTAATTGCGTTGCGCTCACTGCCCG
CTTTCCAGTCGGGAAACCTGTCGTGCCAGCTGCATTAATGAATCGGCCAA
CGCGCGGGGAGAGGCGGTTTGCGTATTGGGCGCCAGGGTGGTTTTTCTTT
TCACCAGTGAGACGGGCAACAGCTGATTGCCCTTCACCGCCTGGCCCTGA
GAGAGTTGCAGCAAGCGGTCCACGCTGGTTTGCCCCAGCAGGCGAAAATC
CTGTTTGATGGTGGTTAACGGCGGGATATAACATGAGCTGTCTTCGGTAT
CGTCGTATCCCACTACCGAGATGTCCGCACCAACGCGCAGCCCGGACTCG
GTAATGGCGCGCATTGCGCCCAGCGCCATCTGATCGTTGGCAACCAGCAT
CGCAGTGGGAACGATGCCCTCATTCAGCATTTGCATGGTTTGTTGAAAAC
CGGACATGGCACTCCAGTCGCCTTCCCGTTCCGCTATCGGCTGAATTTGA
TTGCGAGTGAGATATTTATGCCAGCCAGCCAGACGCAGACGCGCCGAGAC
AGAACTTAATGGGCCCGCTAACAGCGCGATTTGCTGGTGACCCAATGCGA
CCAGATGCTCCACGCCCAGTCGCGTACCGTCTTCATGGGAGAAAATAATA
CTGTTGATGGGTGTCTGGTCAGAGACATCAAGAAATAACGCCGGAACATT
AGTGCAGGCAGCTTCCACAGCAATGGCATCCTGGTCATCCAGCGGATAGT
TAATGATCAGCCCACTGACGCGTTGCGCGAGAAGATTGTGCACCGCCGCT
TTACAGGCTTCGACGCCGCTTCGTTCTACCATCGACACCACCACGCTGGC
ACCCAGTTGATCGGCGCGAGATTTAATCGCCGCGACAATTTGCGACGGCG
CGTGCAGGGCCAGACTGGAGGTGGCAACGCCAATCAGCAACGACTGTTTG
CCCGCCAGTTGTTGTGCCACGCGGTTGGGAATGTAATTCAGCTCCGCCAT
CGCCGCTTCCACTTTTTCCCGCGTTTTCGCAGAAACGTGGCTGGCCTGGT
TCACCACGCGGGAAACGGTCTGATAAGAGACACCGGCATACTCTGCGACA
TCGTATAACGTTACTGGTTTCACATTCACCACCCTGAATTGACTCTCTTC
CGGGCGCTATCATGCCATACCGCGAAAGGTTTTGCGCCATTCGATGGTGT
CCGGGATCTCGACGCTCTCCCTTATGCGACTCCTGCATTAGGAAATTAAT
ACGACTCACTATA
```

3. Creation of a 'tesA, fadD, atfA1 Integration Cassette

The nucleotide sequences, 'tesA, fadD, and aftA1, were integrated into the chromosome of *E. coli* MG1655 Δ4 at the lacZ locus. The sequences were integrated in the order of 'tesA, followed byfadD, and followed by aftA1, and placed under the control of a Trc promoter, as described below.

a) Construction of pACYC-PTrc Plasmid Containing 'tesA, fadD, and atfA1

A pACYC-PTrc vector having the following sequence was used to construct a pACYC-PTrc-'tesA-fadD-atfA1 plasmid. The nucleotide sequence of the pACYC-PTrc vector is as follows:

(SEQ ID NO: 19)
```
ACTCACCAGTCACAGAAAAGCATCTTACGGATGGCATGACAGTAAGAGAA
TTATGCAGTGCTGCCATAACCATGAGTGATAACACTGCGGCCAACTTACT
TCTGACAACGATCGGAGGACCGAAGGAGCTAACCGCTTTTTTGCACAACA
TGGGGGATCATGTAACTCGCCTTGATCGTTGGGAACCGGAGCTGAATGAA
GCCATACCAAACGACGAGCGTGACACCACGATGCCTGCAGCAATGGCAAC
AACGTTGCGCAAACTATTAACTGGCGAACTACTTACTCTAGCTTCCCGGC
AACAATTAATAGACTGGATGGAGGCGGATAAAGTTGCAGGACCACTTCTG
CGCTCGGCCCTTCCGGCTGGCTGGTTTATTGCTGATAAATCTGGAGCCGG
TGAGCGTGGGTCTCGCGGTATCATTGCAGCACTGGGGCCAGATGGTAAGC
CCTCCCGTATCGTAGTTATCTACACGACGGGGAGTCAGGCAACTATGGAT
GAACGAAATAGACAGATCGCTGAGATAGGTGCCTCACTGATTAAGCATTG
GTAACTGTCAGACCAAGTTTACTCATATATACTTTAGATTGATTTAAAAC
TTCATTTTTAATTTAAAAGGATCTAGGTGAAGATCCTTTTTGATAATCTC
ATGACCAAAATCCCTTAACGTGAGTTTTCGTTCCACTGAGCGTCAGACCC
CTTAATAAGATGATCTTCTTGAGATCGTTTTGGTCTGCGCGTAATCTCTT
GCTCTGAAAACGAAAAAACCGCCTTGCAGGGCGGTTTTTCGAAGGTTCTC
TGAGCTACCAACTCTTTGAACCGAGGTAACTGGCTTGGAGGAGCGCAGTC
ACCAAAACTTGTCCTTTCAGTTTAGCCTTAACCGGCGCATGACTTCAAGA
CTAACTCCTCTAAATCAATTACCAGTGGCTGCTGCCAGTGGTGCTTTTGC
ATGTCTTTCCGGGTTGGACTCAAGACGATAGTTACCGGATAAGGCGCAGC
GGTCGGACTGAACGGGGGGTTCGTGCATACAGTCCAGCTTGGAGCGAACT
GCCTACCCGGAACTGAGTGTCAGGCGTGGAATGAGACAAACGCGGCCATA
ACAGCGGAATGACACCGGTAAACCGAAAGGCAGGAACAGGAGAGCGCACG
AGGGAGCCGCCAGGGGGAAACGCCTGGTATCTTTATAGTCCTGTCGGGTT
TCGCCACCACTGATTTGAGCGTCAGATTTCGTGATGCTTGTCAGGGGGGC
GGAGCCTATGGAAAAACGGCTTTGCCGCGGCCCTCTCACTTCCCTGTTAA
GTATCTTCCTGGCATCTTCCAGGAAATCTCCGCCCCGTTCGTAAGCCATT
TCCGCTCGCCGCAGTCGAACGACCGAGCGTAGCGAGTCAGTGAGCGAGGA
AGCGGAATATATCCTGTATCACATATTCTGCTGACGCACCGGTGCAGCCT
TTTTTCTCCTGCCACATGAAGCACTTCACTGACACCCTCATCAGTGCCAA
CATAGTAAGCCAGTATACACTCCGCTAGCGCTGAGGTCTGCCTCGTGAAG
AAGGTGTTGCTGACTCATACCAGGCCTGAATCGCCCCATCATCCAGCCAG
AAAGTGAGGGAGCCACGGTTGATGAGAGCTTTGTTGTAGGTGGACCAGTT
GGTGATTTTGAACTTTTGCTTTGCCACGGAACGGTCTGCGTTGTCGGGAA
GATGCGTGATCTGATCCTTCAACTCAGCAAAAGTTCGATTTATTCAACAA
AGCCACGTTGTGTCTCAAAATCTCTGATGTTACATTGCACAAGATAAAAA
TATATCATCATGAACAATAAAACTGTCTGCTTACATAAACAGTAATACAA
GGGGTGTTATGAGCCATATTCAACGGGAAACGTCTTGCTCGAGGCCGCGA
TTAAATTCCAACATGGATGCTGATTTATATGGGTATAAATGGGCTCGCGA
TAATGTCGGGCAATCAGGTGCGACAATCTATCGATTGTATGGGAAGCCCG
```

-continued

```
ATGCGCCAGAGTTGTTTCTGAAACATGGCAAAGGTAGCGTTGCCAATGAT
GTTACAGATGAGATGGTCAGACTAAACTGGCTGACGGAATTTATGCCTCT
TCCGACCATCAAGCATTTTATCCGTACTCCTGATGATGCATGGTTACTCA
CCACTGCGATCCCCGGGAAAACAGCATTCCAGGTATTAGAAGAATATCCT
GATTCAGGTGAAAATATTGTTGATGCGCTGGCAGTGTTCCTGCGCCGGTT
GCATTCGATTCCTGTTTGTAATTGTCCTTTTAACAGCGATCGCGTATTTC
GTCTCGCTCAGGCGCAATCACGAATGAATAACGGTTTGGTTGATGCGAGT
GATTTTGATGACGAGCGTAATGGCTGGCCTGTTGAACAAGTCTGGAAAGA
AATGCATAAGCTTTTGCCATTCTCACCGGATTCAGTCGTCACTCATGGTG
ATTTCTCACTTGATAACCTTATTTTTGACGAGGGGAAATTAATAGGTTGT
ATTGATGTTGGACGAGTCGGAATCGCAGACCGATACCAGGATCTTGCCAT
CCTATGGAACTGCCTCGGTGAGTTTTCTCCTTCATTACAGAAACGGCTTT
TTCAAAAATATGGTATTGATAATCCTGATATGAATAAATTGCAGTTTCAT
TTGATGCTCGATGAGTTTTTCTAATCAGAATTGGTTAATTGGTTGTAACA
CTGGCAGAGCATTACGCTGACTTGACGGGACGGCGGCTTTGTTGAATAAA
TCGAACTTTTGCTGAGTTGAAGGATCAGATCACGCATCTTCCCGACAACG
CAGACCGTTCCGTGGCAAAGCAAAAGTTCAAAATCACCAACTGGTCCACC
TACAACAAAGCTCTCATCAACCGTGGCTCCCTCACTTTCTGGCTGGATGA
TGGGGCGATTCAGGCCTGGTATGAGTCAGCAACACCTTCTTCACGAGGCA
GACCTCAGCGCTCAAAGATGCAGGGGTAAAAGCTAACCGCATCTTTACCG
ACAAGGCATCCGGCAGTTCAACAGATCGGGAAGGGCTGGATTTGCTGAGG
ATGAAGGTGGAGGAAGGTGATGTCATTCTGGTGAAGAAGCTCGACCGTCT
TGGCCGCGACACCGCCGACATGATCCAACTGATAAAAGAGTTTGATGCTC
AGGGTGTAGCGGTTCGGTTTATTGACGACGGGATCAGTACCGACGGTGAT
ATGGGGCAAATGGTGGTCACCATCCTGTCGGCTGTGGCACAGGCTGAACG
CCGGAGGATCCTAGAGCGCACGAATGAGGGCCGACAGGAAGCAAAGCTGA
AAGGAATCAAATTTGGCCGCAGGCGTACCGTGGACAGGAACGTCGTGCTG
ACGCTTCATCAGAAGGGCACTGGTGCAACGGAAATTGCTCATCAGCTCAG
TATTGCCCGCTCCACGGTTTATAAAATTCTTGAAGACGAAAGGGCCTCGT
GATACGCCTATTTTTATAGGTTAATGTCATGATAATAATGGTTTCTTAGA
CGTCTTAATTAATCAGGAGAGCGTTCACCGACAAACAACAGATAAAACGA
AAGGCCCAGTCTTTCGACTGAGCCTTTCGTTTTATTTGATGCCTGGCAGT
TCCCTACTCTCGCATGGGGAGACCCCACACTACCATCGGCGCTACGGCGT
TTCACTTCTGAGTTCGGCATGGGGTCAGGTGGGACCACCGCGCTACTGCC
GCCAGGCAAATTCTGTTTTATCAGACCGCTTCTGCGTTCTGATTTAATCT
GTATCAGGCTGAAAATCTTCTCTCATCCGCCAAAACAGCCAAGCTGGAGA
CCGTTTAAACTCAATGATGATGATGATGATGGTCGACGGCGCTATTCAGA
TCCTCTTCTGAGATGAGTTTTTGTTCGGGCCCAAGCTTCGAATTCCCATA
TGGTACCAGCTGCAGATCTCGAGCTCGGATCCATGGTTTATTCCTCCTTA
TTTAATCGATACATTAATATATACCTCTTTAATTTTTAATAATAAGTTA
ATCGATAATTCCGGTCGAGTGCCCACACAGATTGTCTGATAAATTGTTAA
```

-continued

```
AGAGCAGTGCCGCTTCGCTTTTTCTCAGCGGCGCTGTTTCCTGTGTGAAA
TTGTTATCCGCTCACAATTCCACACATTATACGAGCCGGATGATTAATTG
TCAACAGCTCATTTCAGAATATTTGCCAGAACCGTTATGATGTCGGCGCA
AAAAACATTATCCAGAACGGGAGTGCGCCTTGAGCGACACGAATTATGCA
GTGATTTACGACCTGCACAGCCATACCACAGCTTCCGATGGCTGCCTGAC
GCCAGAAGCATTGGTGCACCGTGCAGTCGATGATAAGCTGTCAAACCAGA
TCAATTCGCGCTAACTCACATTAATTGCGTTGCGCTCACTGCCCGCTTTC
CAGTCGGGAAACCTGTCGTGCCAGCTGCATTAATGAATCGGCCAACGCGC
GGGGAGAGGCGGTTTGCGTATTGGGCGCCAGGGTGGTTTTTCTTTTCACC
AGTGAGACGGGCAACAGCTGATTGCCCTTCACCGCCTGGCCCTGAGAGAG
TTGCAGCAAGCGGTCCACGCTGGTTTGCCCCAGCAGGCGAAATCCTGTT
TGATGGTGGTTGACGGCGGGATATAACATGAGCTGTCTTCGGTATCGTCG
TATCCCACTACCGAGATATCCGCACCAACGCGCAGCCCGGACTCGGTAAT
GGCGCGCATTGCGCCCAGCGCCATCTGATCGTTGGCAACCAGCATCGCAG
TGGGAACGATGCCCTCATTCAGCATTTGCATGGTTTGTTGAAAACCGGAC
ATGGCACTCCAGTCGCCTTCCCGTTCCGCTATCGGCTGAATTTGATTGCG
AGTGAGATATTTATGCCAGCCAGCCAGACGCAGACGCGCCGAGACAGAAC
TTAATGGGCCCGCTAACAGCGCGATTTGCTGGTGACCCAATGCGACCAGA
TGCTCCACGCCCAGTCGCGTACCGTCTTCATGGGAGAAAATAATACTGTT
GATGGGTGTCTGGTCAGAGACATCAAGAAATAACGCCGGAACATTAGTGC
AGGCAGCTTCCACAGCAATGGCATCCTGGTCATCCAGCGGATAGTTAATG
ATCAGCCCACTGACGCGTTGCGCGAGAAGATTGTGCACCGCCGCTTTACA
GGCTTCGACGCCGCTTCGTTCTACCATCGACACCACCACGCTGGCACCCA
GTTGATCGGCGCGAGATTTAATCGCCGCGACAATTTGCGACGGCGCGTGC
AGGGCCAGACTGGAGGTGGCAACGCCAATCAGCAACGACTGTTTGCCCGC
CAGTTGTTGTGCCACGCGGTTGGGAATGTAATTCAGCTCCGCCATCGCCG
CTTCCACTTTTTCCCGCGTTTTCGCAGAAACGTGGCTGGCCTGGTTCACC
ACGCGGGAAACGGTCTGATAAGAGACACCGGCATACTCTGCGACATCGTA
TAACGTTACTGGTTTCACATTCACCACCCTGAATTGACTCTCTTCCGGGC
GCTATCATGCCATACCGCGAAAGGTTTTGCACCATTCGATGGTGTCAACG
TAAATGCATGCCGCTTCGCCTTCGCGCGCGAATTGATCTGCTGCCTCGCG
CGTTTCGGTGATGACGGTGAAAACCTCTGACACATGCAGCTCCCGGAGAC
GGTCACAGCTTGTCTGTAAGCGGATGCCGGGAGCAGACAAGCCCGTCAGG
GCGCGTCAGCGGGTGTTGGCGGGCCGGCCTCG
```

The 'tesA, fadD, and atfA1 genes were amplified using high fidelity Phusion™ polymerase (New England Biolabs, Inc., Ipswich, Mass.), with the following primers from their respective plasmids, pETDuet-1-'tesA, pHZ1.61, and pHZ1.97-atfA1:

'tesAForward (SEQ ID NO: 20)
5'-CTCTAGAAATAATTTAACTTTAAGTAGGAGAUAGGTACCCATGGCGG

ACACGTTATTGAT

'tesAReverse (SEQ ID NO: 21)
5'-CTTCGAATTCCATTTAAATTATTTCTAGAGTCATTATGAGTCATGAT

TTACTAAAGGC fadDForward (SEQ ID NO: 22)
5'-CTCTAGAAATAATTTTAGTTAAGTATAAGAAGGAGATATACCATGGT

GAAGAAGGTTTGGCTTAA fadDReverse (SEQ ID NO: 23)
5'-CTTCGAATTCCATTTAAATTATTTCTAGAGTTATCAGGCTTTATTGT

CCAC atfA1Forward (SEQ ID NO: 24)
5'-CTCTAGAAATAATTTAGTTAAGTATAAGAAGGAGATATACAT atfA1Reverse (SEQ ID NO: 25)
5'-CTTCGAATTCCATTTAAATTATTTCTAGAGTTACTATTTAATTCCTG

CACCGATTTCC b) Insertion of 'tesA into pACYC-Ptrc Plasmid

Using NcoI and EcoRI sites on both the insert and vector, the 'tesA PCR product amplified from pETDuet-1-'tesA was cloned into the initial position of pACYC-PTrc vector (SEQ ID NO:19). A T4 DNA ligase (New England Biolabs, Ipswich, Mass.) was then used to ligate the pACYC-PTrc vector and 'tesA, producing a pACYC-PTrc-'tesA plasmid. Following overnight ligation, the DNA product was transformed into Top 10 One Shot® cells (Invitrogen, Carlsbad, Calif.). The 'tesA insertion into the pACYC-PTrc vector was confirmed by restriction digestion. An SwaI restriction site as well as overlapping fragments for In-Fusion™ cloning (Clontech, Mountain View, Calif.) was also created at the 3' end of the 'tesA insert.

c) Construction of pACYC-PTrc-'tesA-fadD-atfA1

The pACYC-PTrc-'tesA plasmid was then subject to an overnight digestion by SwaI. fadD amplified from pHZ1.61was cloned after the 'tesA gene using In-Fusion™ cloning. This insertion of fadD was verified with restriction digestion. The insertion of fadD destroys the SwaI site following the 'tesA gene, but recreates a new SwaI site at the 3' end of fadD.

The pACYC-PTrc-'tesA fadD plasmid was again linearized by SwaI, and atfA1 amplified from pHZ 1.97-atfA1 was cloned after the fadD gene using In-Fusion™ cloning. The proper insertion of atfA1 was verified by restriction digestion.

d) Construction of the pOP-80 (pCL) Plasmid

A low copy plasmid pCL1920 (in accordance with Lerner et al., Nucleic Acids Res. 18:4631 (1990)) carrying a strong transcriptional promoter was digested with restriction enzymes AflII and SfoI (New England Biolabs Inc. Ipswich, Mass.). Three DNA sequence fragments were produced by this digestion, among which a 3737 bp fragment was gel-purified using a gel-purification kit (Qiagen, Inc. Valencia, Calif.). In parallel, a fragment containing the Trc-promoter and lacI region from the commercial plasmid pTrcHis2 (Invitrogen, Carlsbad, Calif.) was amplified by PCR using the following primers:

(SEQ ID NO: 26)
LF302:    5'-ATATGACGTCGGCATCCGCTTACAGACA-3'

(SEQ ID NO: 27)
LF303    (5'-AATTCTTAAGTCAGGAGAGCGTTCACCGACAA-3'.

These two primers also introduced recognition sites for ZraI (gacgtc) and AflII (cttaag), at the end of the PCR product. The PCR product was purified using a PCR-purification kit (Qiagen, Inc. Valencia, Calif.) and digested with ZraI and AflII following the recommendations of the supplier (New England BioLabs Inc., Ipswich, Mass.). The digested PCR product was then gel-purified and ligated with the 3737 bp DNA sequence fragment derived from pCL1920. The ligation mixture was transformed in TOP10® chemically competent cells (Invitrogen, Carlsbad, Calif.), and the transformants were plated on Luria agar plates containing 100 µg/mL spectinomycin. After overnight incubation at 37° C., a number of colonies were visible. A select number of these colonies were purified, analyzed with restriction enzymes, and sequenced. One of the plasmids was retained and given the name pOP-80.

e) Construction of pCL-TFW-atfA1

The operon 'tesA-fadD-atfA1 was removed from pACYC-'tesA-fadD-atfA1 using restriction digestion with M/uI and EcoRI (New England Biolabs, Inc., Ipswich, Mass.). It was then cloned into complementary sites on pOP-80 to create the plasmid pCL-TFW-atfA1.

f) Integration of the PTrc-'tesA-fadD-atfA1 operon into the E. coli Δ4 Chromosome at the lacI-lacZ Locus Plasmid pCL-TFW-atfA1 was digested with restriction enzyme HindIII (New England Biolabs, Inc., Ipswich). In parallel, a chloramphenicol gene cassette was obtained from plasmid pLoxPcat2 (GenBank Accession No. AJ401047) by digestion with restriction enzymes BamHI and AvrII (New England Biolabs, Inc., Ipswich, Mass.). Both DNA fragments were blunt-ended using the DNA polymerase Klenow fragment. The resulting fragments were ligated and transformed to generate plasmid pCLTFWcat.

Plasmid placZ constructed and synthesized by DNA2.0 (Menlo Park, Calif.) in accordance to the sequence of SEQ ID NO:28 (below) was used as a template for PCR amplification.

(SEQ ID NO: 28)
CTAGTAACGGCCGCCAGTGTGCTGGAATTCAGGCAGTTCAACCTGTTGAT

AGTACGTACTAAGCTCTCATGTTTCACGTACTAAGCTCTCATGTTTAACG

TACTAAGCTCTCATGTTTAACGAACTAAACCCTCATGGCTAACGTACTAA

GCTCTCATGGCTAACGTACTAAGCTCTCATGTTTCACGTACTAAGCTCTC

ATGTTTGAACAATAAAATTAATATAAATCAGCAACTTAAATAGCCTCTAA

GGTTTTAAGTTTTATAAGAAAAAAAGAATATATAAGGCTTTTAAAGCTT

TTAAGGTTTAACGGTTGTGGACAACAAGCCAGGGATGTAACGCACTGAGA

AGCCCTTAGAGCCTCTCAAAGCAATTTTCAGTGACACAGGAACACTTAAC

GGCTGACAGCCTGAATTCTGCAGATCTGGCGTAATAGCGAAGAGGCCCGC

ACCGATCGCCCTTCCCAACAGTTGCGCAGCCTGAATGGCGAATGGCGCTT

TGCCTGGTTTCCGGTACCAGAAGCGGTGCCGGAAAGCTGGCTGGAGTGCG

ATCTTCCTGAGGCCGATACTGTCGTCGTCCCCTCAAACTGGCAGATGCAC

GGTTACGATGCGCCCATCTACACCAACGTAACCTATCCCATTACGGTCAA

```
TCCGCCGTTTGTTCCCACGGAGAATCCGACGGGTTGTTACTCGCTCACAT
TTAATGTTGATGAAAGCTGGCTACAGGAAGGCCAGACGCGAATTATTTTT
GATGGCGTTAACTCGGCGTTTCATCTGTGGTGCAACGGGCGCTGGGTCGG
TTACGGCCAGGACAGTCGTTTGCCGTCTGAATTTGACCTGAGCGCATTTT
TACGCGCCGGAGAAAACCGCCTCGCGGTGATGGTGCTGCGTTGGAGTGAC
GGCAGTTATCTGGAAGATCAGGATATGTGGCGGATGAGCGGCATTTTCCG
TGACGTCTCGTTGCTGCATAAACCGACTACACAAATCAGCGATTTCCATG
TTGCCACTCGCTTTAATGATGATTTCAGCCGCGCTGTACTGGAGGCTGAA
GTTCAGATGTGCGGCGAGTTGCGTGACTACCTACGGGTAACAGTTTCTTT
ATGGCAGGGTGAAACGCAGGTCGCCAGCGGCACCGCGCCTTTCGGCGGTG
AAATTATCGATGAGCGTGGTGGTTATGCCGATCGCGTCACACTACGTCTG
AACGTCGAAAACCCGAAACTGTGGAGCGCCGAAATCCCGAATCTCTATCG
TGCGGTGGTTGAACTGCACACCGCCGACGGCACGCTGATTGAAGCAGAAG
CCTGCGATGTCGGTTTCCGCGAGGTGCGGATTGAAAATGGTCTGCTGCTG
CTGAACGGCAAGCCGTTGCTGATTCGAGGCGTTAACCGTCACGAGCATCA
TCCTCTGCATGGTCAGGTCATGGATGAGCAGACGATGGTGCAGGATATCC
TGCTGATGAAGCAGAACAACTTTAACGCCGTGCGCTGTTCGCATTATCCG
AACCATCCGCTGTGGTACACGCTGTGCGACCGCTACGGCCTGTATGTGGT
GGATGAAGCCAATATTGAAACCCACGGCATGGTGCCAATGAATCGTCTGA
CCGATGATCCGCGCTGGCTACCGGCGATGAGCGAACGCGTAACGCGAATG
GTGCAGCGCGATCGTAATCACCCGAGTGTGATCATCTGGTCGCTGGGGAA
TGAATCAGGCCACGGCGCTAATCACGACGCGCTGTATCGCTGGATCAAAT
CTGTCGATCCTTCCCGCCCGGTGCAGTATGAAGGCGGCGGAGCCGACACC
ACGGCCACCGATATTATTTGCCCGATGTACGCGCGCGTGGATGAAGACCA
GCCCTTCCCGGCTGTGCCGAAATGGTCCATCAAAAAATGGCTTTCGCTAC
CTGGAGAGACGCGCCCGCTGATCCTTTGCGAATACGCCCACGCGATGGGT
AACAGTCTTGGCGGTTTCGCTAAATACTGGCAGGCGTTTCGTCAGTATCC
CCGTTTACAGGGCGGCTTCGTCTGGGACTGGGTGGATCAGTCGCTGATTA
AATATGATGAAAACGGCAACCCGTGGTCGGCTTACGGCGGTGATTTGGC
GATACGCCGAACGATCGCCAGTTCTGTATGAACGGTCTGGTCTTTGCCGA
CCGCACGCCGCATCCAGCGCTGACGGAAGCAAAACACCAGCAGCAGTTTT
TCCAGTTCCGTTTATCCGGGCAAACCATCGAAGTGACCAGCGAATACCTG
TTCCGTCATAGCGATAACGAGCTCCTGCACTGGATGGTGGCGCTGGATGG
TAAGCCGCTGGCAAGCGGTGAAGTGCCTCTGGATGTCGCTCCACAAGGTA
AACAGTTGATTGAACTGCCTGAACTACCGCAGCCGGAGAGCGCCGGGCAA
CTCTGGCTCACAGTACGCGTAGTGCAACCGAACGCGACCGCATGGTCAGA
AGCCGGGCACATCAGCGCCTGGCAGCAGTGGCGTCTGCGGAAAACCTCA
GTGTGACGCTCCCCGCCGCGTCCCACGCCATCCCGCATCTGACCACCAGC
GAAATGGATTTTTGCATCGAGCTGGGTAATAAGCGTTGGCAATTTAACCG
CCAGTCAGGCTTTCTTTCACAGATGTGGATTGGCGATAAAAAACAACTGC
TGACGCCGCTGCGCGATCAGTTCACCCGTGCACGTCTGCTGTCAGATAAA
GTCTCCCGTGAACTTTACCCGGTGGTGCATATCGGGGATGAAAGCTGGCG
CATGATGACCACCGATATGGCCAGTGTGCCGGTCTCCGTTATCGGGAAG
AAGTGGCTGATCTCAGCCACCGCGAAAATGACATCAAAAACGCCATTAAC
CTGATGTTCTGGGGAATATAAATGTCAGGCATGAGATTATCAAAAAGGAT
CTTCACCTAGATCCTTTTCACGTAGAAAGCCAGTCCGCAGAAACGGTGCT
GACCCCGGATGAATGTCAGCTACTGGGCTATCTGGACAAGGGAAAACGCA
AGCGCAAAGAGAAAGCAGGTAGCTTGCAGTGGGCTTACATGGCGATAGCT
AGACTGGGCGGTTTTATGGACAGCAAGCGAACCGGAATTGCCAGCTGGGG
CGCCCTCTGGTAAGGTTGGGAAGCCCTGCAAAGTAAACTGGATGGCTTTC
TCGCCGCCAAGGATCTGATGGCGCAGGGGATCAAGCTCTGATCAAGAGAC
AGGATGAGGATCGTTTCGCATGATTGAACAAGATGGATTGCACGCAGGTT
CTCCGGCCGCTTGGGTGGAGAGGCTATTCGGCTATGACTGGGCACAACAG
ACAATCGGCTGCTCTGATGCCGCCGTGTTCCGGCTGTCAGCGCAGGGGCG
CCCGGTTCTTTTTGTCAAGACCGACCTGTCCGGTGCCCTGAATGAACTGC
AAGACGAGGCAGCGCGGCTATCGTGGCTGGCCACGACGGGCGTTCCTTGC
GCAGCTGTGCTCGACGTTGTCACTGAAGCGGGAAGGGACTGGCTGCTATT
GGGCGAAGTGCCGGGGCAGGATCTCCTGTCATCTCACCTTGCTCCTGCCG
AGAAAGTATCCATCATGGCTGATGCAATGCGGCGGCTGCATACGCTTGAT
CCGGCTACCTGCCCATTCGACCACCAAGCGAAACATCGCATCGAGCGAGC
ACGTACTCGGATGGAAGCCGGTCTTGTCGATCAGGATGATCTGGACGAAG
AGCATCAGGGGCTCGCGCCAGCCGAACTGTTCGCCAGGCTCAAGGCGAGC
ATGCCCGACGGCGAGGATCTCGTCGTGACCCATGGCGATGCCTGCTTGCC
GAATATCATGGTGGAAAATGGCCGCTTTTCTGGATTCATCGACTGTGGCC
GGCTGGGTGTGGCGGACCGCTATCAGGACATAGCGTTGGCTACCCGTGAT
ATTGCTGAAGAGCTTGGCGGCGAATGGGCTGACCGCTTCCTCGTGCTTTA
CGGTATCGCCGCTCCCGATTCGCAGCGCATCGCCTTCTATCGCCTTCTTG
ACGAGTTCTTCTGAATTATTAACGCTTACAATTTCCTGATGCGGTATTTT
CTCCTTACGCATCTGTGCGGTATTTCACACCGCATACAGGTGGCACTTTT
CGGGGAAATGTGCGCGGAACCCCTATTTGTTTATTTTTCTAAATACATTC
AAATATGTATCCGCTCATGAGACAATAACCCTGATAAATGCTTCAATAAT
AGCACGTGAGGAGGGCCACCATGGCCAAGTTGACCAGTGCCGTTCCGGTG
CTCACCGCGCGCGACGTCGCCGGAGCGGTCGAGTTCTGGACCGACCGGCT
CGGGTTCTCCC
```

PCR primers LacZFnotI and pKDRspeI were designed to create restriction sites for the NotI and SpeI, respectively:

LacZFnotI
(SEQ ID NO: 29)
5'-CAACCAGCGGCCGCGCAGACGATGGTGCAGGATATC pKDRspeI
(SEQ ID NO: 30)
5'-CCACACACTAGTCAGATCTGCAGAATTCAGGCTGTC The resulting DNA fragment was ligated with a DNA fragment from plasmid pCLTFWcat digested with SpeI and NotI enzymes. The ligation mixture was used as a template for another PCR reaction using primers lacIF and lacZR located on the lacI and lacZ regions.

|  |  |
|---|---|
| lacIF | (SEQ ID NO: 31)<br>5'-GGCTGGCTGGCATAAATATCTC |
| lacZR | (SEQ ID NO: 32)<br>5'-CATCGCGTGGGCGTATTCG |

The resulting PCR product ("Integration Cassette") contains approximately 500 bases of homology to lacI or lacZ at each end. This PCR product was used to transform *E. coli* MG1655 44 cells that were made hypercompetent with plasmid pKD46 (see supra).

4. Production of Fatty Acid Ethyl Ester by the Production Strain.

Figure 6:
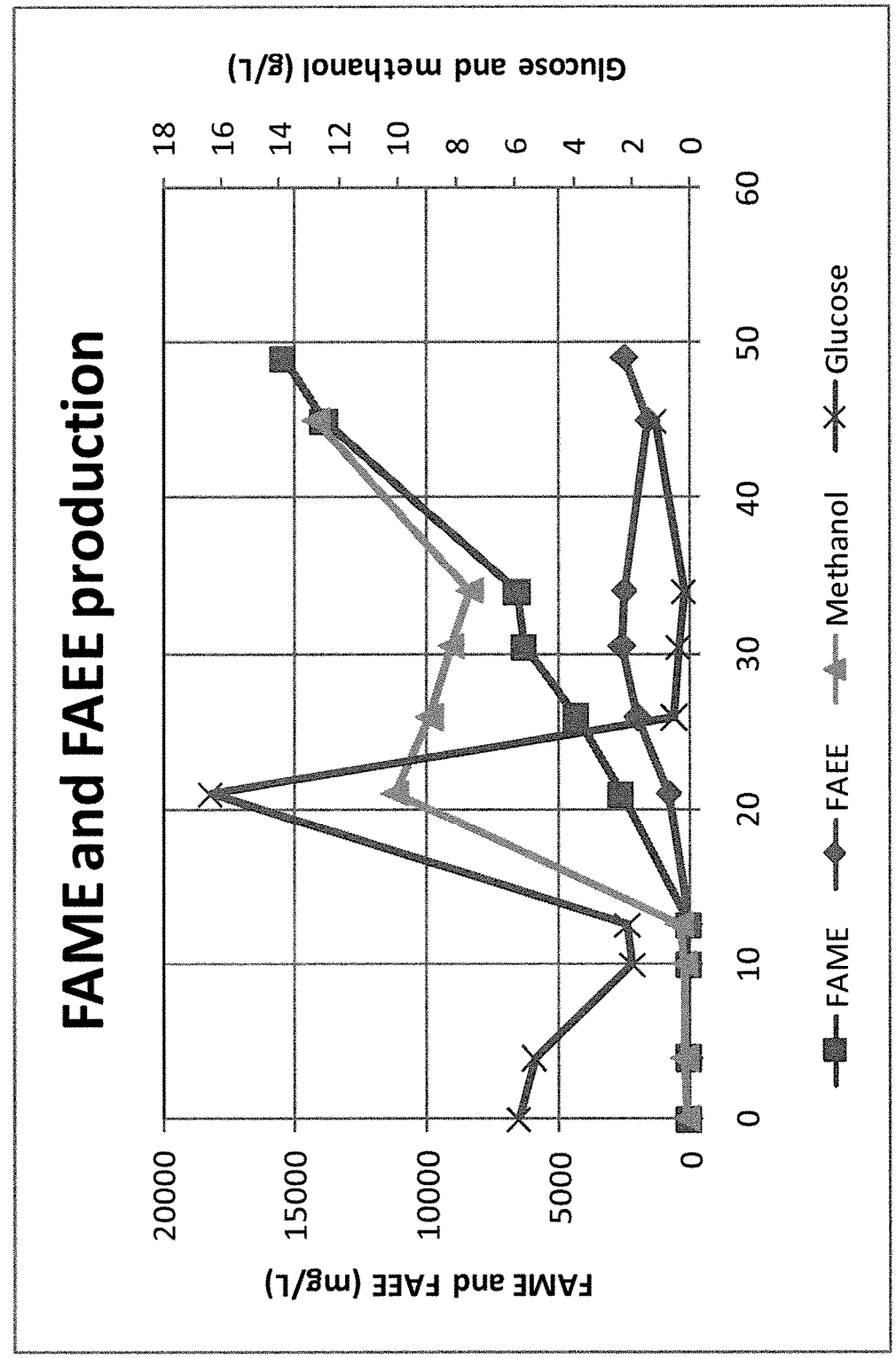
FIG. 6 is a graph of esters produced by a fermentation process using multiple methanol feeds and no exogenous ethanol.

The *E. coli* MG1655 44 strain carrying the 'tesA, fadD, and atfA1 plasmid was grown in fermentors under aerobic conditions favorable for growth and production of FAME. The cells were initially grown with excess glucose and excess oxygen. No accumulation of ethanol was observed. After induction the culture was maintained with a glucose feed lower than consumption, so glucose would not accumulate. Glucose was fed to maintain a glucose limitation. Methanol concentration was about 10 g/L immediately after induction (around 20 h) and increased to around 15 g/L after 48 h. A small amount of glucose accumulated towards the end of the fermentation. In the earlier hours after induction FAME accounted for 71% of the total esters produced while FAEE, with a concentration of around 2 g/L, represented the other 29%. Later in the fermentation, when the methanol concentration was increased, the FAME were produced at a higher rate and the distribution changed to 86% FAME and 14% FAEE, with a concentration of FAEE of about 2.5 g/L. The production profile is shown in FIG. 6. The yield of FAME was 9.3 g FAME per 100 g glucose or 23.3 g FAME per 100 g of carbon in carbon source. The yield of FAEE was 1.6 g FAEE per 100 g glucose or 3.9 g FAEE per 100 g carbon in carbon source. The yield of total product (FAME+FAEE) per amount of glucose used was 10.9 g product per 100 grams glucose or 27.2 g per 100 g carbon in carbon source.

Figure 7:
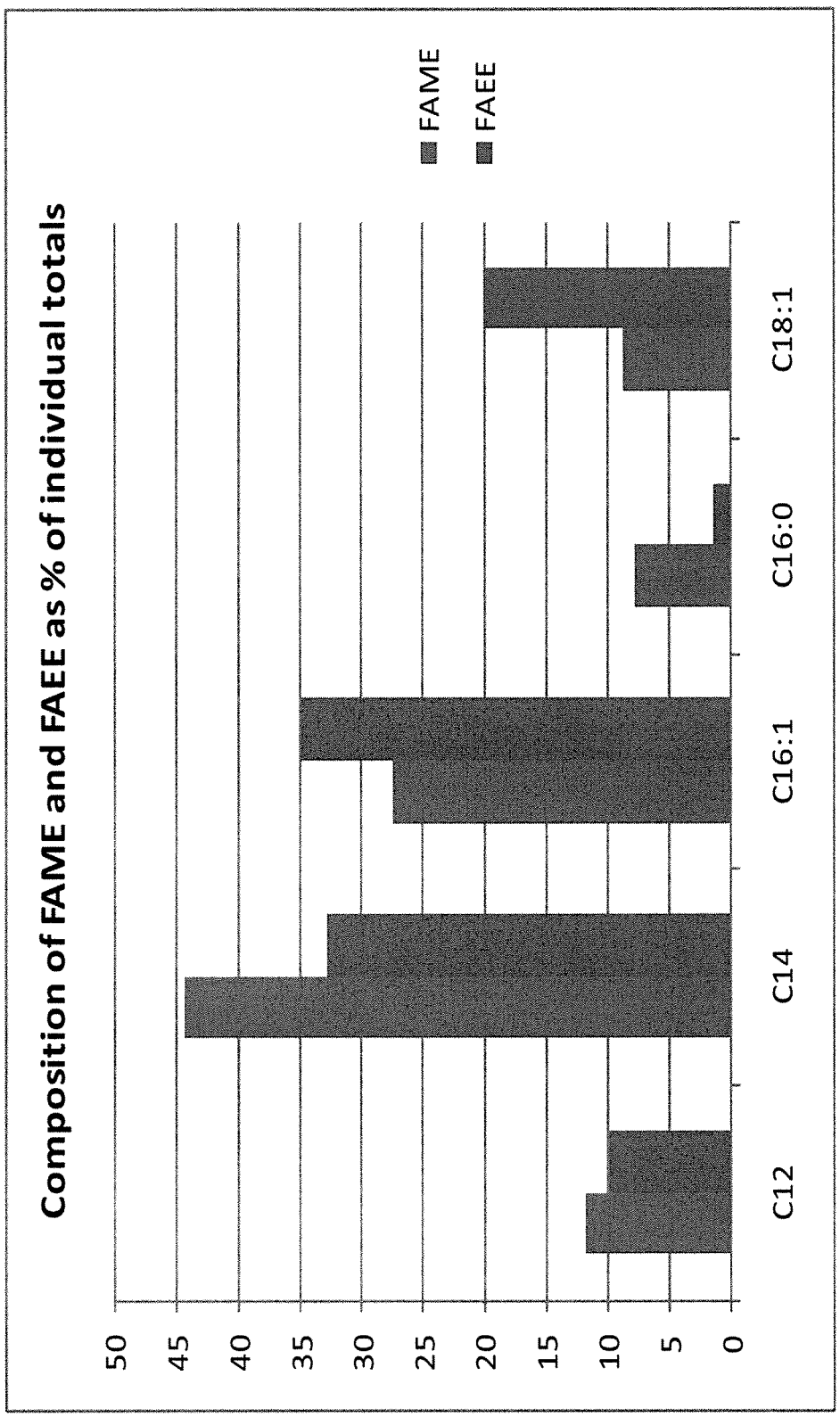
FIG. 7 is a graph of esters as a percentage of total products produced by a fermentation process using multiple methanol feeds and no exogenous ethanol.

The B side of the FAME and the FAEE produced in this process included fatty acids of different length and saturation level. The main components of the mixtures of fatty esters produced in this process were: C1:C12 (methyl laurate), C1:C14 (methyl myristate), C1:C16 (methyl palmitate), C 1:C16:1 (methyl palmitoleate), and C 1:C18:1 (methyl vaccenate); C2:C12 (ethyl laurate), C2:C14 (ethyl myristate), C2:C16 (ethyl palmitate), C2:C16:1 (ethyl palmitoleate), and C2:C18:1 (ethyl vaccenate). A diagram with the percent distribution of each methyl and ethyl ester under the production conditions of the current example is shown in FIG. 7.

Example 2

FAEE Production Without Exogenous Ethanol, Single Methanol Feed

Figure 8:
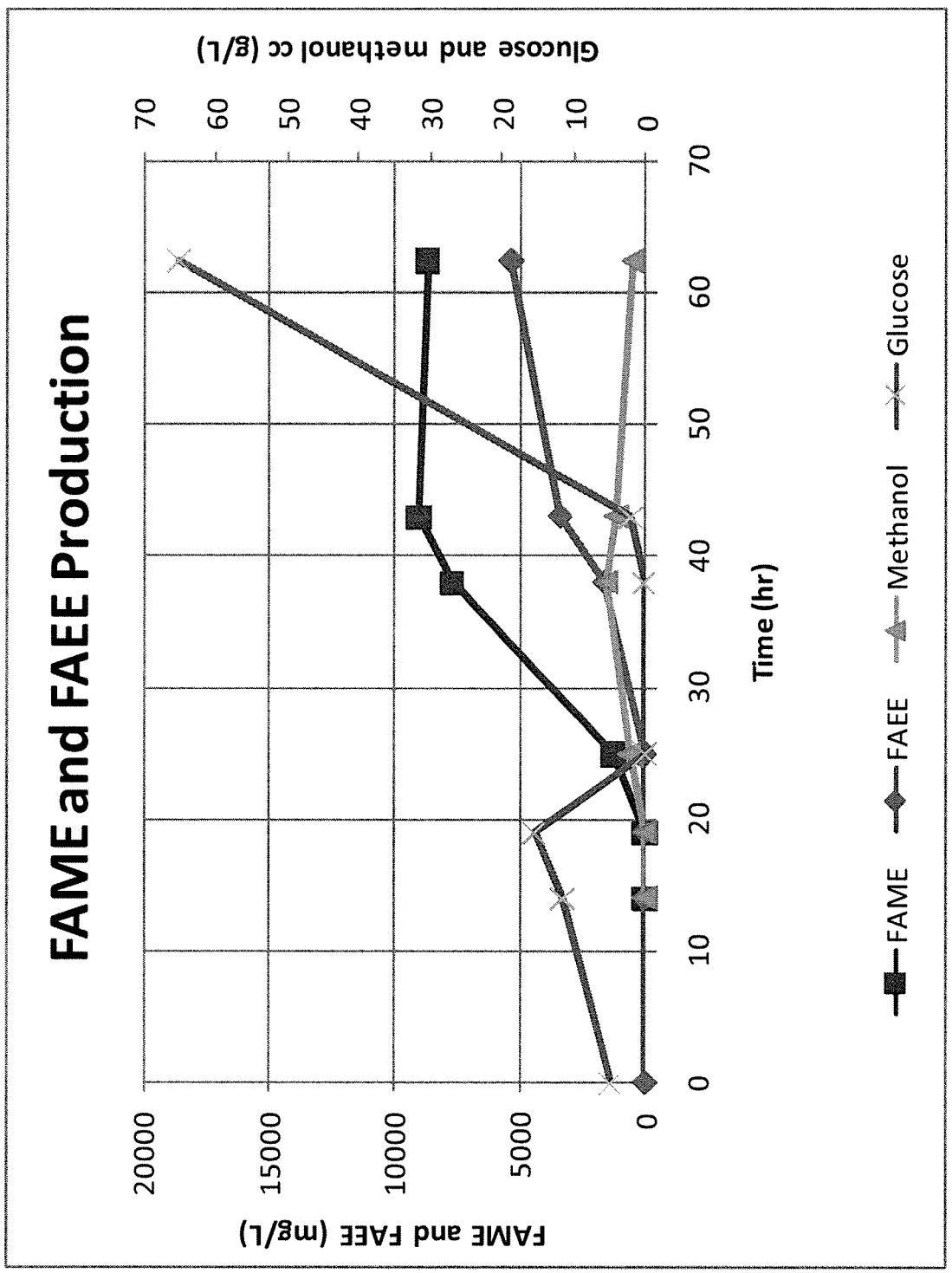
FIG. 8 is a graph of esters produced by a fermentation process using a single methanol feed and no exogenous ethanol.
Figure 9:
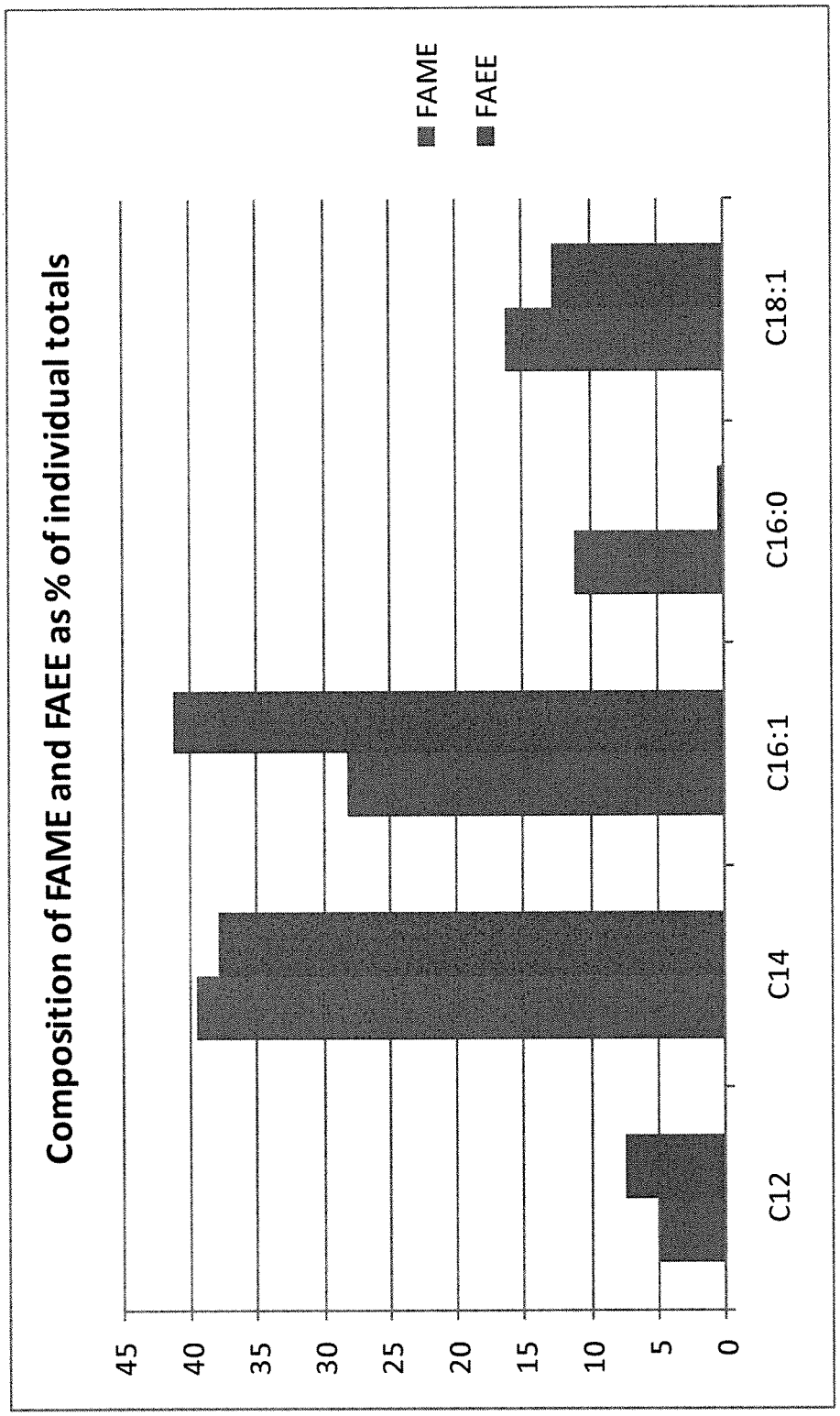
FIG. 9 is a graph of esters as a percentage of total products produced by a fermentation process using a single methanol feed and no exogenous ethanol.

Modified *E. coli* strain A4 (described in Example 1) carrying the plasmid containing 'tesA, fadD, and atfA1 was grown in fermentors under aerobic conditions favorable for growth and production of fatty acid methyl esters. The cells were initially grown with excess glucose and excess oxygen. No accumulation of ethanol was observed. After induction the culture was maintained with a glucose feed lower than consumption, so glucose would not accumulate. Glucose was fed at a faster rate than in Example 1. Methanol was added only once to a concentration of about 10 g/L. In the earlier portion of the fermentation, the results were similar to those of Example 1 with 78% FAME and 22% FAEE. However, later in the run, glucose consumption slowed down, glucose accumulated in the fermentor, and the methanol concentration decreased to about 5 g/L. At this time, the culture almost stopped producing FAME and increased the production of FAEE to a final distribution of 62% FAME and 38% FAEE. Final FAEE concentration was greater than 5 g/L. The fermentation profile is shown in FIG. 8. FIG. 9 presents the percent distribution of the FAME and FAEE produced, differentiated by their B side (fatty acid component). The yield of FAME was 6.5 g FAME per 100 g glucose or 16.3 g FAME per 100 g of carbon in carbon source. The yield of FAEE was 4.0 g FAEE per 100 g glucose or 10.1 g FAEE per 100 g carbon in carbon source. The yield of total product (FAME+FAEE) per amount of glucose used was 10.5 g product per 100 grams glucose or 26.4 g per 100 g carbon in carbon source. All the FAME and FAEE described in Example 1 were present in this case.

Example 3

FAEE Production Without Exogenous Alcohol

*E. coli* strain ID1 (MG1655 ΔfadE with an operon containing the genes 'tesA,fadD and atfA1 integrated in the chromosome under the control of the Trc promoter, constructed in accordance with Example 1) was grown in fermentors under conditions favorable for growth and production of free fatty acids.

Figure 10:
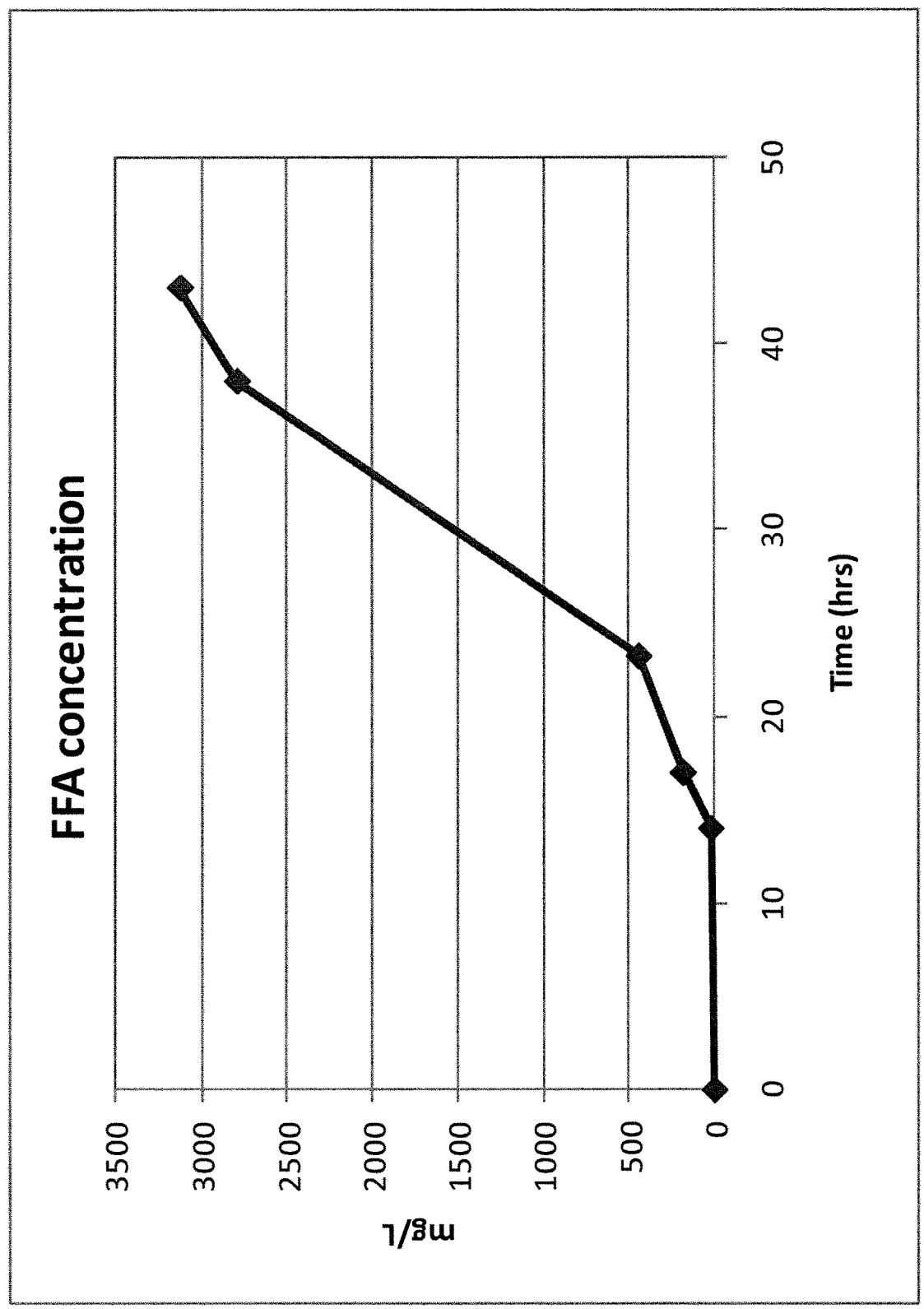
FIG. 10 is a graph of the concentration of free fatty acids produced by a fermentation process using no exogenous alcohol.
Figure 11:
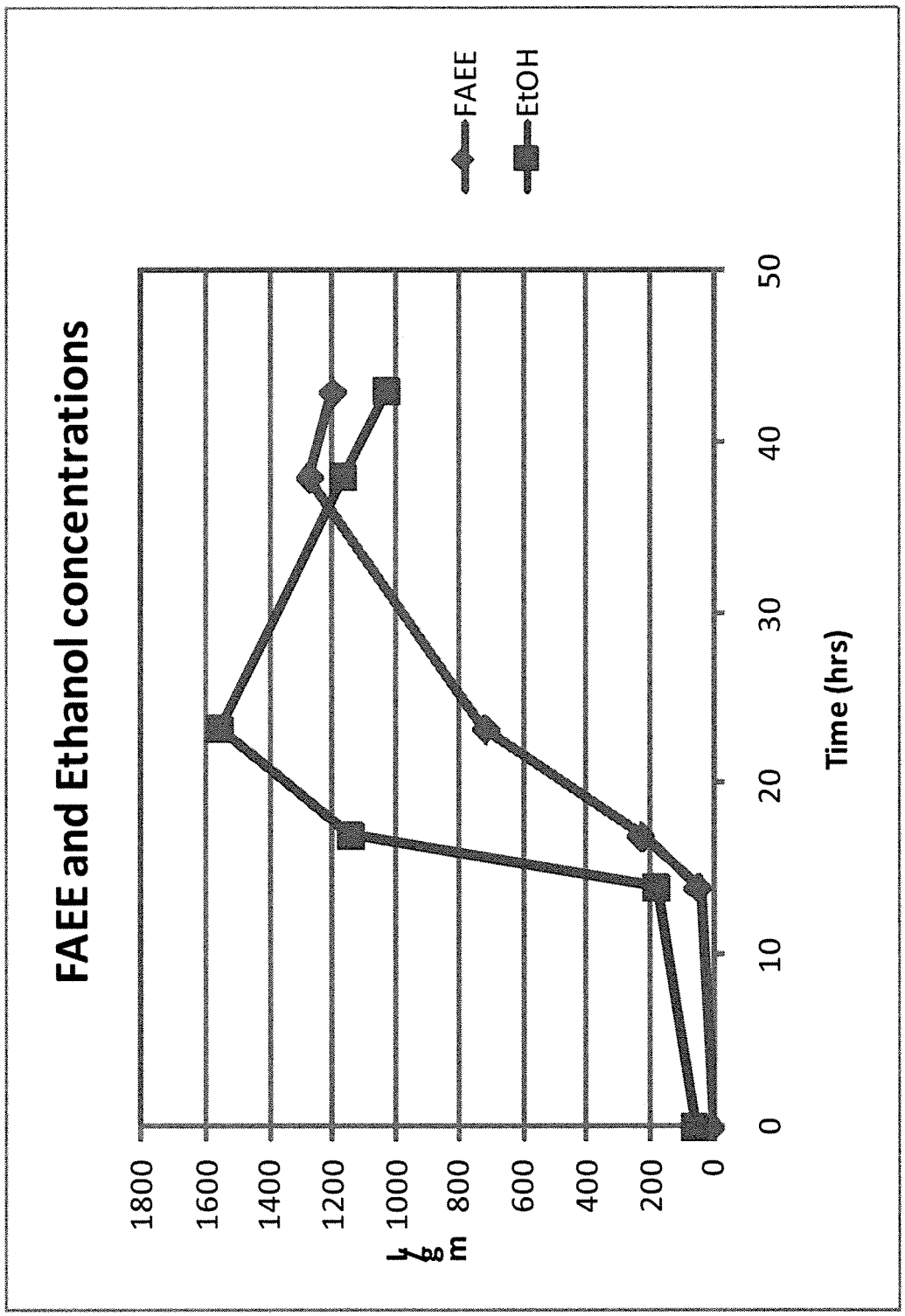
FIG. 11 is a graph of the concentration of FAEE and ethanol produced by a fermentation process using no exogenous alcohol.
Figure 12:
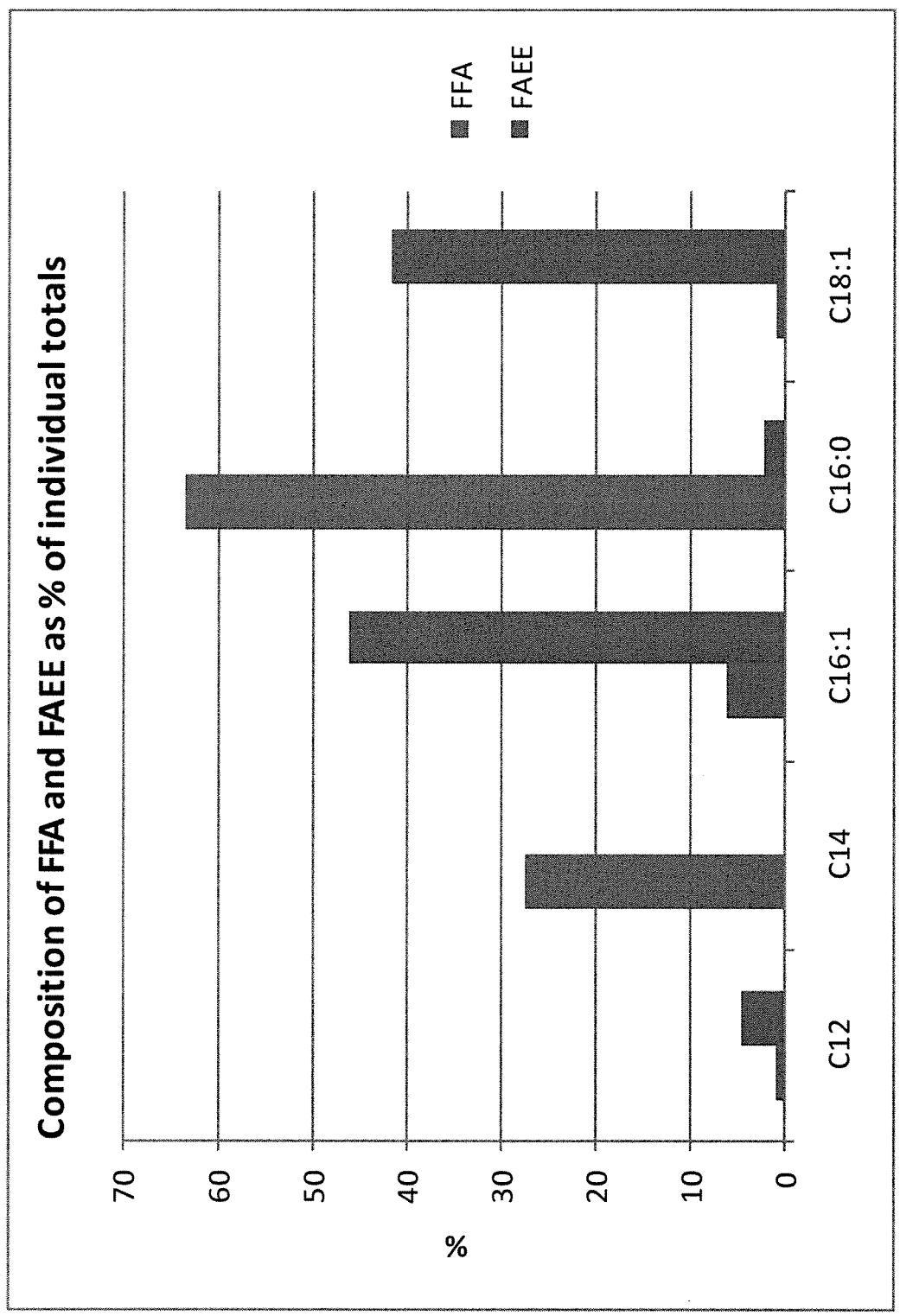
FIG. 12 is a graph of the concentration of free fatty acids and FAEE as a percentage of total products produced by a fermentation process using no exogenous alcohol.

The cells were initially grown with excess glucose (5 g/L) and fed an exponential glucose and mineral feed to allow for cell growth at a rate of 0.3 h$^{-1}$; this feeding was followed by a fixed feed scheme. The culture was maintained fully aerobic throughout the run. No exogenous alcohol was added to the medium. Small quantities of ethanol were produced, and free fatty acids were produced in large amounts. The engineered fatty acid pathway included an ester synthase enzyme, the main enzyme responsible for the production of esters in the presence of added alcohols. In this case, the endogenously produced ethanol was sufficient to act as raw material for the ester synthase enzyme together with the free fatty acids accumulated, resulting in the production and accumulation of FAEE. The accumulation profile for fatty acids, FAEE and ethanol are shown in FIG. 10 and FIG. 11. Free fatty acids accumulated to over 3 g/L in 43 h, while FAEE reached a concentration of 1.2 g/L in the same time. FIG. 12 shows the relative composition of free fatty acids and FAME produced by the process. The yield of FFA was 2.1 g FFA per 100 g glucose or 5.2 g FFA per 100 g of carbon in carbon source. The yield of FAEE was 0.8 g FAEE per 100 g glucose or 2.1 g FAEE per 100 g carbon in carbon source. The combined yield of FFA plus FAEE was 2.9 g per 100 g of glucose or 7.3 g per 100 g carbon in carbon source.

Example 4

FAEE Production Without Exogenous Alcohol in Cyanobacterial Host Cells

Suitable vectors are prepared in order to produce FAEE without exogenous addition of alcohols in cyanobacterial host cells including, for example, cells of *Synechococcus* sp. PCC7002, *Synechococcus elongatus* PCC7942, or *Synechocystis* sp. PCC6803. Suitable genes such as, for example, a plasmid containing a thioesterase gene (e.g., 'tesA from *E. coli*), a fatty acyl-CoA synthase gene (e.g., fadD from *E. coli*) and an ester synthase gene (e.g., atfA1 from *Alcanivorax borkumensis* strain SK2), optionally integrated in the chromosome under the control of a suitable promoter (e.g., PTrc), are then cloned into those vectors. One or more suitable genes that promotes the production of ethanol such as, for example, pdc [GenBank Accession No. YP_163095], adh [GenBank Accession No. YP_162971], adhA [GenBank Accession No. AAA71935], adhB [GenBank Accession No. AAC70367], from *Zymomonas mobilis,* or casA [GenBank Accession No. AAB51563], or casB [GenBank Accession No. AAB51564] of *Klebsiella oxytoca,* are also introduced into these host cells such that FAEE are produced without exogenous addition of alcohol.

A vector is constructed to accomplish homologous recombination in*Synechococcus* sp. PCC7002 pAQ1 [GenBank Accession No. NC_0050525] using 500 bp homologous regions corresponding to positions 3301-3800 and 3801-4300. A selectable marker, such as a spectinomycin resistance cassette containing aminoglycoside 3'-adenyltrasnferase gene, aad, a promoter, and a terminator is derived from the plasmid PCL1920 (in accordance with Lerner et al., *Nucleic Acids Res.* 18:4631 (1990)). That selectable marker is inserted into the homologous regions. A plasmid, such as pACYC177, is prepared in accordance with Chang, et al. *J. Bacteriol.* 134: 1141-1156 (1978). The promoter and ribosome binding site of aminoglycoside phosphotransferase, aph, are added followed by appropriate unique cloning sites that are, for example, NdeI and EcoRI recognition sequences. This complete integration cassette is synthesized and cloned into a pUC19 vector (New England Biolabs, Inc., Ipswich, Mass.). The resulting plasmid, pLS9-7002, allows cloning and expression of a foreign gene and delivery and stable in-vivo integration into *Synechococcus* sp. PCC7002 pAQ1.

A plasmid or synthetic operon containing a thioesterase gene (e.g., 'tesA from *E. coli*), a fatty acyl-CoA synthetase gene (e.g., fadD from *E. coli*) and an ester synthase gene (e.g., atfA1 from *Alcanivorax borkumensis* strain SK2) is created, and subsequently cloned into the NdeI and EcoRI sites of pLS9-7002 downstream of the aph promoter and ribosome binding site. A gene encoding an enzyme promoting ethanol production as described herein is likewise introduced. The resulting plasmid is then transformed into *Synechococcus* sp. PCC7002 using a method described by Stevens et al., *PNAS* 77:6052-56 (1980).

In some embodiments, another vector is constructed for homologous recombination into the *Synechococcus elongatus* PCC7942 genome (GenBank Accession No. CP_000100) using 800 bp homologous regions corresponding to positions 2577844-2578659 and 2578660-2579467. This chromosomal location is known as neutral site one (NS1) (Mackey et al., *Meth. Mol. Biol.* 362:115-129 (2007). A selectable marker, such as, for example, a spectinomycin resistance cassette is derived and introduced as described above. This integration cassette is synthesized and cloned into pUC19 (New England Biolabs, Inc., Ipswich, Mass.). The resulting plasmid, pLS9-7942-NS1, allows cloning and expression of a foreign gene and delivery and stable integration into the Synechococcus elongatus PCC7942 genome. A plasmid or synthetic operon comprising a thioesterase gene, a fatty acyl-CoA synthetase gene, and an ester synthase gene, is created as described above, which is then cloned into the NdeI or EcoRI site of pLS9-7942-NS1. A gene encoding an enzyme promoting ethanol production as described herein is likewise introduced. The resulting plasmid is transformed into *S. elongatus* PCC7942 in accordance with a method described by Mackey et al., supra.

In some embodiments, yet another vector is constructed for homologous recombination into the *Synechocystis* sp. PCC6803 genome (GenBank Accession BA_000022) using 1300 to 1700 bp homologous regions corresponding to positions 2299015-2300690, and 2300691-2302056, respectively. This chromosomal location is known as neutral site RS1/2 (Shao et al., *Appl. Environ. Microbiol.* 68:5026-33 (2002)). A plasmid, such as pACYC177, is prepared in accordance with Chang, et al. *J. Bacteriol.* 134: 1141-1156 (1978). As a selectable marker, a kanamycin resistance cassette (containing aminoglycoside phosphotransferase, aph, promoter, gene and terminator) is derived from the pACYC177 plasmid, and it is added between the homologous regions. Additionally, appropriate unique cloning sites, for example, NdeI and XbaI recognitions sites are added. This integration cassette is synthesized and cloned into pUC19 (New England Biolabs, Inc., Ipswich, Mass.). The resulting plasmid, pLS9-6803-RS, allows cloning and expression of a foreign gene and delivery and stable integration into the *Synechocystis* sp. PCC6803 genome.

A plasmid or synthetic operon containing a thioesterase gene, a fatty acyl-CoA synthetase gene and an ester synthase gene is created as described above, which is then cloned into the NdeI or XbaI site of pLS9-6803-RS. A gene encoding an enzyme promoting ethanol production as described herein is likewise introduced. The resulting plasmid is transformed into *Synechocystis* sp. PCC6803 in accordance with a method described by Zang et al. *J. Microbiol.,* 45:241-45 (2007).

Example 5

FAEE Production Without Exogenous Alcohol in Yeast

A pFBAIN-MOD-1 vector is constructed in accordance with the method of PCT Publication WO2008/147935, the disclosures of which are incorporated herein by reference. This vector is then digested with suitable restriction enzymes, such as, for example, NcoI and NotI (New England Biolabs, Inc., Ipswich, Mass.). A plasmid or synthetic operon containing a thioesterase gene, a fatty acyl-CoA synthase gene, and an ester synthase gene is created as described above, which is then inserted into the pre-digested pFBAIN-MOD-1 vector under standard ligation conditions. A gene encoding an enzyme promoting ethanol production as described herein is optionally likewise introduced. This ligation mixture is then incubated at room temperature for 2 h and used to transform an appropriate competent cell, such as, for example, *E. coli* Top10 Competent cells (Life Technologies, Carlsbad, Calif.). Plasmid DNA from transformants is recovered using a Qiagen Miniprep kit. Correct clones are identified by restriction mapping.

A correct clone is then transformed into a suitable yeast host cell such as a *Yarrowia lipolytica* cell, for example, Y_FOA$^R$. Y_FOA$^R$ is prepared by obtaining *Yarrowia lipolytica* ATCC#20362 cells and plating them on a YPD agar plate (containing 10 g/L of yeast extract (DIFCO, Detroit, Mich.), 20 g/L of bacto pepton (DIFCO, Detroit, Mich.), and 20 g/L of glucose). The cells are then streaked onto a Minimum Medium (MM) plate (containing 75 mg/L each of uracil and uridine, 6.7 g/L YNB (yeast nitrogen base)

with ammonia sulfate, without amino acids, and 20 g/L glucose) containing 250 mg/L 5-FOA (Zymo Research, Orange, Calif.). Plates are incubated at 28° C., and the resulting colonies are patched separately onto MM plates containing 200 mg/L 5-FOA and MM plates lacking uracil and uridine. Ura3 auxotrophy is thus obtained and the resulting strain is the Y_FOA$^R$ strain.

The cells from the transformation are plated onto MM plates lacking uracil (0.17% YNB (DIFCO Labs, Detroit, Mich.) without ammonium sulfate or amino acids, 2% glucose, 0.1% proline, pH 6.1, 20 g/L agar) and maintained at 30° C. for 2 d. The transformants are collected and are optionally used for fermentation under suitable conditions to produce fatty acid ethyl esters. For example, a few transformants are then used to inoculate 25 mL culture in MM medium without ammonium sulfate or amino acids, 2% glucose, 0.1% proline, pH 6.1. Each culture is allowed to grow for 2 d at 30° C., then is switched to 25 mL HGM (High Growth Medium containing 80 g/L glucose, 2.58 g/L KH$_2$PO$_4$, 5.36 g/L K$_2$HPO$_4$) and allowed to grow for about 5 d at 30° C. Total lipids are extracted and the production of fatty acid ethyl esters is ascertained and measured using the methods described herein.

EQUIVALENTS

While specific examples of the subject inventions are explicitly disclosed herein, the above specification and examples herein are illustrative and not restrictive. Many variations of the inventions will become apparent to those skilled in the art upon review of this specification including the examples. The full scope of the inventions should be determined by reference to the examples, along with their full scope of equivalents, and the specification, along with such variations.

All publications, patents, patent applications, and other references cited in this application are herein incorporated by reference in their entirety as if each publication, patent, patent application or other reference were specifically and individually indicated to be incorporated by reference.

---

What is claimed is:

1. A method of producing a fatty acid methyl ester ("FAME") and/or a fatty acid ethyl ester ("FAEE"), the method comprising:
    culturing a recombinant microorganism comprising overexpression of
    (1) an exogenous nucleic acid sequence encoding a thioesterase (EC 3.1.2.),
    (2) an exogenous nucleic acid sequence encoding an acyl-CoA synthase (EC 6.2.1.3), and
    (3) an exogenous nucleic acid sequence encoding a wax synthase (EC 2.3.1.75), in the absence of exogenous alcohol;
    wherein the recombinant microorganism is genetically engineered to overexpress at least one gene selected from the group consisting of pdh, panK, aceEF, accABCD, fabH, fabD, fabG, acpP, fabF, and udhA, relative to a corresponding wild type microorganism; and
    wherein the recombinant microorganism produces the FAME and/or the FAEE when cultured in the presence of a carbohydrate carbon source.

2. The method of claim 1, wherein the recombinant microorganism is genetically engineered to have reduced expression of at least one gene selected from the group consisting of ackA, ackB, adhE, fabF, fabR, fadE, gpsA, ldhA, pflB, plsB, poxB, pta, and glutathione synthase, relative to a corresponding wild type microorganism.

3. The method of claim 1, wherein the recombinant microorganism is genetically engineered to have reduced expression of fabR, relative to a corresponding wild type microorganism.

4. The method of claim 1, further comprising the step of isolating the FAME and/or the FAEE.

5. The method of claim 1, wherein the recombinant microorganism is further genetically engineered to produce ethanol.

6. The method of claim 1, wherein the FAEE is produced at a yield of 5 or 10 grams per 100 grams of glucose.

7. The method of claim 1, wherein the recombinant microorganism is selected from a recombinant *Escherichia coli* cell, a recombinant yeast cell, and a recombinant cyanobacterium cell.

8. A recombinant microorganism for producing a fatty acid methyl ester ("FAME") and/or a fatty acid ethyl ester ("FAEE"), wherein the recombinant microorganism is genetically engineered to overexpress an exogenous nucleic acid sequence encoding a thioesterase (EC 3.1.2.), an exogenous nucleic acid sequence encoding an acyl-CoA synthase (EC 6.2.1.3), and an exogenous nucleic acid sequence encoding a wax synthase (EC 2.3.1.75);
    wherein the recombinant microorganism is genetically engineered to overexpress at least one gene selected from the group consisting ofpdh, panK, aceEF, accABCD, fabH, fabD, fabG, acpP, fabF, and udhA, relative to a corresponding wild type microorganism; and
    wherein the recombinant microorganism produces the FAME and/or the FAEE when cultured in the presence of a carbohydrate carbon source and in the absence of exogenously provided alcohol.

9. The recombinant microorganism of claim 8, wherein the recombinant microorganism is genetically engineered to have reduced expression of at least one gene selected from the group consisting of ackA, ackB, adhE, fabF, fabR, fadE, gpsA, ldhA, pflB, plsB, poxB, pta, and glutathione synthase, relative to a corresponding wild type microorganism.

10. The recombinant microorganism of claim 8, wherein the recombinant microorganism is selected from a recombinant *Escherichia coli* cell, a recombinant yeast cell, and a recombinant cyanobacterium cell.

* * * * *